US012651645B2

(12) United States Patent
Alt et al.

(10) Patent No.: US 12,651,645 B2
(45) Date of Patent: Jun. 9, 2026

(54) METHODS AND COMPOSITIONS RELATING TO DETECTION OF RECOMBINATION AND REARRANGEMENT EVENTS

(71) Applicant: THE CHILDREN'S MEDICAL CENTER CORPORATION, Boston, MA (US)

(72) Inventors: Frederick W. Alt, Cambridge, MA (US); Jiazhi Hu, Boston, MA (US); Sherry Lin, Brookline, MA (US); Zhou Du, Chestnut Hill, MA (US); Yu Zhang, West Roxbury, MA (US); Huan Chen, Cambridge, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 541 days.

(21) Appl. No.: 18/129,274

(22) Filed: Mar. 31, 2023

(65) Prior Publication Data

US 2023/0298702 A1     Sep. 21, 2023

Related U.S. Application Data

(62) Division of application No. 16/481,964, filed as application No. PCT/US2018/017932 on Feb. 13, 2018, now abandoned.

(60) Provisional application No. 62/458,244, filed on Feb. 13, 2017.

(51) Int. Cl.
| | |
|---|---|
| *G16B 30/10* | (2019.01) |
| *C12Q 1/6827* | (2018.01) |
| *C12Q 1/6855* | (2018.01) |
| *C12Q 1/6858* | (2018.01) |
| *C12Q 1/686* | (2018.01) |
| *C12Q 1/6869* | (2018.01) |
| *G16B 30/00* | (2019.01) |

(52) U.S. Cl.
CPC .......... *G16B 30/10* (2019.02); *C12Q 1/6827* (2013.01); *C12Q 1/6855* (2013.01); *C12Q 1/6858* (2013.01); *C12Q 1/686* (2013.01); *C12Q 1/6869* (2013.01); *G16B 30/00* (2019.02); *C12Q 2549/119* (2013.01)

(58) Field of Classification Search
CPC ...... G16B 30/10; G16B 30/00; C12Q 1/6827; C12Q 1/6855; C12Q 1/6858; C12Q 1/686; C12Q 1/6869; C12Q 2549/119; C12Q 1/6806
See application file for complete search history.

(56) References Cited

U.S. PATENT DOCUMENTS

| | | |
|---|---|---|
| 6,514,706 B1 | 2/2003 | Von Kalle et al. |
| 2014/0234847 A1 | 8/2014 | Alt et al. |
| 2016/0040234 A1 | 2/2016 | Hutchins et al. |

FOREIGN PATENT DOCUMENTS

| | | |
|---|---|---|
| WO | 2013/006745 A2 | 1/2013 |
| WO | 2016/081798 A1 | 5/2016 |
| WO | 2018193457 A1 | 10/2018 |

OTHER PUBLICATIONS

Lin et al., PNAS, vol. 113, No. 28, pp. 7846-7851, Jul. 2016.*
Ba et al. "Abstract A033: Mechanisms that mediate intralocus and interlocus regulation of V(D)J recombination at immunoglobulin light chain loci." Cancer Immunology Research 4(11 Supplement): A033 pp. 1-4 (2016).
Chiarle et al., "Genome-wide translocation sequencing reveals mechanisms of chromosome breaks and rearrangements in B cells." Cell 147(1):107-119 (2011).
Dong et al., "Orientation-specific joining of AID-initiated DNA breaks promotes antibody class switching." Nature 525 (7567):134-139 (2015).
Frock et al., "Genome-wide detection of DNA double-stranded breaks induced by engineered nucleases." Nature Biotechnology 33(2):179-186 (2015).
Georgiou et al., "The promise and challenge of high-throughput sequencing of the antibody repertoire", Nature Biotechnology 32(2):158-168 (2014).
GenBank Accession No. AB189968, Mus musculus JH1 gene for immunoglobulin H-chain V-region, partical cds, strain: C57BL/6 (Year: 2005).
Hu et al., "Chromosomal Loop Domains Direct the Recombination of Antigen Receptor Genes." Cell 163(4):947-959 (2015).
Hu et al., "Detecting DNA double-stranded breaks in mammalian genomes by linear amplification-mediated high-throughput genome-wide translocation sequencing." Nature Protocols 11(5):853-871 (2016).
Meng et al., "Convergent transcription at intragenic super-enhancers targets AID-initiated genomic instability." Cell 159(7):1538-1548 (2014).
Rohatgi et al., Systematic design and testing of nested (RT-)PCR primers for specfic amplification of mouse rearranged/expressed immunoglobulin variable region genes from small number of B cells, J. Immunol. Meth,. vol. 339, pp. 205-219 (2008).
Wei et al., "Long Neural Genes Harbor Recurrent DNA Break Clusters in Neural Stem/Progenitor Cells." Cell 164 (4):644-655 (2016).

(Continued)

*Primary Examiner* — Cynthia B Wilder
(74) *Attorney, Agent, or Firm* — NIXON PEABODY LLP; David S. Resnick; Nicole D. Kling

(57) ABSTRACT

Described herein are methods and assays for detection of recombination and/or rearrangement events in a cell. In some embodiments, the methods and/or assays relate to Linear Amplification Mediated (LAM)-PCR. In some embodiments, the recombination event is a V(D)J recombination event.

20 Claims, 123 Drawing Sheets

Specification includes a Sequence Listing.

(56)            References Cited

OTHER PUBLICATIONS

Zhou et al., Mapping genomic hotspots of DNA ganage by single-strand-DNA-compatible and strand-specific CHIP-Sseq method, Genome Res., vol. 23, pp. 705-715 (201.

10x Genomics. "What is a template switch oligo (TSO)?," Article Retrieved from the Internet at <https://kb.10xgenomics.com/s/article/360001493051-What-is-a-template-switch-oligo-TSO>, Article No. 000003028 (Last Published Nov. 3, 2025).

Pinto et al. "A guide for in-house design of template-switch-based 5' rapid amplification of cDNA ends systems." Analytical biochemistry 397.2: 227-232 (2010).

* cited by examiner

*v-Abl* PRO-B CELL LINE
V<sub>K</sub> USAGE

EXAMPLE STITCHED VDJ_H READ FROM PRO-B CELLS

CTGCAATGCTCAGAGAAAACTCCATAACAAAGGTTAAAAATAAAGACCTGGAGAGGCCATTCTTACCTGAG *Jh4*
*LOCUS-SPECIFIC PRIMER*

GAGACGGTGACTGAGGTTCCTTGACCCCAGTAGTCCATAGCCCACTACCGTAGTAATAATTGC *CDR3*
*Dh1-1*

ATCTCTTGCACAGTAATAAATGGCAGTGTCCTCAGCTCTCAGGGCATTCATCTGAAGGTAGAGGATGCTT

TGGGAAGTGTGTCTCTGGAGACGATGAACCACCCTTCACAGATGCACTGTACTCTGTTGTATATCATTA *CDR2*

GCTTTGTTTCTACTTGCAGCAATCCACTCCACTCCAGTCTCTTCCCTGGAGGCTGGCGGGACCCACTCCATGTAG

AAATCACTGAAGGTGAACCCAGAAGTTGCACAGGAGTCTCAGAGAACCCCAGGCTGTACCAAGCCT
*CDR1*

CCTCCAGATTCCACCAGCTTCACCTCACCTCACGGCGCCCTATAGTC
*ADAPTER*

*FIG. 5B*

EXAMPLE STITCHED VJK READ FROM V-Abl CELL LINE

CCGGTTGCCAGGAATGGCTCATTTAGCCAAAATGTCACACAAATTCACACAAGTTACCCAAACAGAACC
LOCUS-SPECIFIC PRIMER

AAAACGTCACAGTCAAAAGTCTACTTACGTTTATTTCCAACTTTGTCCCGAGCCGAAC
JK4

GTGAATGGGAGGAGGATCCCTCATTACTTTTGCTGACAGTAATAGGTTGCAGCATCCTCCTCCCACAGGA
CDR3

TGGATGTTGAGGGGTGAAGTCTGTCCCAGACCCCACTGCCACTAAACCTGGCTGGGATCCCAGATTCTA

GATTGGATGCAGCATAGATGAGGAGTTTGGGTGGCTGTCCTGGTTTCTGTTGGTACCAGTTCATAT
CDR2                                                    CDR1

AACTATCACCATCATCATAATCAACACTTTGGCTGGCCTTGCAGGAGATGGTGGCCCTCTGCCCTAGAG

ACACAGCCAAAGAAGCTGGAGATTGGGTCAGCACAATGTCACCAGTGGGAGCCTGGAATGATAAACAC

ACAGAGCACCAGCGCTGCCTATAGTC
ADAPTER

| Vн FAMILY | VН1 | VН2 | VН3 | VН4 | VН5 | VН6 | VН7 | VН8 | VН9 | VН10 | VН11 | VН12 | VН13 | VН14 | VН15 | VН16 | TOTAL |
|---|---|---|---|---|---|---|---|---|---|---|---|---|---|---|---|---|---|
| FUNCTIONAL V USED | 51 | 7 | 6 | 1 | 10 | 5 | 3 | 8 | 4 | 2 | 2 | 2 | 1 | 4 | 1 | 0 | 107 |
| FUNCTIONAL V NOT USED | 1 | 1 | 0 | 0 | 0 | 0 | 1 | 0 | 0 | 0 | 0 | 0 | 0 | 0 | 0 | 0 | 3 |
| TOTAL FUNCTIONAL Vs | 52 | 8 | 6 | 1 | 10 | 5 | 4 | 8 | 4 | 2 | 2 | 2 | 1 | 4 | 1 | 0 | 110 |
| PSEUDO-V USED | 15 | 1 | 1 | 1 | 2 | 0 | 0 | 1 | 0 | 0 | 0 | 0 | 0 | 0 | 0 | 0 | 21 |
| PSEUDO-V NOT USED | 26 | 2 | 1 | 0 | 9 | 2 | 0 | 7 | 0 | 2 | 0 | 1 | 1 | 0 | 1 | 1 | 53 |
| TOTAL PSUEDO Vs | 41 | 3 | 2 | 1 | 11 | 2 | 0 | 8 | 0 | 2 | 0 | 1 | 1 | 0 | 1 | 1 | 74 |

*FIG. 7C*

| Vₖ FAMILY | Vk1 | Vk2 | Vk3 | Vk4 | Vk5 | Vk6 | Vk7 | Vk8 | Vk9 | Vk10 | Vk11 | Vk12 | Vk13 | Vk14 | Vk15 | Vk16 | Vk17 | Vk18 | Vk19 | Vk20 | TOTAL |
|---|---|---|---|---|---|---|---|---|---|---|---|---|---|---|---|---|---|---|---|---|---|
| FUNCTIONAL V USED | 9 | 3 | 9 | 26 | 5 | 9 | 1 | 11 | 4 | 3 | 1 | 6 | 2 | 4 | 1 | 1 | 2 | 1 | 1 | 1 | 100 |
| FUNCTIONAL V NOT USED | 0 | 0 | 0 | 0 | 0 | 0 | 0 | 0 | 0 | 0 | 0 | 0 | 0 | 0 | 0 | 0 | 0 | 0 | 0 | 0 | 0 |
| TOTAL FUNCTIONAL Vs | 9 | 3 | 9 | 26 | 5 | 9 | 1 | 11 | 4 | 3 | 1 | 6 | 2 | 4 | 1 | 1 | 2 | 1 | 1 | 1 | 100 |
| PSEUDO-V USED | 1 | 0 | 1 | 5 | 0 | 0 | 0 | 0 | 2 | 0 | 0 | 1 | 1 | 0 | 0 | 0 | 0 | 0 | 0 | 0 | 11 |
| PSEUDO-V NOT USED | 3 | 7 | 3 | 2 | 1 | 0 | 0 | 2 | 0 | 0 | 3 | 5 | 16 | 4 | 4 | 0 | 1 | 0 | 0 | 0 | 51 |
| TOTAL PSEUDO-Vs | 4 | 7 | 4 | 7 | 1 | 0 | 0 | 2 | 2 | 0 | 3 | 6 | 17 | 4 | 4 | 0 | 1 | 0 | 0 | 0 | 62 |

*FIG. 9C*

| $V_H$ FAMILY | $V_H1$ | $V_H2$ | $V_H3$ | $V_H4$ | $V_H5$ | $V_H6$ | $V_H7$ | $V_H8$ | $V_H9$ | $V_H10$ | $V_H11$ | $V_H12$ | $V_H13$ | $V_H14$ | $V_H15$ | $V_H16$ | TOTAL |
|---|---|---|---|---|---|---|---|---|---|---|---|---|---|---|---|---|---|
| FUNCTIONAL V USED [2ug] | 51 | 7 | 6 | 1 | 10 | 5 | 3 | 8 | 4 | 2 | 2 | 2 | 1 | 4 | 1 | 0 | 107 |
| FUNCTIONAL V NOT USED [2ug] | 1 | 1 | 0 | 0 | 0 | 0 | 1 | 0 | 0 | 0 | 0 | 0 | 0 | 0 | 0 | 0 | 3 |
| FUNCTIONAL V USED [500ng] | 51 | 7 | 6 | 1 | 10 | 5 | 3 | 8 | 4 | 2 | 2 | 2 | 1 | 4 | 1 | 0 | 107 |
| FUNCTIONAL V NOT USED [500ng] | 1 | 1 | 0 | 0 | 0 | 0 | 1 | 0 | 0 | 0 | 0 | 0 | 0 | 0 | 0 | 0 | 3 |
| FUNCTIONAL V USED [100ng] | 50 | 7 | 6 | 1 | 9 | 3 | 3 | 7 | 4 | 2 | 2 | 2 | 1 | 4 | 1 | 0 | 102 |
| FUNCTIONAL V NOT USED [100ng] | 2 | 1 | 0 | 0 | 1 | 2 | 1 | 1 | 0 | 0 | 0 | 0 | 0 | 0 | 0 | 0 | 8 |
| TOTAL FUNCTIONAL Vs | 52 | 8 | 6 | 1 | 10 | 5 | 4 | 8 | 4 | 2 | 2 | 2 | 1 | 4 | 1 | 0 | 110 |
| PSEUDO-V USED [2ug] | 12 | 1 | 1 | 1 | 2 | 0 | 0 | 1 | 0 | 0 | 0 | 0 | 0 | 0 | 0 | 0 | 18 |
| PSEUDO-V NOT USED [2ug] | 29 | 2 | 1 | 0 | 9 | 2 | 0 | 7 | 0 | 2 | 0 | 1 | 1 | 0 | 1 | 1 | 56 |
| PSEUDO-V USED [500ng] | 11 | 0 | 1 | 0 | 1 | 0 | 0 | 1 | 0 | 0 | 0 | 0 | 0 | 0 | 0 | 0 | 15 |
| PSEUDO-V NOT USED [500ng] | 30 | 3 | 1 | 1 | 10 | 2 | 0 | 7 | 0 | 2 | 0 | 1 | 1 | 0 | 1 | 1 | 59 |
| PSEUDO-V USED [100ng] | 4 | 0 | 1 | 0 | 1 | 0 | 0 | 1 | 0 | 0 | 0 | 0 | 0 | 0 | 0 | 0 | 8 |
| PSEUDO-V NOT USED [100ng] | 37 | 3 | 1 | 1 | 10 | 2 | 0 | 7 | 0 | 2 | 0 | 1 | 1 | 0 | 1 | 1 | 66 |
| TOTAL PSEUDO Vs | 41 | 3 | 2 | 1 | 11 | 2 | 0 | 8 | 0 | 2 | 0 | 1 | 1 | 0 | 1 | 1 | 74 |

| VH FAMILY | VH1 | VH2 | VH3 | VH4 | VH5 | VH6 | VH7 | VH8 | VH9 | VH10 | VH11 | VH12 | VH13 | VH14 | VH15 | TOTAL |
|---|---|---|---|---|---|---|---|---|---|---|---|---|---|---|---|---|
| FUNCTIONAL V USED | 53 | 17 | 6 | 1 | 18 | 5 | 3 | 7 | 6 | 2 | 2 | 3 | 1 | 3 | 1 | 128 |
| FUNCTIONAL V NOT USED | 1 | 1 | 0 | 1 | 1 | 0 | 0 | 1 | 0 | 0 | 0 | 0 | 0 | 0 | 0 | 5 |
| TOTAL FUNCTIONAL Vs | 54 | 18 | 6 | 2 | 19 | 5 | 3 | 8 | 6 | 2 | 2 | 3 | 1 | 3 | 1 | 133 |
| PSEUDO-V USED | 22 | 2 | 2 | 0 | 1 | 0 | 0 | 2 | 0 | 0 | 0 | 3 | 1 | 1 | 0 | 34 |
| PSEUDO-V NOT USED | 15 | 2 | 0 | 0 | 23 | 3 | 1 | 5 | 0 | 2 | 0 | 0 | 0 | 0 | 1 | 52 |
| TOTAL PSEUDO Vs | 37 | 4 | 2 | 0 | 24 | 3 | 1 | 7 | 0 | 2 | 0 | 3 | 1 | 1 | 1 | 86 |

*FIG. 12C*

SP B IgL: GC vs naïve (n= 3 mice, NP10d)

■ SP GC productive   ☐ SP naïve productive

Vκ4-57

*

GC B: SP vs PP (n= 3 mice, NP10d)

r = 0.56

■ SP productive   □ PP productive

Bioinformatic Pipeline

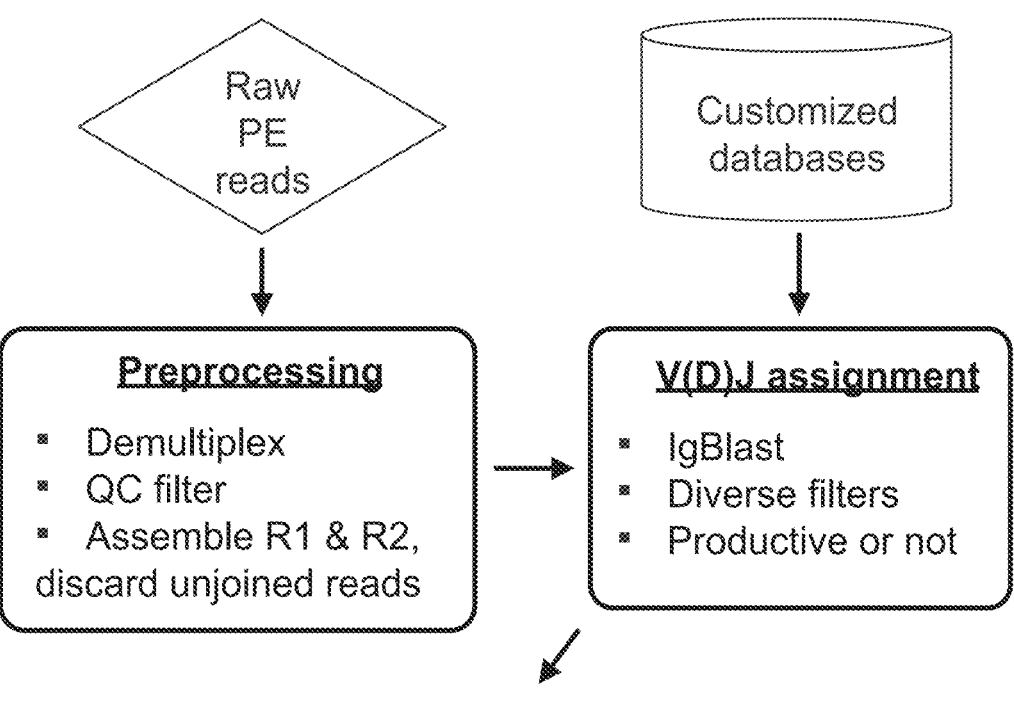

Raw PE reads

Customized databases

Preprocessing
* Demultiplex
* QC filter
* Assemble R1 & R2, discard unjoined reads

V(D)J assignment
* IgBlast
* Diverse filters
* Productive or not

Downstream Analysis

* DNA and protein SHM profile (Intrinsic V mutation database generated from pooled NP sequences.)
* Clonal clustering (CDR3)
* Lineage tree construction
* Mutation selection strength
* Novel V allele identification
* Diversity and Abundance

*FIG. 24 (cont.)*

| bait primer | hV$_{H}$1-2 junctions | J$_{H}$1 | J$_{H}$2 | J$_{H}$3 | J$_{H}$4 | r |
|---|---|---|---|---|---|---|
| hV$_{H}$1-2 | 49704 | 15% | 37% | 23% | 25% | 0.94 |
| mixed J$_{H}$1-4 | 26389 | 15% | 46% | 21% | 18% | |

GC B: SP vs PP (NP10d #3)

■ SP productive   □ PP productive

PP naïve B IgH: WT vs AID-/-

WT productive
AID-/- productive r = 0.98

IGHV2-2
IGHV2-3
IGHV2-4
IGHV2-5
IGHV2-6
IGHV5-12-4
IGHV2-6-8
IGHV5-15
IGHV5-17
IGHV7-2
IGHV4-1
IGHV11-1
IGHV11-2
IGHV9-1
IGHV9-3
IGHV14-4
IGHV7-4
IGHV3-5
IGHV9-4
IGHV13-2
IGHV6-3
IGHV6-5
IGHV6-7
IGHV1-4
IGHV10-3

PP GC IgL productive (AID-/- #1)

$V_K4$-53  $V_K6$-23  $V_K6$-17

METHODS AND COMPOSITIONS RELATING TO DETECTION OF RECOMBINATION AND REARRANGEMENT EVENTS

CROSS-REFERENCE TO RELATED APPLICATIONS

This application is a divisional under 35 U.S.C. § 121 of U.S. Ser. No. 16/481,964 filed Jul. 30, 2019 now abandoned, which is a 35 U.S.C. § 371 National Phase Entry Application of International Application No. PCT/US2018/017932 filed Feb. 13, 2018, which designates the U.S. and claims benefit under 35 U.S.C. § 119(e) of U.S. Provisional Application No. 62/458,244 filed Feb. 13, 2017, the contents of which are incorporated herein by reference in their entireties.

GOVERNMENT SUPPORT

This invention was made with government support under Grant No. AI020047 awarded by the National Institutes of Health. The U.S. government has certain rights in the invention.

SEQUENCE LISTING

The instant application contains a Sequence Listing which has been submitted electronically in XML format and is hereby incorporated by reference in its entirety. Said XML copy, created on Apr. 28, 2023, is named 701039-086701USD1_SL.xml and is 83,619 bytes in size.

TECHNICAL FIELD

The technology described herein relates to detection of recombination and/or rearrangement events in a cell, e.g., V(D)J recombination, via high throughput, genome-wide translocation sequencing (HTGTS)-based methods.

BACKGROUND

The identification and characterization of V(D)J recombination events is of interest both in furthering the understanding of the immune system and for the development and optimization of antibody-based therapeutics. Existing DNA-based methods of detecting V(D)J recombination rely on use of an upstream degenerate V primer and a downstream degenerate J primer, which can cover most, but not all, V(D)J exons and provide uneven coverage of the possible exons. In addition, such approaches only detect rearranged sequences between the two primers and thus would not find RAG-generated joins to most off-target sequences. RNA-based approaches severely underestimate non-productive rearrangements due to decreased transcript levels and miss many off-target rearrangements within a locus due to lack of expression.

SUMMARY

Described herein is an enhanced HTGTS approach for detecting recombination and/or rearrangements events at, e.g., Ig loci. The assays and methods described herein permit the detection and characterization of any such events with greater sensitivity and less bias than the existing methods.

In one aspect of any of the embodiments, described herein is a method for high throughput, genome-wide translocation sequencing (HTGTS)-based detection of recombination and/or rearrangement events in a cell, the method comprising the steps of:

a. extracting genomic DNA and/or mRNA from a cell;

b. optionally, producing a fragmented DNA and/or mRNA sample;

c. producing:

a single-stranded PCR product from genomic DNA by Linear Amplification Mediated (LAM)-PCR with at least one primary locus-specific primer; and/or cDNA from mRNA by reverse-transcription with at least one primary locus-specific primer;

d. producing a ligated DNA and/or cDNA product by ligating the single-stranded PCR product or cDNA produced in step (c) to an adaptor, wherein the adaptor comprises:

a distal portion of known DNA sequence that can be used to design PCR primers for a nested PCR amplification;

a proximal portion of random nucleotides; and a 3' overhang;

e. producing a nested PCR product by performing a nested-PCR with an adaptor-specific primer and at least one secondary locus-specific primer using the ligated product of step (d), thereby amplifying the nucleic acid sequence comprising the recombination and/or rearrangement event;

f. optionally, digesting the PCR product of step (e) with a restriction enzyme to block un-rearranged bait-containing fragments;

g. producing a sequenced nested PCR product by sequencing the nested PCR product; and h. aligning the sequenced nested PCR product against a reference sequence or antigen receptor database.

In some embodiments of any of the aspects, the recombination event is a V(D)J recombination event. In some embodiments of any of the aspects, the cell is selected from a group consisting of: a mature B lymphocyte, developing B lymphocyte, mature T lymphocyte, or developing T lymphocyte. In some embodiments of any of the aspects, the method further comprises providing the cell, wherein the cell was obtained from an animal immunized with an antigen. In some embodiments of any of the aspects, the method further comprises providing the cell, wherein the cell comprises a V(D)J exon which has undergone somatic hypermutation. In some embodiments of any of the aspects, the cell is a germinal center B lymphocyte.

In some embodiments of any of the aspects, the method further comprises the steps of: immunizing an animal with an antigen; and obtaining a cell from the animal; before performing step (a).

In some embodiments of any of the aspects, the method further comprises the use of multiple primary locus-specific primers and/or secondary locus-specific primers. In some embodiments of any of the aspects, the multiple primers specifically anneal to different V, D, or J gene segments.

In some embodiments of any of the aspects, the method further comprises a step of differentiating a source cell or tissue to initiate V(D)J recombination prior to performing step (a). In some embodiments of any of the aspects, the source cell is an induced pluripotent stem cell. In some embodiments of any of the aspects, the source cell is a primary stem cell.

In some embodiments of any of the aspects, the cell or source is transduced with RAG1/2 endonuclease to initiate V(D)J recombination prior to performing step (a). In some embodiments of any of the aspects, the method further comprises a step of contacting the cell with one or more reagents that initiate V(D)J recombination. In some embodiments of any of the aspects, the reagent that initiates V(D)J recombination is Imatinib.

In some embodiments of any of the aspects, the cell is a v-abl virus-transformed B cell.

In some embodiments of any of the aspects, the rearrangement event involves an oncogene and/or a RAG off-target cutting site. In some embodiments of any of the aspects, the cell is selected from the group consisting of: a cell expressing AID; a cancer cell; a cell expressing RAG endonuclease; or a nervous system cell.

In some embodiments of any of the aspects, the primary locus-specific primer comprises an affinity tag. In some embodiments of any of the aspects, the method further comprises isolating the products of step (c) by affinity purification. In some embodiments of any of the aspects, the affinity tag is biotin. In some embodiments of any of the aspects, the affinity purification comprises binding biotin with streptavidin. In some embodiments of any of the aspects, the affinity purification comprises binding the products of step (c) to a substrate. In some embodiments of any of the aspects, the substrate is a bead.

In some embodiments of any of the aspects, the primers used for the nested PCR step comprise barcode sequences.

In some embodiments of any of the aspects, the fragmenting is performed by sonication or restriction enzyme digest. In some embodiments of any of the aspects, the fragmenting is performed by randomly shearing genomic DNA or with a frequently cutting restriction enzyme. In some embodiments of any of the aspects, ligating the product of step (c) to an adaptor comprises contacting the product with a population of adaptors having the same distal portion and random proximal portion sequences.

In some embodiments of any of the aspects, the proximal portion of the adaptor is 3-10 nucleotides in length. In some embodiments of any of the aspects, the proximal portion of the adaptor is 5-6 nucleotides in length.

In some embodiments of any of the aspects, the adaptor comprises barcode sequences between distal and proximal portions.

In some embodiments of any of the aspects, the PCR products produced in step (e) are size selected prior to sequencing. In some embodiments of any of the aspects, the cell is present in a tissue prior to step (a). In some embodiments of any of the aspects, the sequencing is performed using a next generation sequencing method. In some embodiments of any of the aspects, the step of aligning is performed by a non-human machine. In some embodiments of any of the aspects, the non-human machine comprises a computer executable software.

In some embodiments of any of the aspects, the method further comprises providing a display module for displaying the results of the step of aligning.

In some embodiments of any of the aspects, the result of the alignment step is a mutation profile of a nucleotide or amino acid sequence across a set of V(D)J rearrangements.

In some embodiments of any of the aspects, the cell is a mammalian cell. In some embodiments of any of the aspects, the blocking digestion step (f) is omitted. In some embodiments of any of the aspects, end repair is not performed prior to step (c).

BRIEF DESCRIPTION OF THE DRAWINGS

FIG. 3A depicts a locus-wide view of V-DJ or D-J junctions identified in the IgH locus from representative splenic B or bone marrow pro-B cells from two libraries. White boxes represent the JH segments and shaded triangles represent recombination signal sequences (RSSs). The arrow indicates primer site and orientation. The black lines above the linear plot indicate the positions of V, D, and J segments. The convention that the VH sequence is read from upstream leader sequences to the downstream RSSs is defined by a (+); the opposite orientation is defined by a (−). FIG. 3B depicts the proportion of pseudo or functional VHs utilized in either splenic B or pro-B cell repertoires. FIG. 3C depicts a locus-wide view of V-J junctions identified in the Igκ locus from v-Abl virus transformed B cell lines from a representative library. Labels as in (FIG. 3A). Grey box represents a pseudo Jκ. RS indicates a bona fide RSS without an adjoining V or J segment; it is often utilized during V(D)J recombination to partially delete the Igκ locus on an allele for which an unproductive VJκ is generated. FIG. 3D depicts the proportion of pseudo or functional VKs utilized in the v-Abl transformed B cell line repertoire.

FIG. 4A depicts a frequency plot of utilized functional VHs in splenic B or pro-B cells. Y axis shows the number of combined in-frame and out-of-frame reads on individual VHs from the representative libraries in FIGS. 3A-3D. The data was extracted after IgBlast analysis. FIG. 4B depicts as in FIG. 4A, for Vκ in v-Abl-transformed B cell lines.

FIGS. 5A-5C depicts two examples of stitched paired-end Ilumina Miseq sequences extracted from IgH or Igk libraries. FIG. 5A depicts the distribution of the length of VHs captured from a representative pro-B cell library. ~33% of the VDJ exons recovered had VH alignments longer than or equal to 285 bp (3353/11431). This percentage can readily be greatly improved by using high-throughput sequencing methods which yield longer read lengths. FIG. 5B depicts example stitched paired-end read sequence extracted from a representative $J_H4$ library. The locus-specific primer, located downstream $J_H4$, is indicated. JH and DH segments are indicated. VH CDR1, CDR2, and CDR3 are indicated. Adaptor sequence (ligated onto linear-amplified PCR fragments) is indicated. FIG. 5B discloses SEQ ID NO: 33. FIG. 5C is as shown in FIG. 5A, but the example stitched VJκ read is shown. FIG. 5C discloses SEQ ID NO: 34.

FIGS. 7A-7F depict HTGTS-Rep-seq of $V_HDJ_H$ and $DJ_H$ repertoire in partially enriched pro-B cells and purified splenic B cells of C57BL/6 mice. FIG. 7A depicts a schematic of the murine IgH locus showing $V_{HS}$, $D_{HS}$, $J_{HS}$, and $C_H$ region. The arrow indicates the $J_H4$ coding end bait primer. FIG. 7B depicts $V_H$ repertoire with productive and non-productive information from $V_HDJ_H$ joins in pro-B cells (upper) and IgM$^+$ splenic B cells (lower). Some of the most frequently utilized $V_{HS}$ are highlighted with arrows as indicated. FIG. 7C depicts the utilization numbers of functional $V_{HS}$ and pseudo $V_{HS}$ across 16 families in HTGTS-Rep-seq libraries described in FIG. 7B. FIG. 7D depicts a pie chart showing the average overall percentage of productive and non-productive $V_HDJ_H$ joins from libraries described in FIG. 7B. FIG. 7E depicts D usage in $V_HDJ_H$ and $DJ_H$ joins in pro-B cells and IgM$^+$ splenic B cells as indicated. FIG. 7F depicts $DJ_H:V_HDJ_H$ ratios in pro-B cells and IgM$^+$ splenic B cells as indicated. All the data are showed by mean±SEM, N=3.

FIG. 8A depicts the $V_H$ repertoire with productive and non-productive information from $V_HDJ_H$ joins (left) and pie chart showing the average overall percentage of productive and non-productive $V_HDJ_H$ joins (right) in IgM$^+$ splenic B cells using each $J_H$ coding end bait primers as indicated. FIG. 8B depicts a comparison of D usage in $DJ_H$ joins in IgM$^+$ splenic B cells using each $J_H$ coding end bait primers. FIG. 8C depicts a comparison of $DJ_H:V_HDJ_H$ ratios in IgM$^+$ splenic B cells using each $J_H$ coding end bait primers. Mean±SEM, N=3 for all the data. Other analysis details are as described for FIGS. 7A-7F.

FIGS. 9A-9C demonstrate HTGTS-Rep-seq of VJκ repertoire in IgM$^+$ splenic B cells of C57BL/6 mice using Jκ5 bait primer. FIG. 9A depicts a schematic of the murine Igκ locus showing Vκs and Jκs. Grey bars indicate functional Vκs with convergent and tandem transcriptional orientations, respectively, to the downstream Jκs. Black bars indicate pseudo Vκs. arrow indicates the Jκ5 coding end bait primer. In FIG. 9B: Left panel: Vκ repertoire with productive and non-productive information from VJκ joins in IgM$^+$ splenic B cells with Jκ5 bait primer either individually (upper) or from combined Jκ bait primers (lower). Some differentially utilized Vκs among 4 different Jκs are highlighted with arrows as indicated. Right panel: Pie chart showing overall percentage of productive and non-productive VJκ joins. Representative results from two repeats are showed. FIG. 9C depicts utilization numbers of functional and pseudo Vκs across 20 families in libraries described in FIG. 9B.

FIGS. 10A-10B demonstrate that a representative $V_HDJ_H$ repertoire can be generated from small amounts of starting genomic DNA. FIG. 10A depicts $V_H$ repertoire with productive and non-productive information from $V_HDJ_H$ joins (left) and pie chart showing the average overall percentage of productive and non-productive $V_HDJ_H$ joins (right) in IgM$^+$ splenic B cells cloned from indicated amounts of genomic DNA using $J_H4$ coding end bait primer. Mean±SEM, N=3. FIG. 10B depicts $V_H$ utilization numbers separated by family, organized as in FIG. 7C.

FIG. 11A depicts a schematic of the generation of DJ and VDJ rearrangements via V(D)J recombination showing Vs (dark grey), Ds (black), and Js (light grey). Representative DJ and VDJ joining events are shown. FIG. 11B depicts a schematic of the HTGTS-Rep-seq method overview. Briefly, genomic DNA from B cell populations are sonicated and linearly amplified with a biotinylated primer that anneals downstream of one specific J segment. The biotin-labeled single-stranded DNA products are enriched with Streptavidin beads and 3' ends are ligated in an unbiased manner with a bridge adaptor containing 6-nucleotide random nucleotide (highlighted in the rectangular box). Products were then prepared for 2×300 bp sequencing on an Illumina Miseq. Generated reads were analyzed with the Ig/TCR-Repertoire analysis pipeline described in the methods.

FIGS. 12A-12F depict HTGTS-Rep-seq of $V_HDJ_H$ and $DJ_H$ repertoire in pro-B cells and IgM$^+$ splenic B cells of 129SVE mice. FIG. 12A depicts a schematic of the murine IgH locus showing $V_{HS}$ (functional=grey; pseudo=black), $D_{HS}$, and $J_{HS}$. Arrow indicates the $J_H4$ coding end bait primer. FIG. 12B demonstrates $V_H$ repertoire with productive and non-productive information from $V_HDJ_H$ joins in pro-B cells (upper) and IgM$^+$ splenic B cells (lower). Some of the most frequently utilized $V_{HS}$ are highlighted with arrows as indicated. Mean±SEM, N=3. FIG. 12C depicts utilization numbers of functional or pseudo $V_{HS}$ across 16 families in the HTGTS-Rep-seq libraries described in FIG. 12B. FIG. 12D depicts a pie chart showing the average overall percentage ±SEM of productive and non-productive $V_HDJ_H$ joins in pro-B cells (upper) and IgM$^+$ splenic B cells (lower). FIG. 12E depicts D usage in $DJ_H$ joins in pro-B cells and IgM$^+$ splenic B cells as indicated. Mean±SEM, N=3. FIG. 12F depicts a comparison of $DJ_H:V_HDJ_H$ ratios in pro-B cells and IgM$^+$ splenic B cells as indicated. Mean±SEM, N=3. details of the analysis are as described for FIG. 7A-7F.

FIG. 13A depicts $V_H$ repertoire with productive and non-productive information from $V_HDJ_H$ joins (left) and pie chart showing the average overall percentage ±SEM of productive and non-productive $V_HDJ_H$ joins (right) in IgM$^+$ splenic B cells using individual $J_H$ coding end bait primers. FIG. 13B depicts a comparison of D usage in $DJ_H$ joins in IgM$^+$ splenic B cells using each $J_H$ coding end bait primers. FIG. 13C depicts a comparison of $DJ_H:V_HDJ_H$ ratios in IgM$^+$ splenic B cells using each $J_H$ coding end bait primers. Mean±SEM, N=3 for all the panels. Other analysis details are as described for FIGS. 7A-7F.

FIG. 14A depicts an alignment of the germline sequences of $J_H1$-4. The sequences were extracted from the mm9 genome and are highly conserved between 129SVE and C57BL/6. The WGXG-encoding sequences are in red. $J_H$ length is marked with arrowheads, with 1 indicating the nucleotide most proximal to the bait primer. FIG. 14A discloses SEQ ID NOS 35-38, respectively, in order of appearance. In FIG. 14B, line plots show the number per 10,000 total V(D)J joins that retained indicated $J_H$ length for each $J_H$ bait (right x-axis). Bar graphs show the percentage of in-frame V(D)J exons at each retained $J_H$ length (left x-axis). Mean±SEM, N=3.

FIG. 15A depicts a schematic of IgH locus as in FIG. 7A-7F. Red arrows indicate mixed primers that bind downstream of each $J_H$. FIG. 15B depicts $V_H$ usage profiles separated by $J_H$ segment baits. One representative profile was shown here from two repeats of combined primer HTGTS-Rep-seq libraries. FIG. 15C depicts D usage in DJ$_H$ joins in IgM$^+$ splenic B cells using each J$_H$ coding end bait primers.

FIG. 16A depicts a schematic of Igκ locus, as in FIG. 3. Arrows indicate the position of used Jκ bait primers. FIG. 16B depicts Vκ usage profiles and overall productive/non-productive ratios of VJκ separated by Jκ baits in IgM$^+$ splenic B cells. In each panel, representative Vκ repertoires with productive and non-productive information from VJκ joins with each Jκ bait primer either individually (upper) or from combined Jκ primers (lower) are showed. Some differentially utilized Vκs among 4 different Jκs are highlighted with arrows as indicated (see also FIG. 9). Representative results from two repeats are showed.

FIG. 17A depicts CDR3 length distribution of productive V$_H$DJ$_H$ exons in C57BL/6 partially enriched pro-B libraries made with J$_H$4 bait primer. Consensus CDR3 motif plots were made for the subset of 11-13aa length CDR3 sequences, flanked on either end by the consensus cysteine and tryptophan. FIG. 17B: As in FIG. 17A, for C57BL/6 splenic B libraries made with J$_H$4 bait primer. FIG. 17C: As in FIG. 17A, for C57BL/6 splenic B libraries made with the four J$_H$ bait primers. Mean±SEM, N=3 for (FIG. 17A-17C). FIG. 17D: As in FIG. 17A, for C57BL/6 splenic B libraries made with Jκ5 primer. Note that we noticed some errors in our CDR3 sequence analyses due to the basal levels of sequencing errors of current high-throughput sequencing methods, including Illumina Miseq, and the read length (maximum 600 bp) that are not sufficient to cover entire sequences of longer DNA fragments containing V(D)J exons. However, we eliminated such potential ambiguities by including in our analyses only overlapping joined reads and/or by increasing thresholds for read quality.

FIG. 18A depict the proportion of unique CDR3 sequences for each technical repeat library from FIG. 10. Mean±SEM, N=3. FIG. 18B depicts the number of identical CDR3 sequences between technical repeat libraries at varying amounts of starting material.

FIG. 25A discloses SEQ ID NOS 39-42, respectively, in order of appearance.

DETAILED DESCRIPTION

Figure 1:
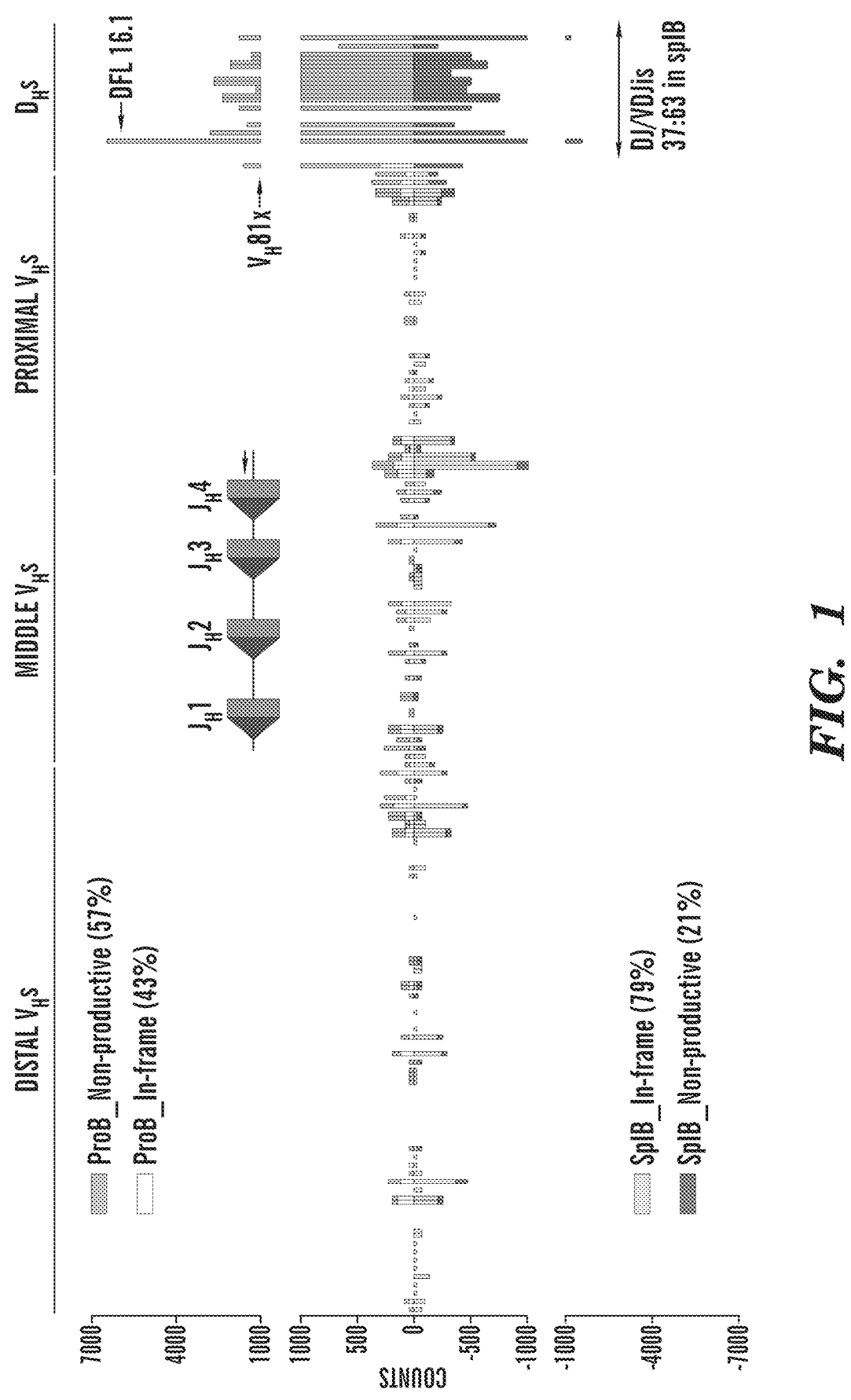
FIG. 1 depicts a graph of linear amplification-mediated high throughput genome-wide translocation sequencing adapted repertoire sequencing (HTGTS-Rep-seq) of VH and DH usage in progenitor (pro)-B cells and splenic B cells. VH repertoire and in-frame or non-productive information from VDJH joins is indicated on left; D usage in DJH joins is indicated on the right. Libraries were generated using a $J_H4$ coding end primer, as indicated by the primer on the schematic at the top. Libraries were prepared from wild-type 129sve DNA from purified pro-B and splenic B cells.
Figure 2:
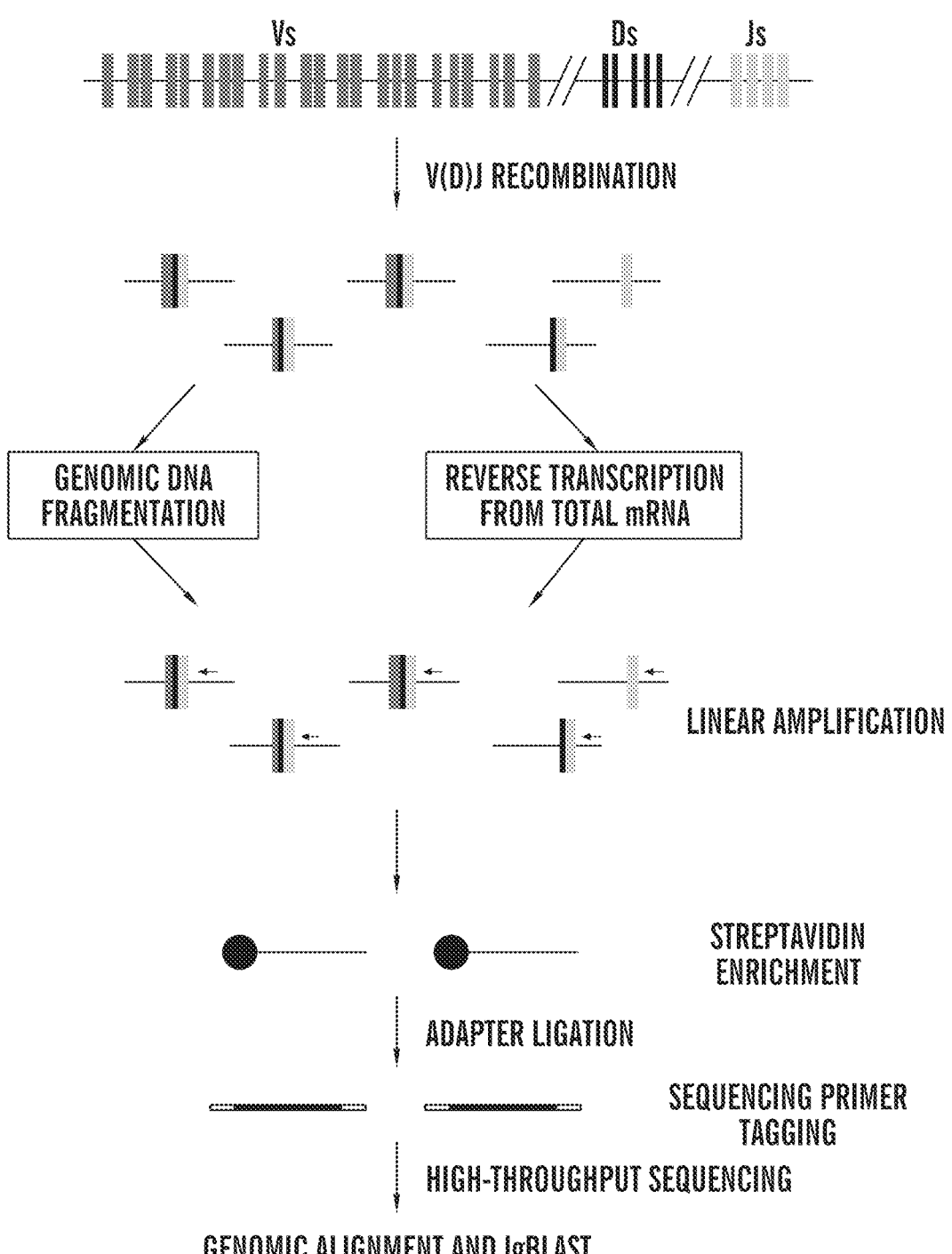
FIG. 2 depicts a schematic of HTGTS-Rep-seq. A simplified IgH locus is shown at the top as an example. V(D)J sequences together with DJ sequences and J germ-line sequences are linearly amplified from reverse-transcribed total messenger RNA (mRNA) or from fragmented whole genomic DNA with a JH-specific biotinylated primer. Amplified products are then enriched and prepared as HTGTS libraries (Frock et al., *Nat Biotech,* 2015; Hu et al., *Nat Protoc,* 2016) for paired-end sequencing by Illumina Miseq or other high-throughput sequencing methods. Sequencing data are then subjected to a custom pipeline for genomic alignments and IgBlast.

Described herein is a robust linear amplification-mediated high-throughput genome-wide translocation sequencing (HTGTS) method that identifies recombination and/or rearrangement events in a cell. In some embodiments of any of the aspects, the recombination event is a V(D)J recombination event. The method is particularly relevant for identifying recombination and/or rearrangements at Ig loci.

The method is therefore useful, for example, for anyone wishing to identify and/or characterize, e.g., V(D)J recombination. The same method can also be used to screen the effects of agents on V(D)J recombination.

In one aspect of any of the embodiments, described herein is a method for high throughput, genome-wide translocation sequencing (HTGTS)-based detection of recombination and/or rearrangement events in a cell, the method comprising the steps of: (a) extracting genomic DNA and/or mRNA from a cell; (b) optionally, producing a fragmented DNA and/or mRNA sample; (c) producing i) a single-stranded polymerase chain reaction (PCR) product from genomic DNA by Linear Amplification Mediated (LAM)-PCR with at least one primary locus-specific primer; and/or ii) complementary DNA (cDNA) from mRNA by reverse-transcription with at least one primary locus-specific primer; (d) producing a ligated DNA and/or cDNA product by ligating the single-stranded PCR product or cDNA produced in step (c) to an adaptor, wherein the adaptor comprises: a distal portion of known DNA sequence that can be used to design PCR primers for a nested PCR amplification; a proximal portion of random nucleotides; and a 3' overhang; (e) producing a nested PCR product by performing a nested-PCR with an adaptor-specific primer and at least one secondary locus-specific primer using the ligated product of step (d), thereby amplifying the nucleic acid sequence comprising the recombination and/or rearrangement event; (f) optionally, digesting the PCR product of step (e) with a restriction enzyme to block un-rearranged bait-containing fragments; (g) producing a sequenced nested PCR product by sequencing the nested PCR product; and (h) aligning the sequenced nested PCR product against a reference sequence or antigen receptor database.

In one aspect of any of the embodiments, described herein is a method for high throughput, repertoire sequencing-based detection of Ig repertoire sequences in a cell, the method comprising the steps of:

a. extracting genomic DNA and/or mRNA from a cell;

b. optionally, producing a fragmented DNA and/or mRNA sample;

c. producing:

a single-stranded PCR product from genomic DNA by Linear Amplification Mediated (LAM)-PCR with at least one primary locus-specific primer; and/or cDNA from mRNA by reverse-transcription with at least one primary locus-specific primer;

d. producing a ligated DNA and/or cDNA product by ligating the single-stranded PCR product or cDNA produced in step (c) to an adaptor, wherein the adaptor comprises:

a distal portion of known DNA sequence that can be used to design PCR primers for a nested PCR amplification;

a proximal portion of random nucleotides; and a 3' overhang;

e. producing a nested PCR product by performing a nested-PCR with an adaptor-specific primer and at least one secondary locus-specific primer using the ligated product of step (d), thereby amplifying the nucleic acid sequence comprising the Ig repertoire sequence;

f. optionally, digesting the PCR product of step (e) with a restriction enzyme to block un-rearranged bait-containing fragments;

g. producing a sequenced nested PCR product by sequencing the nested PCR product; and h. aligning the sequenced nested PCR product against a reference sequence or antigen receptor database.

As used herein, "Ig repertoire" refers to the group of sequences (or a portion of such sequences) of the Ig genes that arise in a cell or organism after at least one of V(D)J recombination, somatic hypermutation, activation, selection, and the like occur. The Ig repertoire of individual cells obtained from a single organism can vary. In detecting an Ig repertoire, one can detect all Ig sequences in a sample (e.g., a cell or a group of cells) or can detect portions of those sequences (e.g., the J gene segments used, but not the V gene segments used; or the J gene segments used but not the SHM). The methods described herein are suitable for detecting all portions of the Ig repertoire.

In some embodiments of any of the aspects, detecting the Ig repertoire comprises detecting at least V(D)J recombination events and/or somatic hypermutations (SMH). In some embodiments of any of the aspects, detecting the Ig repertoire comprises detecting one or more of Ig heavy chains, Ig light chains, V usage, D usage, J usage, and CDR repertoires.

Methods of extracting genomic DNA or mRNA are well-known in the art, see, e.g., Tan and Yiap. J Biomed and Biotechnol 2009; and Varma et al. Biotechnol J 2007 2:386-392; each of which is incorporated by reference herein in its entirety. In some embodiments of any of the aspects, genomic DNA or mRNA extraction can be performed using a commercially available kit, e.g. WIZARD Genomic DNA Purification Kit (Cat. No. A1120; Promega, Madison, WI) or ReliaPrep™ RNA Cell and Tissue Miniprep Systems (Cat. No. Z6010; Promega, Madison WI).

DNA and/or mRNA samples can be fragmented by any method known in the art, including but not limited to sonication, restriction enzyme digest, random shearing, restriction with a frequently-cutting restriction enzyme, nebulization, acoustic shearing, point-sink shearing, needle shearing, and a French press. In some embodiments of any of the aspects, the fragmenting of a nucleic acid sample can be performed by restriction enzyme digest. Frequently cutting enzymes, which typically cut every 4 bp are well known to one skilled in the art and one can screen for their effect on a target genome in silico using a target genome sequence as a template. For example, MspI is a suitable frequently-cutting enzyme in human cells, but a skilled artisan can easily substitute the enzyme according to the need for any given genome. As used herein, the term "fragmented DNA sample" or "fragmented "mRNA sample" refers to a sample of nucleic acid which has been subjected to a fragmentation process such that a statistically significant greater number of double-stranded breaks (DSBs) exist in the sample as compared to prior to the fragmentation process. In some embodiments of any of the aspects, a fragmented nucleic acid sample no longer comprises intact chromosomes. One of skill in the art can readily select a fragmentation process, including strength and duration thereof, that will provide a desired degree of fragmentation, e.g., that will result in a population of nucleic acid molecules of the desired sizes.

In some embodiments of any of the aspects, the fragmenting of a nucleic acid sample can be performed by sonication. Sonication provides random, unbiased fragmentation, which differs from the specific fragmentation achieved by restriction digest, e.g., as described in US Patent Publication 20140234847; which is incorporated by reference herein in its entirety. In some embodiments of any of the aspects, end repair is performed after fragmentation and before LAM-PCR. In some embodiments of any of the aspects, end repair is not performed after fragmentation but before LAM-PCR.

In some embodiments of the various aspects described herein, genomic DNA and/or mRNA is sheared, rather than digested by specific frequent cutter enzymes. Enzymes can have a bias injunction enrichment genome-wide.

In some embodiments of any of the aspects, the methods and compositions described herein relate to performing a PCR. PCR refers to a process of specifically amplifying, i.e., increasing the abundance of, a nucleic acid sequence of interest, and in some embodiments of any of the aspects, the exponential amplification occurring when the products of a previous polymerase extension serve as templates for the successive rounds of extension. A PCR amplification regimen according to the invention comprises at least one, e.g., at least 1, at least 2, at least 5, 10, 15, 20, 25, 30, 35 or more iterative cycles, where each cycle comprises the steps of: 1) strand separation (e.g., thermal denaturation); 2) oligonucleotide primer annealing to template molecules; and 3) nucleic acid polymerase extension of the annealed primers. Conditions and times necessary for each of these steps can be devised by one of ordinary skill in the art. An amplification regimen according to the methods described herein is preferably performed in a thermal cycler, many of which are commercially available.

Linear Amplification Mediated PCR (LAM-PCR) is a type of PCR in which a primer to a known sequence (bait) is used to produce single-stranded DNA (ssDNA) from a target nucleic acid sequence, where the PCR product comprises sequence downstream from the site at which the primer anneals. The PCR product's sequence can be unknown, e.g. if a recombination and/or rearrangement event has occurred near the bait sequence. The ssDNA is then converted to double-stranded DNA (dsDNA) and further LAM-PCR amplification reactions can be conducted. LAM-PCR is described in further detail at, e.g., Schmidt et al. Nature Methods 2007 4:1051-7; U.S. Pat. No. 6,514,706; U.S. Pat. App. US2007/0037139 and Harkey et al., (2007) Stem Cells Dev., June; 16(3): 381-392; each of which is incorporated by reference herein in its entirety. In some embodiments of any of the aspects, the LAM-PCR step can produce a single-stranded PCR product from genomic DNA.

In some embodiments of any of the aspects, the methods and compositions described herein relate to performing a reverse-transcriptase reaction e.g, by performing a reaction using a RNA template (the cDNA), a primer, and a RNA-dependent DNA polymerase. Protocols and reagents for performing reverse transcription are well known in the art and commercially available. In some embodiments of any of the aspects, the reverse-transcription step can produce a cDNA product from mRNA.

In some embodiments of any of the aspects, the LAM-PCR step is performed using a primary locus-specific primer. In some embodiments of any of the aspects, the reverse transcription step is performed using a primary locus-specific primer.

A primary locus-specific primer is a primer that can specifically anneal to a known sequence at at least one V, D, or J segment, a sequence flanking a V, D, or J segment, or a sequence flanking a sequence known/suspected to be involved in a rearrangement. In some embodiments of any of the aspects, the primary locus-specific primer is a primer that can specifically anneal to a known sequence of at least one V, D, or J segment. In some embodiments of any of the aspects, the primary locus-specific primer is a primer that can specifically anneal to a sequence flanking a V, D, or J segment, e.g., a sequence within 10 bp, 20 bp, 30 bp, 50 bp, 100 bp, 200 bp, 300 bp, 400 bp, 500 bp, or 1 kb of a V, D, or J segment. In some embodiments of any of the aspects, the primary locus-specific primer is a primer that can specifically anneal to a sequence flanking a V, D, or J segment, e.g., a sequence within 10 bp, 20 bp, 30 bp, 50 bp, 100 bp, 200 bp, 300 bp, or 400 bp of a V, D, or J segment. In some embodiments of any of the aspects, the primary locus-specific primer is a primer that can specifically anneal to a sequence flanking a sequence known or suspected to be involved in a rearrangement, e.g., a sequence within 10 bp, 20 bp, 30 bp, 50 bp, 100 bp, 200 bp, 300 bp, 400 bp, 500 bp, or 1 kb of a sequence known or suspected to be involved in a rearrangement. In some embodiments of any of the aspects, the primary locus-specific primer is a primer that can specifically anneal to a sequence flanking a sequence known or suspected to be involved in a rearrangement, e.g., a sequence within 10 bp, 20 bp, 30 bp, 50 bp, 100 bp, 200 bp, 300 bp, or 400 bp of a sequence known or suspected to be involved in a rearrangement.

In some embodiments of any of the aspects, multiple primary locus-specific primers and/or multiple secondary locus-specific primers can be used, e.g., to detect recombination and/or rearrangement at multiple loci and/or to detect multiple individual recombination and/or rearrangement events at the same locus. In some embodiments of any of the aspects, multiple primary locus-specific primers and/or multiple secondary locus-specific primers can be used, e.g., to detect multiple possible recombination and/or rearrangement events, e.g., to screen for an event or events which occurs amongst multiple possible events. In some embodiments of any of the aspects, the multiple primary or secondary locus-specific primers specifically anneal to different V, D, or J gene segments, to sequences flanking different V, D, or J segments, to different portions of the same V, D, or J gene segment, and/or to different sequences flanking the same V, D, or J segments. In some embodiments of any of the aspects, one or both of the LAM-PCR, reverse transcriptase, and/or nested PCR steps can be performed in a multiplex fashion, e.g., the multiple primers are present in the same reaction mixture. In some embodiments of any of the aspects, the multiple primers are present in separate reaction mixtures, e.g., they are used in parallel.

In some embodiments of any of the aspects, the at least one primary locus-specific primer specifically anneals to J gene segments. In some embodiments of any of the aspects, multiple primary locus-specific primers are used and each primary locus-specific primer specifically anneals to a different J gene segment. In some embodiments of any of the aspects, multiple primary locus-specific primers are used and collectively, the primary locus-specific primers specifically anneal to each different J gene segment present in the genome of the cell or organism as it exists prior to V(D)J recombination. In some embodiments of any of the aspects, multiple primary locus-specific primers are used and collectively, the primary locus-specific primers specifically anneal to each of $J_H1$, $J_H2$, $J_H3$, and $J_H4$. In some embodiments of any of the aspects, multiple primary locus-specific primers are used and collectively, the primary locus-specific primers specifically anneal to each different $J_H$, $J_\kappa$, and $J_\lambda$, gene segment present in the genome of the cell or organism prior to V(D)J recombination.

In some embodiments of any of the aspects, multiple primary locus-specific primers are used and each primary locus-specific primer specifically anneals to a different V, D, and/or J gene segment. In some embodiments of any of the aspects, multiple primary locus-specific primers are used and collectively, the primary locus-specific primers specifically anneal to each different V, D, and/or J gene segment present in the genome of the cell or organism as it exists prior to V(D)J recombination.

In some embodiments of any of the aspects, a primary locus-specific primer specifically anneals to a degenerate region of the targeted gene segment. In some embodiments of any of the aspects, a primary locus-specific primer specifically anneals to the most degenerate region of the targeted gene segment.

In some embodiments of any of the aspects, the primary locus-specific primer can comprise an affinity tag, e.g. for affinity purification using a substrate with the appropriate affinity domain. An affinity domain and tag pair can complex two molecules by non-covalent means. In some embodiments of any of the aspects, the first locus-specific primer can comprise an affinity tag to which the affinity domain can specifically bind. A number of affinity tags and domains are well known in the art and are described, e.g., in Lichty et al. Protein Expr Purif 2005 41:98-105; Zhao et al. J Analytical Methods in Chemistry 2013; Kimple et al. Current Protocols in Protein Science 2004 36:939:9.1-9.9.19; and Giannone et al. Methods and Protocols "Protein Affinity Tags" Humana Press 2014; each of which is incorporated by reference herein in its entirety. Non-limiting examples of compatible affinity domain and affinity tag pairings can include an antibody or antigen-binding fragment thereof and an epitope; an anti-His antibody or antigen-binding fragment thereof and a His tag; an anti-HA antibody or antigen-binding fragment thereof and a HA tag; an anti-FLAG antibody or antigen-binding fragment thereof and a FLAG tag; an anti-myc antibody or antigen-binding fragment thereof and a myc tag; an anti-V5 antibody or antigen-binding fragment thereof and a V5 tag; an anti-GST antibody or antigen-binding fragment thereof and a GST tag; an anti-MBP antibody or antigen-binding fragment thereof and a MBP tag; an aptamer and the target molecule recognized by that aptamer; e.g., streptavidin and biotin. In some embodiments of any of the aspects, an affinity tag and/or domain is located at or near one terminus of the molecule, e.g. within 10 nucleotides of a terminus. Affinity tags and/or domains can be, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule. In some embodiments of any of the aspects, the affinity domain can be an aptamer.

One example of using affinity domains and tags to complex two molecules is the biotin-avidin or biotin-streptavidin conjugation. In this approach, one of the members of molecules to be conjugated together (e.g., the nuclease or the template nucleic acid) is biotinylated and the other is conjugated with avidin or streptavidin. Many commercial kits are available for biotinylating molecules, such as proteins. For example, an aminooxy-biotin (AOB) can be used to covalently attach biotin to a molecule with an aldehyde or ketone group. Moreover, the primer can be coupled to a biotin acceptor peptide, for example, the AviTag or Acceptor Peptide (referred to as AP; Chen et al., 2 Nat. Methods 99 (2005)). The Acceptor Peptide sequence allows site-specific biotinylation by the *E. coli* enzyme biotin ligase (BirA; Id.). Another non-limiting example of using conjugation with an affinity domain/tag is the biotin-sandwich method. See, e.g., Davis et al., 103 PNAS 8155 (2006). In this approach, the two molecules to be conjugated together are biotinylated and then conjugated together using tetravalent streptavidin. In some embodiments of any of the aspects, the affinity tag can be biotin.

In some embodiments of any of the aspects, the method can further comprise isolating the PCR products produced in step (c) (the products of LAM-PCR or reverse transcription) by affinity purification. In some embodiments of any of the aspects, affinity purification can comprise binding the PCR and/or reverse transcription products produced in step (c) to a substrate, e.g. a bead and/or a column. In some embodiments of any of the aspects, the substrate can be a bead. In some embodiments of any of the aspects, affinity purification can comprise binding biotin with streptavidin, e.g., binding biotin-tagged PCR products to beads, substrates, and/or columns comprising streptavidin.

The product resulting from reverse transcription and/or PCR with the primary locus-specific primer, optionally after isolation (e.g. affinity purification), can be ligated to an adaptor molecule. In the ligation step, typically, one uses nucleic acid (e.g., DNA) that is concentrated at less than 1.5 ng/microL. Concentrations varying from about 1.0 to about 2.5 ng/microL can be used and a skilled artisan will be able to optimize the nucleic acid concentrations using routine methods.

The adaptor molecule is a double-stranded oligonucleotide, e.g. a dsDNA molecule comprising a distal portion of known DNA sequence that can be used to design PCR primers for a nested PCR amplification; and a proximal portion comprising random nucleotides and a 3' overhang. In some embodiments of any of the aspects, the 3' ends of the distal and proximal portions of the adaptor are modified to prevent self ligation, e.g. by providing a 3' dideoxynucleotide, e.g. a 3' ddC. In some embodiments of any of the aspects, the end of the adaptor which does not comprise the 3' overhang, e.g. the end comprising the distal portion, is blunt-ended. In some embodiments of any of the aspects, the 3' overhang can anneal to the ssDNA PCR product and/or reverse transcription product.

In some embodiments of any of the aspects, the proximal portion of the adaptor can be 3-10 nucleotides in length. In some embodiments of any of the aspects, the proximal portion of the adaptor can be 5-6 nucleotides in length. In some embodiments the proximal portion can have some nucleotides fixed.

In some embodiments of any of the aspects, the proximal portion of the adaptor molecule can consist of a 3' overhang. In some embodiments of any of the aspects, the proximal portion of the adaptor can be 3-10 nucleotides in length. In some embodiments of any of the aspects, the proximal portion of the adaptor can be 5-6 nucleotides in length.

In some embodiments of any of the aspects, the adaptor can further comprise a barcode sequence, e.g., between the distal and proximal portions. In some embodiments of any of the aspects, the distal portion of the adaptor comprises a sequence that is complementary to the adaptor-specific primer used in the nested PCR step.

In some embodiments of any of the aspects, ligating the single-stranded PCR products to an adaptor can comprise contacting the PCR product with a population of adaptors having the same distal portion and varying random proximal portion sequences.

In the nested-PCR step, a PCR reaction is performed using primers that anneal to the amplified sequence produced by a first reaction, e.g., the LAM-PCR reaction and/or the reverse transcription reaction, to increase specificity of the final product. Accordingly, nested-PCR performed on the ligated DNA product with an adaptor- and at least one secondary locus-specific primer will amplify and/or replicate the nucleic acid sequence surrounding the site of the recombination and/or rearrangement. In theory, there is not a minimum or a maximum for how many rounds of nested PCR can be used. In some embodiments of any of the aspects, the nested PCR comprises at least one round, at least 2 rounds, or at least 3 rounds. In some embodiments of any of the aspects, the nested PCR comprises one round, 2 rounds, or 3 rounds. In some embodiments of any of the aspects, the nested PCR comprises one round, 2 rounds, 3 rounds, 1-2 rounds, 1-3 rounds, or 1-5 rounds. More rounds can be less useful since they can just increase the amplification of already overrepresented sequences—Nested PCR (with typically 2 rounds) is used to increase specificity of the amplification reaction, by using independent sets of primers for the same locus. In some embodiments of any of the aspects, a third round or reaction can add the barcodes necessary for sequencing, e.g., 454 sequencing. Such a third round or reaction can be skipped if barcoded primers are used at round 2 (or the nested-PCR step) or if one uses other sequencing methods where additional bar codes are not needed. In some aspects of all the embodiments of the invention, one performs 1 round of nested PCR and an additional round to introduce a tag or a label into the PCR products thus allowing a specific sequencing protocol to be applied to analyze the sequences of the site of the recombination and/or rearrangement. In some aspects of all the embodiments of the invention, one performs 2 rounds of nested PCR and an additional round to introduce a tag or a label into the PCR products thus allowing a specific sequencing protocol to be applied to analyze the sequences of the site of the recombination and/or rearrangement.

In some embodiments of any of the aspects, the secondary locus-specific primer used in the nested-PCR step can overlap with the primary locus-specific primer used in the LAM-PCR or reverse transcription step. In some embodiments of any of the aspects, the primers are designed such that 3' end of the secondary locus-specific primer anneals closer (e.g. at least one nucleotide closer, 1-2 nucleotides closer, 1-3 nucleotides closer, 1-5 nucleotides closer, etc.) to the site of the recombination and/or rearrangement than the 3' end of the primary locus-specific primer. In some embodiments of any of the aspects, the sequence of the secondary locus-specific primer can comprise a portion of the sequence of the primary locus-specific primer. In some embodiments of any of the aspects, the sequence of the secondary locus-specific primer can comprise a 3' portion of the sequence of the primary locus-specific primer. In some embodiments of any of the aspects, the sequence of the secondary locus-specific primer can comprise the sequence of the primary locus-specific primer.

In some embodiments of any of the aspects, one or more of the primers used for the nested PCR step can comprise barcode sequences. As used herein, "barcode" refers to a DNA sequence used as a barcode or tag for identification of a target molecule. In some embodiments of any of the aspects, the DNA sequence is exogenous and/or foreign relative to the genomes of the organism being analyzed.

In some embodiments of any of the aspects, the ligated DNA can be digested with a blocking enzyme, e.g., 1) after nested PCR but prior to sequencing or 2) prior to nested PCR. The blocking enzyme digestion can block amplification of unrecombined and/or unrearranged targeted alleles in subsequent steps, e.g., during nested PCR or sequencing. Blocking enzymes typically need to be selected in each individual case based on the DNA sequence of the locus where the recombination or rearrangement occurs—any common restriction enzyme that cuts in the unrecombined/unrearranged product past the enzyme restriction site, such as I-SceI restriction site, and therefore should be absent from the recombined/rearranged product, can be used as a blocking enzyme. The selection is routine and based on each individual sequence. Thus, a skilled artisan can readily find a suitable blocking enzyme for the assays. In some embodiments of any of the aspects, the blocking digestion is not performed, e.g., it is omitted.

As used herein, the term "blocking enzyme" refers to a restriction enzyme that cuts in the unrecombined and/or unrearranged product distal, relative to the primary locus-specific primer, of a site of recombination and/or rearrangement. A blocking enzyme will not cut in the unrecombined/unrearranged product proximal, relative to the primary locus-specific primer, of the site of recombination and/or rearrangement. Thus, a blocking enzyme, and its sequence specificity, is determined by the particular sequence of the DNA and/or mRNA used in the method, the sequence of the primary locus-specific primer, and the recombination and/or rearrangement. Any restriction enzyme with the appropriate specificity can be utilized. One of skill in the art is readily able to select a restriction enzyme with the necessary specificity given such parameters.

DNA sequencing of the nested-PCR product can be performed by any method known in the art. In some embodiments of any of the aspects, the sequencing can be performed by a next generation sequencing method. As used herein "next-generation sequencing" refers to oligonucleotide sequencing technologies that have the capacity to sequence oligonucleotides at speeds above those possible with conventional sequencing methods (e.g. Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina): SOLiD technology (Applied Biosystems); Ion semiconductor sequencing (ION Torrent); DNA nanoball sequencing (Complete Genomics); and technologies available from Pacific Biosciences, Intelligen Biosystems, Oxford Nanopore Technologies, and Helicos Biosciences. In some embodiments of any of the aspects, the sequencing primers can comprise portions compatible with the selected next-generation sequencing method. Next-generation sequencing technologies and the constraints and design parameters of associated sequencing primers are well known in the art (see, e.g. Shendure, et al., "Next-generation DNA sequencing," Nature, 2008, vol. 26, No. 10, 1135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11(3):333-43; Zhang et al., "The impact of next-generation sequencing on genomics", J Genet Genomics, 2011, 38(3):95-109; (Nyren, P. et al. Anal Biochem 208: 17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties).

In some embodiments of any of the aspects, the nested-PCR products can be size selected prior to sequencing. Any reasonable size can be selected, e.g., to exclude non-specific amplification products, such as poly-primer amplification products. In some embodiments of any of the aspects, nested-PCR products of from about 400 bp to about 1 kb can be selected for, e.g., to exclude non-specific poly-primer amplification products. In some embodiments of any of the aspects, nested-PCR products of from about 200 bp to about 1 kb can be selected for, e.g., to exclude non-specific poly-primer amplification products.

In some embodiments of any of the aspects, the sequence of the nested-PCR product can be aligned against a reference sequence and/or an antigen receptor database to identify, e.g., the sequence resulting from the recombination and/or rearrangement, the V, D, and/or J segments involved in a recombination event, or the presence of variants, mutations, and/or hypermutations associated with a recombination and/or rearrangement. In some embodiments of any of the aspects, the sequence of the nested-PCR product can be aligned against a reference sequence. A reference sequence can be a sequence comprising the DNA sequences which participated in the recombination and/or rearrangement. Alternatively, a reference sequence can be a sequence comprising known recombination and/or rearrangement products that occur at the relevant locus (loci). The reference sequence can be, e.g., a genomic sequence(s) from type of cell being analyzed.

In some embodiments of any of the aspects, the sequence of the nested-PCR product can be aligned against an antigen receptor database. An antigen receptor database comprises sequences, which encode or can be recombined to encode antigen receptors, e.g. Ig genes, V gene segments, D gene segments, and/or J gene segments. Antigen receptor databases are known in the art or can be assembled from data. An exemplary database is IgBLAST, which is freely available on the world wide web at ncbi.nlm.nih.gov/igblast/ and which allows users to input a recombined sequence and obtain matches from a database of germline gene sequences.

In some embodiments of any of the aspects, the step of aligning can be performed by a non-human machine. In some embodiments of any of the aspects, the non-human machine can comprise a computer executable software. In some embodiments of any of the aspects, the method can further comprise a display module for displaying the results of the step of aligning.

Figure 6:
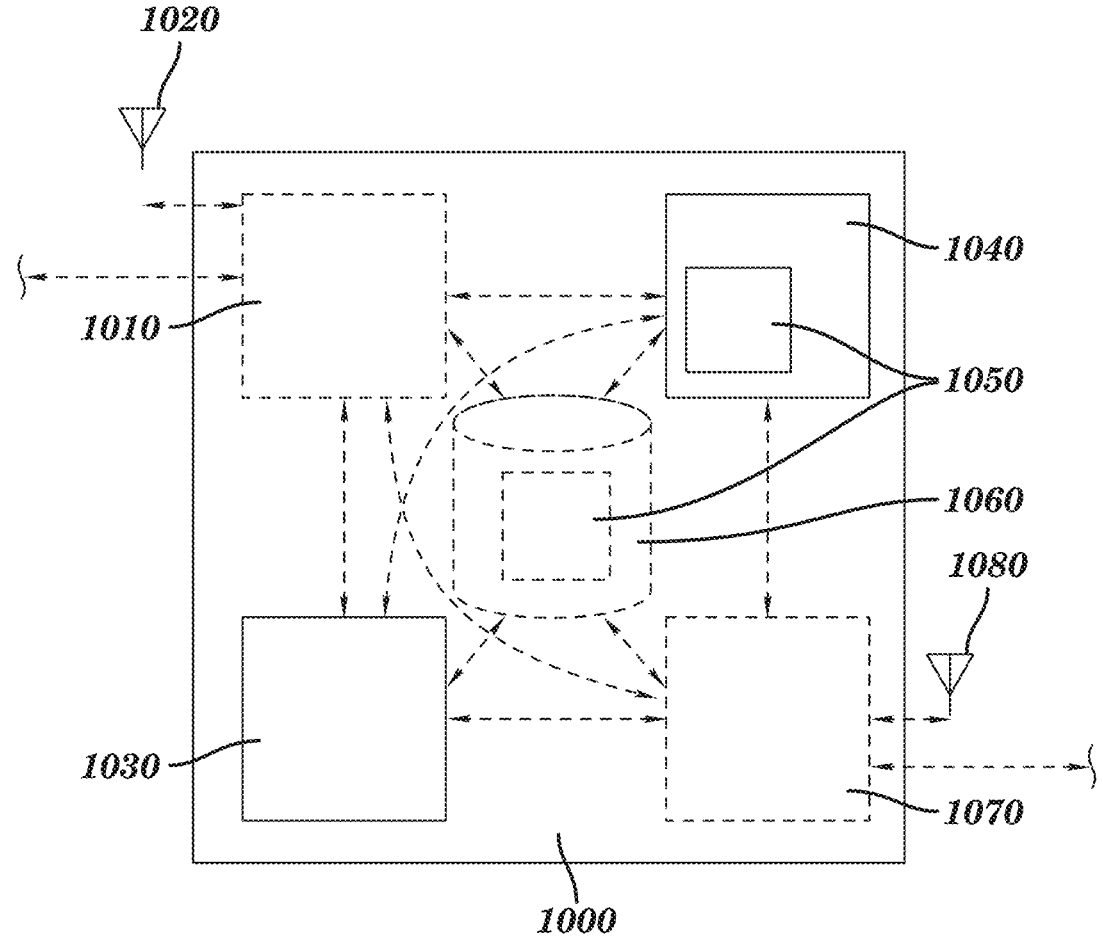
FIG. 6 depicts a computer device or system 1000 comprising one or more processors 1030 and a memory 1040 storing one or more programs 1050 for execution by the one or more processors 1030.

FIG. 6 depicts a computer device or system 1000 comprising one or more processors 1030 and a memory 1040 storing one or more programs 1050 for execution by the one or more processors 1030.

In some embodiments of any of the aspects, the device or computer system 1000 can further comprise a non-transitory computer-readable storage medium 1060 storing the one or more programs 1050 for execution by the one or more processors 1030 of the device or computer system 1000.

In some embodiments of any of the aspects, the device or computer system 1000 can further comprise one or more input devices 1010, which can be configured to send or receive information to or from any one from the group consisting of: an external device (not shown), the one or more processors 1030, the memory 1040, the non-transitory computer-readable storage medium 1060, and one or more output devices 1070. The one or more input devices 1010 can be configured to wirelessly send or receive information to or from the external device via a means for wireless communication, such as an antenna 1020, a transceiver (not shown) or the like.

In some embodiments of any of the aspects, the device or computer system 1000 can further comprise one or more output devices 1070, which can be configured to send or receive information to or from any one from the group consisting of: an external device (not shown), the one or more input devices 1010, the one or more processors 1030, the memory 1040, and the non-transitory computer-readable storage medium 1060. The one or more output devices 1070 can be configured to wirelessly send or receive information to or from the external device via a means for wireless communication, such as an antenna 1080, a transceiver (not shown) or the like.

In one aspect, described herein is a computer implemented method for high throughput, genome-wide translocation sequencing (HTGTS) and detection of recombination and/or rearrangement events, comprising: on a device having one or more processors and a memory storing one or more programs for execution by the one or more processors, the one or more programs including instructions for: aligning a sequenced nested PCR product against a reference sequence to identify a site of recombination and/or rearrangement event and the parent sequences which participated in the event.

In some embodiments of any of the aspects, the aligning step is performed by an aligning program. In some embodiments of any of the aspects, the aligning program is Bowtie2. In some embodiments of any of the aspects, the aligning step comprises a best-path search algorithm to determine alignments. In some embodiments of any of the aspects, the aligning step comprises de-multiplexing sequence reads. In some embodiments of any of the aspects, the de-multiplexing sequence reads comprises using a fastq-multx tool. In some embodiments of any of the aspects, the aligning step comprises trimming an adaptor sequence. In some embodiments of any of the aspects, the trimming the adaptor sequence comprises using a SeqPrep utility. In some embodiments of any of the aspects, the aligning step comprises mapping reads to a referenced sequence or database using the Bowtie2 with the top fifty alignments reported that had an alignment score above 50, representing a perfect 25 nt local alignment.

In some embodiments of any of the aspects, the aligning step comprises a best-path searching algorithm to select an optimal sequence of alignments that describe the read's composition. In some embodiments of any of the aspects, the aligning step comprises filtering. In some embodiments of any of the aspects, the filtering comprises a bait alignment and a prey alignment. As used herein, "bait" refers to a sequence to which the primary locus-specific primer would anneal, or which is adjacent to that sequence. A "prey" sequence is a sequence which is not contiguous with the bait sequence prior to the recombination and/or rearrangement event, but which is contiguous with the bait sequence after the recombination and/or rearrangement sequence. In some embodiments of any of the aspects, the bait alignment does not extend more than 10 nucleotides beyond a targeted site (e.g., the site the primer anneals to). In some embodiments of any of the aspects, the aligning step comprises vector controls, off-set nicking with multiple sites, and use of a distal targeted site. In some embodiments of any of the aspects, the aligning step comprises comparing discarded alignments to a selected prey alignment. In some embodiments of any of the aspects, if any of the discarded alignments surpasses both a coverage and score threshold with respect to the prey alignment, the read is filtered due to low mapping quality. In some embodiments of any of the aspects, the aligning step comprises extending the bait alignment 10 nucleotides past the primer to remove possible mispriming events and other artifacts. In some embodiments of any of the aspects, the aligning step comprises removing potential duplicates by comparing coordinates of an end of a bait alignment and a start of a prey alignment across all reads. In some embodiments of any of the aspects, the aligning step comprises marking a read as a duplicate if it has a bait alignment off-set within 2 nt and a prey alignment offset within 2 nt of another read's bait and prey alignments. In some embodiments of any of the aspects, the aligning step comprises applying post-filter stringency to remove junctions with gaps larger than 30 nt and bait sequences shorter than 50 nt. In some embodiments of any of the aspects, the aligning step comprises removing reads with prey alignments to telomere repeat sequences.

In some embodiments of any of the aspects, the computer implemented method is used with a method for high throughput, genome-wide translocation sequencing (HTGTS)-based detection of recombination and/or rearrangement events in a cell, the method comprising the steps of: (a) extracting genomic DNA and/or mRNA from a cell; (b) optionally, producing a fragmented DNA and/or mRNA sample; (c) producing: a single-stranded PCR product from genomic DNA by Linear Amplification Mediated (LAM)-PCR with at least one primary locus-specific primer; and/or cDNA from mRNA by reverse-transcription with at least one primary locus-specific primer; (d) producing a ligated DNA and/or cDNA product by ligating the single-stranded PCR product or cDNA produced in step (c) to an adaptor, wherein the adaptor comprises: a distal portion of known DNA sequence that can be used to design PCR primers for a nested PCR amplification; a proximal portion of random nucleotides; and a 3' overhang; (e) producing a nested PCR product by performing a nested-PCR with an adaptor-specific primer and at least one secondary locus-specific primer using the ligated product of step (d), thereby amplifying the nucleic acid sequence comprising the recombination and/or rearrangement event; (f) optionally, digesting the PCR product of step (e) with a restriction enzyme to block un-rearranged bait-containing fragments; (g) producing a sequenced nested PCR product by sequencing the nested PCR product; and (h) aligning the sequenced nested PCR product against a reference sequence or antigen receptor database.

In one aspect, described herein is a computer system for high throughput, genome-wide translocation sequencing (HTGTS)-based detection of recombination and/or rearrangement events in a cell, comprising: one or more processors and memory to store one or more programs, the one or more programs comprising instructions for: aligning a sequenced nested PCR product against a reference sequence and/or database to identify and/or characterize the recombination and/or rearrangement event.

In one aspect, described herein is a non-transitory computer-readable storage medium storing one or more programs for high throughput, genome-wide translocation sequencing (HTGTS)-based detection of recombination and/or rearrangement events in a cell, the one or more programs for execution by one or more processors of a computer system, the one or more programs comprising instructions for: aligning a sequenced nested PCR product against a reference sequence and/or database to identify and/or characterize the recombination and/or rearrangement event.

In some embodiments of any of the aspects, a modern alignment program, e.g., BOWTIE2™, is used to align to a reference sequence. In some embodiments of any of the aspects, a best-path search algorithm can be used to determine alignments. Use of such algorithms permits further characterization of the breakpoints at junctions and/or use of paired-end reads.

In an exemplary embodiment, sequence reads can be de-multiplexed and adaptor sequence trimmed using the FASTQ-MULTX™ tool from ea-utils (available on the World Wide Web at code.google.com/p/eautils/) and the SEQPREP™ utility (available on the World Wide Web at github.com/jstjohn/SeqPrep), respectively. Reads can be mapped to the reference sequence using BOWTIE2™ (available on the World Wide Web at bowtiebio.sourcefor-ge.net/bowtie2/manual.shtml). The top alignments, e.g. the top ten, twenty, thirty, forty, fifty, or more alignments can be used. In some embodiments of any of the aspects, alignments (or top alignments) with an alignment score above a threshold alignment score can be used. In some embodiments of any of the aspects, the threshold alignment score can be 50, representing a perfect 25 nt local alignment.

In some embodiments of any of the aspects, a best-path searching algorithm can be used to select the optimal sequence of alignments that describe the read's composition, typically finding the alignments. Aligned reads can be filtered, e.g., on the following conditions: (1) reads must include both a bait alignment and a prey alignment and (2) the bait alignment cannot extend more than 10 nucleotides beyond the targeted site. In some embodiments of any of the aspects, for vector controls and off-set nicking with multiple sites, the distal targeted site can be used. Discarded alignments can be compared to the selected prey alignment; if any of the discarded alignments surpass both a coverage and score threshold with respect to the prey alignment, the read can be filtered due to low mapping quality.

In some embodiments of any of the aspects, to remove possible mispriming events and other potential artifacts, the bait alignment can extend 10 nucleotides past the primer. Potential duplicates can be removed by comparing the coordinates of the end of the bait alignment and the start of the prey alignment across all reads. A read can be marked as a duplicate if it has a bait alignment off-set within 2 nt and a prey alignment offset within 2 nt of another read's bait and prey alignments. Post-filter stringency can be applied to remove junctions with gaps larger than a predetermined nucleotide length (e.g., 10 nt, 20 nt, 30 nt, 40 nt, 50 nt, etc) and bait sequences shorter than a predetermined length (e.g., 70 nt, 60 nt, 50 nt, 40 nt, 30 nt, etc.). Reads with prey alignments to telomere repeat sequences can also be removed.

Each of the above identified modules or programs corresponds to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments of any of the aspects, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

In some embodiments of any of the aspects, the result of the aligning step is displayed on a display module. In some embodiments of any of the aspects, the result of the aligning step is displayed on a computer monitor. In some embodiments of any of the aspects, the result of the aligning step is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, California, or any other type of processor, visual display devices such as flat panel displays, cathode ray tubes and the like, as well as computer printers of various types.

In some embodiments of any of the aspects, a World Wide Web browser is used for providing a user interface for display of the content based on the aligning results. It should be understood that other modules of the invention can be adapted to have a web browser interface. Through the Web browser, a user can construct requests for retrieving data from the alignment results. Thus, the user will typically point and click to user interface elements such as buttons, pull down menus, scroll bars and the like conventionally employed in graphical user interfaces.

In some embodiments of any of the aspects, the result of the alignment step is a mutation profile of a nucleotide or amino acid sequence across a set of V(D)J rearrangements. In some embodiments of any of the aspects, the result of the alignment step is displayed as a mutation profile of a nucleotide or amino acid sequence across a set of V(D)J rearrangements. Detecting of a number of recombination and/or rearrangement events, either in parallel or multiplex reactions and alignment of the events to the reference sequence/database can result in identification of point mutations, indels, and/or variations of the recombination/rearrangement junction and optionally, the relative frequency of such events.

The cell of the methods and assays described herein can be any type of cell, including, but not limited to, a eukaryotic cell, a mammalian cell, a human cell, a plant cell, a neuronal cell, a fibroblast, an in vitro cell, or an in vivo cell. The cell can be of any type, so long as it contains DNA. In some embodiments of any of the aspects, the cell can be a cell that can be maintained in culture. The cell can be a primary cell or an immortalized cell. One can also use differentiated cells as well as partially differentiated cells, pluripotent cells and stem cells, including embryonic stem cells. In some embodiments of any of the aspects, the cell is a mammalian cell. In some embodiments of any of the aspects, the cell is a human cell.

In some embodiments of any of the aspects, the cell can be a cell comprising a V(D)J exon which has undergone somatic hypermutation, e.g., the cell can be a germinal center B lymphocyte. In some embodiments of any of the aspects, the cell is a mature B lymphocyte, a developing B lymphocyte, a mature T lymphocyte, or a developing T lymphocyte. In some embodiments of any of the aspects, a mature B lymphocyte, a developing B lymphocyte, a mature T lymphocyte, a developing T lymphocyte, a cell obtained from a germinal center, and/or a cell obtained from a Peyer's Patch. In some embodiments of any of the aspects, the cell is a germinal center or Peyer's Patch B lymphocyte. In some embodiments of any of the aspects, cells can be activated using activating conditions well known to one skilled in the art to induce cell division and recombination events.

In some embodiments of any of the aspects, the cell can be present in a tissue, e.g., in vivo, prior to step (a). In some embodiments of any of the aspects, the cell can be present in an animal prior to step (a). In some embodiments of any of the aspects, the cell can be present in an animal immunized with an antigen prior to step (a). In some embodiments of any of the aspects, the method further comprises providing the cell, wherein the cell was obtained from an animal immunized with an antigen. In some embodiments of any of the aspects, the method further comprises immunizing an animal with an antigen and isolating a cell from the animal prior to step (a).

V(D)J recombination can be induced in a cell or the source of the cell prior to performing step (a). By way of non-limiting example, V(D)J recombination can be induced in a cell, tissue, or animal by transduction and/or ectopic expression of RAG1/2 endonuclease. A further non-limiting example of an agent that can induce V(D)J recombination is imatinib (i.e. GLEEVEC, mesylate, or STI-571). In some embodiments of any of the aspects, the cell is a v-abl-transformed B cell.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments of any of the aspects, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments of any of the aspects, the method can further comprise a step of differentiating a source cell or tissue to initiate V(D)J recombination prior to performing step (a). In some embodiments of any of the aspects, the source cell is a primary stem cell. In some embodiments of any of the aspects, the source cell is an induced pluripotent stem cell (IPSC). Methods of differentiation particular cells and/or tissues to, initiate V(D)J recombination are known in the art, e.g., methods of differentiating cells into the B lymphocyte or T lymphocyte lineages.

In some embodiments of any of the aspects, the rearrangement event involves an oncogene and/or a RAG off-target cutting site.

In some embodiments of any of the aspects, the cell can be a cell expressing AID; a cancer cell; a cell expressing RAG endonuclease; or a nervous system cell.

In one aspect, described herein is a kit comprising at least one primary locus-specific primer that will specifically anneal within 400 bp of a V, D, or J segment. In some embodiments of any of the aspects, the kit can further comprise an adaptor, the adaptor comprising: a distal portion of known DNA sequence that can be used to design PCR primers for a nested PCR amplification; a proximal portion of random nucleotides; and a 3' overhang. In some embodiments of any of the aspects, the kit can further comprise at least one secondary locus-specific primer. In some embodiments of any of the aspects, the kit can further comprise at least one nested PCR primer. In some embodiments of any of the aspects, the kit can further comprise a substrate comprising an affinity domain, wherein the primary or secondary locus-specific primer comprises an affinity tag. In some embodiments of any of the aspects, the kit can further comprise a cell.

A kit is any manufacture (e.g., a package or container) comprising at least one reagent, e.g., a primary and/or secondary locus-specific primer, the manufacture being promoted, distributed, or sold as a unit for performing the methods described herein. The kits described herein can optionally comprise additional components useful for performing the methods described herein. By way of example, the kit can comprise fluids and compositions (e.g., buffers, dNTPs, etc.) suitable for performing one or more of the reactions according to the methods described herein, an instructional material which describes performance of a method as described herein, and the like. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

In various embodiments, the methods described herein relate to performing a PCR amplification regimen with at least one primer, e.g., an oligonucleotide primer. As used herein, "primer" refers to a DNA or RNA polynucleotide molecule or an analog thereof capable of sequence-specifically annealing to a polynucleotide template and providing a 3' end that serves as a substrate for a template-dependent polymerase to produce an extension product which is complementary to the polynucleotide template. The conditions for initiation and extension usually include the presence of at least one, but more preferably all four different deoxyribonucleoside triphosphates and a polymerization-inducing agent such as DNA polymerase or reverse transcriptase, in a suitable buffer (in this context "buffer" includes solvents (generally aqueous) plus necessary cofactors and reagents which affect pH, ionic strength, etc.) and at a suitable temperature. A primer useful in the methods described herein is generally single-stranded, and a primer and its complement can anneal to form a double-stranded polynucleotide. Primers according to the methods and compositions described herein can be less than or equal to 300 nucleotides in length, e.g., less than or equal to 300, or 250, or 200, or 150, or 100, or 90, or 80, or 70, or 60, or 50, or 40, and preferably 30 or fewer, or 20 or fewer, or 15 or fewer, but at least 10 nucleotides in length.

In some embodiments of any of the aspects, the PCR reactions described herein relate to the use of a set of primers. As used herein, the term "set of primers" refers to a group of at least two primers, including a forward primer and a reverse primer, one of which anneals to a first strand of a target nucleic acid sequence and the other of which anneals to a complement of the first strand. In some embodiments of any of the aspects, the first primer of a primer pair subset can anneal to a first strand of the target nucleic acid sequence and the second primer of a primer pair subset (e.g., reverse primer), can anneal to the complement of that strand. The orientation of the primers when annealed to the target and/or its complement can be such that nucleic acid synthesis proceeding from primer extension of a one primer of the primer pair subset would produce a nucleic acid sequence that is complementary to at least one region of the second primer of the primer pair subset. The "first strand" of a nucleic acid target and/or sequence can be either strand of a double-stranded nucleic acid comprising the sequence of the target nucleotide and/or target site locus, but once chosen, defines its complement as the second strand. Thus, as used herein, a "forward primer" is a primer which anneals to a first strand of a nucleic acid target, while a "reverse primer" of the same set is a primer which anneals to the complement of the first strand of the nucleic acid target. As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

Methods of making primers are well known in the art, and numerous commercial sources offer oligonucleotide synthesis services suitable for providing primers according to the methods and compositions described herein, e.g. INVITRO-GEN™ Custom DNA Oligos; Life Technologies; Grand Island, NY or custom DNA Oligos from IDT; Coralville, IA).

In some embodiments of any of the aspects, one or more of the primers can be selected from SEQ ID Nos: 1-32 or 43-65. In some embodiments of any of the aspects, one or more of the primers can comprise a sequence selected from SEQ ID Nos: 1-32 or 43-65.

TABLE 4

| Name | Sequence | Purpose | SEQ ID NO |
|---|---|---|---|
| J$_H$1-bio | /5BiosG/CTGCAGCATGCA GAGTGTG | HTGTS bio primer for J$_H$1 coding end | 1 |
| J$_H$1-red | TGACATGGGGAGATCTG AGA | HTGTS red primer for J$_H$1 coding end | 2 |
| J$_H$2-bio | /5BiosG/ACCCTTTCTGAC TCCCAAGG | HTGTS bio primer for J$_H$2 coding end | 3 |
| J$_H$2-red | CCCCAACAAATGCAGTA AAATCT | HTGTS red primer for J$_H$2 coding end | 4 |
| J$_H$3-bio | /5BiosG/GGGACAAAGGG GTTGAATCT | HTGTS bio primer for J$_H$3 coding end | 5 |
| J$_H$3-red | CCCGTTTGCAGAGAATC TT | HTGTS red primer for J$_H$3 coding end | 6 |
| J$_H$4_bio | /5BiosG/CCCTCAGGGACA AATATCCA | HTGTS bio primer for J$_H$4 coding end | 7 |
| J$_H$4_red | CTGCAATGCTCAGAAAA CTCC | HTGTS red primer for J$_H$4 coding end | 8 |
| Jκ1_bio | /5Biosg/TTCCCAGCTTTG CTTACGGAG | HTGTS bio primer for Jκ1 coding end | 9 |
| Jκ1_red | AGTGCCAGAATCTGGTT TCAGAG | HTGTS red primer for Jκ1 coding end | 10 |
| Jκ2_bio | /5Biosg/ATTCCAACCTCT TGTGGGACAG | HTGTS bio primer for Jκ2 coding end | 11 |
| Jκ2_red | TCCCTCCTTAACACCTG ATCTGAG | HTGTS red primer for Jκ2 coding end | 12 |
| Jκ4_bio | /5BiosG/CGCTCAGCTTTC ACACTGACTC | HTGTS bio primer for Jκ4 coding end | 13 |
| Jκ4_red | CAGGTTGCCAGGAATGG CTC | HTGTS red primer for Jκ4 coding end | 14 |
| Jκ5_bio | /5Biosg/GCCCCTAATCTC ACTAGCTTGA | HTGTS bio primer for Jκ5 coding end | 15 |
| Jκ5_red | GTCAACTGATAATGAGC CCTCTCC | HTGTS red primer for Jκ5 coding end | 16 |
|  | CTGCAGCATGCAGAGTG TG | HTGTS primer for J$_H$1 coding end | 17 |
|  | TGACATGGGGAGATCTG AGA | HTGTS primer for J$_H$1 coding end | 18 |
|  | ACCCTTTCTGACTCCCA AGG | HTGTS primer for J$_H$2 coding end | 19 |
|  | CCCCAACAAATGCAGTA AAATCT | HTGTS primer for J$_H$2 coding end | 20 |
|  | GGGACAAAGGGGTTGA ATCT | HTGTS primer for J$_H$3 coding end | 21 |
|  | CCCGTTTGCAGAGAATC TT | HTGTS primer for J$_H$3 coding end | 22 |
|  | CCCTCAGGGACAAATAT CCA | HTGTS primer for J$_H$4 coding end | 23 |
|  | CTGCAATGCTCAGAAAA CTCC | HTGTS primer for J$_H$4 coding end | 24 |
|  | TTCCCAGCTTTGCTTACG GAG | HTGTS primer for Jκ1 coding end | 25 |
|  | AGTGCCAGAATCTGGTT TCAGAG | HTGTS primer for Jκ1 coding end | 26 |

TABLE 4-continued

| Name | Sequence | Purpose | SEQ ID NO |
|------|----------|---------|-----------|
| | ATTCCAACCTCTTGTGG GACAG | HTGTS primer for Jκ2 coding end | 27 |
| | TCCCTCCTTAACACCTG ATCTGAG | HTGTS primer for Jκ2 coding end | 28 |
| | CGCTCAGCTTTCACACT GACTC | HTGTS primer for Jκ4 coding end | 29 |
| | CAGGTTGCCAGGAATGG CTC | HTGTS primer for Jκ4 coding end | 30 |
| | GCCCCTAATCTCACTAG CTTGA | HTGTS primer for Jκ5 coding end | 31 |
| | GTCAACTGATAATGAGC CCTCTCC | HTGTS primer for Jκ5 coding end | 32 |

PCR requires the use of a nucleic acid polymerase. As used herein, the phrase "nucleic acid polymerase" refers an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and commercially available. One group of preferred nucleic acid polymerases are thermostable, i.e., they retain function after being subjected to temperatures sufficient to denature annealed strands of complementary nucleic acids, e.g. 94° C., or sometimes higher. As understood in the art, PCR can require cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. More specifically, strand separation according to the methods described herein is achieved by heating the nucleic acid sample above its Tm. Generally, for a sample containing nucleic acid molecules in buffer suitable for a nucleic acid polymerase, heating to 94° C. is sufficient to achieve strand separation. An exemplary buffer contains 50 mM KCl, 10 mM Tric-HCl (pH 8.8@25° C.), 0.5 to 3 mM MgCl2, and 0.1% BSA.

As also understood in the art, PCR requires annealing primers to template nucleic acids. As used herein, "anneal" refers to permitting two complementary or substantially complementary nucleic acids strands to hybridize, and more particularly, when used in the context of PCR, to hybridize such that a primer extension substrate for a template-dependent polymerase enzyme is formed. Conditions for primer-target nucleic acid annealing vary with the length and sequence of the primer and are based upon the calculated Tm for the primer. Generally, an annealing step in an amplification regimen involves reducing the temperature following the strand separation step to a temperature based on the calculated Tm for the primer sequence, for a time sufficient to permit such annealing. Tm can be readily predicted by one of skill in the art using any of a number of widely available algorithms (e.g., OLIGO™ (Molecular Biology Insights Inc. Colorado) primer design software and VENTRO NTI™ (Invitrogen, Inc. California) primer design software and programs available on the internet, including Primer3 and Oligo Calculator). For example, Tm's can be calculated using the NetPrimer software (Premier Biosoft; Palo Alto, CA; and freely available on the world wide web at http://www.premierbiosoft.com/netprimer/netprlaunch/Help/xnet-prlaunch.html). The Tm of a primer can also be calculated using the following formula, which is used by NetPrimer software and is described in more detail in Freier et al. PNAS 1986 83:9373-9377 which is incorporated by reference herein in its entirety. $Tm=\Delta H/(\Delta S+R*\ln(C/4))+16.6$ log $([K+]/(1+0.7 [K+]))-273.15$ wherein, $\Delta H$ is enthalpy for helix formation; $\Delta S$ is entropy for helix formation; R is molar gas constant (1.987 cal/° C.*mol); C is the nucleic acid concentration; and [K+] is salt concentration. For most amplification regimens, the annealing temperature is selected to be about 5° C. below the predicted Tm, although temperatures closer to and above the Tm (e.g., between 1° C. and 5° C. below the predicted Tm or between 1° C. and 5° C. above the predicted Tm) can be used, as can, for example, temperatures more than 5° C. below the predicted Tm (e.g., 6° C. below, 8° C. below, 10° C. below or lower). Generally, the closer the annealing temperature is to the Tm, the more specific is the annealing. The time allowed for primer annealing during a PCR amplification regimen depends largely upon the volume of the reaction, with larger volumes requiring longer times, but also depends upon primer and template concentrations, with higher relative concentrations of primer to template requiring less time than lower relative concentrations. Depending upon volume and relative primer/template concentration, primer annealing steps in an amplification regimen can be on the order of 1 second to 5 minutes, but will generally be between 10 seconds and 2 minutes, preferably on the order of 30 seconds to 2 minutes. As used herein, "substantially anneal" refers to a degree of annealing during a PCR amplification regimen which is sufficient to produce a detectable level of a specifically amplified product.

PCR also relies upon polymerase extension of annealed primers at each cycle. As used herein, the term "polymerase extension" means the template-dependent incorporation of at least one complementary nucleotide, by a nucleic acid polymerase, onto the 3' end of an annealed primer. Polymerase extension preferably adds more than one nucleotide, preferably up to and including nucleotides corresponding to the full length of the template. Conditions for polymerase extension vary with the identity of the polymerase. The temperature used for polymerase extension is generally based upon the known activity properties of the enzyme.

Although, where annealing temperatures are required to be, for example, below the optimal temperatures for the enzyme, it will often be acceptable to use a lower extension temperature. In general, although the enzymes retain at least partial activity below their optimal extension temperatures, polymerase extension by the most commonly used thermostable polymerases (e.g., Taq polymerase and variants thereof) is performed at 65° C. to 75° C., e.g, 68-72° C.

Primer extension is performed under conditions that permit the extension of annealed oligonucleotide primers. As used herein, the term "conditions that permit the extension of an annealed oligonucleotide such that extension products are generated" refers to the set of conditions including, for example temperature, salt and co-factor concentrations, pH, and enzyme concentration under which a nucleic acid polymerase catalyzes primer extension. Such conditions will vary with the identity of the nucleic acid polymerase being used, but the conditions for a large number of useful polymerase enzymes are well known to those skilled in the art. One exemplary set of conditions is 50 mM KCl, 10 mM Tric-HCl (pH 8.8@25° C.), 0.5 to 3 mM MgCl2, 200 uM each dNTP, and 0.1% BSA at 72° C., under which Taq polymerase catalyzes primer extension.

As used herein, "amplified product" or "PCR product" refers to polynucleotides resulting from a PCR reaction that are copies of a portion of a particular target nucleic acid sequence and/or its complementary sequence, which correspond in nucleotide sequence to the template nucleic acid sequence and/or its complementary sequence. An amplified product can be double or single stranded.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method for high throughput, genome-wide translocation sequencing (HTGTS)-based detection of recombination and/or rearrangement events in a cell, the method comprising the steps of:
   a. extracting genomic DNA and/or mRNA from a cell;
   b. optionally, producing a fragmented DNA and/or mRNA sample;
   c. producing:
      a single-stranded PCR product from genomic DNA by Linear Amplification Mediated (LAM)-PCR with at least one primary locus-specific primer; and/or
      cDNA from mRNA by reverse-transcription with at least one primary locus-specific primer;
   d. producing a ligated DNA and/or cDNA product by ligating the single-stranded PCR product or cDNA produced in step (c) to an adaptor, wherein the adaptor comprises:

a distal portion of known DNA sequence that can be used to design PCR primers for a nested PCR amplification;
      a proximal portion of random nucleotides; and
      a 3' overhang;
   e. producing a nested PCR product by performing a nested-PCR with an adaptor-specific primer and at least one secondary locus-specific primer using the ligated product of step (d), thereby amplifying the nucleic acid sequence comprising the recombination and/or rearrangement event;
   f. optionally, digesting the PCR product of step (e) with a restriction enzyme to blocks un-rearranged bait-containing fragments;
   g. producing a sequenced nested PCR product by sequencing the nested PCR product; and
   h. aligning the sequenced nested PCR product against a reference sequence or antigen receptor database.

2. The method of paragraph 1, wherein the recombination event is a V(D)J recombination event.

3. The method of paragraph 2, wherein the cell is selected from a group consisting of:
   a mature B lymphocyte, developing B lymphocyte, mature T lymphocyte, or developing T lymphocyte.

4. The method of any of paragraphs 2-3, wherein the method further comprises providing the cell, wherein the cell was obtained from an animal immunized with an antigen.

5. The method of any of paragraphs 2-4, wherein the method further comprises providing the cell, wherein the cell comprises a V(D)J exon which has undergone somatic hypermutation.

6. The method of paragraph 5, wherein the cell is a germinal center B lymphocyte.

7. The method of any of paragraphs 2-6, further comprising the steps of:
   immunizing an animal with an antigen; and
   obtaining a cell from the animal;
   before performing step (a).

8. The method of any of paragraphs 1-7, wherein the method further comprises the use of multiple primary locus-specific primers and/or secondary locus-specific primers.

9. The method of paragraph 8, wherein the multiple primers specifically anneal to different V, D, or J gene segments.

10. The method of any of paragraphs 1-9, further comprising a step of differentiating a source cell or tissue to initiate V(D)J recombination prior to performing step (a).

11. The method of paragraph 10, wherein the source cell is an induced pluripotent stem cell.

12. The method of paragraph 10, wherein the source cell is a primary stem cell.

13. The method of any of paragraphs 1-12, wherein the cell or source is transduced with RAG1/2 endonuclease to initiate V(D)J recombination prior to performing step (a).

14. The method of any of paragraphs 1-13, further comprising a step of contacting the cell with one or more reagents that initiate V(D)J recombination.

15. The method of paragraph 14, wherein the reagent that initiates V(D)J recombination is Imatinib.

16. The method of paragraph 15, wherein the cell is a v-abl virus-transformed B cell.

17. The method of paragraph 1, wherein the rearrangement event involves an oncogene and/or a RAG off-target cutting site.

18. The method of paragraphs 1 or 17, wherein the cell is selected from the group consisting of:

a cell expressing AID; a cancer cell; a cell expressing RAG endonuclease; or a nervous system cell.

19. The method of any of paragraphs 1-18, wherein the primary locus-specific primer comprises an affinity tag.

20. The method of paragraph 19, wherein the method further comprises isolating the products of step (c) by affinity purification.

21. The method of any of paragraphs 19-20, wherein the affinity tag is biotin.

22. The method of paragraph 21, wherein the affinity purification comprises binding biotin with streptavidin.

23. The method of any of paragraphs 20-22, wherein the affinity purification comprises binding the products of step (c) to a substrate.

24. The method of paragraph 23, wherein the substrate is a bead.

25. The method of any of paragraphs 1-24, wherein the primers used for the nested PCR step comprise barcode sequences;

26. The method of any of paragraphs 1-25, wherein the fragmenting is performed by sonication or restriction enzyme digest.

27. The method of any of paragraphs 1-26, wherein the fragmenting is performed by randomly shearing genomic DNA or with a frequently cutting restriction enzyme.

28. The method of any of paragraphs 1-27, wherein ligating the product of step (c) to an adaptor comprises contacting the product with a population of adaptors having the same distal portion and random proximal portion sequences.

29. The method of any of paragraphs 1-28, wherein the proximal portion of the adaptor is 3-10 nucleotides in length.

30. The method of any of paragraphs 1-29, wherein the proximal portion of the adaptor is 5-6 nucleotides in length.

31. The method of any of paragraphs 1-30, wherein the adaptor comprises barcode sequences between distal and proximal portions.

32. The method of any of paragraphs 1-31, wherein the PCR products produced in step (e) are size selected prior to sequencing.

33. The method of any of paragraphs 1-32, wherein the cell is present in a tissue prior to step (a).

34. The method of any of paragraphs 1-33, wherein the sequencing is performed using a next generation sequencing method.

35. The method of any of paragraphs 1-34, wherein the step of aligning is performed by a non-human machine.

36. The method of paragraph 35, wherein the non-human machine comprises a computer executable software.

37. The method of paragraph 35, further comprising a display module for displaying the results of the step of aligning.

38. The method of any of paragraphs 34-37, wherein the result of the alignment step is a mutation profile of a nucleotide or amino acid sequence across a set of V(D)J rearrangements.

39. The method of any of paragraphs 1-38, wherein the cell is a mammalian cell.

40. The method of any of paragraphs 1-39, wherein the blocking digestion step (f) is omitted.

41. The method of any of paragraphs 1-40, wherein end repair is not performed prior to step (c).

42. The method of any of paragraphs 1-41, wherein one or more of the primers comprises a sequence selected from SEQ ID Nos: 1-32.

43. The method of any of paragraphs 1-41, wherein one or more of the primers is selected from SEQ ID Nos: 1-32.

Some embodiments of the technology described herein can be defined according to any of the following numbered paragraphs:

1. A method for high throughput, genome-wide translocation sequencing (HTGTS)-based detection of recombination and/or rearrangement events in a cell, the method comprising the steps of:

a. extracting genomic DNA and/or mRNA from a cell;

b. optionally, producing a fragmented DNA and/or mRNA sample;

c. producing:

a single-stranded PCR product from genomic DNA by Linear Amplification Mediated (LAM)-PCR with at least one primary locus-specific primer; and/or cDNA from mRNA by reverse-transcription with at least one primary locus-specific primer;

d. producing a ligated DNA and/or cDNA product by ligating the single-stranded PCR product or cDNA produced in step (c) to an adaptor, wherein the adaptor comprises:

a distal portion of known DNA sequence that can be used to design PCR primers for a nested PCR amplification;

a proximal portion of random nucleotides; and a 3' overhang;

e. producing a nested PCR product by performing a nested-PCR with an adaptor-specific primer and at least one secondary locus-specific primer using the ligated product of step (d), thereby amplifying the nucleic acid sequence comprising the recombination and/or rearrangement event;

f. optionally, digesting the PCR product of step (e) with a restriction enzyme to blocks un-rearranged bait-containing fragments;

g. producing a sequenced nested PCR product by sequencing the nested PCR product; and h. aligning the sequenced nested PCR product against a reference sequence or antigen receptor database.

2. The method of paragraph 1, wherein the recombination event is a V(D)J recombination event.

3. A method for high throughput, repertoire sequencing-based detection of Ig repertoire sequences in a cell, the method comprising the steps of:

a. extracting genomic DNA and/or mRNA from a cell;

b. optionally, producing a fragmented DNA and/or mRNA sample;

c. producing:

a single-stranded PCR product from genomic DNA by Linear Amplification Mediated (LAM)-PCR with at least one primary locus-specific primer; and/or cDNA from mRNA by reverse-transcription with at least one primary locus-specific primer;

d. producing a ligated DNA and/or cDNA product by ligating the single-stranded PCR product or cDNA produced in step (c) to an adaptor, wherein the adaptor comprises:

a distal portion of known DNA sequence that can be used to design PCR primers for a nested PCR amplification;

a proximal portion of random nucleotides; and a 3' overhang;

e. producing a nested PCR product by performing a nested-PCR with an adaptor-specific primer and at least one secondary locus-specific primer using the ligated product of step (d), thereby amplifying the nucleic acid sequence comprising the Ig repertoire sequence;

f. optionally, digesting the PCR product of step (e) with a restriction enzyme to block un-rearranged bait-containing fragments;

g. producing a sequenced nested PCR product by sequencing the nested PCR product; and h. aligning the sequenced nested PCR product against a reference sequence or antigen receptor database.

4. The method of paragraph 3, wherein the repertoire detected comprises V(D)J recombination events and/or somatic hypermutations (SMH).

5. The method of any of paragraphs 3-4, wherein the repertoire detected comprises Ig heavy chains, Ig light chains, V usage, and CDR3 repertoires.

6. The method of any of paragraphs 1-5, wherein the cell is selected from a group consisting of:

a mature B lymphocyte, a developing B lymphocyte, a mature T lymphocyte, a developing T lymphocyte, a cell obtained from a germinal center, and a cell obtained from a Peyer's Patch.

7. The method of any of paragraphs 1-6, wherein the method further comprises providing the cell, wherein the cell was obtained from an animal immunized with an antigen.

8. The method of any of paragraphs 1-7, wherein the method further comprises providing the cell, wherein the cell comprises a V(D)J exon which has undergone somatic hypermutation.

9. The method of paragraph 8, wherein the cell is a germinal center or Peyer's Patch B lymphocyte.

10. The method of any of paragraphs 1-9, further comprising the steps of:

immunizing an animal with an antigen; and obtaining a cell from the animal;

before performing step (a).

11. The method of any of paragraphs 1-10, wherein the at least one primary locus-specific primer specifically anneal to J gene segments.

12. The method of any of paragraphs 1-11, wherein the method further comprises the use of multiple primary locus-specific primers and/or secondary locus-specific primers.

13. The method of paragraph 12, wherein each of the multiple primers specifically anneal to different V, D, and/or J gene segments.

14. The method of paragraph 13, wherein each of the multiple primers specifically anneal to each different J gene segment present in the genome of the cell or organism prior to V(D)J recombination.

15. The method of paragraph 14, wherein, collectively, the multiple primers specifically anneal to a sequence in each of $J_H1$, $J_H2$, $J_H3$, or $J_H4$.

16. The method of paragraph 14, wherein, collectively, the multiple primers specifically anneal to at least one sequence in each of the $J_H$, $J_K$, and $J_L$ gene segments present in the genome of the cell or organism prior to V(D)J recombination.

17. The method of any of paragraphs 1-16, wherein the at least one primary locus-specific primer specifically anneals to a degenerate region(s) of the targeted gene segment(s).

18. The method of any of paragraphs 1-17, further comprising a step of differentiating a source cell or tissue to initiate V(D)J recombination prior to performing step (a).

19. The method of paragraph 18, wherein the source cell is an induced pluripotent stem cell.

20. The method of paragraph 18, wherein the source cell is a primary stem cell.

21. The method of any of paragraphs 1-20, wherein the cell or source is transduced with RAG1/2 endonuclease to initiate V(D)J recombination prior to performing step (a).

22. The method of any of paragraphs 1-21, further comprising a step of contacting the cell with one or more reagents that initiate V(D)J recombination or SHM.

23. The method of paragraph 22, wherein the reagent that initiates V(D)J recombination is Imatinib.

24. The method of paragraph 23, wherein the cell is a v-abl virus-transformed B cell.

25. The method of paragraphs 1-24, wherein the rearrangement event involves an oncogene and/or a RAG off-target cutting site.

26. The method of any of paragraphs 1-25, wherein the cell is selected from the group consisting of:

a cell expressing AID; a cancer cell; a cell expressing RAG endonuclease; or a nervous system cell.

27. The method of any of paragraphs 1-26, wherein the primary locus-specific primer comprises an affinity tag.

28. The method of paragraph 27, wherein the method further comprises isolating the products of step (c) by affinity purification.

29. The method of any of paragraphs 27-28, wherein the affinity tag is biotin.

30. The method of paragraph 29, wherein the affinity purification comprises binding biotin with streptavidin.

31. The method of any of paragraphs 28-30, wherein the affinity purification comprises binding the products of step (c) to a substrate.

32. The method of paragraph 31, wherein the substrate is a bead.

33. The method of any of paragraphs 1-32, wherein the primers used for the nested PCR step comprise barcode sequences;

34. The method of any of paragraphs 1-33, wherein the fragmenting is performed by sonication or restriction enzyme digest.

35. The method of any of paragraphs 1-34, wherein the fragmenting is performed by randomly shearing genomic DNA or with a frequently cutting restriction enzyme.

36. The method of any of paragraphs 1-35, wherein ligating the product of step (c) to an adaptor comprises contacting the product with a population of adaptors having the same distal portion and random proximal portion sequences.

37. The method of any of paragraphs 1-36, wherein the proximal portion of the adaptor is 3-10 nucleotides in length.

38. The method of any of paragraphs 1-37, wherein the proximal portion of the adaptor is 5-6 nucleotides in length.

39. The method of any of paragraphs 1-38, wherein the adaptor comprises barcode sequences between distal and proximal portions.

40. The method of any of paragraphs 1-39, wherein the PCR products produced in step (e) are size selected prior to sequencing.

41. The method of any of paragraphs 1-40, wherein the cell is present in a tissue prior to step (a).

42. The method of any of paragraphs 1-41, wherein the sequencing is performed using a next generation sequencing method.

43. The method of any of paragraphs 1-42, wherein the step of aligning is performed by a non-human machine.

44. The method of paragraph 43, wherein the non-human machine comprises a computer executable software.

45. The method of paragraph 43, further comprising a display module for displaying the results of the step of aligning.

46. The method of any of paragraphs 1-45, wherein the result of the alignment step is a mutation profile of a nucleotide or amino acid sequence across a set of V(D)J rearrangements.

47. The method of any of paragraphs 1-46, wherein the cell is a mammalian cell.

48. The method of any of paragraphs 1-47, wherein the blocking digestion step (f) is omitted.

49. The method of any of paragraphs 1-48, wherein end repair is not performed prior to step (c).

50. The method of any of paragraphs 1-49, wherein one or more of the primers comprises a sequence selected from SEQ ID Nos: 1-32 or 43-65.

51. The method of any of paragraphs 1-50, wherein one or more of the primers is selected from SEQ ID Nos: 1-32 and 43-65.

EXAMPLES

Example 1: LAM-HTGTS Approaches to Study RAG On- and Off-Targets

LAM-HTGTS identifies prey sequences that join to DSB-associated bait sequences (Frock et al. 2015). Because V(D)J recombination generates rearrangements with junctions at borders of V, D, and J segments, primers for any of these gene segments can be employed as bait to identify sites of RAG-generated DSBs both in progenitor or precursor lymphocytes undergoing V(D)J recombination, as well as in mature lymphocytes to identify V(D)J recombination events that occurred earlier in development retrospectively. LAM-HTGTS employing endogenous RAG-generated DSBs identifies RAG-generated on- and off-target junctions in developing B- and T-lineage cells that could not be detected by prior assays (Hu et al., 2015; Zhao et al.; also see below). Depending on which side of the DSBs the bait primer resides, LAM-HTGTS identifies all V(D)J coding joins or the corresponding RSS joins (e.g. Hu et al., 2015) including those present in the chromosome or in excision circles (Hu et al., 2015). Besides being quantitative and tremendously sensitive, LAM-HTGTS is unbiased with respect to productive and non-productive joins, requires only a single bait PCR primer, reads out both deletional and inversional joins, and readily identifies even very low frequency recombination events such as those that occur at CAC off-targets, that were invisible to prior assays. LAM-HTGTS also detects these joins across several Mb long recombination domains (Hu et al., 2015). In addition, LAM-HTGTS can be used to follow joining of various types of V(D)J join intermediates, for example by following joining of particular $DJ_H$ rearrangements (Hu et al., 2015). LAM-HTGTS also reveals joining of individual Ds or Vs by using them as LAM-HTGTS baits.

To convert LAM-HTGTS into a more standard repertoire sequencing method, termed HTGTS-Rep-seq, modifications to the method were made, including moving bait primers closer to the coding end of bait Js and employing MiSeq 300bpx2 paired end sequencing to capture the length of the V sequence in recovered junctions. LAM-HTGTS pipeline was also modified to include IgBLAST to generate an analysis pipeline that provides comprehensive information on in-frame or non-productive junctions, complementarity determining regions (CDRs), and mutations. HTGTS-Rep-seq is superior to prior approaches. In this regard, prior DNA based approaches rely on use of an upstream degenerate V primer and a downstream degenerate J primer, which would cover most, but not all, V(D)J exons and likely not all equally. In addition, such approaches only detect rearranged sequences between the two primers and thus would not find RAG-generated joins to most off-target sequences (Georgiou et al., 2014). RNA-based approaches only require one downstream primer (from the J or constant region) and thus obviate biases in prior DNA-based assays, but these approaches severely underestimate non-productive rearrangements due to decreased transcript levels and would miss many off-target rearrangements within a locus due to lack of expression (Georgiou et al., 2014). In contrast, HTGTS-Rep-seq requires linear extension from a single or class of primers (e.g. J or D primers) and detects in-frame and out-of-frame rearrangements and even detects robust classes of joins in some loci secondary to RSS fusion that are invisible to prior assays (Hu et al., 2015).

HTGTS-Rep-seq has been employed to analyze V(D)J repertoires from mouse and human IgH, Igλ and Igκ loci by using primers for a given J. To illustrate the approach and repertoire data generated, HTGTS-Rep-seq analysis of RAG-generated $J_H4$ segment coding ends as bait on DNA from mouse pro-B cells shown above the axis and mature splenic B cells below the axis to allow direct comparison of repertoires, as shown in FIG. 1. Note that the assay relatively quantitatively provides relative utilization of different D segments in $DJ_H4$ rearrangements and relative utilization of different $V_H$ segments both in-frame and non-productive (FIG. 1). Thus, in purified pro-B cells, the frequency of $DJ_H4$ rearrangements greatly exceeds that of V(D)$J_H4$ rearrangements whereas in spleen they occur at levels more closely approximating the idealized 30/70 ratio (FIG. 1). In addition, while $V_H81X$ rearrangements are by far the most abundant rearrangement in pro-B cells (with twice as many non-productive as in frame), $V_H81X$ rearrangements represent a low proportion of the total in splenic B cells and nearly all are non-productive, as expected due to negative selection of $V_H81X$ in-frame rearrangements (Guo et al., 2011b; Alt et al., 2013). Proportions of the various rearrangements types are consistent across all experiments, including preferential rearrangement of certain distal $V_{HS}$ and preferential representation of some of these in mature repertoires (FIG. 1). This approach works well for the various mouse Ig and TCR loci, and for all human Ig loci. The method is fast, relatively inexpensive, and can utilize as little as 200 ng of DNA from purified B or T lineage populations.

Example 2

The immunotherapy market and antibody research field currently both urgently seek an unbiased high-throughput assay that can facilitate the discovery of new high-affinity antibodies for antigens of interest and to help understand vaccine development. Such an assay would also facilitate the engineered design of new antibodies. To address this need, described herein is a novel approach to perform repertoire sequencing and reveal somatic hypermutations via a high throughput approach.

The methods described herein relate to a linear amplification method with a single primer that specifically recognizes regions downstream of given J segments to amplify V(D)J exons for sequencing; thus, the present assay overcomes the bias inherent to existing methods which employ degenerate V primers that cannot equally bind all the V segment families. LAM-HTGTS can determine and quantify V(D)J exons from all the V segment families in genomic DNA (or mRNA) (although our method obviates the reasons mRNA is current in some approaches) from any cell origin, e.g. progenitor cells, precursor cells, peripheral cells, and cell lines.

To demonstrate the method, VH and Vκ usage was examined. FIG. 3A-3D depict example VH usage patterns from progenitor B (pro-B) cells and peripheral splenic B cells, and an example Vκ usage pattern from pro-B cell lines. Notably, the majority of the functional VH's from all the VH families are utilized in pro-B and mature B cells, and all but one functional VK was utilized in v-Abl-transformed pro-B cell lines. These data demonstrate that the present method has no obvious bias, in contrast to existing methods.

Figure 4A:
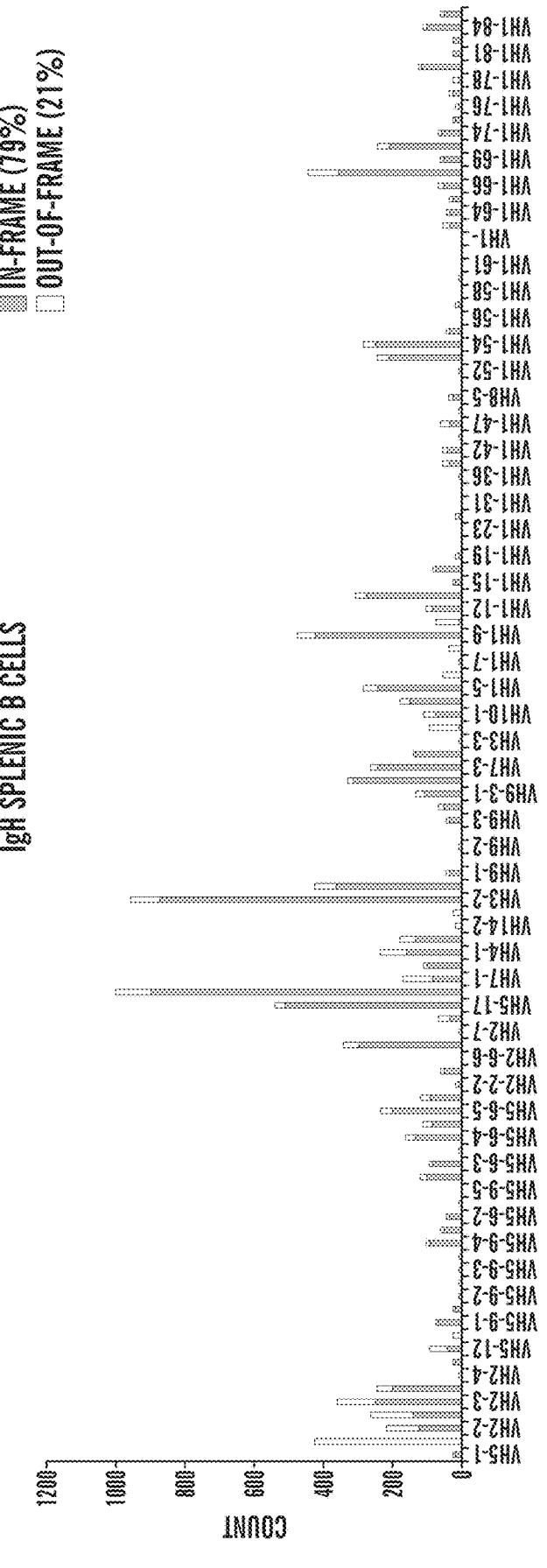
FIGS. 4A-4B demonstrate that the assay can also be used to distinguish and quantify in-frame and out-of-frame V(D)J exons.
Figure 4A:
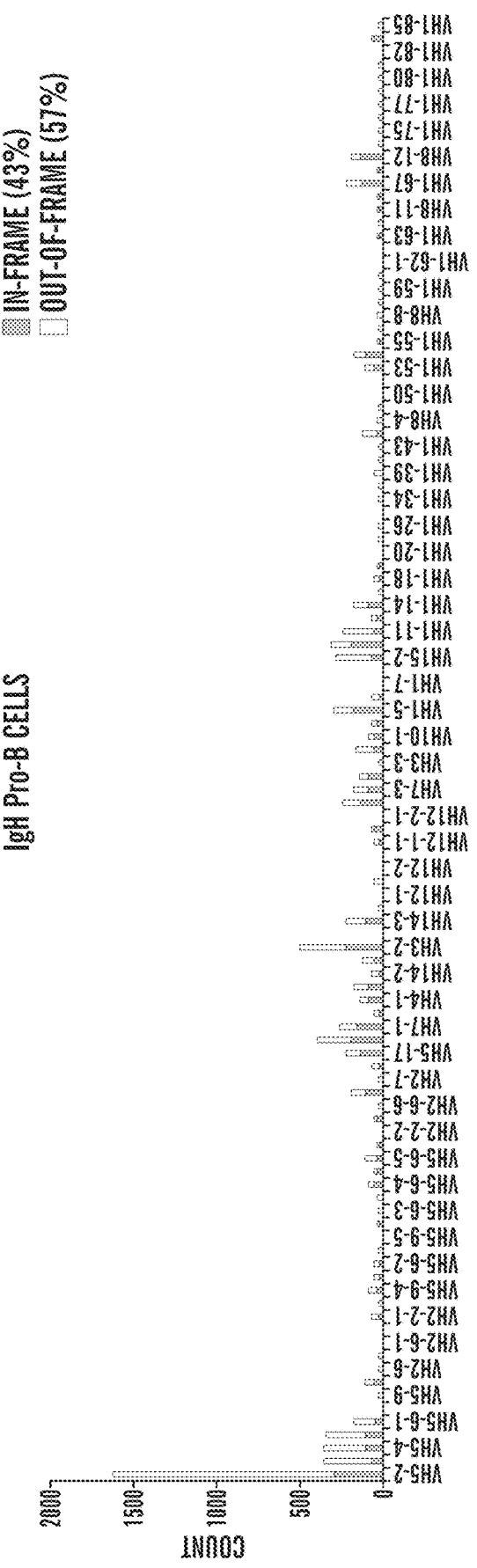
Figure 4B:
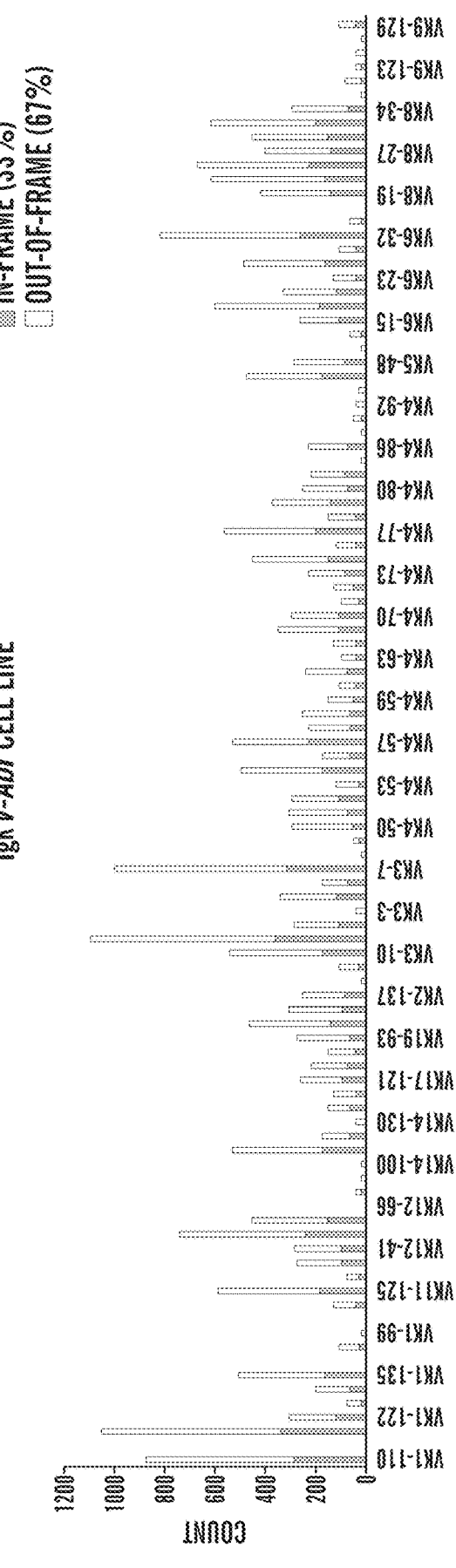
Figure 5A:
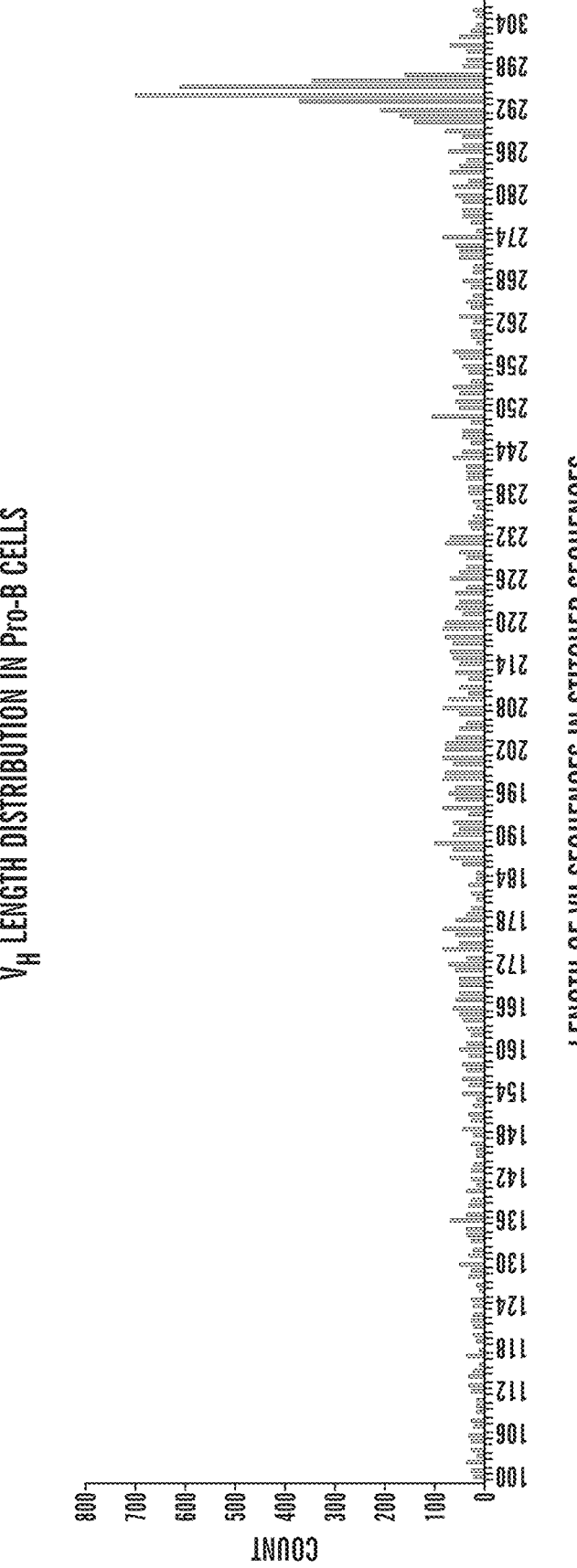

FIGS. 4A-4B demonstrate that the assay can also be used to distinguish and quantify in-frame and out-of-frame V(D)J exons. Stitched paired-end Illumina Miseq sequences extracted from IgH or Igκ libraries. The full CDR1, CDR2, and CDR3 were included in the more than 30% of the total stitched sequences; thus this method can be used to study somatic hypermutation (FIGS. 5A-5C). Thus far, this property which is critical for following specific immune responses (e.g. during vaccination experiments) has not been reported for any other methods.

Example 3

The methods described herein differ from earlier methods in that:
1. mRNA can be used for generating HTGTS-Rep-seq libraries.
2. The primers can be placed 20-50 bp-downstream of the intended bait coding ends; in prior methods, primers were at least 100 bp from the coding ends.
3. The primers described herein are universal primers, and can be used for HTGTS-Rep-seq libraries from all users:

TABLE 1

| Name | Sequence | Purpose | SEQ ID NO |
|---|---|---|---|
| $J_H1$-bio | /5BiosG/CTGCAGCATGCA GAGTGTG | HTGTS bio primer for $J_H1$ coding end | 1 |
| $J_H1$-red | TGACATGGGGAGATCTG AGA | HTGTS red primer for $J_H1$ coding end | 2 |

TABLE 1-continued

| Name | Sequence | Purpose | SEQ ID NO |
|---|---|---|---|
| $J_H2$-bio | /5BiosG/ACCCTTTCTGAC TCCCAAGG | HTGTS bio primer for $J_H2$ coding end | 3 |
| $J_H2$-red | CCCCAACAAATGCAGTA AAATCT | HTGTS red primer for $J_H2$ coding end | 4 |
| $J_H3$-bio | /5BiosG/GGGACAAAGGG GTTGAATCT | HTGTS bio primer for $J_H3$ coding end | 5 |
| $J_H3$-red | CCCGTTTGCAGAGAATC TT | HTGTS red primer for $J_H3$ coding end | 6 |
| $J_H4$_bio | /5BiosG/CCCTCAGGGACA AATATCCA | HTGTS bio primer for $J_H4$ coding end | 7 |
| $J_H4$_red | CTGCAATGCTCAGAAAA CTCC | HTGTS red primer for $J_H4$ coding end | 8 |
| Jκ1_bio | /5Biosg/TTCCCAGCTTTG CTTACGGAG | HTGTS bio primer for Jκ1 coding end | 9 |
| Jκ1_red | AGTGCCAGAATCTGGTT TCAGAG | HTGTS red primer for Jκ1 coding end | 10 |
| Jκ2_bio | /5Biosg/ATTCCAACCTCT TGTGGGACAG | HTGTS bio primer for Jκ2 coding end | 11 |
| Jκ2_red | TCCCTCCTTAACACCTG ATCTGAG | HTGTS red primer for Jκ2 coding end | 12 |
| Jκ4_bio | /5BiosG/CGCTCAGCTTTC ACACTGACTC | HTGTS bio primer for Jκ4 coding end | 13 |
| Jκ4_red | CAGGTTGCCAGGAATGG CTC | HTGTS red primer for Jκ4 coding end | 14 |
| Jκ5_bio | /5Biosg/GCCCCTAATCTC ACTAGCTTGA | HTGTS bio primer for Jκ5 coding end | 15 |
| Jκ5_red | GTCAACTGATAATGAGC CCTCTCC | HTGTS red primer for Jκ5 coding end | 16 |

4. No enzyme blocking is needed for HTGTS-Rep-seq, whereas most prior HTGTS applications require enzyme blocking.
5. Lower amounts of starting material usually can be used for HTGTS-Rep-seq than prior methods, since V(D)J rearrangements are in most applications expected to occur more frequently than general translocations.
6. All the duplicates are usually kept in HTGTS-Rep-seq analyses, while this is not the case for most of the prior HTGTS applications.
7. IgBlast is used to analyze HTGTS-Rep-seq libraries; thus HTGTS-Rep-seq gives information on the usage of Vs, D, and Js within antigen receptor loci.
8. HTGTS-Rep-seq pipeline (using IgBlast) provides productive and non-productive rearrangement information about V(D)J exons isolated.
9. HTGTS-Rep-seq pipeline provides CDR3 information for V(D)J exons isolated.
10. HTGTS-Rep-seq pipeline provides somatic hypermutation information for some V(D)J exons, while mutations are ignored in prior application analysis pipelines.
11. HTGTS-Rep-seq pipeline provides information for one (V-J recombination) or two (V-D-J recombination) V-containing joins in sequenced fragments.
12. LAM-HTGTS pipeline gives information for D-J joins and RAG off-target joins in sequenced fragments.
13. HTGTS-Rep-seq can be used to identify clonal lineages defined by sequence read similarity and to identify unannotated V alleles and/or segments.

300 bp×2 miseq sequencing can be utilized for HTGTS-Rep-seq.

Example 4: A Highly Sensitive and Unbiased Approach for Elucidating Antibody Repertoires Developing B lymphocytes undergo V(D)J recombination to assemble germline V, D, and J gene segments into exons that encode the antigen-binding variable region of immunoglobulin (Ig) heavy (H) and light (L) chains. IgH and IgL chains associate to form the B cell receptor (BCR), which upon antigen binding activates B cells to secrete BCR as an antibody. Each of the huge number of clonally independent B cells expresses a unique set of IgH and IgL variable regions. Ability of V(D)J recombination to generate vast primary B cell repertoires results from combinatorial assortment of large numbers of different V, D, and J segments, coupled with diversification of the junctions between them to generate the complementary determining region 3 (CDR3) for antigen contact. Approaches to evaluate in depth the content of primary antibody repertoires and, ultimately, to study how they are further molded by secondary mutation and affinity maturation processes are of great importance to the B cell development, vaccine, and antibody fields. Described herein is an unbiased, sensitive, and readily accessible assay, referred to as HTGTS repertoire sequencing (HTGTS-Rep-seq), to quantify antibody repertoires. HTGTS-Rep-seq quantitatively identifies the vast majority of IgH and IgL V(D)J exons, including their unique CDR3 sequences, from progenitor and mature mouse B lineage cells via the use of specific J primers. HTGTS-Rep-seq also accurately quantifies $DJ_H$ intermediates and V(D)J exons in either productive or non-productive configurations. HTGTS-Rep-seq should be useful for studies of human samples, including clonal B-cell expansions and also for following antibody affinity maturation processes.

Antibodies are generated by B cells of the adaptive immune system to eliminate various pathogens. A somatic gene rearrangement process, termed V(D)J recombination, assembles antibody gene segments to form sequences encoding the antigen-binding regions of antibodies. Each of the multitude of newly generated B cells produces a different antibody with a unique antigen-binding sequence; which collectively form the primary antibody repertoire of an individual. Given the utility of specific antibodies for treating various human diseases, approaches to elucidate primary antibody repertoires are of great importance. Described herein is a new method for high-coverage analysis of antibody repertoires termed HTGTS-Rep-seq, which is both unbiased and highly sensitive.

Introduction

The B lymphocyte antigen receptor (BCR) is comprised of identical immunoglobulin heavy (IgH) and Ig light (IgL) chains. Antibodies are the secreted form of the BCR. The V(D)J recombination process assembles germline V, D, and J gene segments into exons that encode the antigen-binding variable region exons of the BCR. The RAG 1 and 2 endonuclease (RAG) initiates V(D)J recombination by generating DNA double-stranded breaks (DSBs) between V, D, and J gene segments and their flanking recombination signal sequences (RSSs) (1). In this process, the V, D, and J coding ends are generated as covalent hairpins that must be opened, and which are often further processed, prior to being joined by classical non-homologous end joining (2). Processing of V, D, J coding ends can involve generation of deletions or insertions of nucleotides at the junction regions (2); including the frequent de novo addition of nucleotides by the terminal deoxynucleotidyl transferase component of the V(D)J recombination process (3). Notably the V(D)J junctional region encodes a major antigen contact region of the antibody variable region, known as complementarity determining region 3 (CDR3), and thus these junctional diversification processes make a huge contribution to antibody diversity.

The mouse IgH locus spans 2.7 megabases (Mbs). There are 100s of $V_{HS}$ in the several Mb distal portion of the IgH, with the number varying substantially in certain mouse strains (4). The $V_{HS}$ lie approximately 100 kb upstream from a 50 kb region containing 13 $D_{HS}$, which is followed several kb downstream by a 2 kb region containing 4 $J_{HS}$. The IgH constant region ($C_H$) exons lie downstream of the $J_{HS}$. Following assembly of a $V_H DJ_H$ exon, transcription initiates upstream of the $V_H$ and terminates downstream of the $C_H$ exons, with V(D)J and $C_H$ portions being fused into the ultimate IgH messenger RNA (mRNA) via splicing of the primary transcript. Due to the random junctional diversification mechanisms, only about ⅓ of assembled IgH V(D)J exons are able to generate in-frame splicing events that place the V(D)J and $C_H$ exons in the same reading frame to generate productive (in-frame with functional $V_H$) rearrangements that encode an IgH polypeptide with the remainder being non-productive (out-of-frame, in-frame with a stop codon, or utilizing a pseudo-$V_H$) (5). IgL chain variable region exons are assembled from just V and J segments but otherwise follow similar basic principles to those of IgH. The mouse Igκ light chain locus spans 3.2 Mbs with 100s of Vκs in a 3.1-Mb region separated by 20 kb from 5 Jκs downstream; while the Igλ light chain locus is smaller and less complex (6). RNA splicing again joins assembled $VJ_L$ exons to corresponding $C_L$ exons.

Figure 11A:
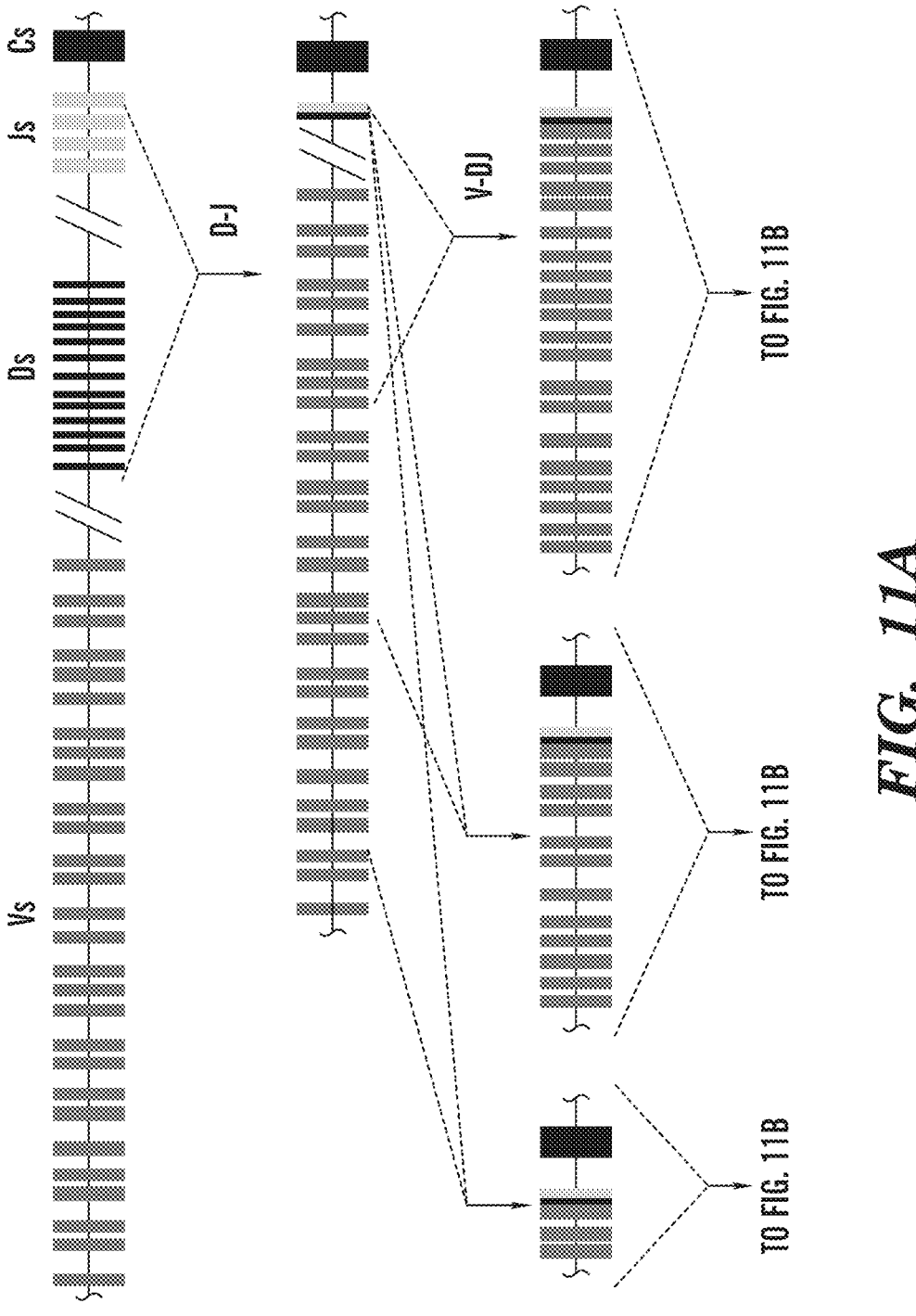
FIGS. 11A-11B depict a schematic for HTGTS-Rep-seq.

During B cell development, V(D)J recombination is regulated to ensure specific repertoires and prevent undesired rearrangements. IgH V(D)J recombination occurs stage-specifically in progenitor B (pro-B) cells before that of IgL loci which occur in precursor B (pre-B) cells. IgH V(D)J recombination is ordered, with D to $J_H$ joining occurring, usually on both alleles, before appendage of a $V_H$ to a $DJ_H$ complex (FIG. 11A) (2). In addition, the $V_H$ to $DJ_H$ step of IgH V(D)J recombination is feedback regulated with a productive rearrangement leading to cessation of V(D)J recombination on the other allele if it is still in $DJ_H$ configuration (2). In contrast, initial non-productive IgH V(D)J rearrangements do not prevent $V_H$ to $DJ_H$ rearrangements from occurring on the other allele. Such feedback regulation generally leads to the typical 40/60 ratio of mature B cells with two IgH V(D)J rearrangements (one productive) versus one IgH V(D)J plus a $DJ_H$ rearrangement (7). $V_H$ to $DJ_H$ rearrangement is also regulated to generate diverse utilization of the 100s of upstream $V_{HS}$. While proximal $V_{HS}$, notably the most proximal $V_H$ ($V_H$81X), are somewhat over-utilized in pro-B V(D)J rearrangements, the sequestering of the $D_{HS}$ and $J_{HS}$ in a separate chromosomal domain from that of the $V_{HS}$ (8, 9), coupled with the phenomenon of locus contraction (10, 11), allows even the most distal $V_{HS}$ to be utilized. Subsequently, the somewhat biased primary $V_H$ repertoire in pro-B cells is subjected to cellular selection mechanisms to generate a more normalized primary repertoire in newly generated B cells (12).

Each B cell expresses a unique BCR, and each individual mouse or human has the capacity to generate up to $10^{13}$ or more distinct BCRs in the primary repertoire (13), with a large fraction of these being generated by junctional diversification of IgH and IgL CDR3s (14). In this regard, the ability to quantitatively identify the IgH and IgL variable region exons that contribute to the primary antibody reper-toire is of great interest in elucidating contributions of this repertoire to immune responses and to immune diseases (15). Several important repertoire sequencing assays that utilize next-generation sequencing have been developed. These approaches involve the generation of repertoire librar-ies from either genomic DNA or mRNA (15). Most prior DNA-based approaches rely on use of upstream degenerate V primers, each designed to identify members of particular $V_H$ families, and a downstream degenerate J primer; an approach that covers many, but not necessarily all, V(D)J exons and likely not all equally. RNA-based approaches generally only require one downstream primer (from the J or constant region) and thus obviate biases in prior DNA-based assays; but these approaches can severely underestimate non-productive rearrangements due to decreased transcript levels (15). In addition, the long length of the 5'RACE-derived complementary DNAs can also pose a challenge, as sequencing technologies cannot always cover the entire length of the V(D)J exons.

The methods described herein employs a single primer for a DSB-associated bait sequence to perform linear amplifi-cation across bait-prey junctions to identify all prey sequences joined to the bait DSBs in an unbiased manner. As V(D)J recombination generates rearrangements with junc-tions at borders of V, D, and J segments; primers for any of these gene segments can be employed as bait to identify sites of RAG-generated DSBs, both in progenitor or precursor lymphocytes undergoing V(D)J recombination, as well as in mature lymphocytes to retrospectively identify V(D)J recombination events that occurred earlier in development. Notably, the methods described herein identified RAG-generated $DJ_H$ joins, RSS joins in excision circles, and off-target junctions in developing B-lineage cells that were not detected by prior assays (22), illustrating the high sensitivity of the assay.

Results

Overview of LAM-HTGTS Adapted Repertoire Sequenc-ing.

Figure 11B:
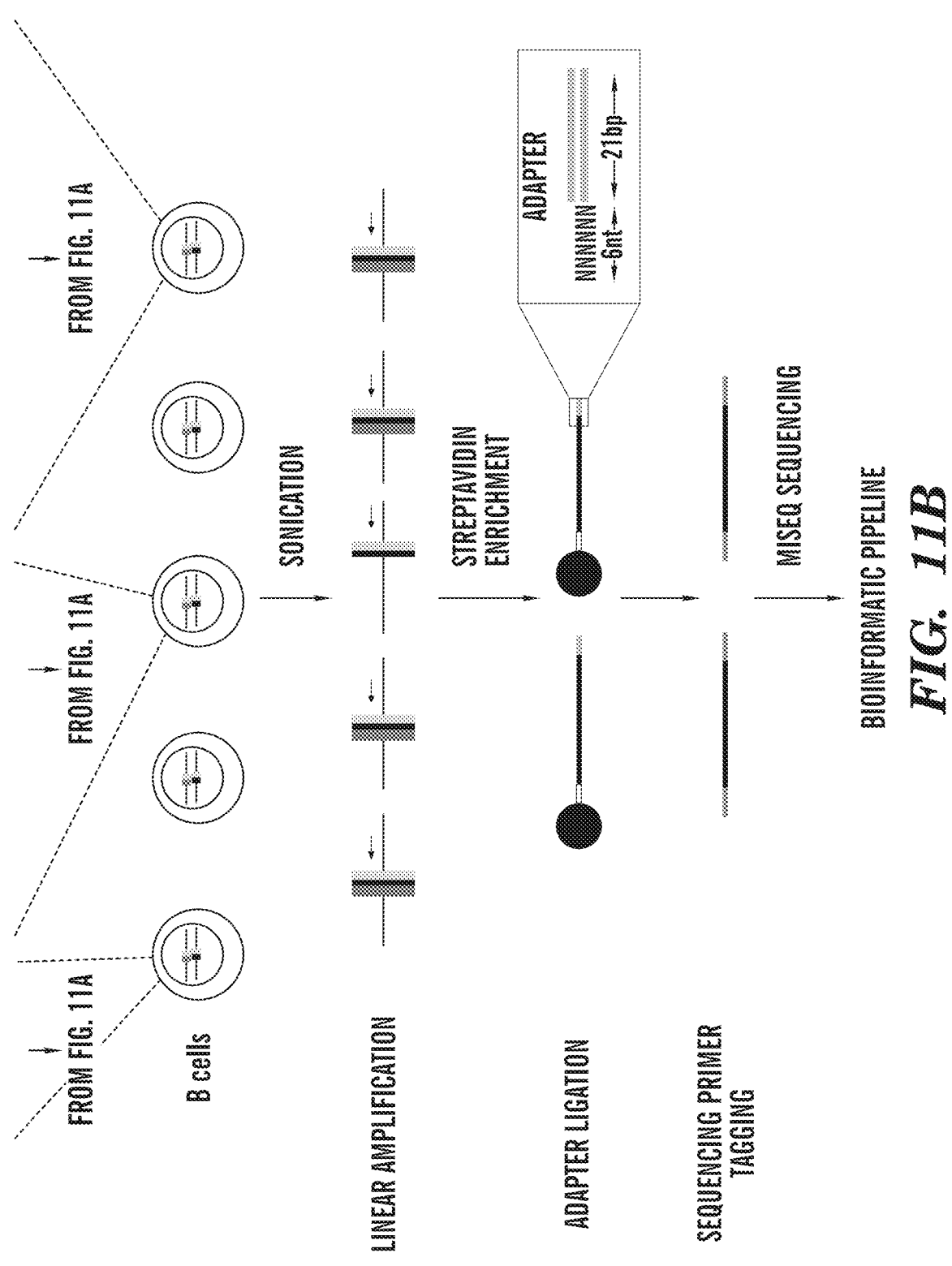

For HTGTS-Rep-seq libraries, bait coding ends of J segments were utilized to identify, in unbiased fashion, mouse IgH $DJ_H$ repertoires along with both productive and non-productive IgH V(D)J repertoires from both pro-B and peripheral B cells. Similarly, mouse productive and non-productive Igκ repertoires from peripheral B cells were also identified. For all samples analyzed, genomic DNA isolated from a pool of the given type of B cells was sonicated to generate fragments with an average size of approximately 1 kb and which, thus, would be expected to harbor IgH V(D)J or DJ rearrangements, Igκ VJ rearrangements, or un-rear-ranged $J_{HS}$ or Jκs (FIG. 11B).

Biotinylated bait primers that anneal to sequences down-stream of the coding end of a particular $J_H$ or Jκ segment will allow linear amplification of any fragments containing the bait J segment(s). Subsequent streptavidin purification, adapter ligation, and library construction steps are carried out as previously described (16)(FIG. 11B). To generate longer sequencing reads for more accurate alignment of Vs and Ds, bait primers were positioned closer to the coding ends of bait Js and MiSeq 2×300 bp paired-end sequencing was employed to capture full-length V(D)J sequences in recovered junctions. For bioinformatic analysis, the LAM-HTGTS pipeline was combined with IgBlast (23) to gener-ate an analysis pipeline that provides comprehensive infor-mation on productive or non-productive junctions and CDR3 sequences.

For the HTGTS-Rep-seq all recovered junctions includ-ing all duplicates can be kept for analysis for reasons described previously (22). To control for experimental varia-tions, 3 technical repeat HTGTS-Rep-seq libraries were generated from the same splenic B cell DNA samples which yield highly reproducible repertoires with correlation coef-ficient (r) values of 0.99 (Table 2). Even for biological repeat IgH or IgL HTGTS-Rep-seq libraries from pro-B or splenic B cells of 3 different mice, correlation analyses revealed highly reproducible repertoires with r values greater than 0.9 in most of the data sets (Tables 2 and 3). However, as described below, detailed analyses of certain aspects of such libraries, such as the fraction of unique CDR3s in the total repertoire, reveal expected biological variations (Table 2).

Figures 7A, 7B:
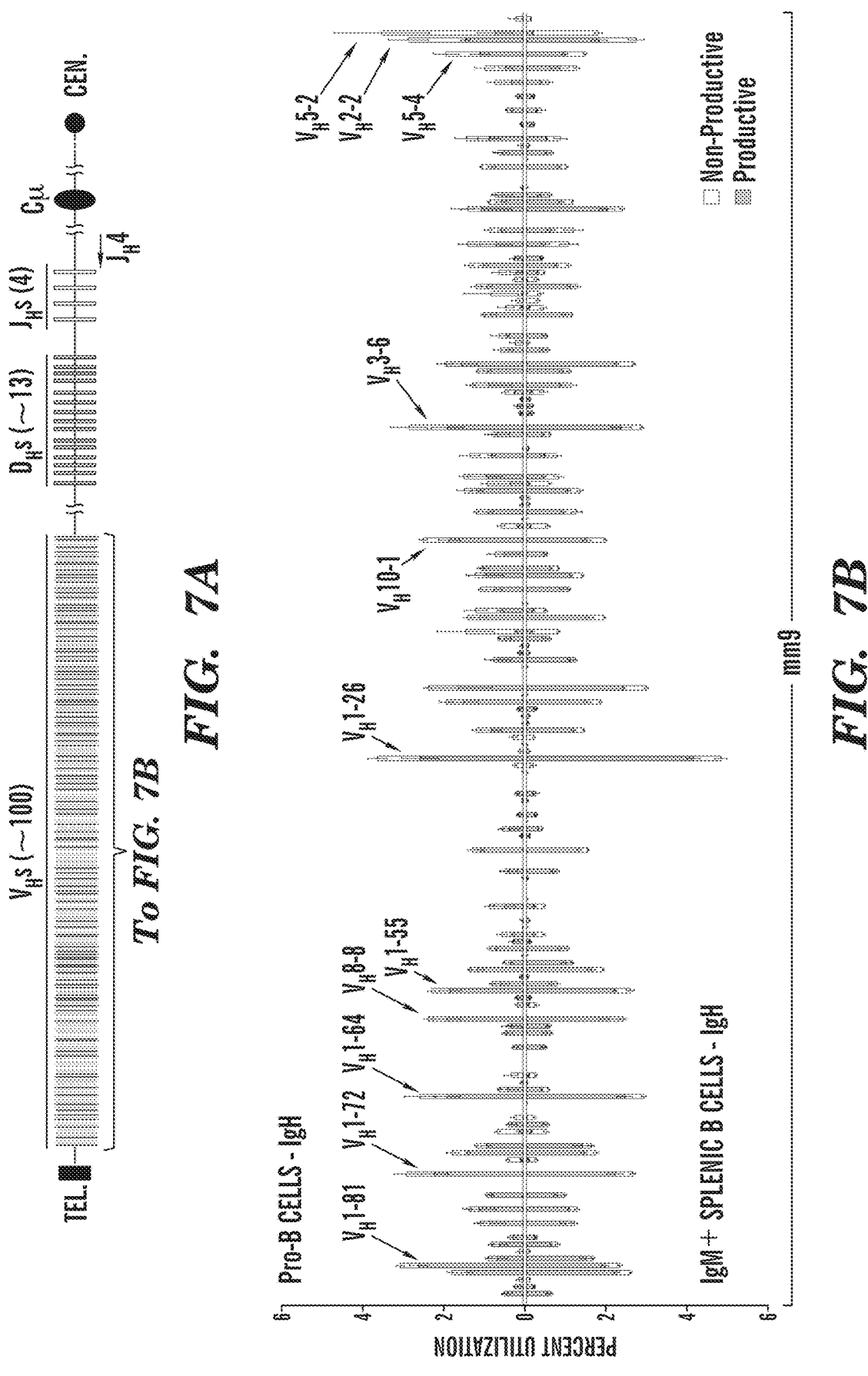
Figure 17A:
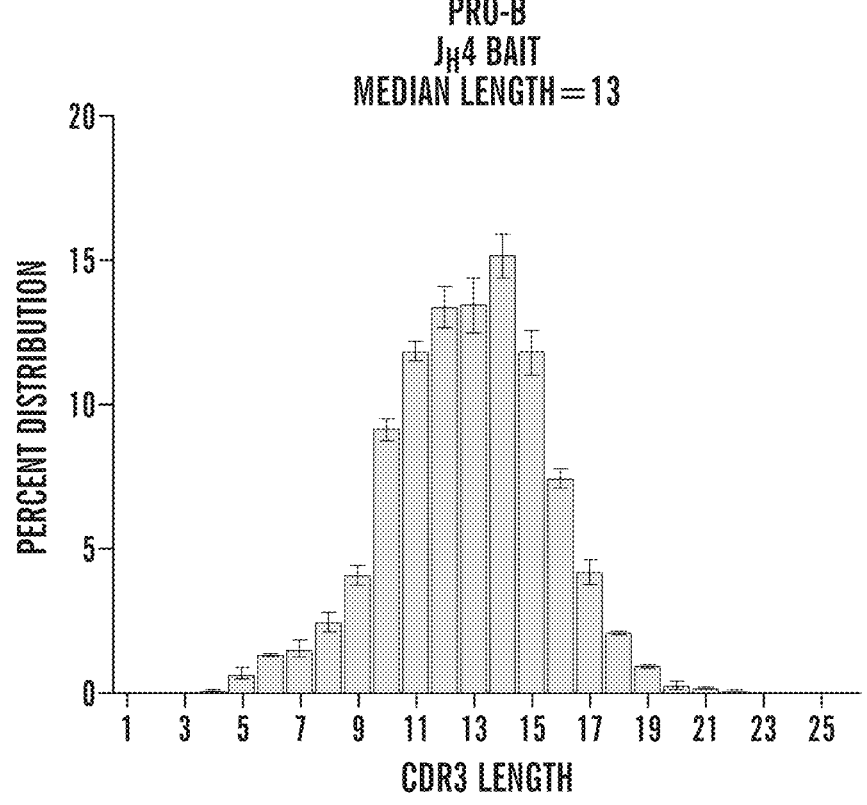
FIGS. 17A-17D depict CDR3 length distribution and consensus motif of productive V$_H$DJ$_H$ and VJκ exons.
Figure 17A:
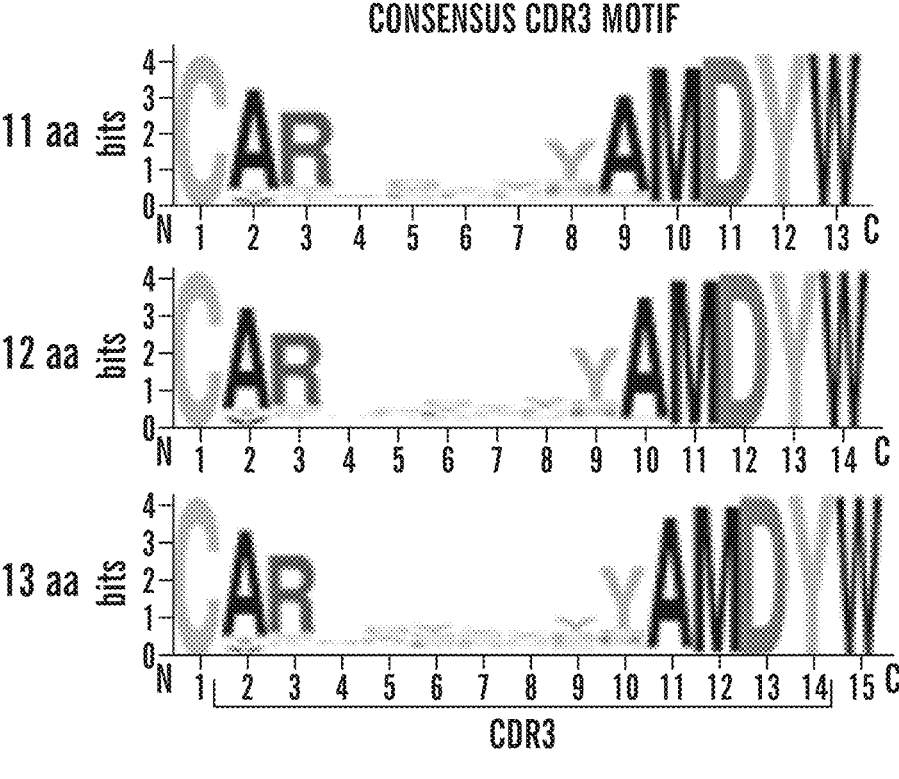
Figure 17B:
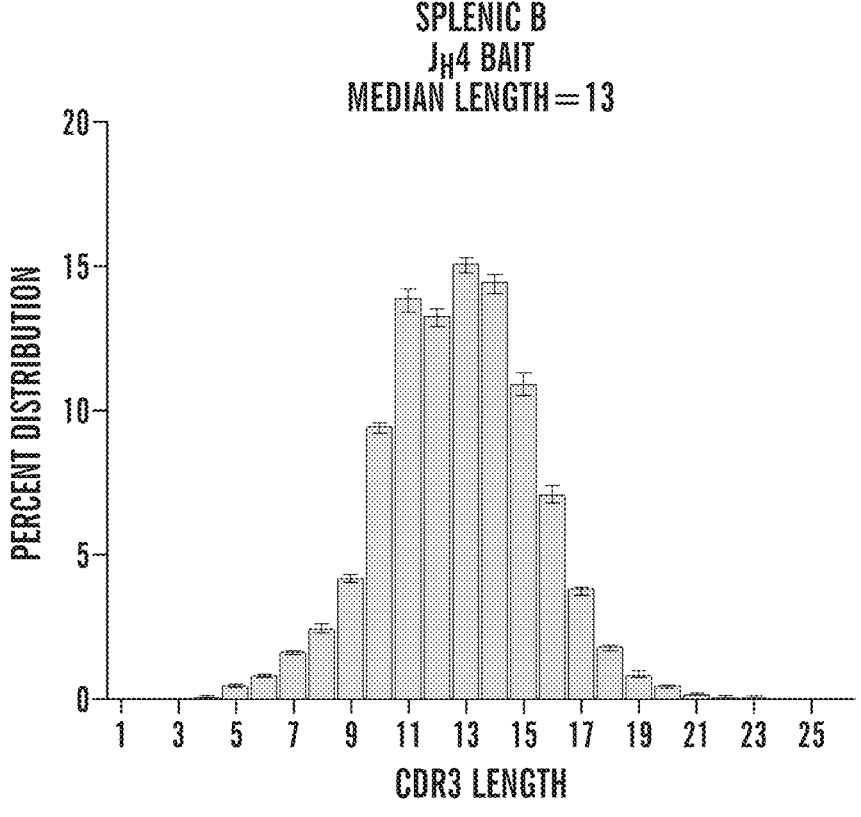
Figure 17B:
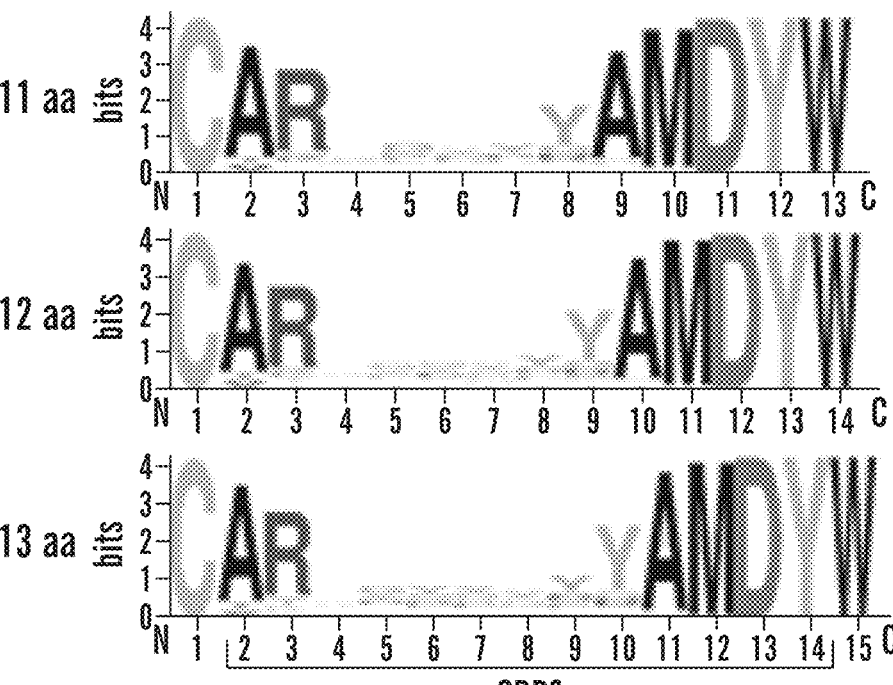
Figure 17C:
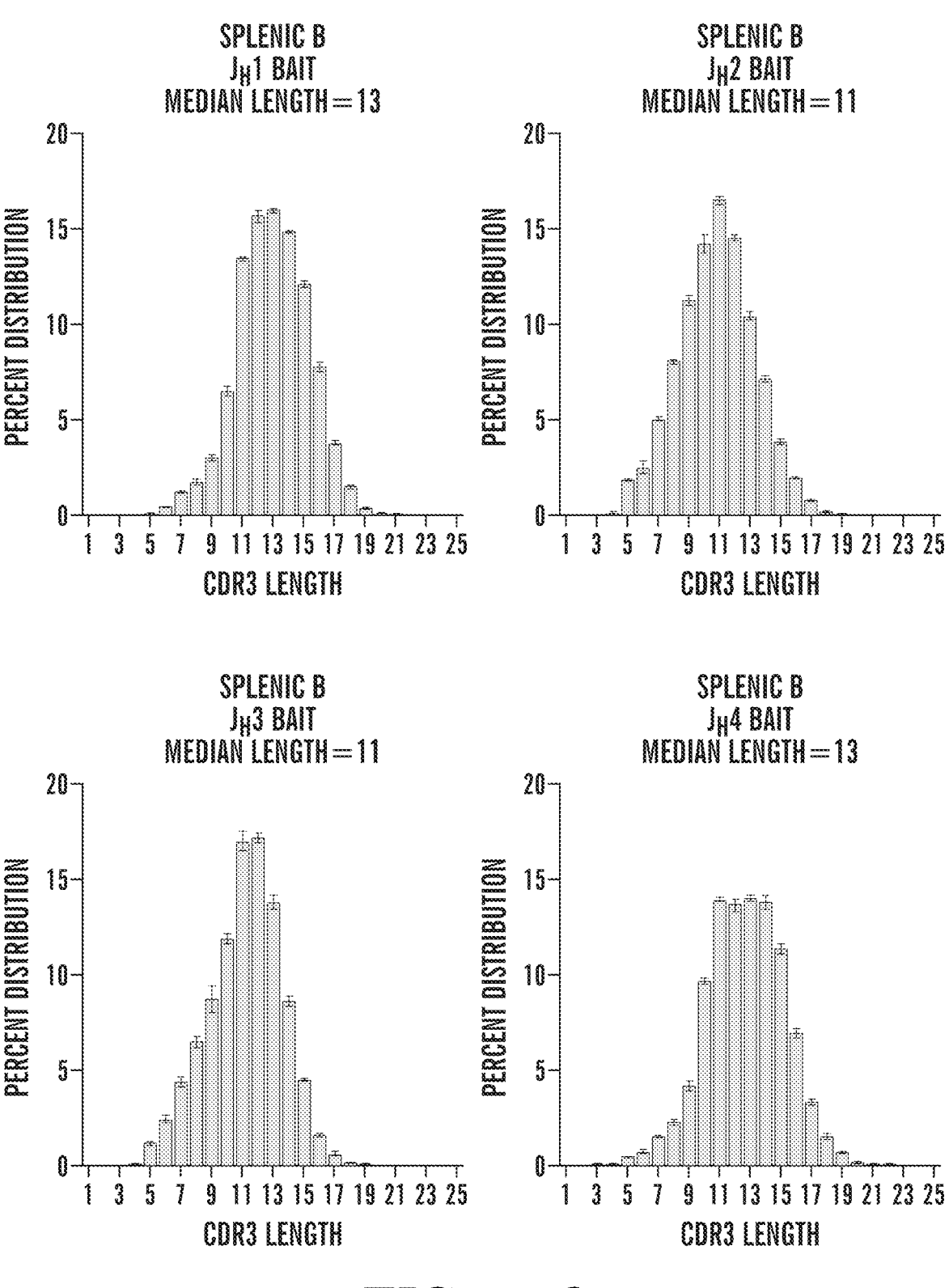

HTGTS-Rep-seq Reveals IgH $V_H DJ_H$ and $DJ_H$ Repertoires in Developing and Mature B Cells To test ability of HTGTS-Rep-seq to detect differences between primary pro-B cell IgH repertoires versus those of peripheral B lymphocytes, primary $B220^+CD43^+IgM^-$ pro-B cells were enriched from the bone marrow and $B220^+IgM^+$ B cells were purified from the spleen of wild-type C57BL/6 mice. 2 µg genomic DNA isolated from these cell populations was used to perform HTGTS-Rep-seq with a $J_H4$ coding end bait primer to capture $V_H DJ_{H4}$ and $DJ_{H4}$ rearrangements (FIG. 7A; Table 2). Libraries from both cell types showed broad usage of $V_{HS}$ in $V_H DJ_{H4}$ rearrangements throughout the IgH variable region locus with some $V_{HS}$ utilized more frequently (e.g. $V_H5$-2, $V_H2$-2, $V_H3$-6, $V_H1$-26, $V_H1$-64, $V_H1$-72, $V_H1$-81) (FIG. 7B). The C57BL/6 IgH locus has approximately 110 potentially functional $V_{HS}$ and 74 pseudo $V_{HS}$ categorized into 16 families (24). In the IgH repertoire libraries generated with a $J_H4$ coding end bait, there were detected in $V_H DJ_H$ exons 107 functional $V_{HS}$ from all 16 families, as well as 21 pseudo $V_{HS}$ with relatively conserved RSSs (FIG. 17C). Notably, the three "functional" $V_{HS}$ ($V_H1$-62-1, $V_H2$-6-8, $V_H7$-2) not detected by HTGTS-Rep-seq also were not found by another high-throughput repertoire sequencing method (25), indicating that they may actually be non-functional with respect to the ability to undergo V(D)J recombination.

Figure 7D:
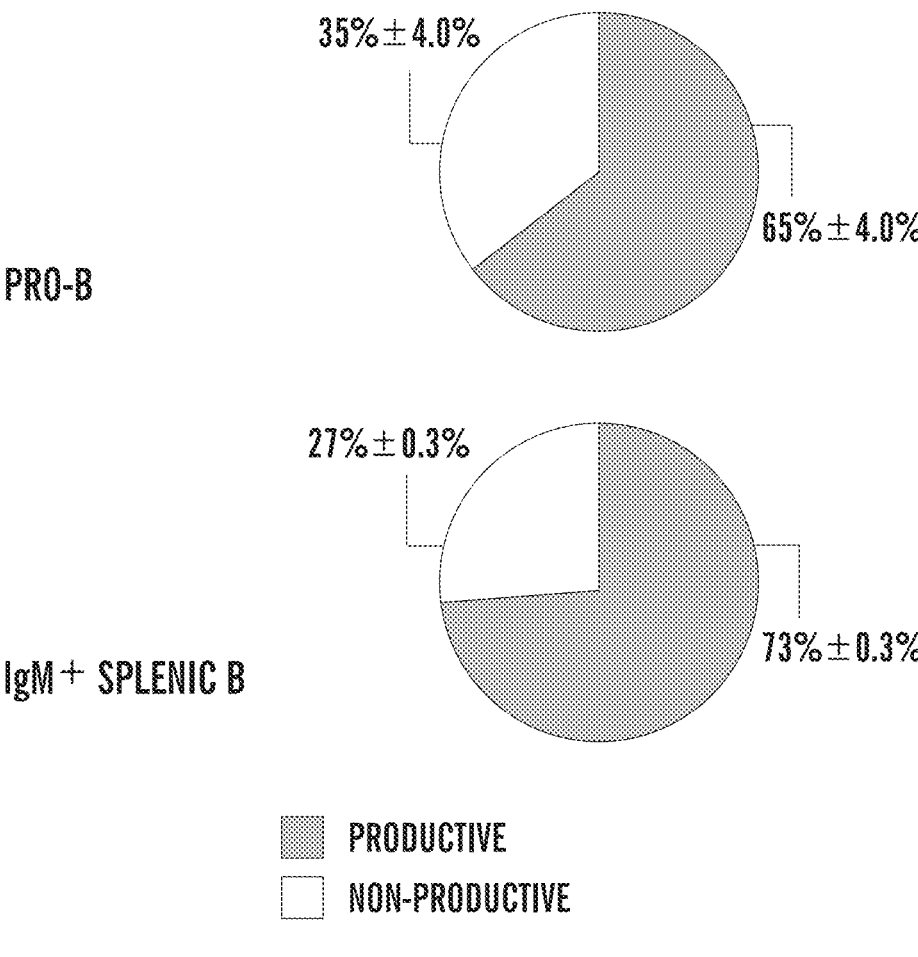
Figure 7E:
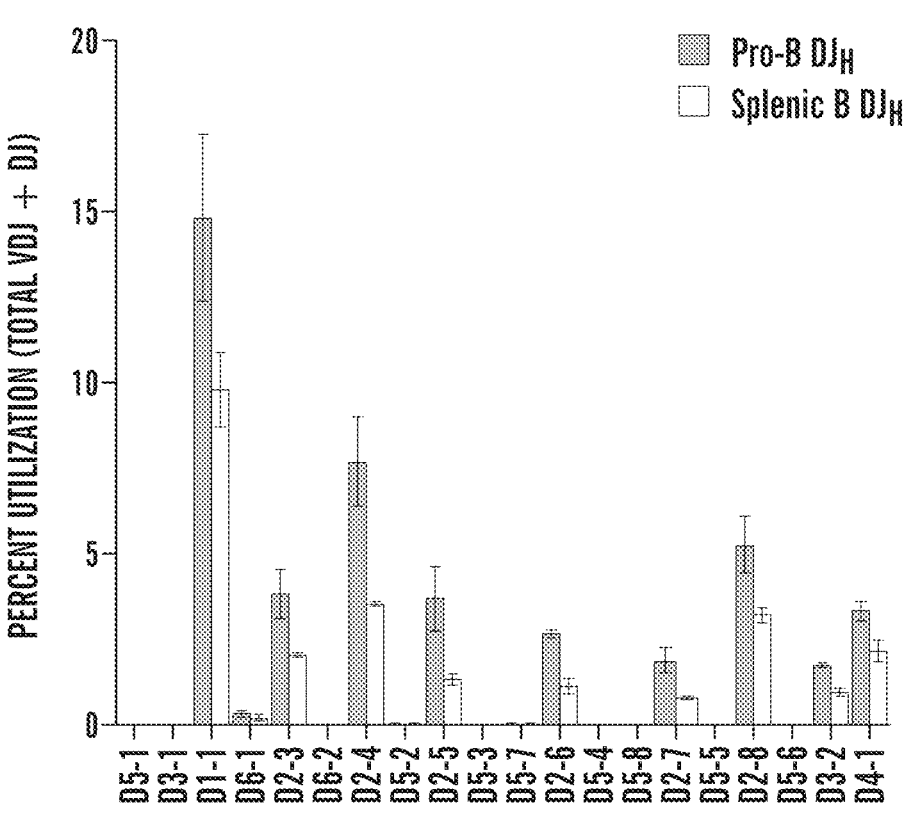
Figure 7F:
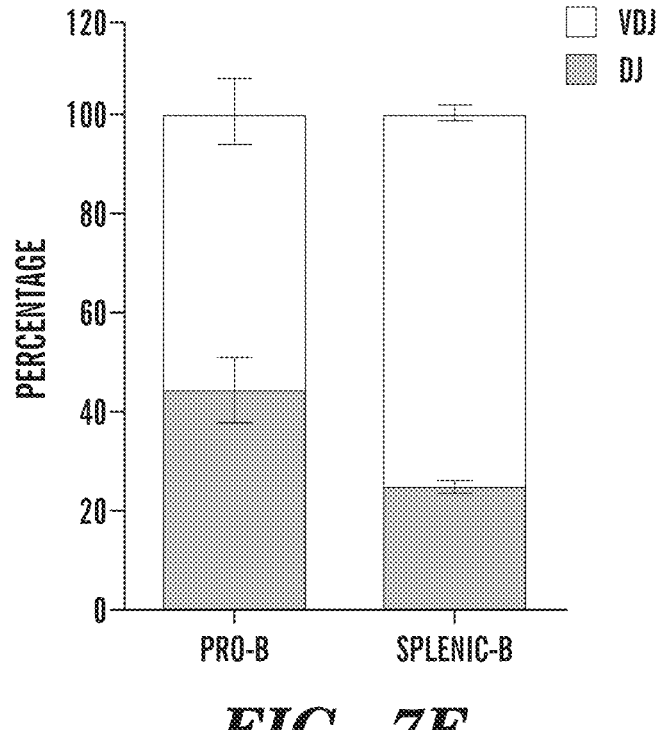

$V_H$ to $DJ_H$ rearrangements occur at the pro-B stage, with only one in three expected to be in-frame (5). In the $V_H DJ_H4$ exons HTGTS-Rep-seq identified, on average 65%, as pro-ductive and, correspondingly, 35% were non-productive (FIG. 7D). This ratio likely reflects a dynamic differentiation process in which pro-B cells with two non-productive rear-rangements are negatively selected and those with a pro-ductive rearrangement on one allele are positively selected (12). Due in large part to feedback mechanisms from pro-ductive V(D)J$_H$ rearrangements during pro-B cell develop-ment, approximately 40% of splenic B cells display $V_H DJ_H$ rearrangements on both alleles (one productive and one non-productive) and the remaining 60% have one productive $V_H DJ_H$ and one $DJ_H$ rearrangement (5). Thus, a population of splenic B cells theoretically would be expected to have about 71% productive $V_H DJ_H$ exons and 29% non-produc-tive $V_H DJ_H$ exons. Indeed, a very similar ratio of productive/non-productive $V_H DJ_H4$ exons (73:27) were observed in the HTGTS-Rep-seq libraries from splenic B cell DNA (FIG. 7D). In the $DJ_H$ joins revealed by HTGTS-Rep-seq, $D_H1$-1 (also known as DFL16.1) was used most frequently in libraries from both pro-B and splenic mature B cells (FIG. 7E). Moreover, a much higher percentage of $DJ_H$ exons were observed in pro-B cells compared to that of splenic B cells (45% vs. 25%; FIG. 7E, 7F), in line with D to $J_H$ rearrange-ment on both alleles preceding $V_H$ to $DJ_H$ rearrangement in developing pro-B cells (5, 26, 27).

Biased Proximal $V_H$ Usage in 129SVE Mice Revealed by HTGTS-Rep-seq.

The 129SVE mouse strain IgH locus contains more $V_{HS}$ than the C57BL/6 IgH locus with a somewhat different organization (24). Given that 129SVE mice and cell lines have frequently been used in V(D)J recombination studies, the same $J_H4$ bait primers were used to also generate HTGTS-Rep-seq libraries from 129SVE bone marrow pro-B cells and splenic B cells (Table 3). The 129SVE IgH locus $V_H$ sequences are annotated up to approximately 1 Mb into the variable $V_H$ region, but $V_H$ sequences lying within the relatively large more distal region of the locus are not completely annotated. Thus, to generate an approximate 129SVE $V_HDJ_H$ repertoire, Igblast analyses were run against a combination of all the known 129SVE $V_H$ sequences and the annotated distal $V_H$ sequences from the C57BL/6 background starting from $V_H8$-2 (FIG. 12A, 12B). As with the C57BL/6 libraries, the $V_{HS}$ were widely used and 128 functional $V_{HS}$ out of 133 distinct members of the 15 $V_H$ families plus 34 pseudo $V_{HS}$ were detected (FIG. 12C).

Figures 12A, 12B:
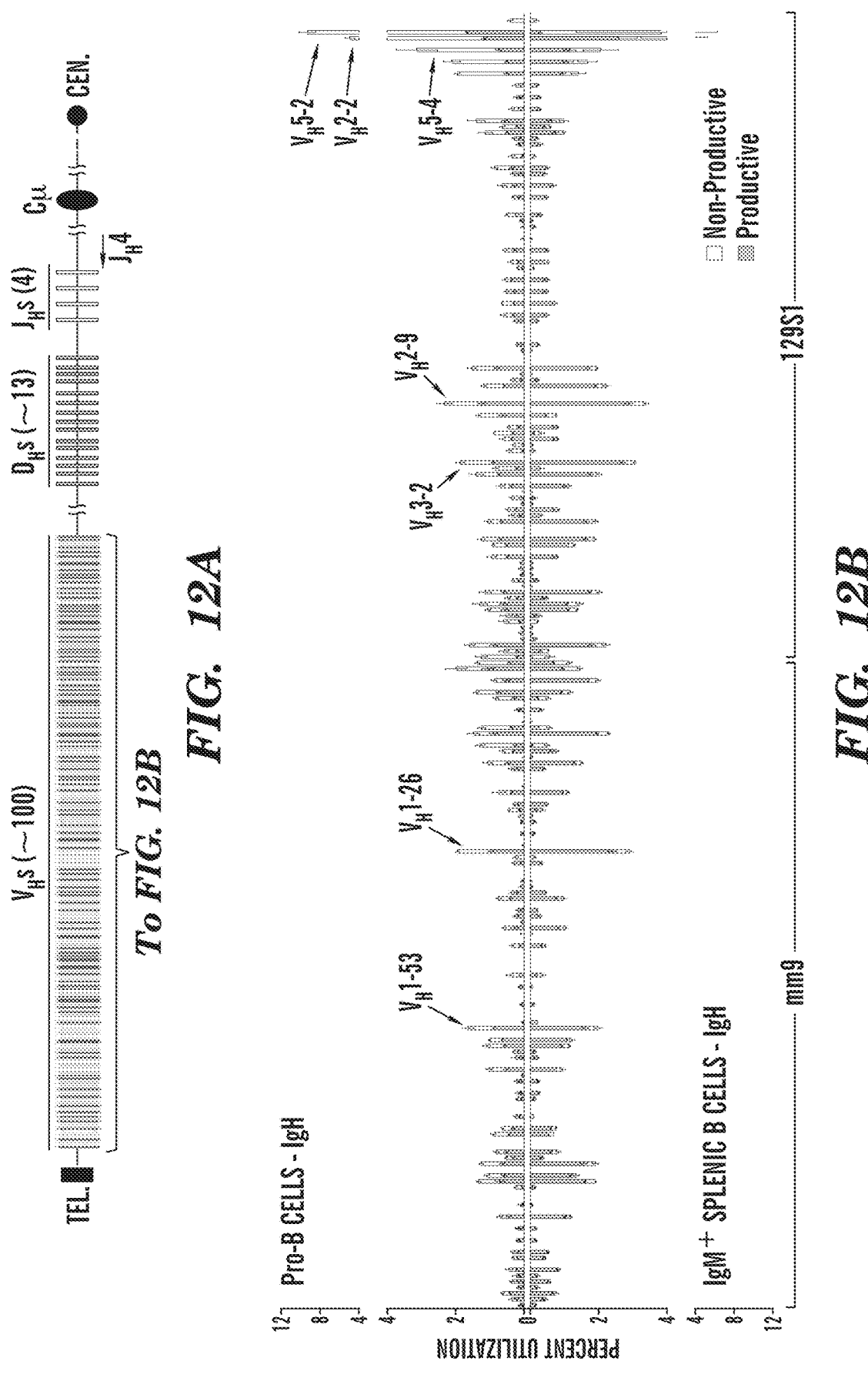
Figure 12D:
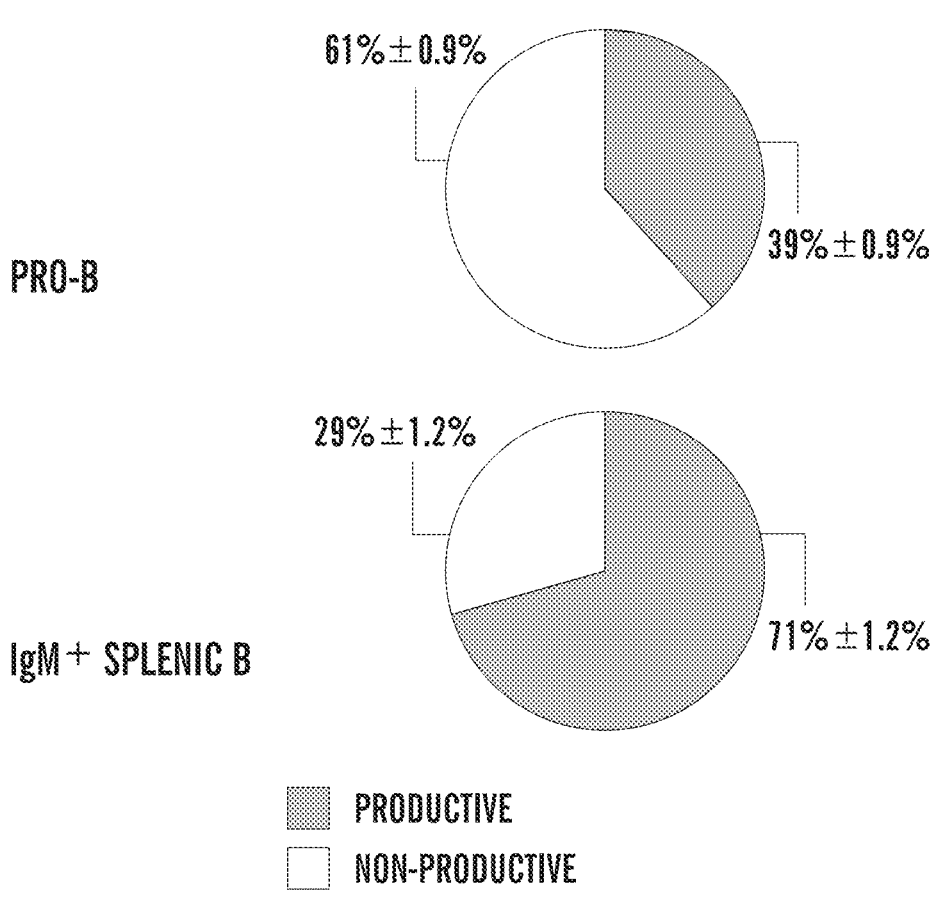
Figure 12E:
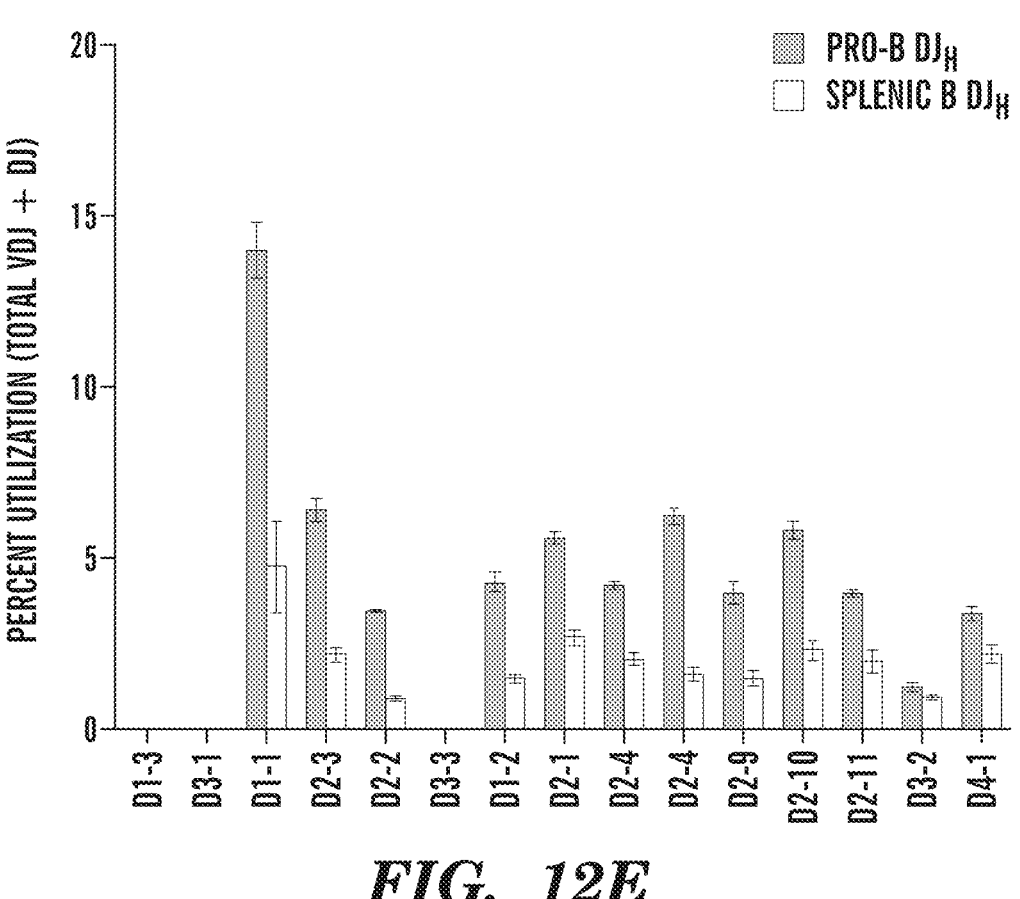
Figure 12F:
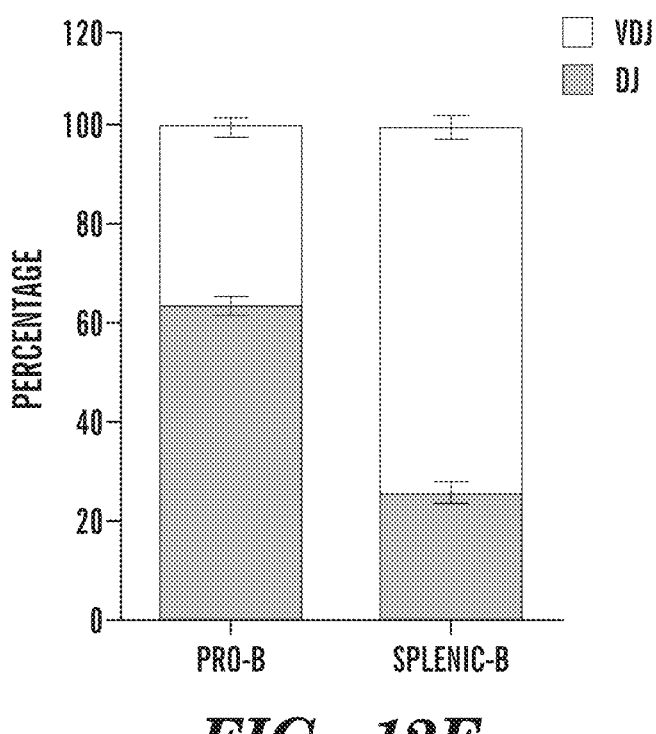

In contrast to the IgH $V_HDJ_{H4}$ repertoire in C57BL/6 mice, a highly biased usage of proximal $V_{HS}$, especially $V_H5$-2 (also known as $V_H81X$) and $V_H2$-2, in 129SVE mice was found (FIGS. 7B, 12B). The D-proximal $V_H5$-2 was used in 9.5% (1.7% productive; 7.7% non-productive) of all $V_HDJ_{H4}$ exons in pro-B cells and about 4% (0.3% productive; 3.5% non-productive) of all $V_HDJ_{H4}$ exons in splenic B cells of 129SVE mice (FIG. 12B). In contrast, $V_H5$-2 appeared in only about 3.5% (0.7% productive; 2.8% non-productive) and about 1.8% (0.15% productive; 1.6% non-productive) of the $V_HDJ_{H4}$ exons in C57BL/6 enriched pro-B and purified splenic B cells, respectively (FIG. 7B). The majority of $V_H5$-2-containing $V_HDJ_{H4}$ joins in splenic B cells were non-productive in both mouse strains, in contrast to other highly utilized $V_{HS}$ throughout both alleles ($V_H2$-2, $V_H5$-4, $V_H3$-6, $V_H1$-26, $V_H1$-55, $V_H8$-8, $V_H1$-64, $V_H1$-72, $V_H1$-81), consistent with previous reports that most $V_H5$-2-containing productive rearrangements are selected against due to their auto-reactive properties or inability to proper pair with IgL or surrogate IgL chains (28-30). As the $V_H5$-2 gene body, RSS and downstream are conserved in C57BL/6 versus 129SVE mouse strains, the basis for greatly increased $V_H5$-2 utilization in primary repertoires of the 129SVE strain remain to be determined.

A comparison of $V_HDJ_H$ and $DJ_H$ rearrangements in 129SVE pro-B cell libraries also revealed a relatively lower ratio of productive/non-productive $V_HDJ_H$ exons (39:61 in 129SVE vs. 65:35 in C57BL/6), as well as a lower ratio of $V_HDJ_H/DJ_H$ rearrangements (about 45:55 in 129SVE vs. about 55:45 in C57BL/6) (FIG. 7D-7F; 12D-12F). $V_H5$-2 rearrangements did not substantially contribute to these differences. Both pro-B cell libraries were generated in 4-week old mice, suggesting that the lower relative proportion of productive $V_HDJ_H$ exons in 129SVE compared to C57BL/6 pro-B cells might be attributed to differential timing of B cell checkpoint selection in these two mouse strains. For both mouse strains, the splenic B cell libraries showed comparable productive/non-productive and VDJ/DJ ratios (FIGS. 7D-7F; 12D-12F).

IgM+ Splenic B Cell $V_HDJ_H$ Exons Display Similar $V_H$ Usage Profiles Across Different $J_{HS}$.

Figure 8A:
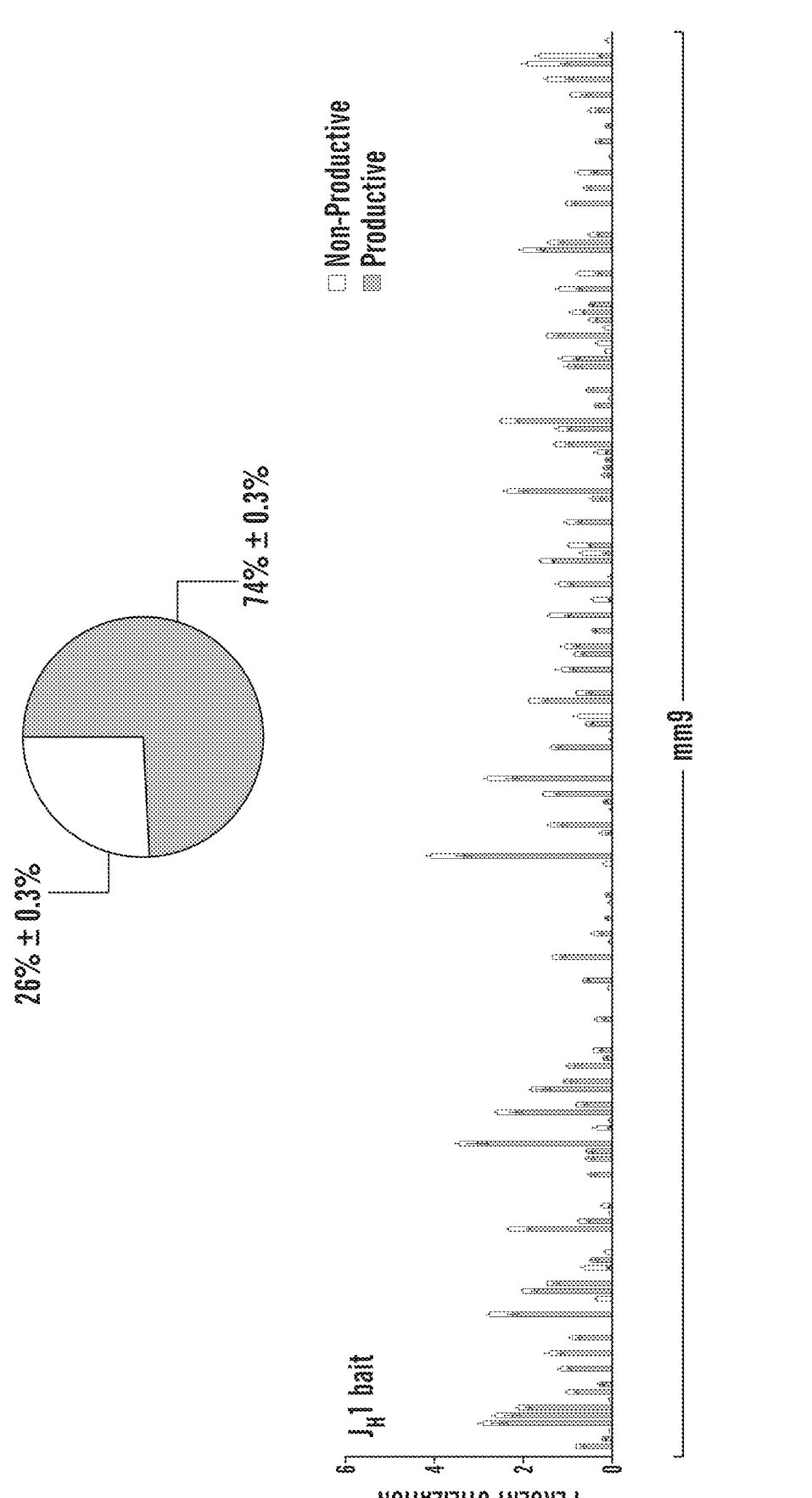
FIGS. 8A-8C depict $V_HDJ_H$ and $DJ_H$ repertoires in IgM$^+$ splenic B cells across four $J_H$ baits.
Figure 8A:
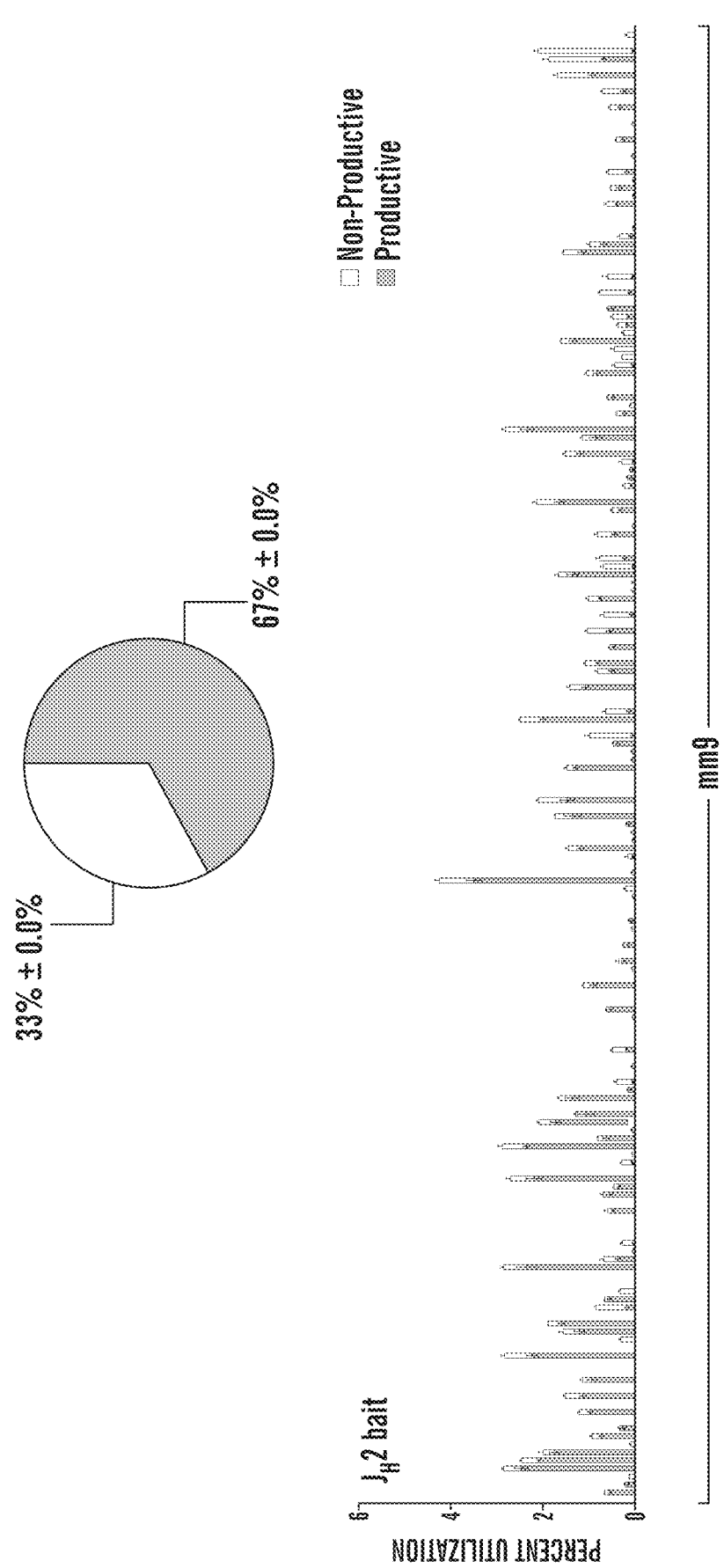
Figure 8A:
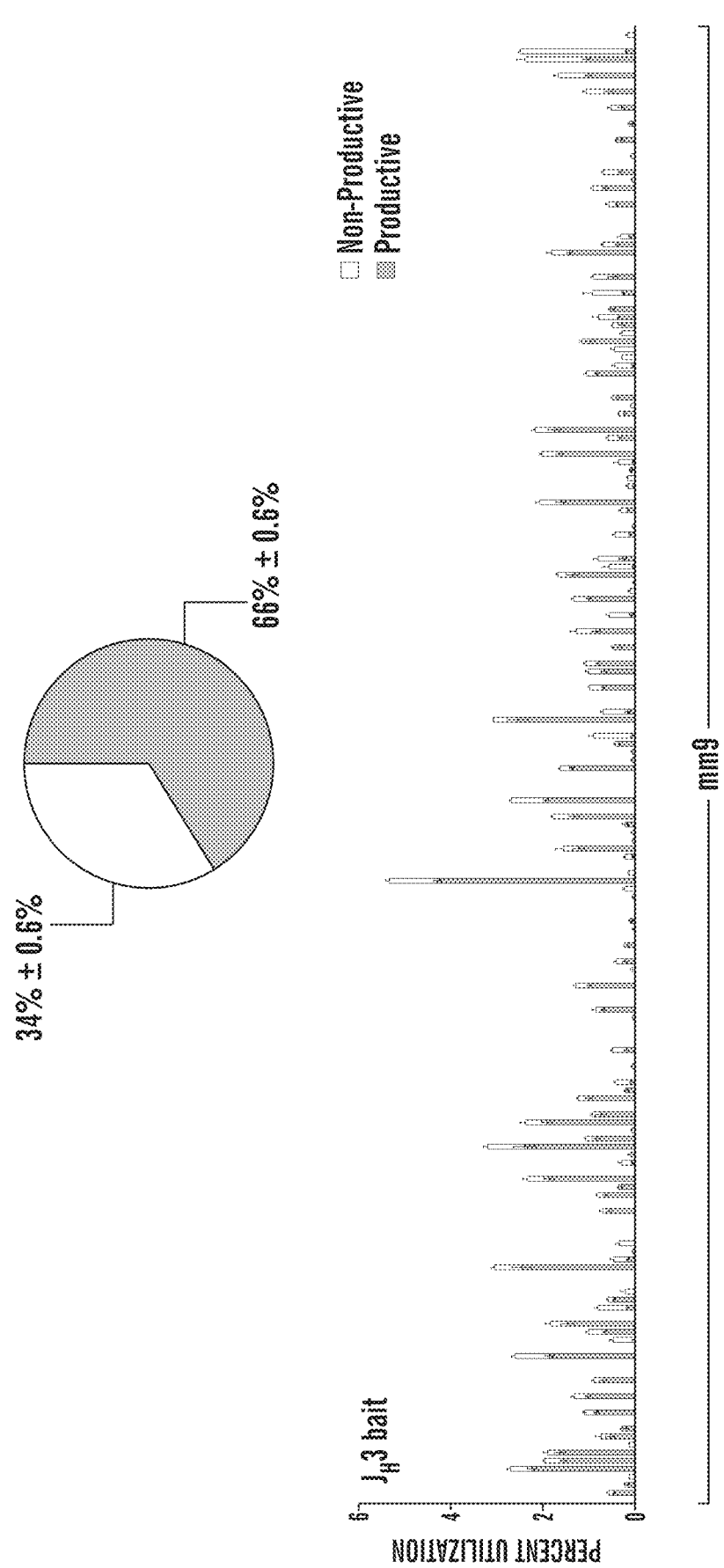
Figure 8A:
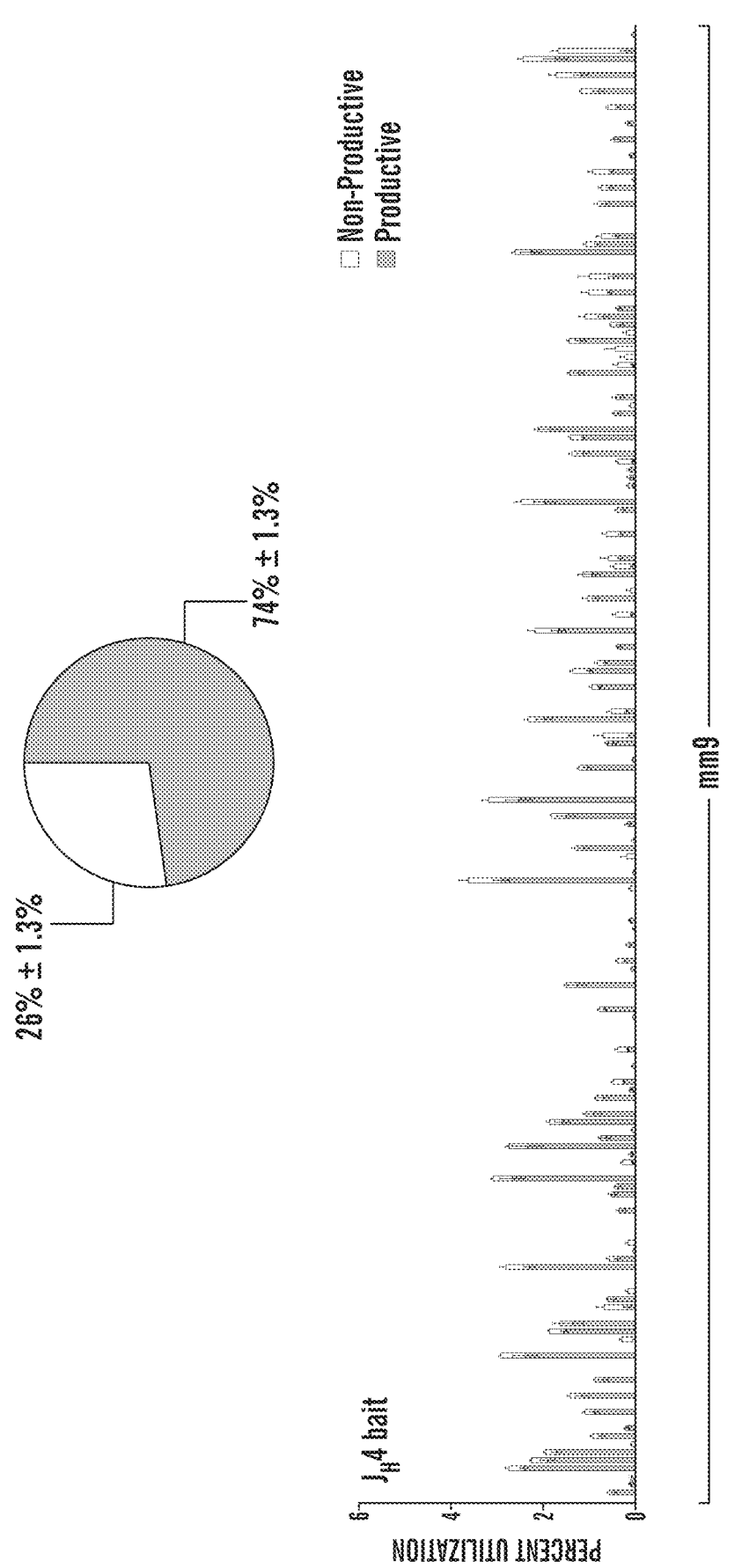
Figure 8B:
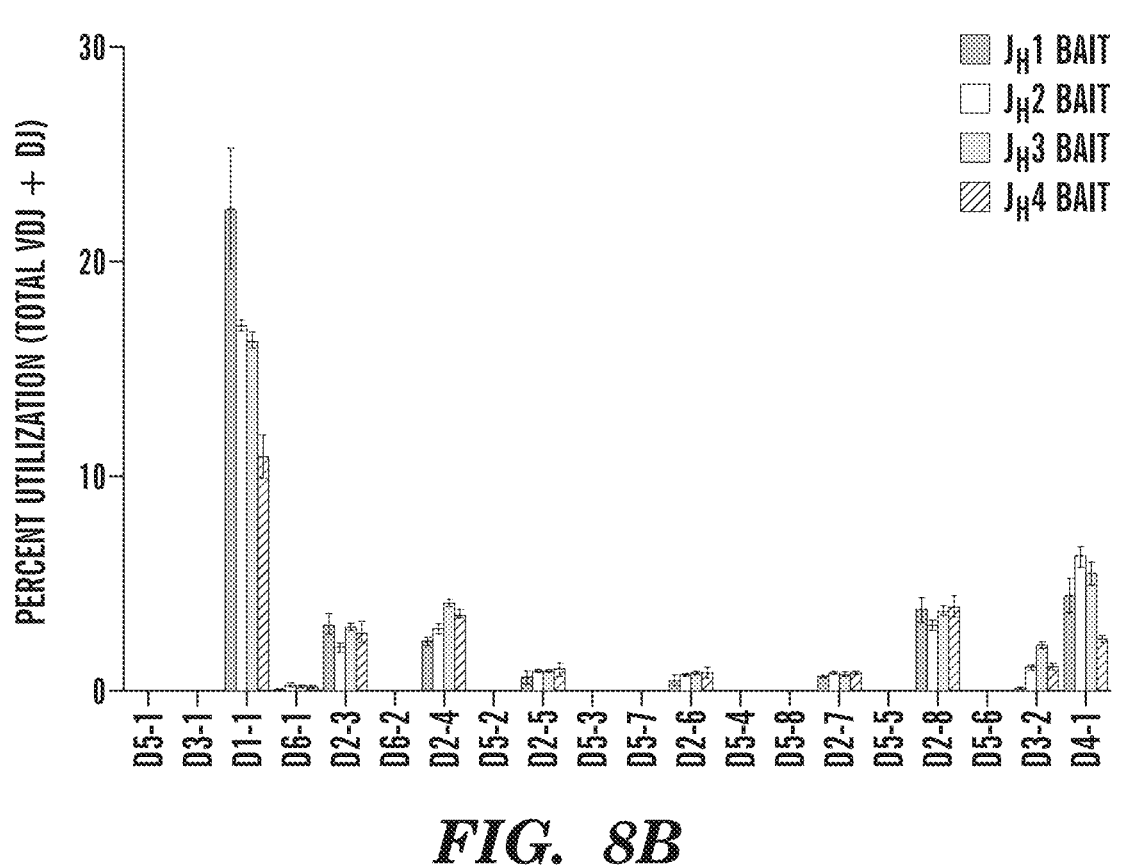
Figure 8C:
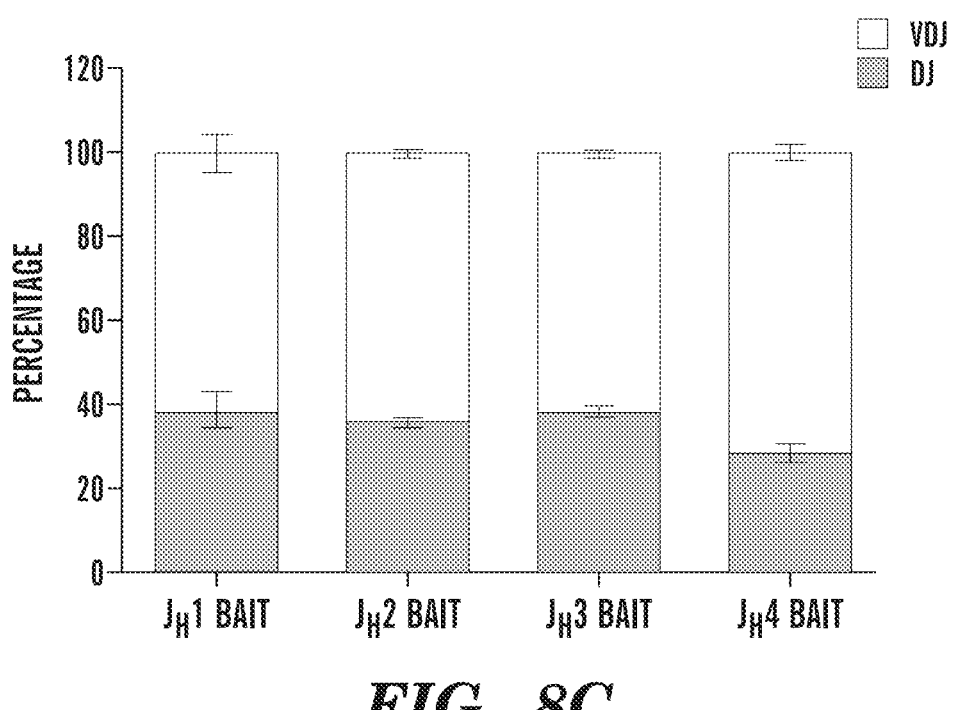
Figure 13A:
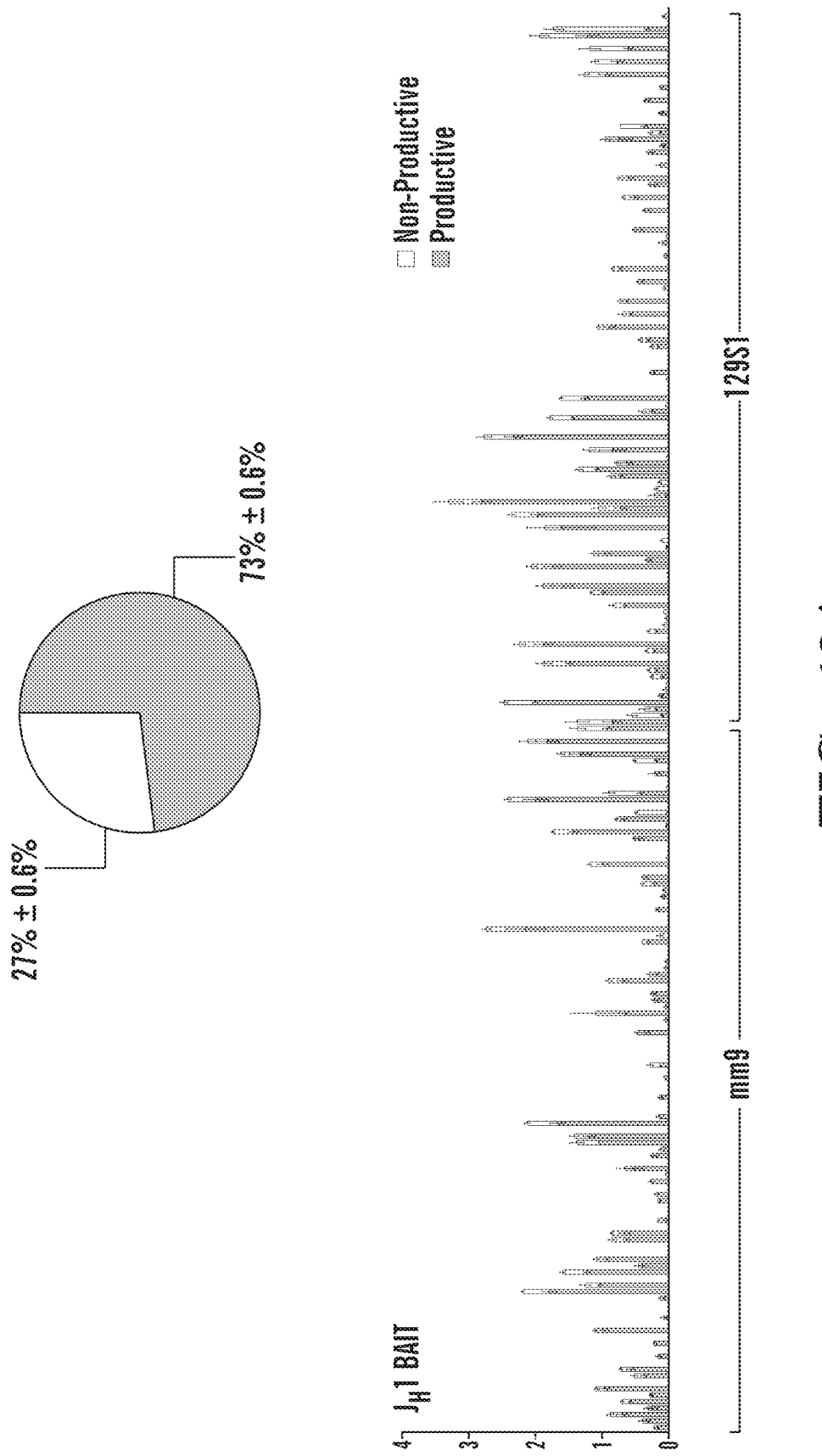
FIGS. 13A-13C depict a comparison of $V_HDJ_H$ and $DJ_H$ repertoire in IgM$^+$ splenic B cells of 129SVE mice using four different $J_H$ baits.
Figure 13A:
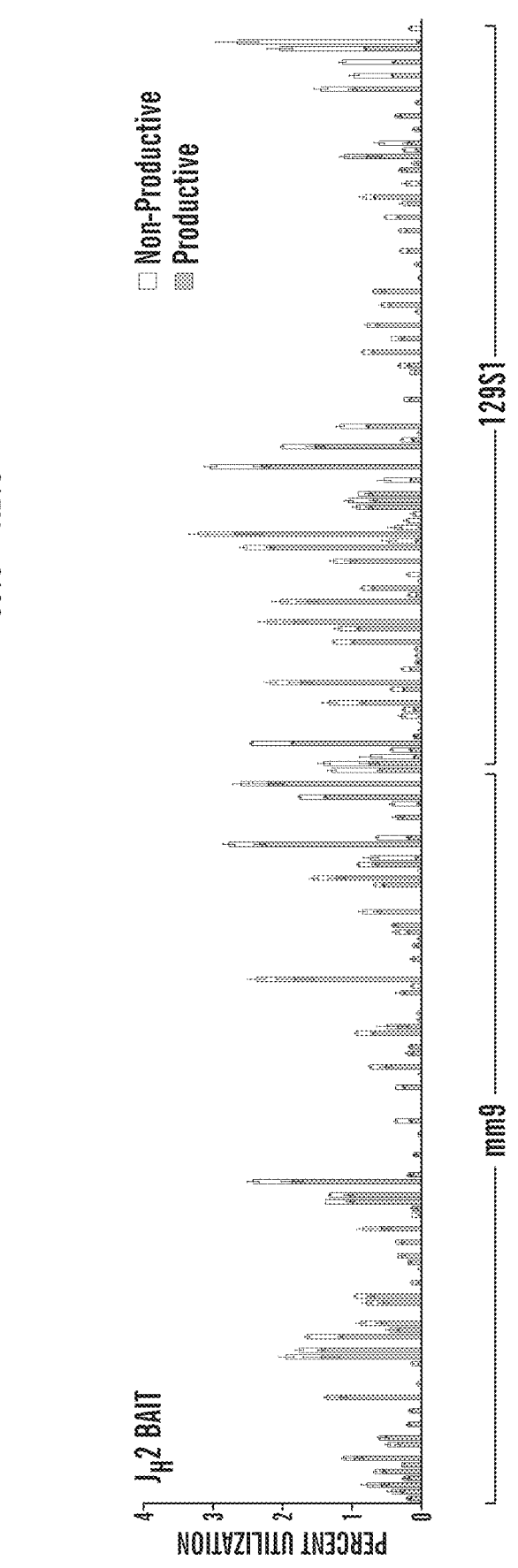
Figure 13A:
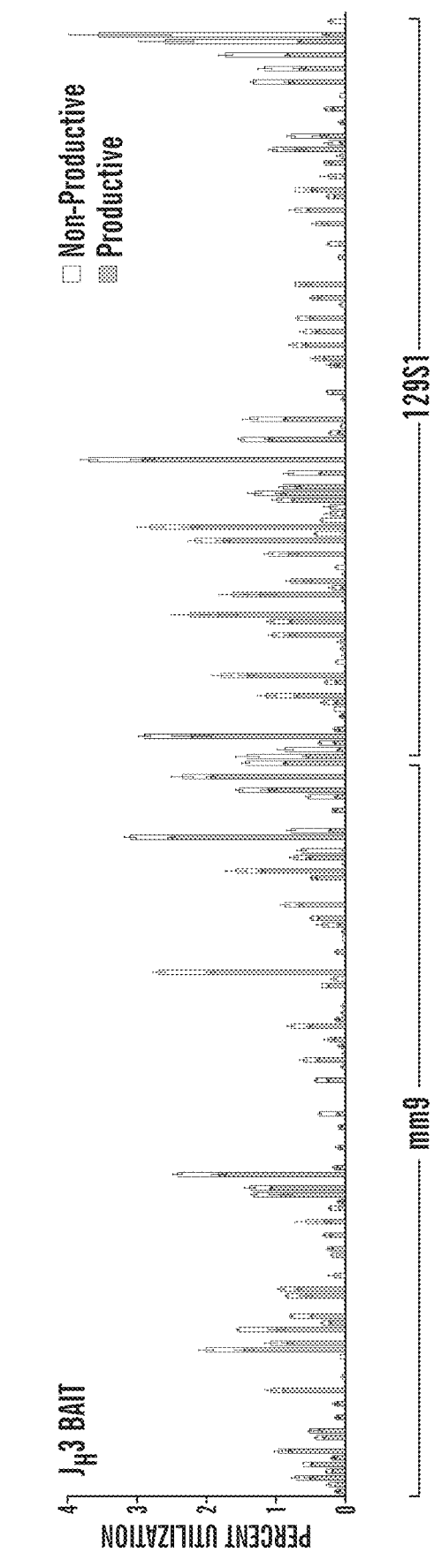
Figure 13A:
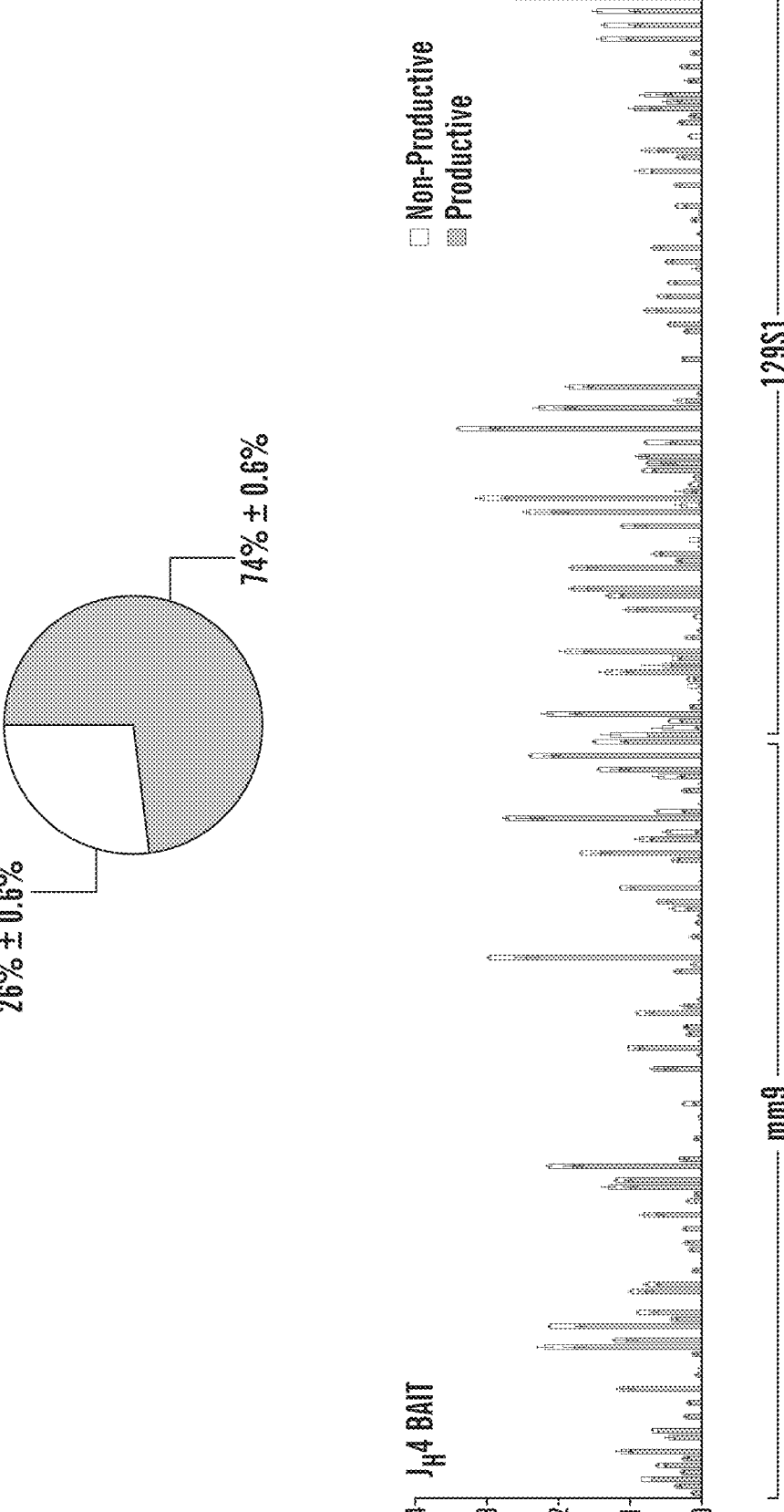
Figure 13B:
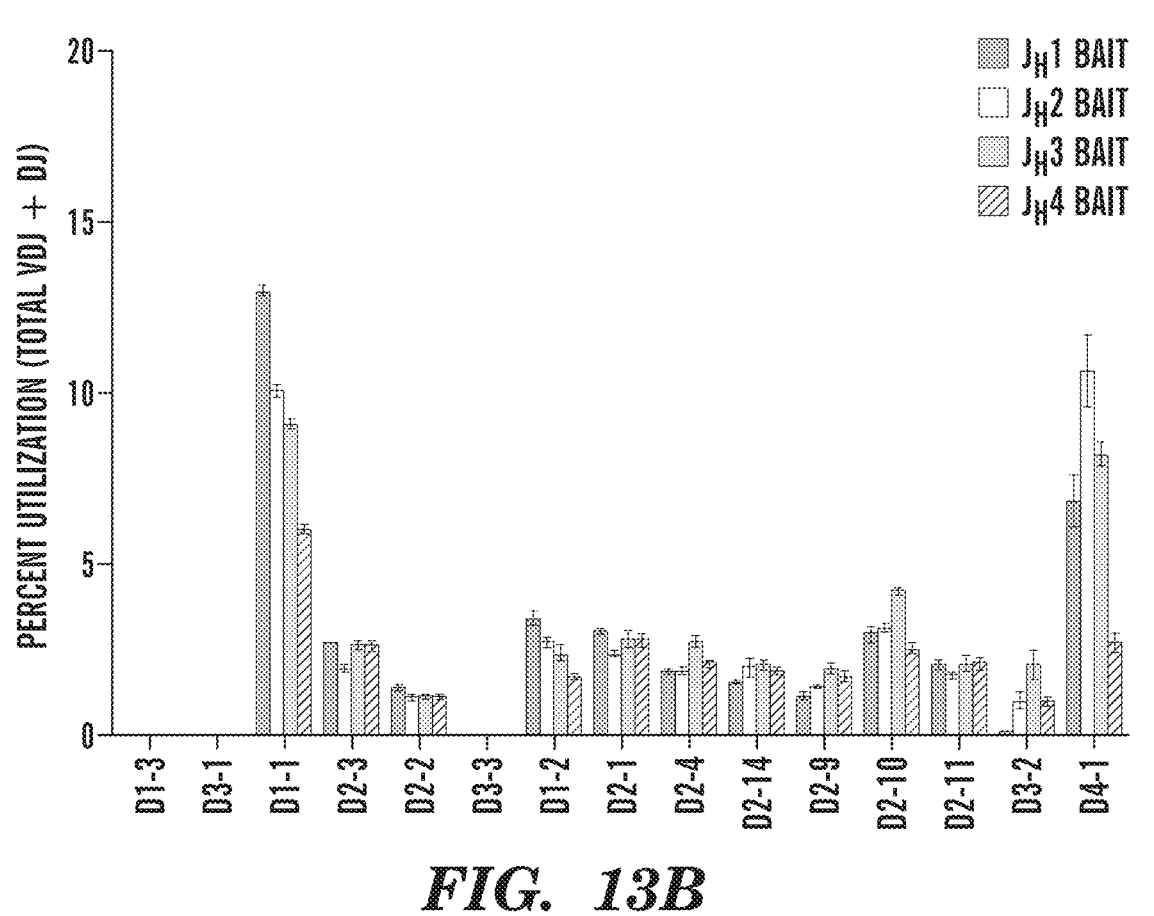
Figure 13C:
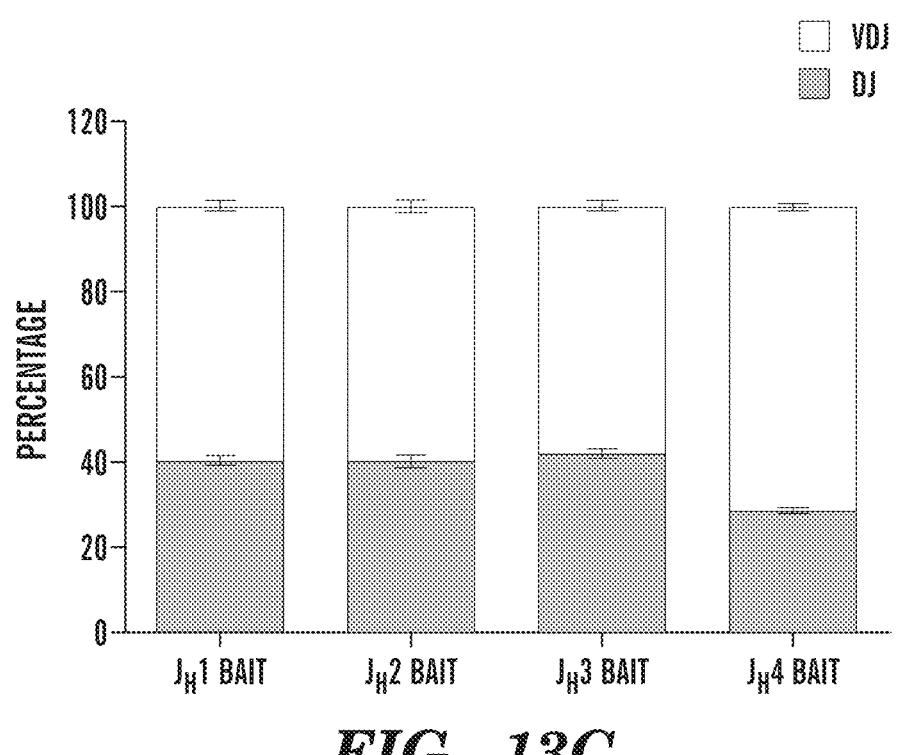
Figure 14A:
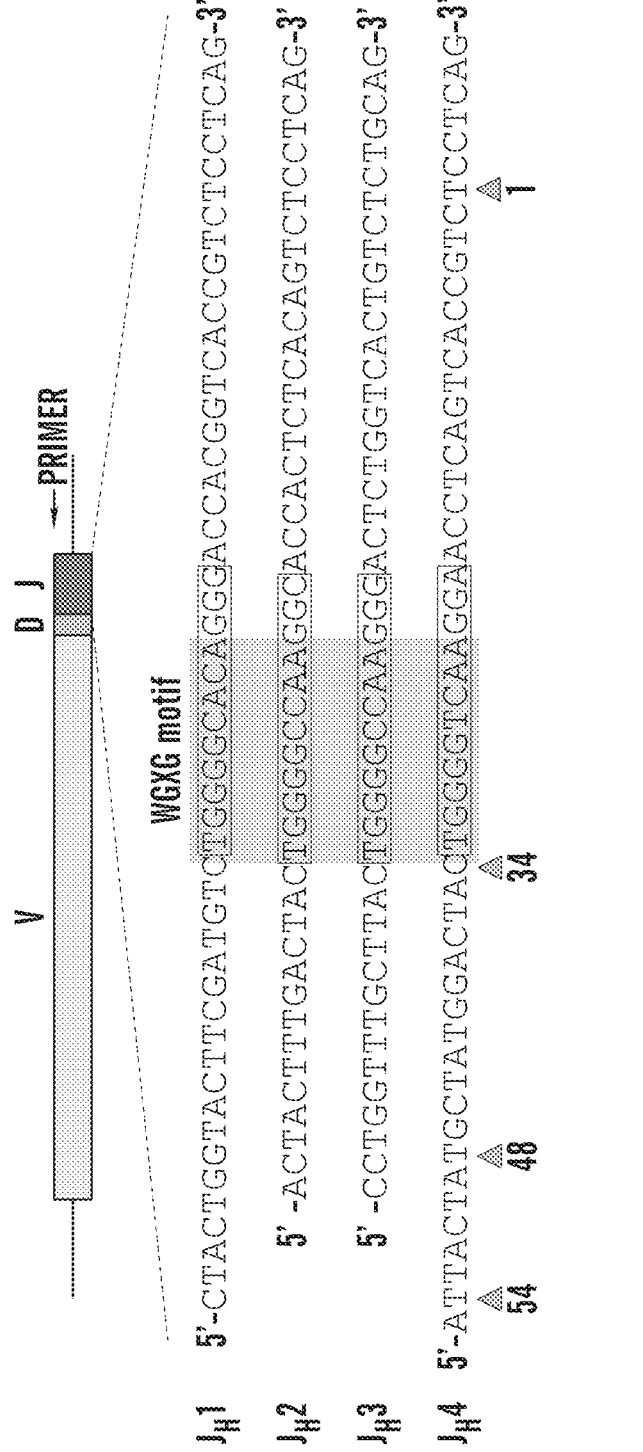
FIGS. 14A-14B demonstrate in-frame $V_HDJ_H$ proportions across $J_H$ coding end lengths for $J_H1$-4.
Figure 14B:
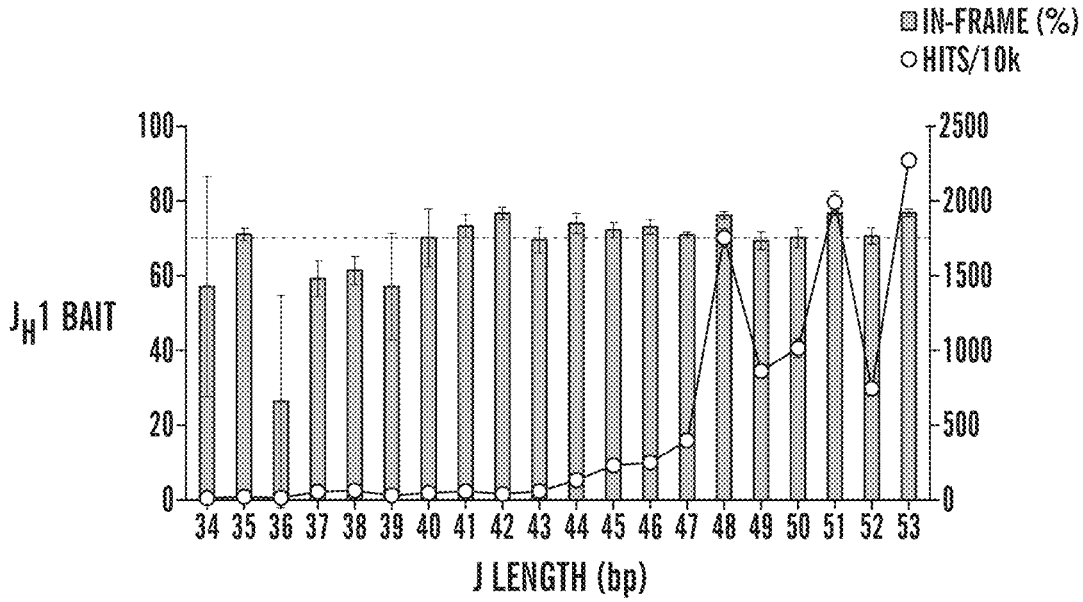
Figure 14B:
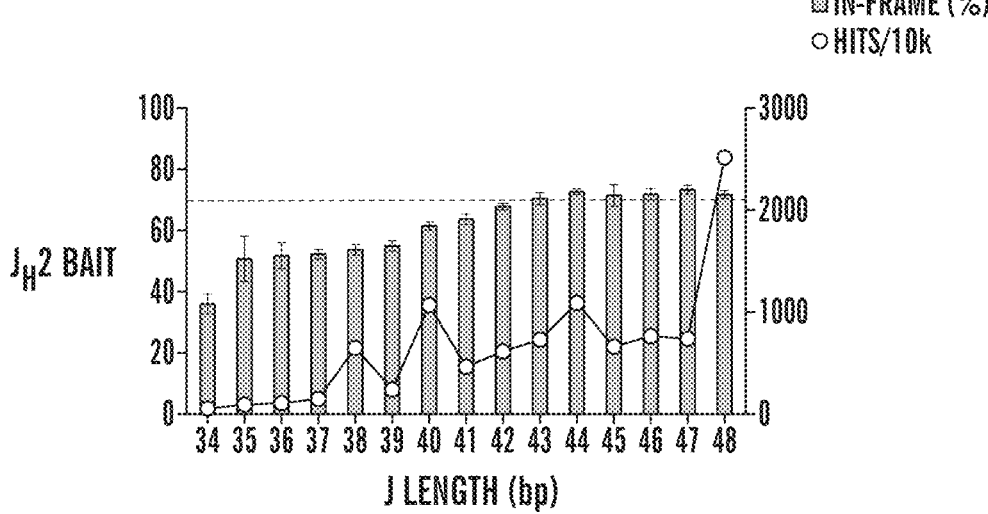
Figure 14B:
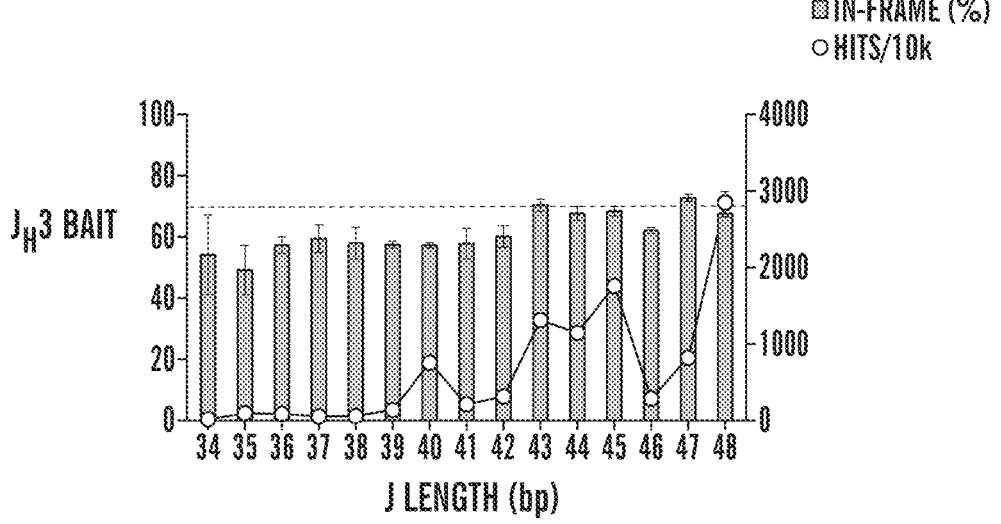
Figure 14B:
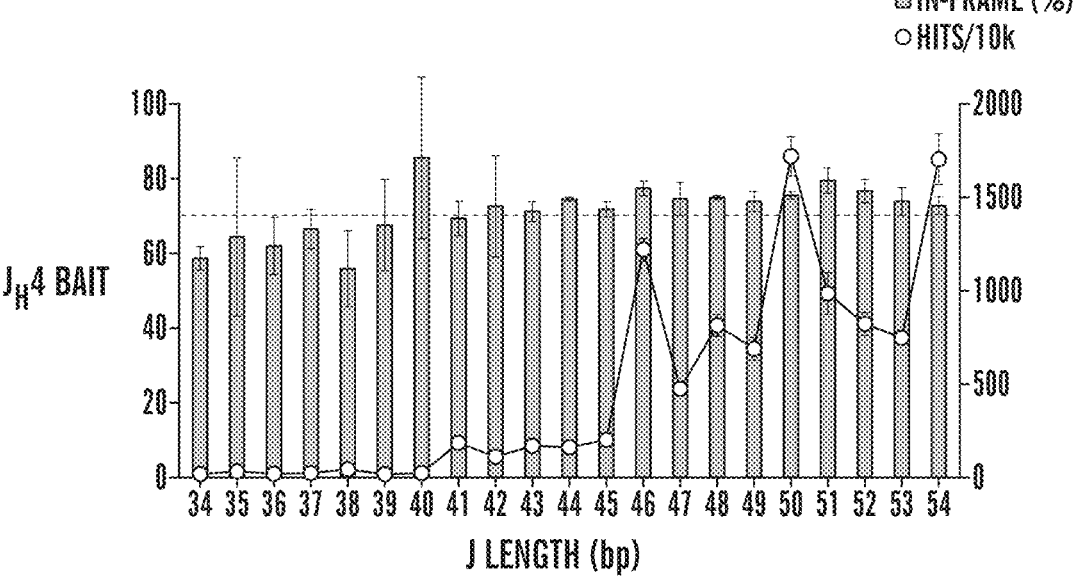
Figure 15A:
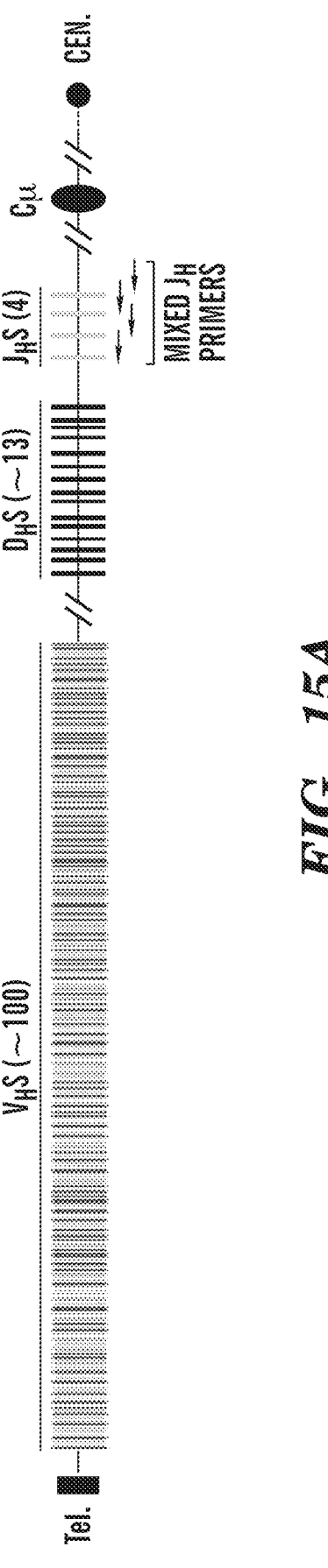
FIGS. 15A-15C depict IgM$^+$ splenic B cell $V_HDJ_H$ usage profiles in a 129SVE mouse using four $J_H$ baits combined.
Figure 15B:
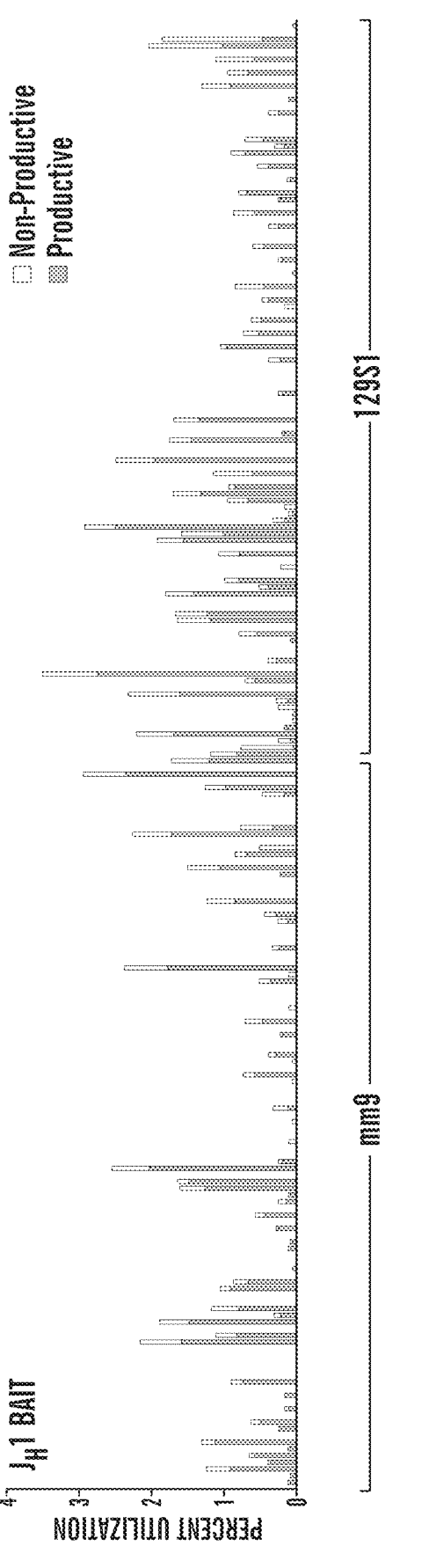
Figure 15B:
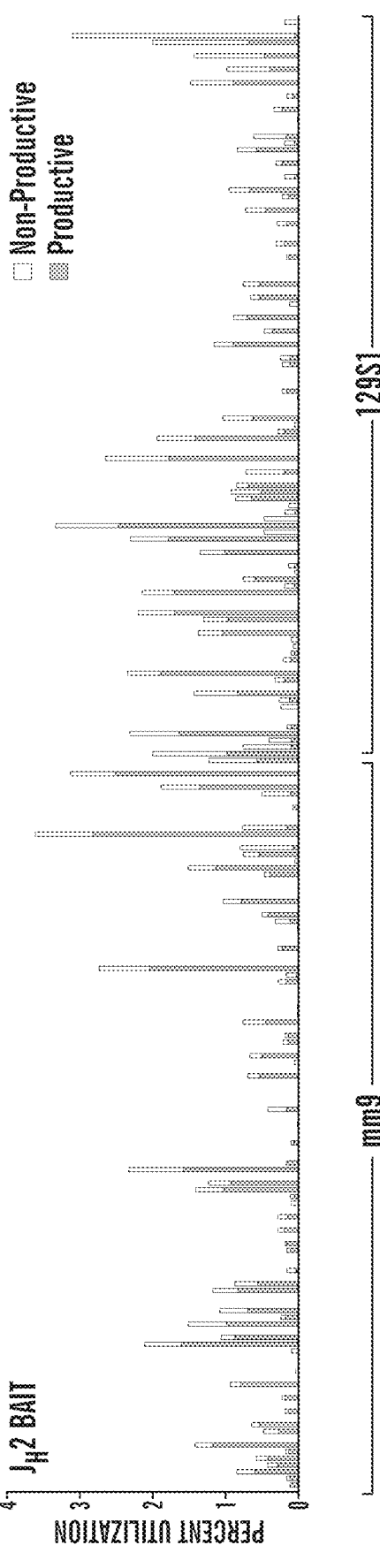
Figure 15B:
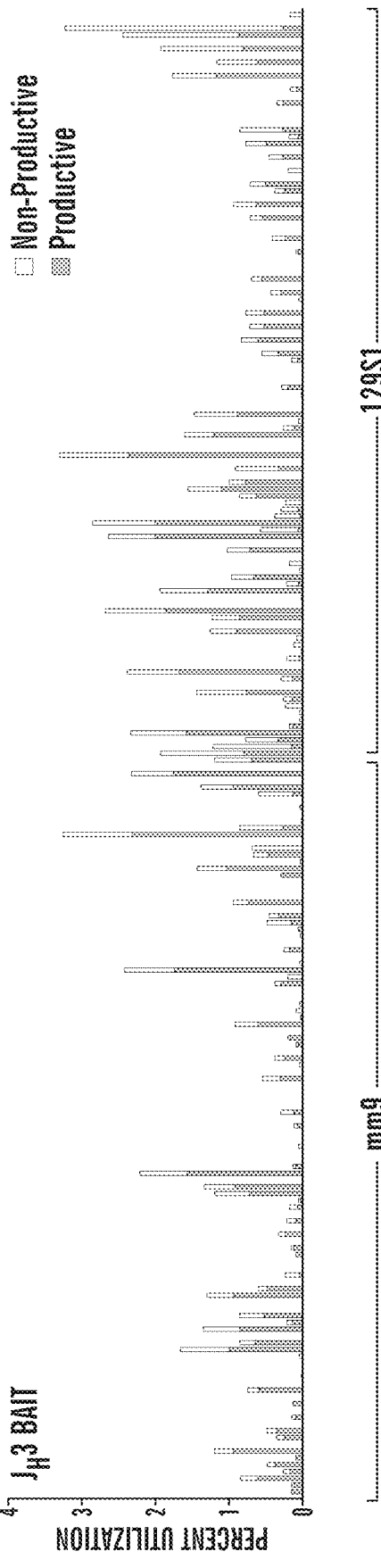
Figure 15B:
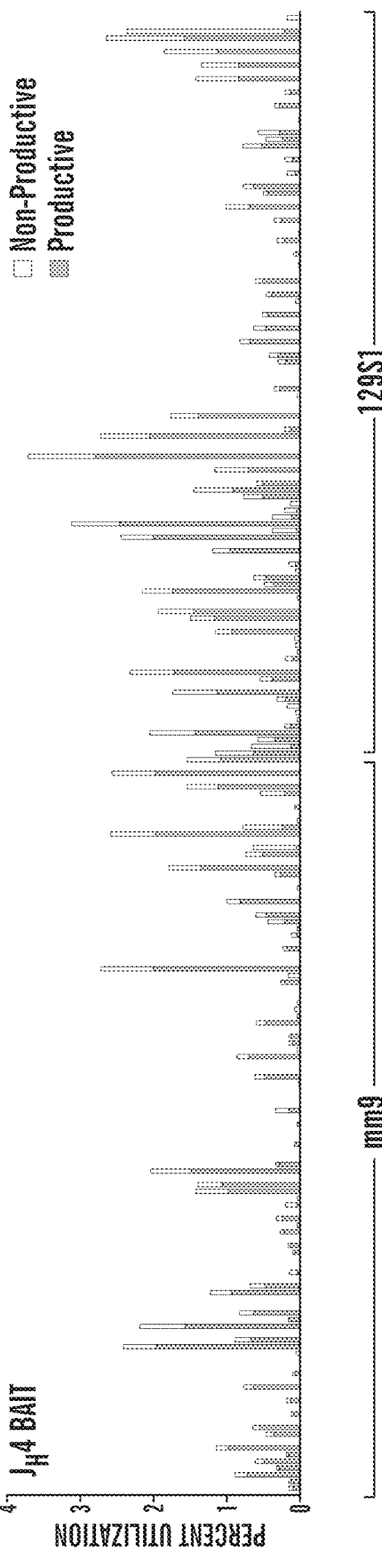
Figure 15C:
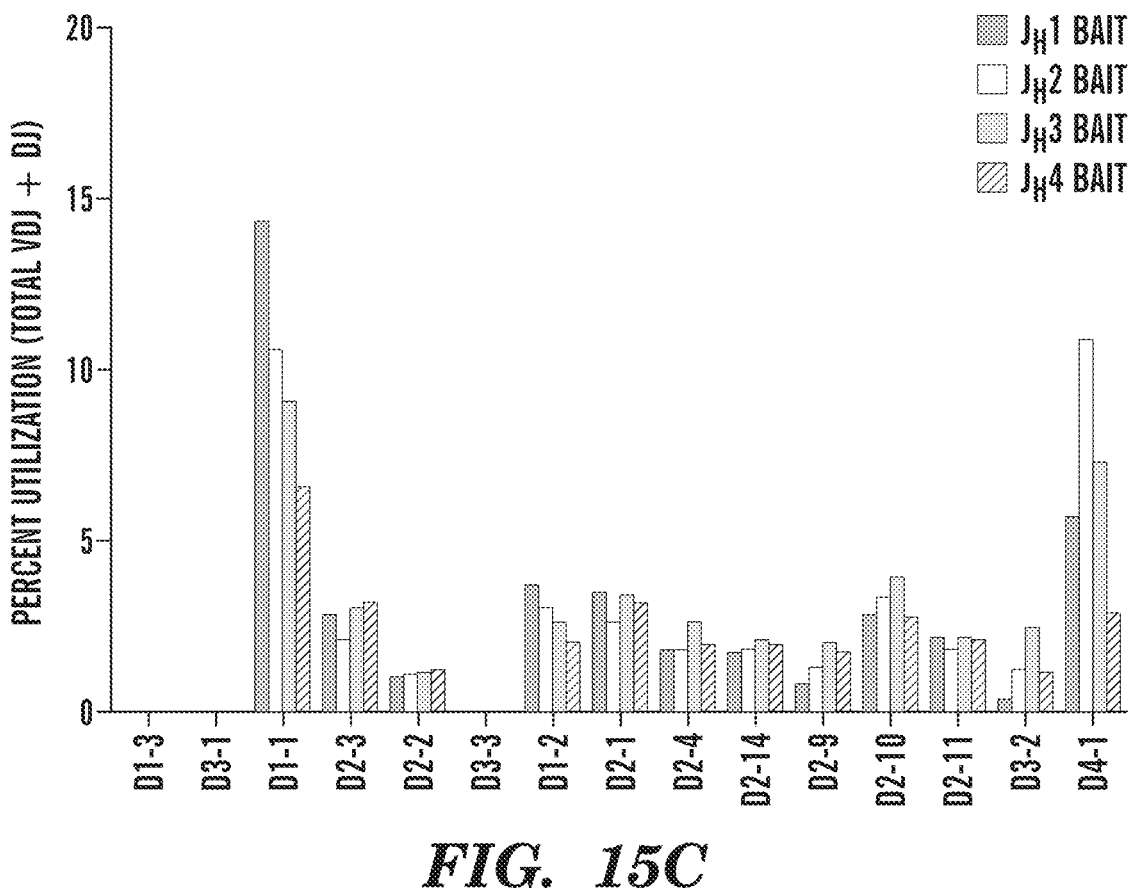
Figures 16A, 16B:
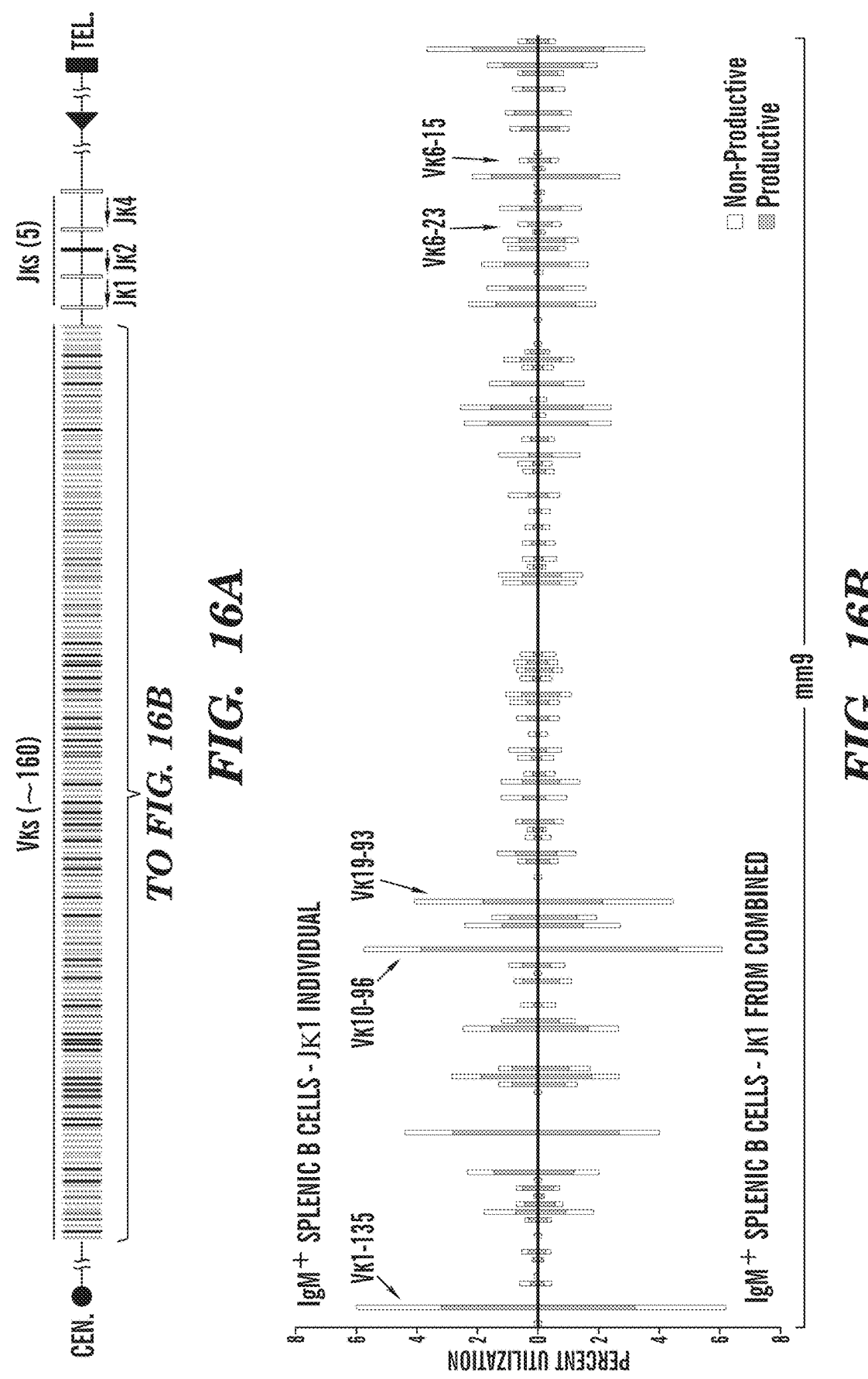
FIGS. 16A-16B depict Igκ repertoire in IgM$^+$ splenic B cells of C57BL/6 mice using different Jκ baits.
Figure 16B:
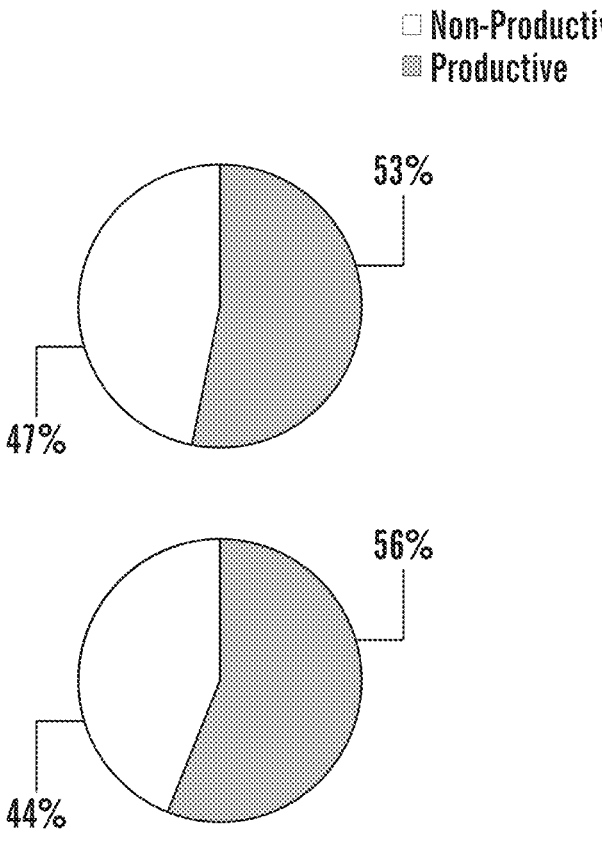
Figure 16B:
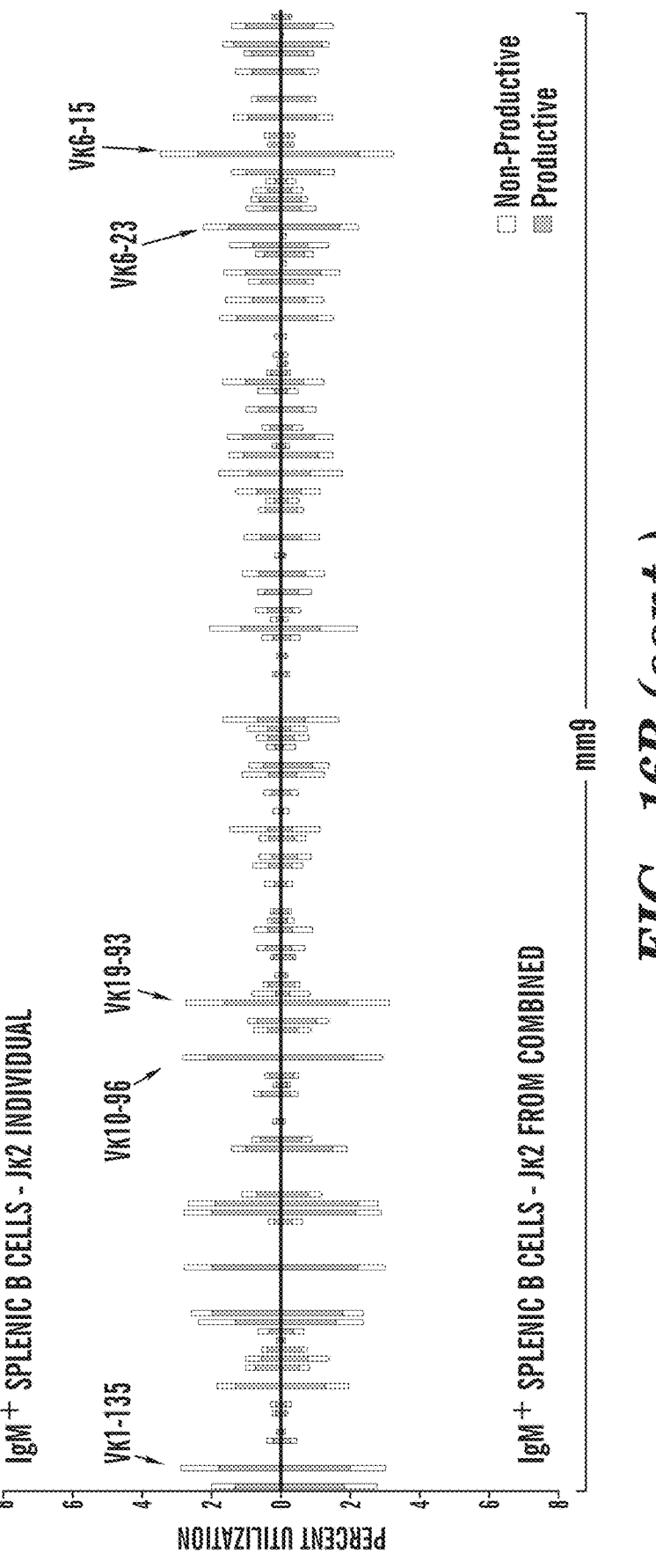
Figure 16B:
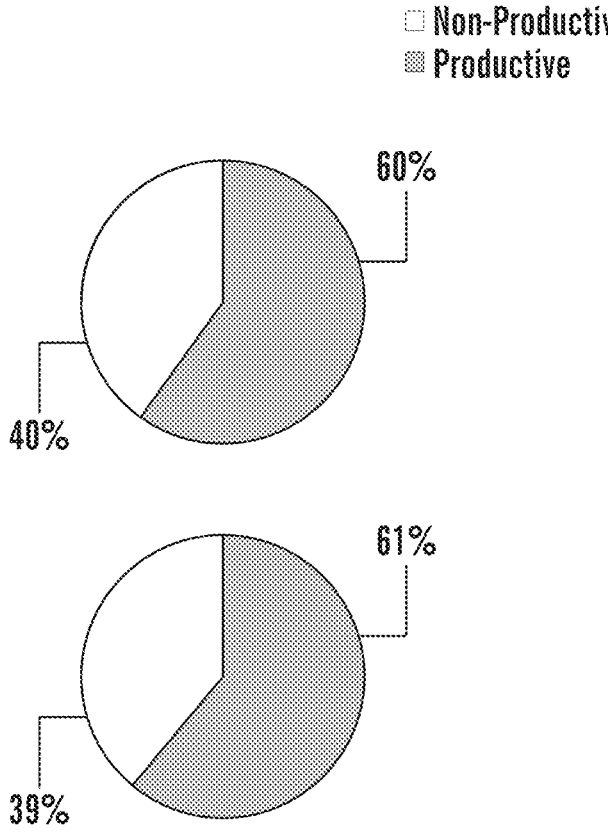
Figure 16B:
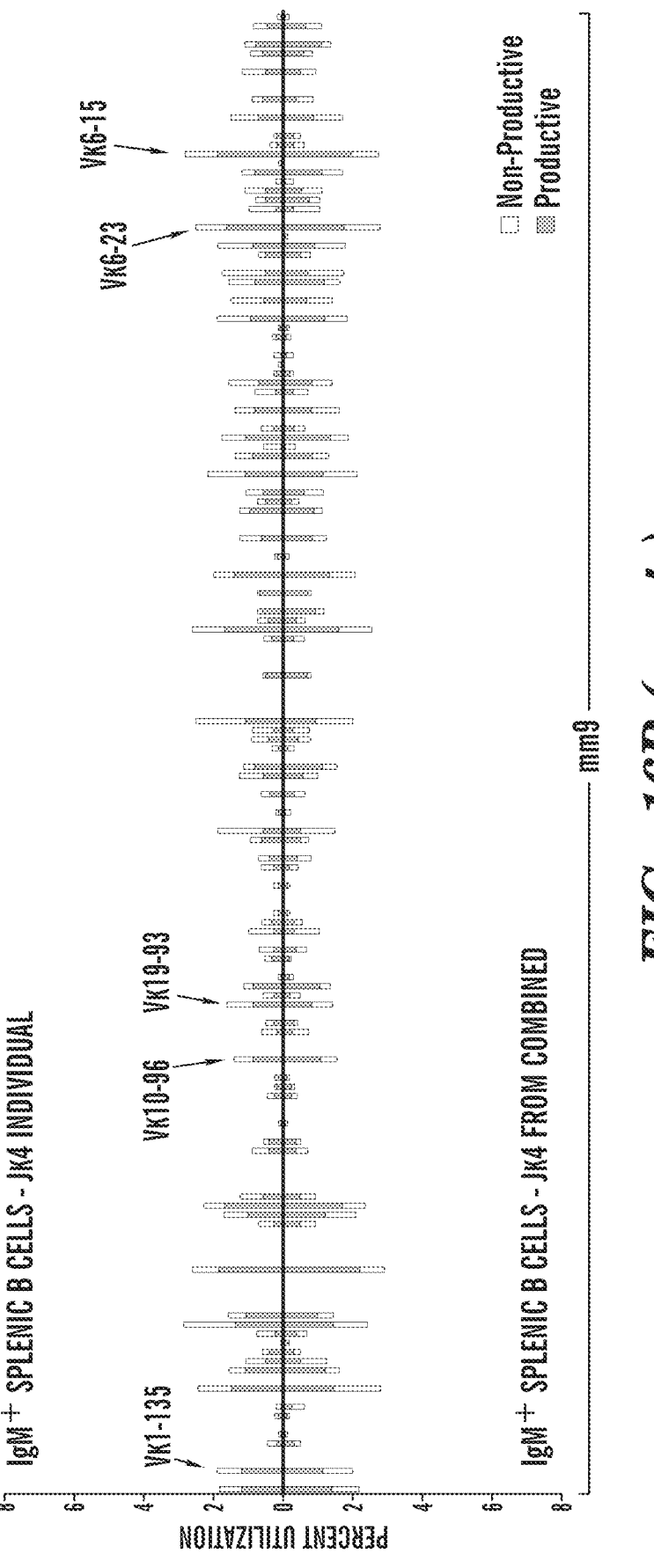
Figure 16B:
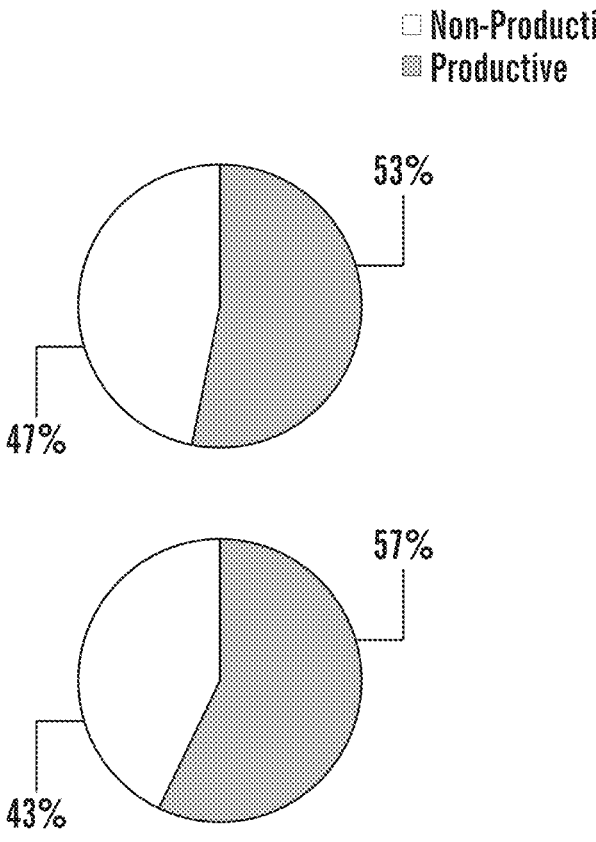

Bait primers were also designed to the other three $J_{HS}$ in the IgH locus and libraries made from splenic B cells of both C57BL/6 and 129SVE mice to compare $V_H$ and D utilization among the different $J_{HS}$. These assays revealed similar $V_H$ and D utilization repertoires for the four different $J_{HS}$, indicating that selection for a particular $V_{HS}$ or D in a $V_HDJ_H$ join did not vary substantially between the $J_{HS}$ in both C57BL/6 and 129SVE mice (FIGS. 8A, 13A). However, higher proportions of non-productive $V_HDJ_H$ rearrangements were found using the $J_H2$ and $J_H3$ baits, compared to the $J_H1$ and $J_H4$ bait libraries (FIGS. 8A, 13A). In this regard, the stretch of sequence from the $J_H$ coding ends to the highly conserved WGXG-motif that is crucial for a stable antibody structure (24) is shorter in the $J_H2$ and $J_H3$ segments relative to the $J_H1$ and $J_H4$ segments (FIG. 14A). Thus, some $V_HDJ_{H2}$ and $V_HDJ_{H3}$ joins sites could lie too close to the WGXG-encoded sequences and be selected against due to unstable antibody structure (FIG. 14B). Moreover, moderate differences wetr observed in the $D_H$ usage profiles among the four $J_{HS}$ and a larger ratio of $V_HDJ_H$:$DJ_H$ joins for the $J_H4$ bait libraries, which potentially could reflect the relative positions of these $J_{HS}$ in the recombination center that initiates V(D)J recombination (31) (FIGS. 8B,8C and 13B, 13C). Finally, HTGTS-Rep-seq libraries were prepared from 129SVE splenic B cells with four sets of $J_H$ HTGTS-Rep-seq primers combined (FIG. 15A, Table 3). This approach, which allowed us to detect all $V_HDJ_{H1-4}$ exons in one HTGTS-Rep-seq library, revealed general V(D)J repertoires similar to those detected with individual $J_H$ primers (FIG. 15 vs 13).

HTGTS-Rep-seq Detects Diverse Igκ VJ Rearrangements.

Figure 3A:
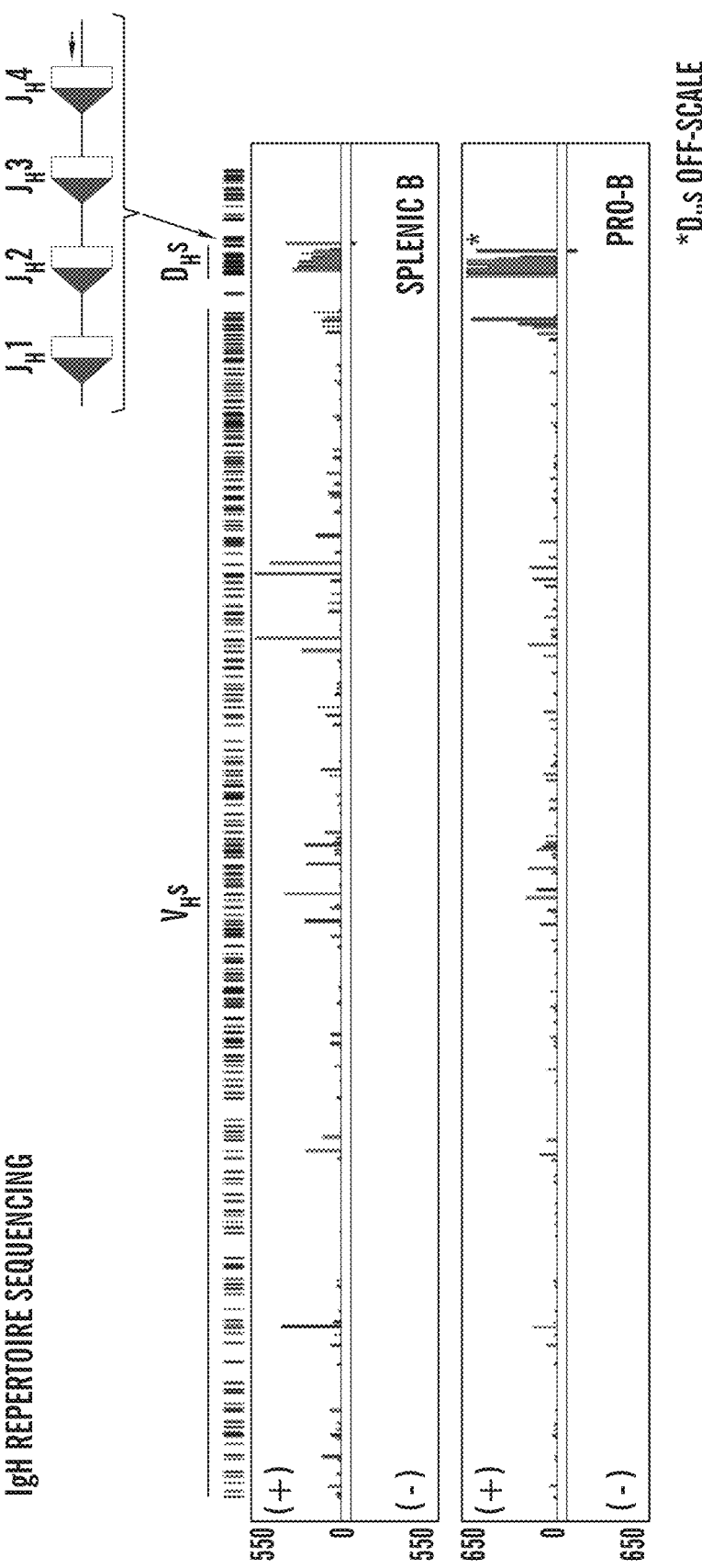
FIGS. 3A-3D.
Figure 3B:
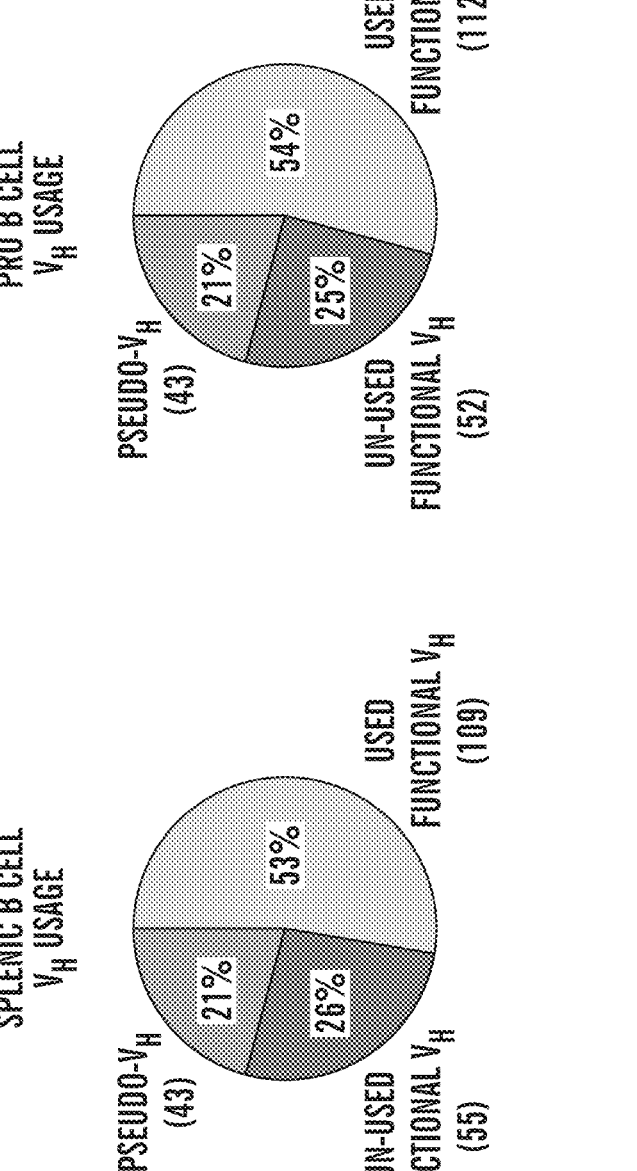
Figure 3C:
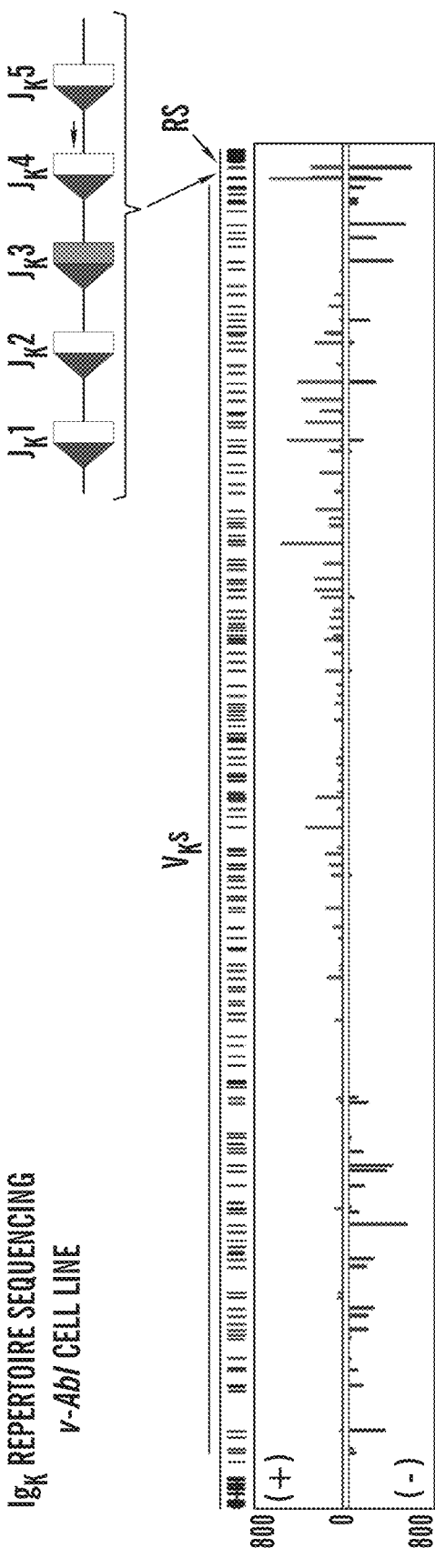
Figure 3D:
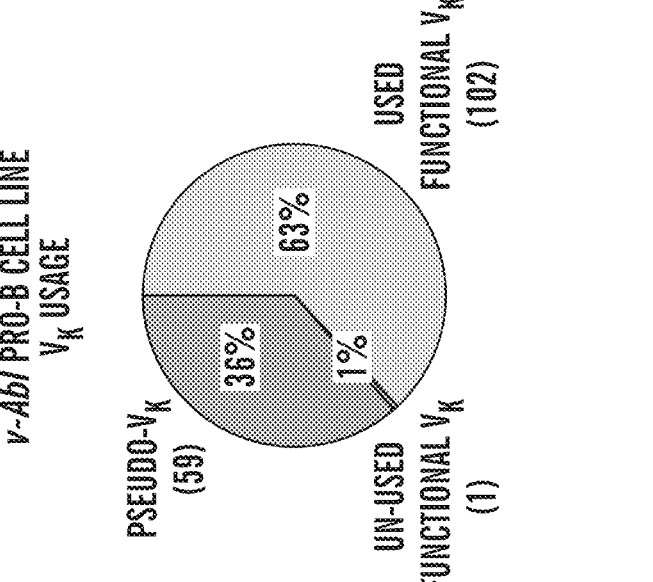
Figures 9A, 9B:
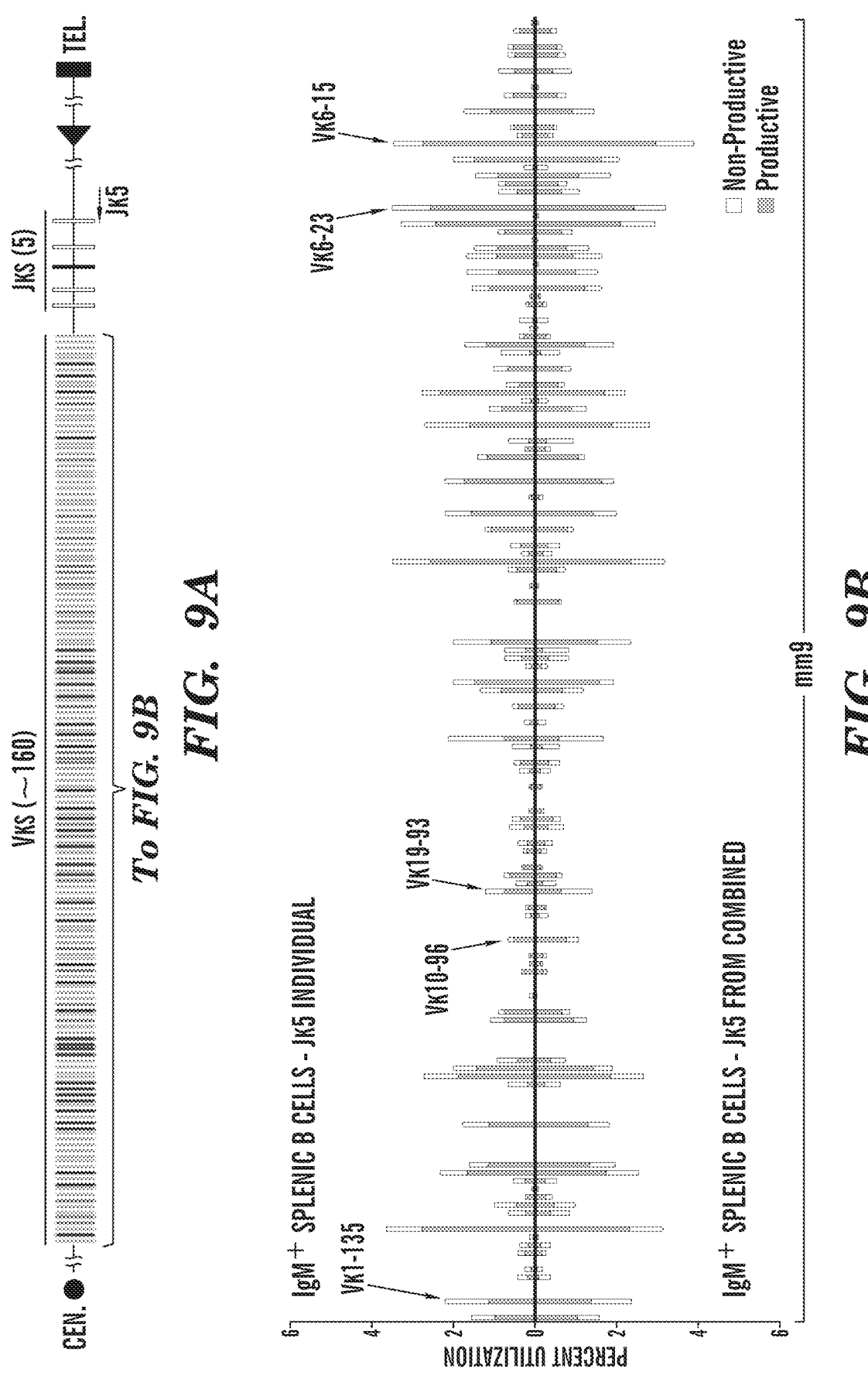
Figure 9B:
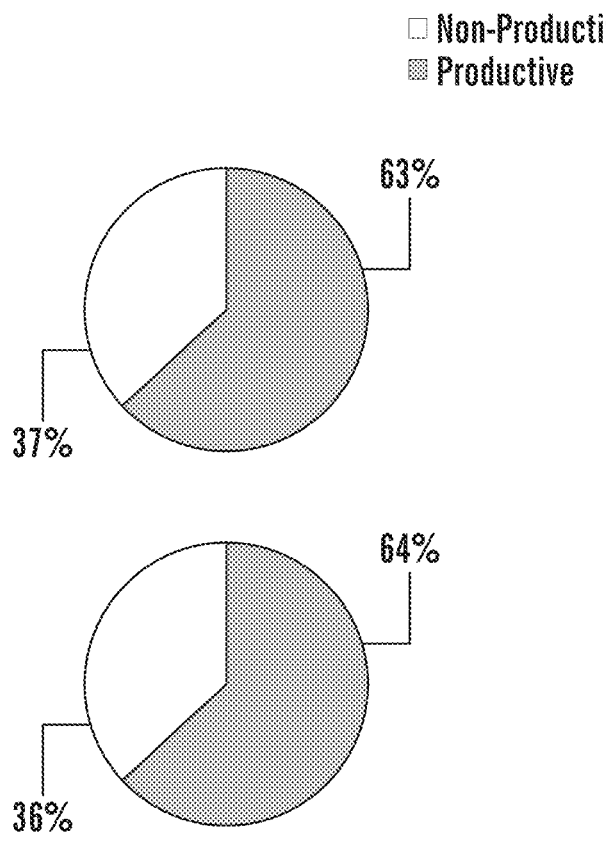

In mice, the Igκ locus generates the majority of IgL-expressing B cells (32). The Vκ locus organization is distinct from that of the $V_H$ locus. Besides not having D segments and, therefore, undergoing direct Vκ to Jκ rearrangements, the Vκ locus contains V segments organized in both direct and inverted orientation relative to the Jκ segments (6) (FIG. 9A). Thus, for some Vκs, joining to Jκ occurs deletionally like $V_H$ to $DJ_H$ joining, but for others it occurs via inversion of the intervening sequence. Direct and inverted Vκs generally occur in distinct clusters but also can be individually interspersed (FIG. 9A). To first assess the Igκ repertoire, HTGTS-Rep-seq was performed on 1 μg of genomic DNA from C57BL/6 splenic B cells using a Ji5 coding end bait primer. Similar to the IgH locus, widespread usage of Vκs was also observed across the entire locus to the Jκs (FIG. 3A, B). All of the 100 functional Vκs across 20 Vκ families were detected by HTGTS-Rep-seq, and 11 out of 62 pseudo Vκs were also detected (FIG. 9C). We saw productive/non-productive VJi joins at a 63:37 ratio in splenic B cells (FIG. 9B), which is slightly lower than the predicted 67:33 ratios (33). This small deviation might reflect the presence of non-productive VJκ joins in Igλ positive cells (32)

HTGTS-Rep-seq libraries were also generated from splenic B cell DNAs to capture VJκ joins from the three other functional Jκ segments separately or in a combination of all 4 Jκ primers. In contrast to IgH repertoires with different $J_H$ primers, the Igκ repertoires showed apparently different utilization of some Vκs (e.g. Vκ6-15, Vκ6-23, Vκ19-93, Vκ10-96, Vκ1-135) between different Jκ baits. Moreover, the productive/non-productive ratios from the other Jκ primer libraries were slightly lower than that observed with the Jκ5 primer (Jκ1: 53:47, Jκ2; 60:40, Jκ4: 53:47 vs Jκ5: 63:37) (FIG. 16). These differences in utilization and ratios likely reflect the occurrence of sequential VJκ recombination events (34). In this context, alleles containing non-productive VJκ joins with the three Jκs upstream of Jκ5 have the ability for an un-rearranged Vκ upstream the non-productive VJκ to join to a remaining Jκ (34). If this secondary rearrangement is inversional, the non-productive VJκ joins would be retained in the genome and add to the non-productive fraction of VJκ1, VJκ2, or VJκ4 joins that are detected by HTGTS-Rep-seq. Given this scenario, VJκ5 rearrangements, which are terminal rearrangement events, would be expected to reflect the theoretical productive/non-productive ratios, as described herein.

HTGTS-Rep-seq Revealed Characteristic CDR3 Properties.

Figure 17D:
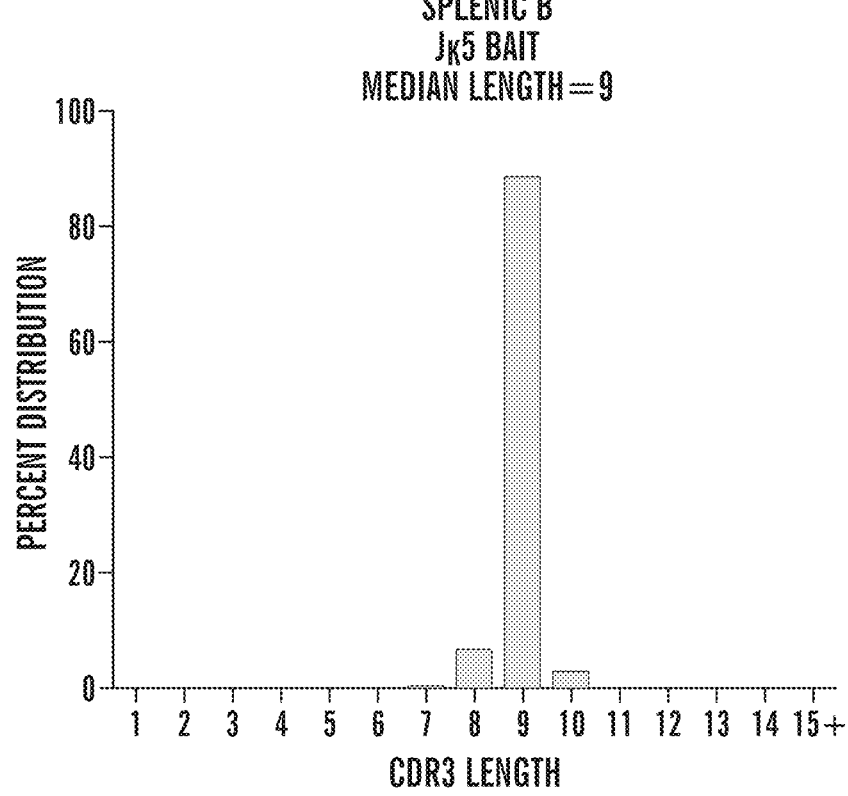
Figure 17D:
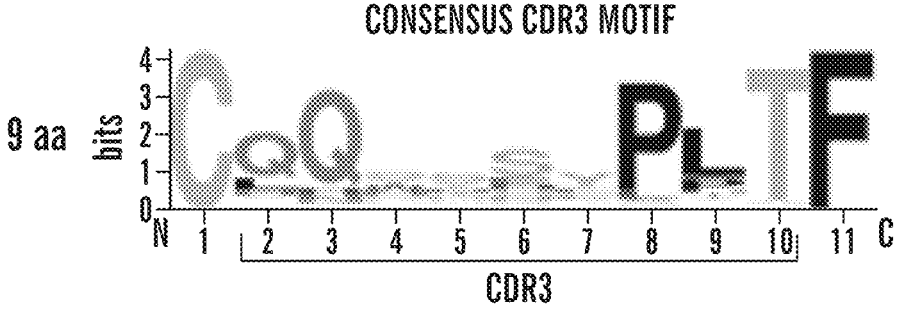

The CDR3 sequences from productive $V_HDJ_H$ and VJκ rearrangements in pro-B and splenic B cells were analyzed. The CDR3 of productive $V_HDJ_H$ exons in pro-B and splenic B cells showed a diverse range of lengths from 3 to 24 amino acids (aa) with a peak at 11-15 aa (FIG. 17A, 17B). The consensus CDR3 motifs of these $V_HDJ_H$ exons, made from the unique subset, from un-immunized pro-B and splenic B cells shared the same $V_H$ contributed and $J_H4$ contributed aa sequences as anticipated (FIG. 17A,17B). Given that the gene bodies of $J_H2$ and $J_H3$ are shorter than those of $J_H1$ and $J_H4$, the average lengths of $V_HDJ_{H2}$ and $V_HDJ_{H3}$ exons were shorter than those of $V_HDJ_{H1}$ and $V_HDJ_{H4}$ (median length 11 aa vs 13 aa) (FIG. 17C). In contrast to productive $V_HDJ_H$ exons, approximately 85% productive VJκ exons from splenic B cells showed a CDR3 length of 9 aa. The VJκ CDR3 motif also showed the expected flanking cysteine and phenylalanine (FIG. 17D). Thus, HTGTS-Rep-seq produces sequences with CDR3 characteristics expected from the various bait loci.

HTGTS-Rep-seq can be Utilized with Low Amounts of Starting Material.

Figure 10A:
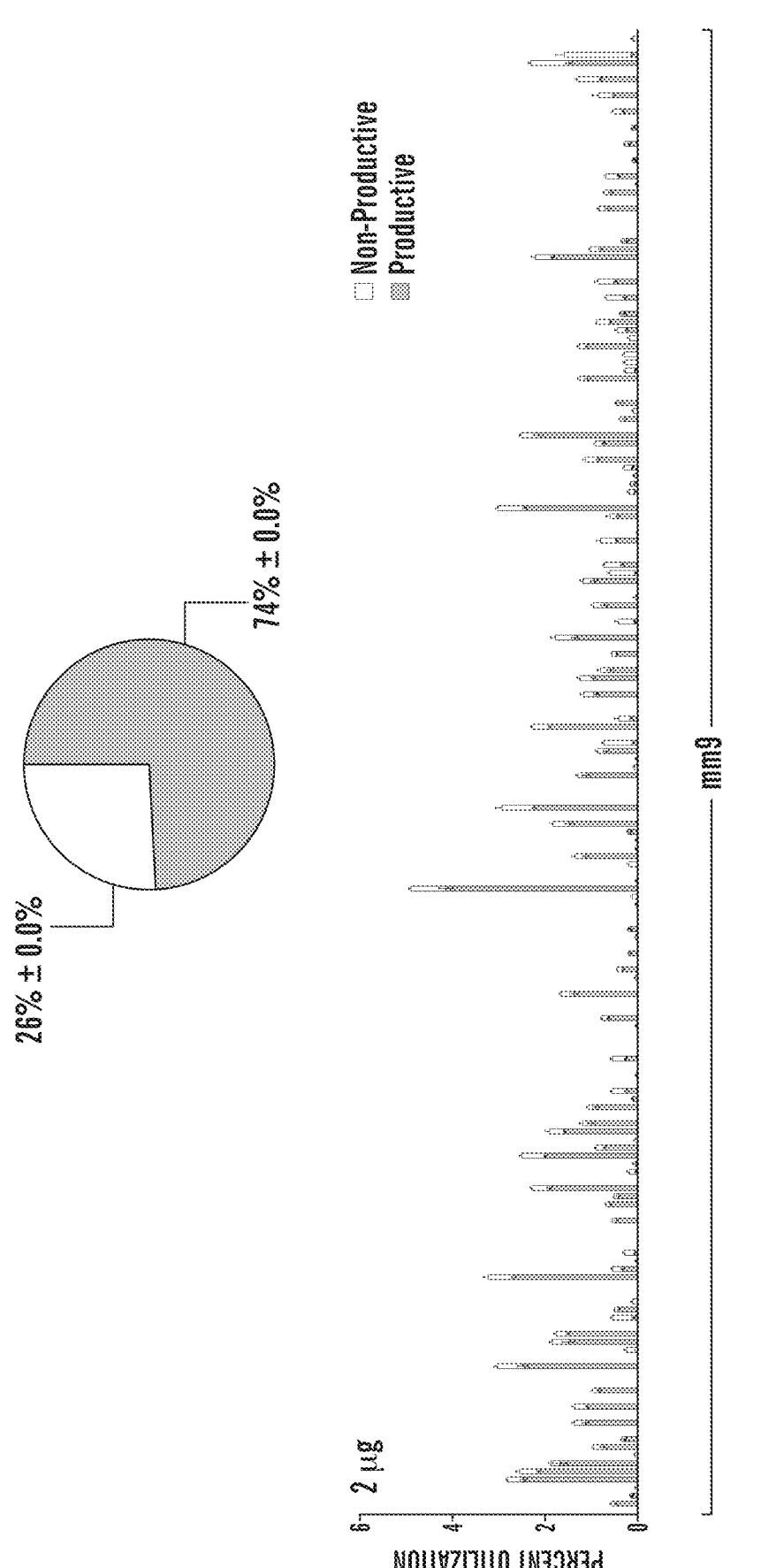
Figure 10A:
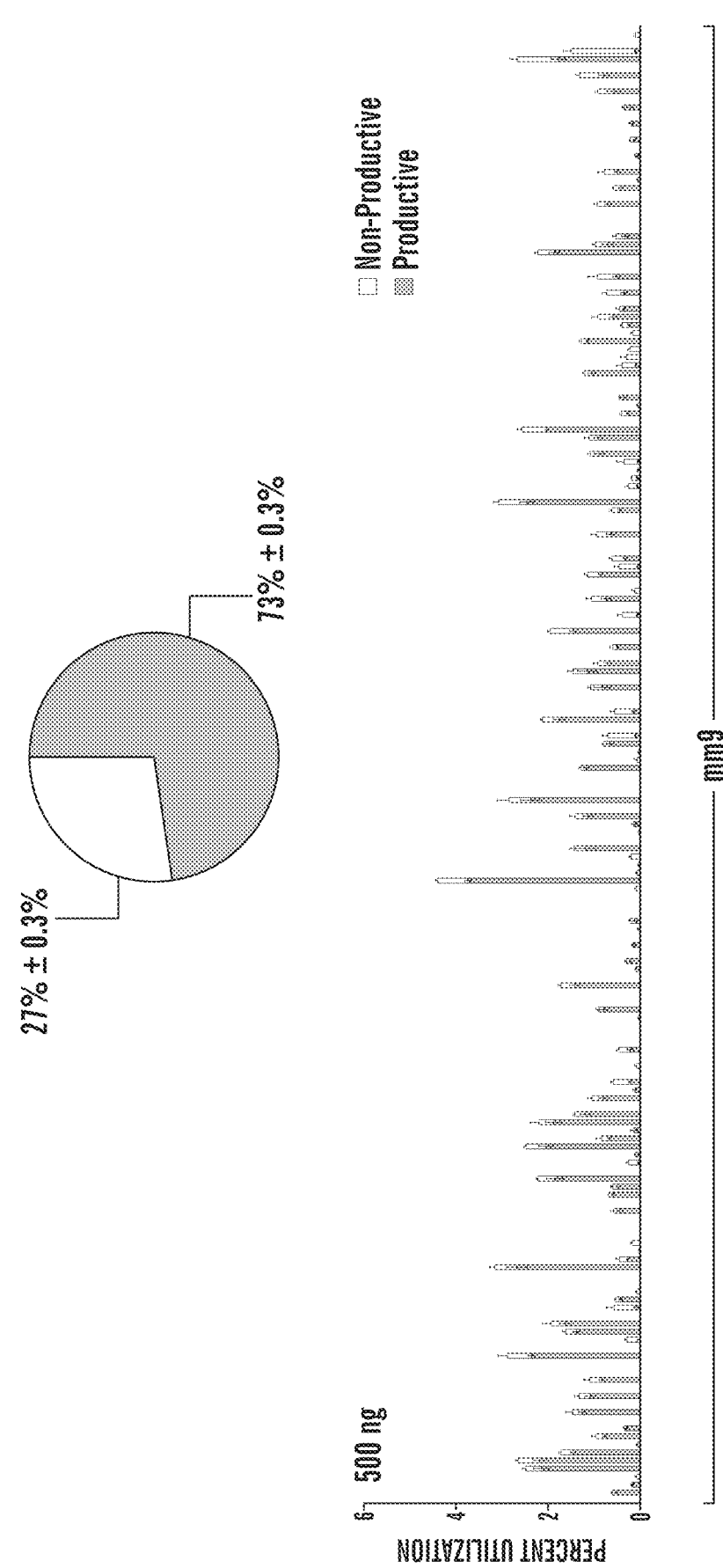
Figure 10A:
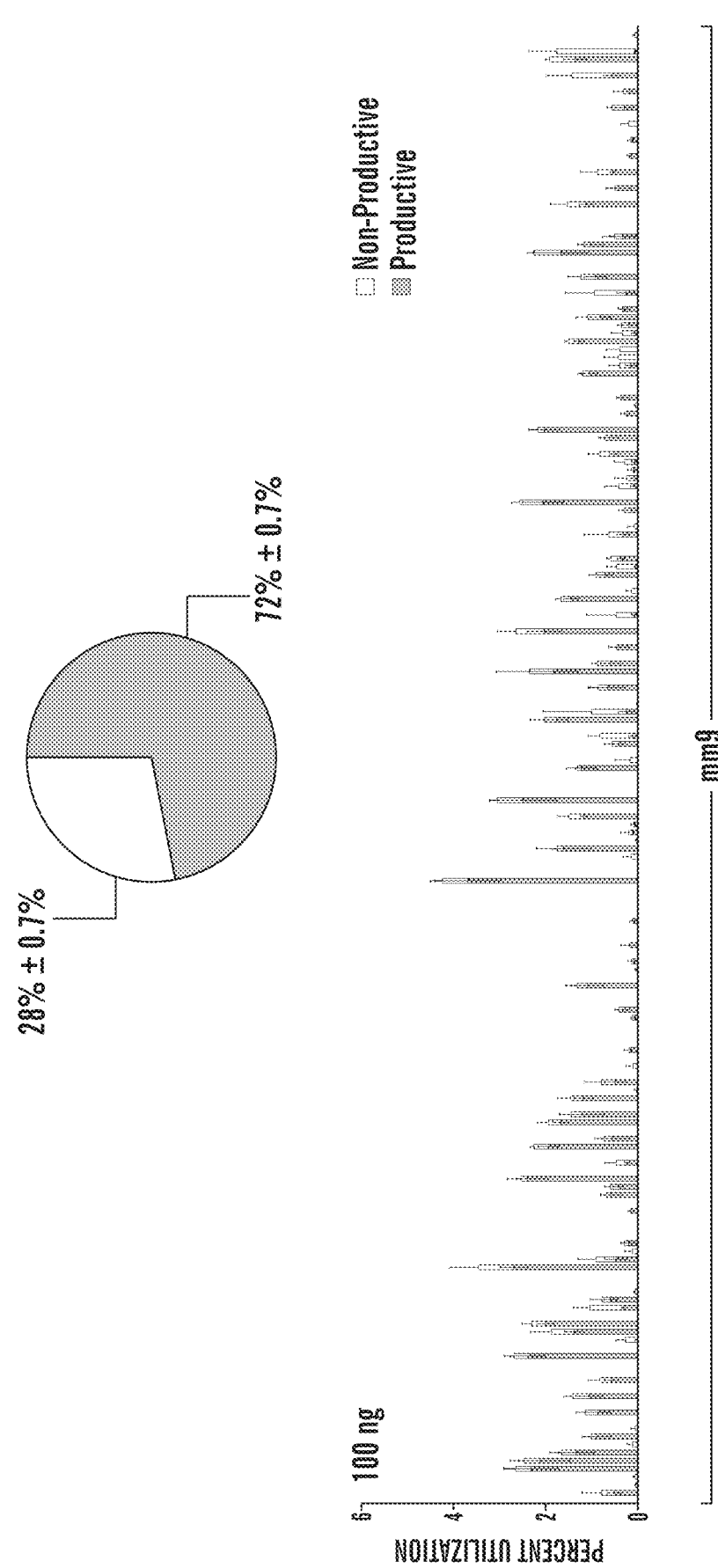

Libraries were generated from $J_H4$ coding end baits with starting DNA amounts of 2 μg, 500 ng, and 100 ng, each purified from the splenic B cells of the same C57BL/6 mouse. Libraries generated from 2 μg and 500 ng genomic DNA were almost identical (r>0.97) in $V_H$ usage and productive/non-productive rearrangement ratios (FIG. 10A, 10B; Table 2). Even though a slight decrease in the number of detected $V_{HS}$ from the libraries generated from 100 ng of genomic DNA was seen, they still displayed a similar repertoire profile (r=~0.8) and productive/non-productive ratio (FIG. 10A, 10B), demonstrating that HTGTS-Rep-seq can be used to generate a quite representative $V_HDJ_H$ repertoire library from as little as 20,000 B cells.

Figure 18A:
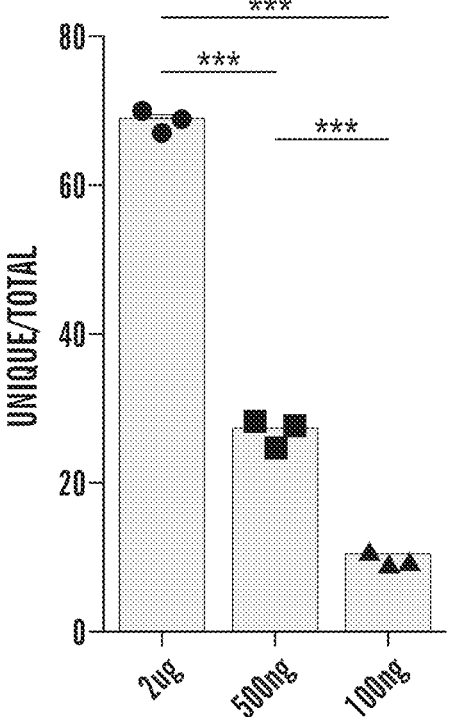
FIGS. 18A-18B depict characterization of unique CDR3 reads.
Figure 18B:
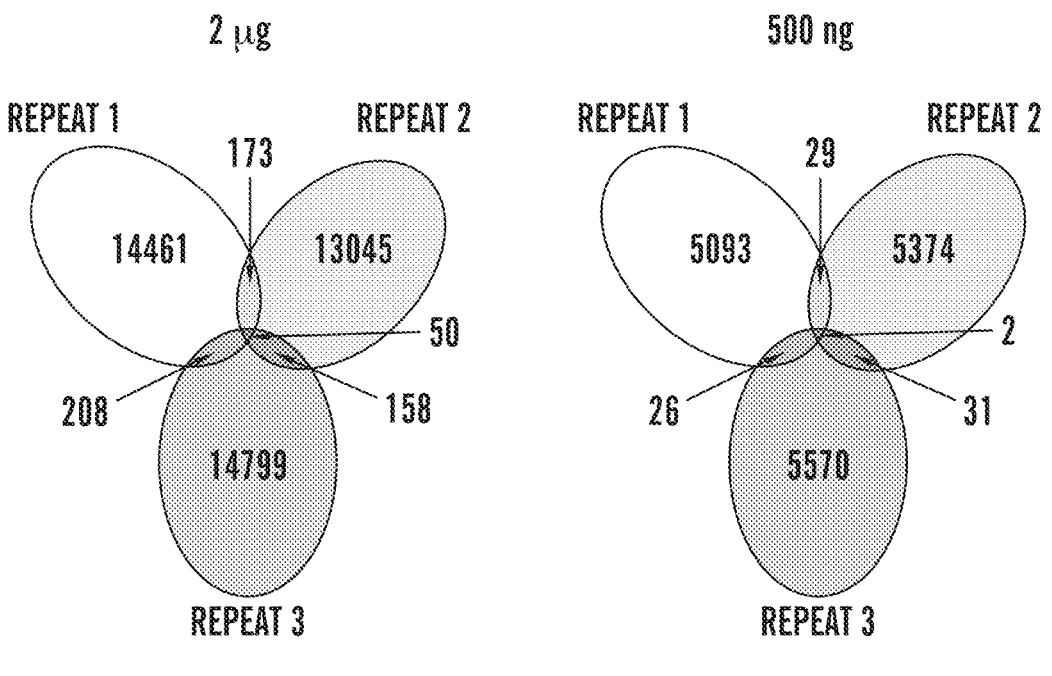
Figure 18B:
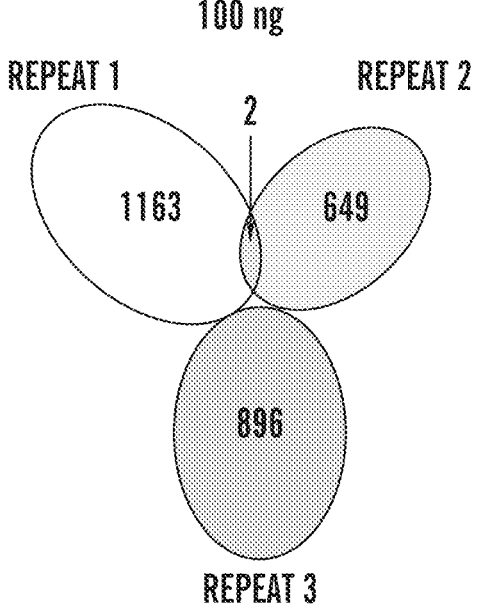

$V(D)J_H$ junctional diversities were further evaluated in these titrated libraries by comparing the percentages of unique CDR3 sequences (35). It was found that the proportion of V(D)J exons containing unique CDR3 sequences substantially decreased with reduced amounts of starting material (FIG. 18A), indicating that higher amounts of DNA starting material allows the detection of a greater fraction of the highly diverse IgH CDR3 repertoire. While sequencing errors might in theory lead to minor overestimation of CDR3 diversity, the enormous biological diversity of CDR3 in these samples was such high that a very small overlap portion was observed in detected $V(D)J_H$ CDR3 sequences (<1%) between the three technical repeats of 2 μg DNA libraries and even less between 500 ng or 100 ng DNA library repeat subsets (FIG. 18B). Thus, 100 ng DNA is enough to generate a representative $V(D)J_H$ library with respect to $V_H$ usage, but even 2 μg of DNA reveals only a very small fraction of the immense diversity IgH CDR3s.

Discussion

HTGTS-Rep-seq is a DNA-based method that requires only a single bait PCR primer, reads out both deletional and inversional V(D)J joins, and can readily be adapted to identify low frequency recombination events invisible to prior repertoire sequencing assays (22). In addition, HTGTS-Rep-seq can be used to comprehensively study productive and non-productive V exon usage. HTGTS-Rep-seq can also be utilized to developmentally assess the frequency of V(D)J intermediates, most notably by quantitatively identifying the frequency of particular $DJ_H$ rearrangements (22) (FIG. 7E, 7F). HTGTS-Rep-seq also could be adapted for revealing joining patterns of individual Ds or Vs by using them as baits. Thus, this assay, or adaptations of it, are useful for detecting changes in repertoires that occur during development, or during an immune response.

HTGTS-Rep-seq requires as little as 100 ng of genomic DNA (and potentially less) from mouse splenic B cells to capture a representative profile of $V_H$ usage. Thus, this technique can be applied to relatively small numbers of cells and yield accurate repertoire profiles. In some embodiments, the methods described herein can include an initial step to enrich for sonicated DNA fragments, e.g., those containing sequences just downstream of the whole Jκ region.

The ability to use linear amplification with only a single J primer or set of J primers by HTGTS-Rep-seq avoids the necessity of employing sets of degenerate V primers (along with J primers) required by prior DNA-based repertoire sequencing methods, which could lead to variable amplification efficiencies of different V families or Vs within a family (15). Being DNA-based, HTGTS-Rep-seq also bypasses a major limitation of RNA-based methods for certain applications by quantitatively capturing the frequency of Ig rearrangements in a population regardless of their expression level or whether they are productive or non-productive. Current means to address biases due to multiplex PCR or varying expression levels between cells include the use of universal identifiers (25, 36, 37) or single cell methods (38), but HTGTS-Rep-seq can accurately identify a population repertoire profile without the additional cost or steps of synthesizing primers with random barcodes, or sorting for single cells.

It is striking that in experiments where about 15,000 unique V(D)J rearrangements were sequence from each of 3 technical repeats, less than 1% overlap of unique CDR3 sequences was found, emphasizing the great sensitivity of the approach. This highly sensitive HTGTS-Rep-seq approach can easily be adapted for application to human samples. In that regard, the sensitivity of HTGTS-Rep-seq provides a low cost and rapid method for identifying clonal rearrangements (even $DJ_H$ rearrangements) that would be diagnostic of clonal B or T lymphocyte expansions that occur in the context of certain immune system diseases including cancers. Finally, in our libraries, approximately one third of the joined sequences cover the entire length of the approximately 370 bp V(D)J exons, making HTGTS-Rep-seq applicable to tracking dominant populations of particular V(D)J exons, including particular CDRs, that appear in the B cell repertoire during antibody affinity maturation in an immune response. This application can be enhanced as high throughput sequencing technologies are advanced to achieve greater lengths and accuracy.

Materials and Methods

Mice.

Wild-type 129SVE and C57BL/6 mice were purchased from Charles River Laboratories International. All animal experiments were performed under protocols approved by the Institutional Animal Care and Use Committee of Boston Children's Hospital.

B Cell Isolation from Bone Marrow and Spleen.

Bone marrow-derived pro-B ($B220^+IgM^-CD43^+$) cells were purified from 129SVE or enriched from C57BL/6 mice by sorting and after the depletion of erythrocytes. Single cell suspensions were stained with B220-APC, CD43-PE, and IgM-FITC antibodies. Splenic resting B cells were purified using biotin/streptavidin bead methods (B220 positive selection (Miltenyi #130-049-501)) or EasySep™ CD43-negative B cell selection (Stem Cell Technologies #19754). HTGTS-Rep-seq.

HTGTS-Rep-seq was performed as described (16). Primers are listed in Table 1. For the $DJ_H$ joins analysis, the standard LAM-HTGTS bioinformatic pipeline (16) was employed. For the $V_HDJ_H$ and VJκ identification, MiSeq reads were de-multiplexed using the fastq-multx tool in ea-utils suite (code.google.com/p/ea-utils/) and trimmed adaptors with cutadapt software (code.google.com/p/cut-adapt/). The paired reads were then joined using fastq-join tool from ea-utils suite (overlap region ≥10 bp and mismatch rate ≤8%). Reads are then grouped as joined reads and unjoined, and analyzed separately in the following analysis. Igblastn (23) was utilized using joined reads and unjoined reads against V(D)J gene databases using default parameters. The V(D)J gene sequences were obtained from IMGT (24), manually curated, and used to generate igblastn sequence databases. Various stringencies were applied to filter reads that can align to V, D, J genes (igblast score >150, total alignment length >100, overall mismatch ratio <0.1). In unjoined reads, the top V gene identified in R1 and R2 reads must match. The usage of V genes can be computed based on the processed igblast results. A pipeline named "HTGTS-rep" is developed to conduct above-mentioned processing and analyzing and can be downloaded at Bitbucket. bitbucket.org/adugduzhou/htgtsrep. Sequencing and processed data were deposited into GEO database GSE82126.

REFERENCES

1. Teng G, Schatz D G (2015) Regulation and Evolution of the RAG Recombinase. *Adv Immunol* 128:1-39.
2. Alt F W, Zhang Y, Meng F-L, Guo C, Schwer B (2013) Mechanisms of programmed DNA lesions and genomic instability in the immune system. *Cell* 152(3):417-429.
3. Alt F W, Baltimore D (1982) Joining of immunoglobulin heavy chain gene segments: implications from a chromosome with evidence of three D-JH fusions. *Proc Natl Acad Sci USA* 79(13):4118-4122.
4. Retter I, et al. (2007) Sequence and characterization of the Ig heavy chain constant and partial variable region of the mouse strain 129S1. *J Immunol* 179(4):2419-2427.
5. Yancopoulos G D, Alt F W (1986) Regulation of the assembly and expression of variable-region genes. *Annu Rev Immunol* 4:339-368.
6. Proudhon C, Hao B, Raviram R, Chaumeil J, Skok J A (2015) Long-Range Regulation of V(D)J Recombination. *Adv Immunol* 128:123-182.
7. Jung D, Giallourakis C, Mostoslavsky R, Alt F W (2006) Mechanism and control of V(D)J recombination at the immunoglobulin heavy chain locus. *Annu Rev Immunol* 24:541-570.
8. Guo C, et al. (2011) CTCF-binding elements mediate control of V(D)J recombination. *Nature* 477(7365):424-430.
9. Lin S G, Guo C, Su A, Zhang Y, Alt F W (2015) CTCF-binding elements 1 and 2 in the Igh intergenic control region cooperatively regulate V(D)J recombination. *Proc Natl Acad Sci USA* 112(6):1815-1820.
10. Fuxa M, et al. (2004) Pax5 induces V-to-DJ rearrangements and locus contraction of the immunoglobulin heavy-chain gene. *Genes Dev* 18(4):411-422.
11. Jhunjhunwala S, et al. (2008) The 3D structure of the immunoglobulin heavy-chain locus: implications for long-range genomic interactions. *Cell* 133(2):265-279.

12. Melchers F (2015) Checkpoints that control B cell development. *J Clin Invest* 125(6):2203-2210.
13. Granato A, Chen Y, Wesemann D R (2015) Primary immunoglobulin repertoire development: time and space matter. *Curr Opin Immunol* 33:126-131.
14. Schroeder H W, Zemlin M, Khass M, Nguyen H H, Schelonka R L (2010) Genetic control of DH reading frame and its effect on B-cell development and antigen-specific antibody production. *Crit Rev Immunol* 30(4):327-344.
15. Georgiou G, et al. (2014) The promise and challenge of high-throughput sequencing of the antibody repertoire. *Nat Biotechnol* 32(2):158-168.
16. Hu J, et al. (2016) Detecting DNA double-stranded breaks in mammalian genomes by linear amplification-mediated high-throughput genome-wide translocation sequencing. *Nature Protoc* 11(5):853-871.
17. Chiarle R, et al. (2011) Genome-wide translocation sequencing reveals mechanisms of chromosome breaks and rearrangements in B cells. *Cell* 147(1):107-119.
18. Frock R L, et al. (2015) Genome-wide detection of DNA double-stranded breaks induced by engineered nucleases. *Nat Biotechnol* 33(2):179-186.
19. Meng F-L, et al. (2014) Convergent transcription at intragenic super-enhancers targets AID-initiated genomic instability. *Cell* 159(7):1538-1548.
20. Wei P-C, et al. (2016) Long Neural Genes Harbor Recurrent DNA Break Clusters in Neural Stem/Progenitor Cells. *Cell* 164(4):644-655.
21. Dong J, et al. (2015) Orientation-specific joining of AID-initiated DNA breaks promotes antibody class switching. *Nature* 525(7567):134-139.
22. Hu J, et al. (2015) Chromosomal Loop Domains Direct the Recombination of Antigen Receptor Genes. *Cell* 163(4):947-959.
23. Ye J, Ma N, Madden T L, Ostell J M (2013) IgBLAST: an immunoglobulin variable domain sequence analysis tool. *Nucleic Acids Res* 41(Web Server issue):W34-40.
24. Lefranc M-P, et al. (2015) IMGT®, the international ImMunoGeneTics information System® 25 years on. *Nucleic Acids Res* 43(Database issue):D413-22.
25. Khan T A, et al. (2016) Accurate and predictive antibody repertoire profiling by molecular amplification finger-printing. *Sci Adv* 2(3):e1501371-e1501371.
26. Alt F W, et al. (1984) Ordered rearrangement of immunoglobulin heavy chain variable region segments. *EMBO J* 3(6):1209-1219.
27. Daly J, Licence S, Nanou A, Morgan G, Mårtensson I-L (2007) Transcription of productive and nonproductive VDJ-recombined alleles after IgH allelic exclusion. *EMBO J* 26(19):4273-4282.
28. Yancopoulos G D, et al. (1984) Preferential utilization of the most JH-proximal VH gene segments in pre-B-cell lines. *Nature* 311(5988):727-733.
29. Malynn B A, Yancopoulos G D, Barth J E, Bona C A, Alt F W (1990) Biased expression of JH-proximal VH genes occurs in the newly generated repertoire of neonatal and adult mice. *J Exp Med* 171(3):843-859.
30. Boekel ten E, Melchers F, Rolink A G (1997) Changes in the V(H) gene repertoire of developing precursor B lymphocytes in mouse bone marrow mediated by the pre-B cell receptor. *Immunity* 7(3):357-368.
31. Schatz D G, Ji Y (2011) Recombination centres and the orchestration of V(D)J recombination. *Nat Rev Immunol* 11(4):251-263.

32. Gorman J R, Alt F W (1998) Regulation of immuno-globulin light chain isotype expression. *Adv Immunol* 69:113-181.

33. Mostoslavsky R, Alt F W, Rajewsky K (2004) The lingering enigma of the allelic exclusion mechanism. *Cell* 118(5):539-544.

34. Melchers F, Boekel ten E, Yamagami T, Andersson J, Rolink A (1999) The roles of preB and B cell receptors in the stepwise allelic exclusion of mouse IgH and L chain gene loci. *Semin Immunol* 11(5):307-317.

35. Pieper K, Grimbacher B, Eibel H (2013) B-cell biology and development. *J Allergy Clin Immunol* 131(4):959-971.

36. Vollmers C, Sit R V, Weinstein J A, Dekker C L, Quake S R (2013) Genetic measurement of memory B-cell recall using antibody repertoire sequencing. *Proc Natl Acad Sci USA* 110(33):13463-13468.

37. Egorov E S, et al. (2015) Quantitative profiling of immune repertoires for minor lymphocyte counts using unique molecular identifiers. *J Immunol* 194(12):6155-6163.

38. Sundling C, et al. (2014) Single-cell and deep sequencing of IgG-switched macaque B cells reveal a diverse Ig repertoire following immunization. *J Immunol* 192(8):3637-3644.

TABLE 2

Summary of $VDJ_H$ joins analysis from HTGTS-Rep-seq Libraries of C57BL/6 mice

| Cell type | Locus | Input DNA | Coding end primer | &Exp | # V(D)J Junctions including duplicates | *Correlation between % Productive V(D)J subsets | # Unique CDR3 Junctions | *Correlation between % Productive V(D)J subsets |
|---|---|---|---|---|---|---|---|---|
| Pro-B | IgH | 2 ug | $J_H4$ | Mouse 1 | 8,299 | vs M2: 0.88 | 1,639 | vs. Total: 0.97 |
| | | | | Mouse 2 | 25,957 | vs M3: 0.98 | 9,133 | vs. Total: 0.99 |
| | | | | Mouse 3 | 22,613 | vs M1: 0.85 | 8,894 | vs. Total: 0.99 |
| Splenic B | IgH | 2 ug | $J_H4$ | Mouse 1 | 45,857 | vs M2: 0.99 | 20,583 | vs. Total: 0.97 |
| | | | | Mouse 2 | 57,477 | vs M3: 0.97 | 38,091 | vs. Total: 0.99 |
| | | | | Mouse 3 | 16,504 | vs M1: 0.96 | 7,053 | vs. Total: 0.97 |
| Splenic B | IgH | 2 ug | $J_H1$ | Mouse 1 | 54,172 | vs M2: 0.98 | | |
| | | | | Mouse 2 | 77,670 | vs M3: 0.98 | | |
| | | | | Mouse 3 | 37,648 | vs M1: 0.98 | | |
| Splenic B | IgH | 2 ug | $J_H2$ | Mouse 1 | 66,589 | vs M2: 0.98 | | |
| | | | | Mouse 2 | 81,547 | vs M3: 0.98 | | |
| | | | | Mouse 3 | 74,857 | vs M1: 0.99 | | |
| Splenic B | IgH | 2 ug | $J_H3$ | Mouse 1 | 26,586 | vs M2: 0.99 | | |
| | | | | Mouse 2 | 29,619 | vs M3: 0.98 | | |
| | | | | Mouse 3 | 23,097 | vs M1: 0.99 | | |
| Splenic B | IgH | 2 ug | $J_H4$ | Mouse 1 | 21,532 | vs M2: 0.97 | | |
| | | | | Mouse 2 | 26,838 | vs M3: 0.95 | | |
| | | | | Mouse 3 | 12,669 | vs M1: 0.95 | | |
| Splenic B | IgH | 2 ug | $J_H4$ | Repeat 1 | 20,703 | vs R2: 0.99 | 14,461 | vs. Total: 1.00 |
| | | | | Repeat 2 | 18.959 | vs R3: 0.99 | 13,045 | vs. Total: 1.00 |
| | | | | Repeat 3 | 22,118 | vs R1: 0.99 | 14,799 | vs. Total: 1.00 |
| Splenic B | IgH | 500 ng | $J_H4$ | Repeat 1 | 20,605 | vs R2: 0.98 | 5,093 | vs. Total: 0.99 |
| | | | | Repeat 2 | 18,897 | vs R3: 0.97 | 5,374 | vs. Total: 0.99 |
| | | | | Repeat 3 | 20,105 | vs R1: 0.97 | 5,570 | vs. Total: 0.99 |
| Splenic B | IgH | 100 ng | $J_H4$ | Repeat 1 | 12,007 | vs R2: 0.77 | 1,163 | vs. Total: 0.96 |
| | | | | Repeat 2 | 6,968 | vs R3: 0.79 | 649 | vs. Total: 0.92 |
| | | | | Repeat 3 | 8,106 | vs R1: 0.86 | 896 | vs. Total: 0.96 |
| Splenic B | $Ig_\kappa$ | 1 ug | $J_\kappa1$ | Mouse 1 | 46,554 | vs C1: 0.99 | | |
| | | | $J_\kappa2$ | Mouse 1 | 26,117 | vs C1: 0.98 | | |
| | | | $J_\kappa4$ | Mouse 1 | 16,047 | vs C1: 0.98 | | |
| | | | $J_\kappa5$ | Mouse 1 | 9,782 | vs C1: 0.98 | | |
| Splenic B | $Ig_\kappa$ | 1 ug | $J_\kappa1$ | Combined | 10,988 | vs M1: 0.99 | | |
| | | | $J_\kappa2$ | | 10,159 | vs M1: 0.98 | | |
| | | | $J_\kappa4$ | | 8,613 | vs M1: 0.98 | | |
| | | | $J_\kappa5$ | | 17,750 | vs M1: 0.98 | | |

&Mouse 1, 2, 3 mean the experiments were performed from three different mice; Repeat 1, 2, 3 mean the experiments were performed using DNA from the same mouse.
*The correlation coefficient values (r) were derived from two sets of productive V(D)J exons (%) via CORREL function in excel. The bigger the value, the more similar the two sets of data.

TABLE 3

Summary of HTGTS-Rep-seq Libraries from 129SVE mice

| Cell type | Locus | Input DNA | Coding end primer | Experiment | # Junctions including duplicates | Correlation between Productive V(D)J subsets |
|---|---|---|---|---|---|---|
| Pro-B | IgH | 2 ug | $J_H4$ | Mouse 1 | 20,081 | vs. M2: 0.95 |
| | | | | Mouse 2 | 14,950 | vs. M3: 0.93 |
| | | | | Mouse 3 | 21,701 | vs. M1: 0.96 |
| Splenic B | IgH | 2 ug | $J_H4$ | Mouse 1 | 52,140 | vs. M2: 0.98 |
| | | | | Mouse 2 | 67,885 | vs. M3: 0.95 |
| | | | | Mouse 3 | 68,337 | vs. M1: 0.96 |

TABLE 3-continued

Summary of HTGTS-Rep-seq Libraries from 129SVE mice

| Cell type | Locus | Input DNA | Coding end primer | Experiment | # Junctions including duplicates | Correlation between Productive V(D)J subsets |
|---|---|---|---|---|---|---|
| Splenic B | IgH | 2 ug | $J_H1$ | Mouse 1 | 165,224 | vs. M2: 0.94 |
| | | | | Mouse 2 | 102,858 | vs. M3: 0.95 |
| | | | | Mouse 3 | 97,125 | vs. M1: 0.96 |
| Splenic B | IgH | 2 ug | $J_H2$ | Mouse 1 | 191,016 | vs. M2: 0.98 |
| | | | | Mouse 2 | 123,362 | vs. M3: 0.96 |
| | | | | Mouse 3 | 95,336 | vs. M1: 0.96 |
| Splenic B | IgH | 2 ug | $J_H3$ | Mouse 1 | 77,966 | vs. M2: 0.97 |
| | | | | Mouse 2 | 50,202 | vs. M3: 0.97 |
| | | | | Mouse 3 | 43,512 | vs. M1: 0.97 |
| Splenic B | IgH | 2 ug | $J_H4$ | Mouse 1 | 85,649 | vs. M2: 0.96 |
| | | | | Mouse 2 | 37,247 | vs. M3: 0.96 |
| | | | | Mouse 3 | 40,422 | vs. M1: 0.97 |
| Splenic B | IgH | 2 ug | JH1 | Combined | 3,652 | |
| | | | JH2 | | 27,701 | |
| | | | JH3 | | 11,104 | |
| | | | JH4 | | 12,713 | |

Example 5: HTGTS-V(D)J SHM-seq Reveals Insights in the Nature of Antibody Repertoires Generated in Peyer's Patch Germinal Centers B3 Cells B lymphocytes diversify their antigen receptor repertoire through two major mechanisms: V(D)J recombination and SHM[1]. V(D)J recombination occurs in the bone marrow and involves the combinatorial assembly of germline V, (D), and J segments coupled with diversification of the junctions between them to generate the complementary determining region 3 (CDR3) for antigen contact[1]. In antigen activated germinal center B cells[2], activation induced cytidine deaminase (AID)-initiated SHM introduces point mutations at short hot spot motifs throughout V(D)J sequences[3]. Once naïve B cells residing in the follicles get activated by antigen, they migrate to the interfollicular region to interact with cognate T cells, leading to full activation of these B cells and acquisition of T follicular helper ($T_{FH}$) cell phenotype for the T cells. The $T_{FH}$ cells and B cells with relatively high antigen affinity then migrate back to the center of follicle to seed the formation of GCs[2,4]. Inside GCs, B cells undergo rapid proliferation and SHM in the dark zone and channel to the light zone to be selected by antigen presenting follicular dendritic cells (FDCs) and $T_{FH}$ cells[5], where B cells with improved antigen-binding affinity are positively selected to re-enter dark zone and those with decreased affinity or inactivated B cell receptor (BCR) are negatively selected to undergo apoptosis. Recirculation between the two zones facilitates repeated rounds of B cell proliferation, SHM and selection, leading to BCR clonal expansion and affinity maturation. Selected B cells also undergo AID-initiated class switch recombination (CSR) to change the class of antibody they produce and ultimately can differentiate into plasma cells and memory B cells.

Different from systemic secondary lymphoid tissues, Peyer's Patches (PPs) are gut-associated lymphoid tissues (GALT) with constitutive GC activity in the absence of specific immunization or infection by pathogens[6]. These GCs are highly dependent on gut microbiome since germ-free mice possess much smaller PPs and minimal GC B cells[7,8]. Like conventional GC at other sites, PP GC responses against commensal bacterial are strongly T cell- and CD40-dependent[9,10]. Nevertheless, it has been suggested by several studies that the antigen recognition requirements for inducing and sustaining GC responses in PP may be less stringent than in other lymphoid tissues. In mice carrying the EBV LMP2A gene in place of their endogenous immunoglobulin heavy chain (IgH) gene, which maintains BCR pathway signaling without producing real BCRs, GCs were able to form in PPs but not in spleen[11]. In mice with a unique pre-rearranged VDJ knock-in (encoding a 4-hydroxy-3-nitrophenylacetyl (NP)-specific heavy chain) a normal amount of GC B cells from PPs were detected and the $V_H$ exon contained extensive SHMs with intrinsic pattern[12].

These above findings raised the question of whether PP GCs could serve as sites of antibody diversification in an antigen non-specific manner in mouse and human, as indicated in chicken, sheep and rabbits, by SHM and/or gene conversion[13-15]. On the other hand, repeated oral immunization with NP-hapten conjugated to cholera toxin (NP-CT) in C57BL/6 mice was found to stimulate a strong GC response in PP generating oligoclonal and affinity-matured NP-specific antibodies[16], indicating mouse PP GC can function in a conventional BCR-dependent manner. It was unclear whether oral immunization of NP-CT induces the same type of GC response as that by gut microbiome-derived antigen. Yet the transgenic mice studies are limited by their scope of interpretation. Thus it remained a most intriguing question in the field how GCs form and function in PP B cells and the B cell receptors/antibodies they produce in the absence of a specific immunization, potentially in response to gut microbiome. To address this major question in the immunology field in WT C57BL/6 mice with a full primary V(D)J repertoire, described herein is a high throughput repertoire sequencing assay, namely HTGTS-V(D)J SHM-seq, to study BCR V(D)J repertoires and SHMs of spontaneous PP GC, with sensitivity enough to assay the repertoire, including full SHMs of IgH and IgL chains involved, in GCs from a single PP, and compare them to those of splenic GC B cells in response to immunization.

Summary

To elucidate the physiological antibody repertoire of splenic or PP germinal center B cells and gain into mechanisms that may select or mature it, a high throughput antibody repertoire sequencing assay (HTGTS-V(D)J SHM-seq) was developed, which is sensitive enough to follow splenic B cell antigen specific responses and to elucidate full IgH and IgL repertoires of V usage, CDR3 and now SHM patterns in PP GC B cells. C57BL/6 mice PPs and spleen samples from a universal naïve B cell repertoire were used and from that repertoire cells were selected to form GC repertoires in distinct fashion. In PP GCs specific $V_H$ and clonotype selections were observed across mice and even across individual PPs, but which show extensive somatic hypermutations (SHMs) of patterns that largely represent intrinsic SHM targeting patterns in the absence of specific antigen selection. AID is not essential for this restricted BCR selection to occur in PP GCs but does affect the spectrum of VDJs selected.

It is further shown that a similar phenomenon occurs with respect to Igκ light chain repertoires in PP GCs. Comparison of dominant IgH and IgL clonotypes in GCs from individual PPs from the same or different mice permits deduction of specific pairs of IgH and IgL chains that are likely selected together to form a selected BCR and, thereby, a specific antibody. These findings indicate that there is a very strong selection for B cells bearing specific, rare BCRs in mouse chronic PP GCs, consistent with the intriguing possibility that the BCRs represent "innate PP BCRs" with sequence intrinsic affinity maturation that may contribute to their recognition of gut antigens.

This new method can be applied to human PPs in the context of health or intestinal disease. Because these rare antibodies can be identified, the mouse studies can be extended by producing particular antibodies that are found to assay their target specificity and further define their biological activity. The new modification of the repertoire sequencing method can also permit the following of immune responses in HIV mouse vaccination models following vaccination with antigens designed to induce generation of broadly neutralizing antibodies. Additionally, the data demonstrates that the PP responses occur in the context of microbiota or food antigens Results Overview of HTGTS-V(D)J-SHM-seq HTGTS-V(D)J SHM-seq provides full length V(D)J SHM profiles across an entire repertoire of both Ig heavy and light chains, in addition to the V usage and CDR3 repertoires. This method is highly unbiased in that it is DNA-based and employs linear amplification using only J segment primers. For the IgH repertoire (FIG. 24), from sonicated genomic DNA (e.g. from GC B cells), mixed biotinylated $J_H1$, $J_H2$, $J_H3$, $J_H4$ bait primers were used to linearly amplify all the VDJ junctions. The amplification products were then enriched with streptavidin beads and tagged for Illumina Miseq™-based next generation sequencing as previously described[17,18].

Figure 25A:
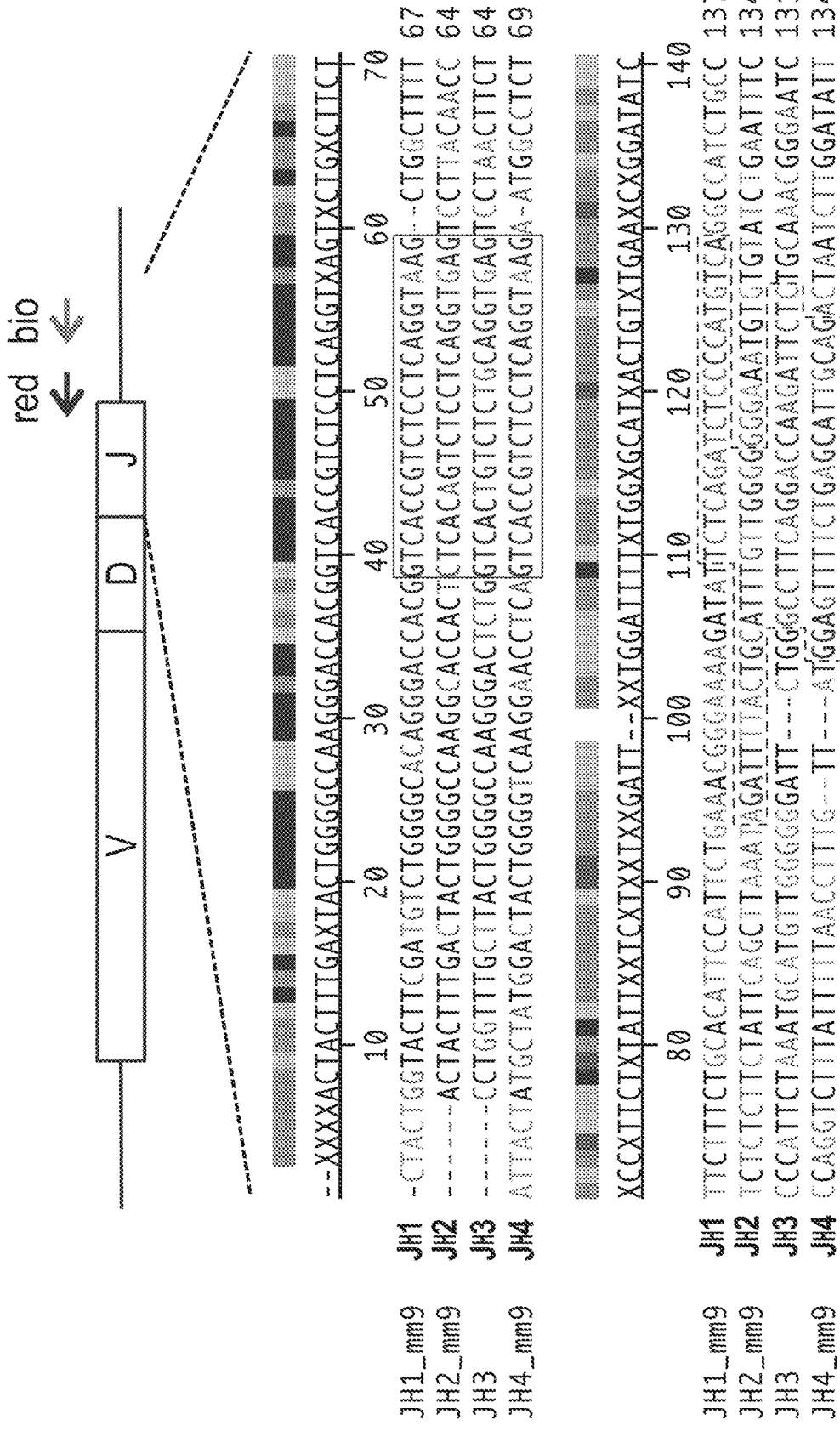
FIG. 25A depicts the location of J$_H$1-4 primers, which were selected from a highly degenerative region.
Figure 25B:
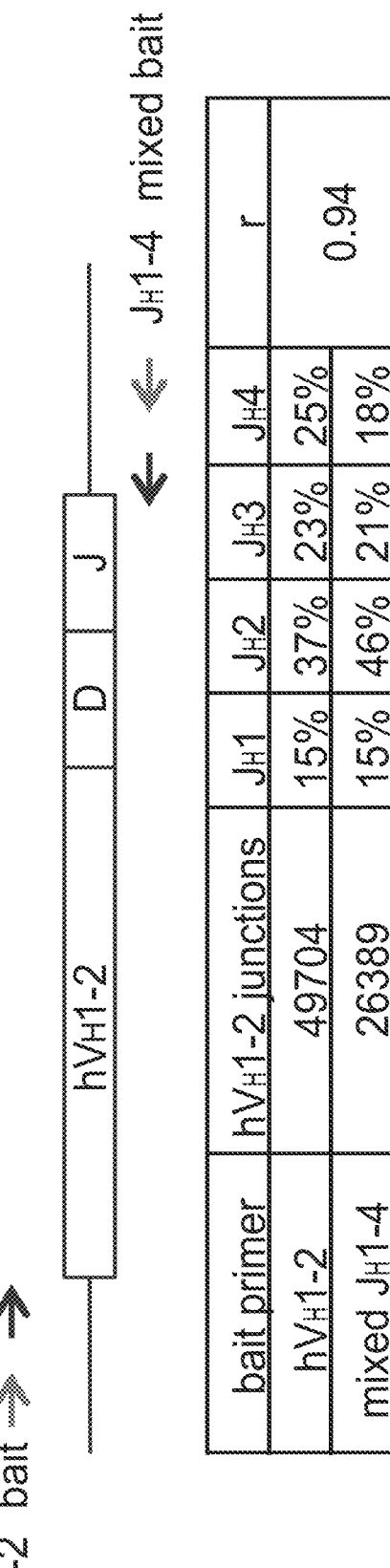
FIG. 25B depicts the ratio of each J$_H$ in hV$_H$1-2DJ junctions made from hV$_H$1-2 bait and compared with the library made from mixed J$_H$1-4 baits.

To capture full-length V(D)J sequences in recovered junctions for SHM analysis, bait primers were positioned closest to the coding ends of $J_{HS}$ and MiSeq 2×300-bp paired-end sequencing was used. The $J_H1$-4 primers were selected from a highly degenerate region (FIG. 25A), so that their usage reflects the genuine composition of $J_H1$-4 VDJ junctions. In this regard, a mouse model with human $V_H1$-2 ($hV_H1$-2) replacing the mouse $V_H81X$ with IGCR1 deletion was employed so that $hV_H1$-2 accounts for half of the $V_H$ usage in mature splenic B cell repertoire[19], where a library was made from $hV_H1$-2 bait to determine the ratio of each $J_H$ in $hV_H1$-2DJ/junctions and compared with the library made from mixed $J_H1$-4 baits (FIG. 25B).

Figure 28A:
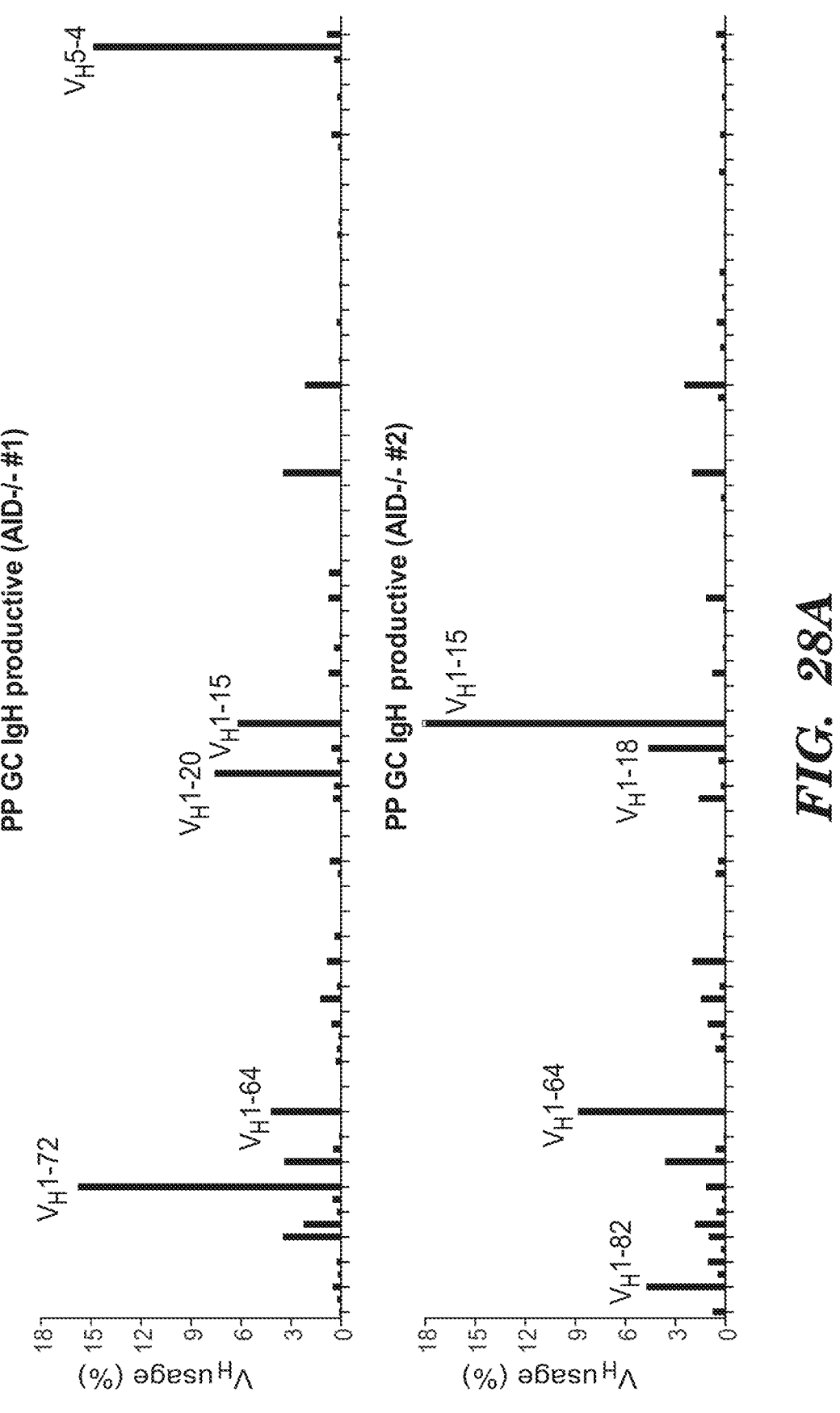
FIGS. 28A-28B depict V$_H$ usage of PP GC vs naïve B cells from individual AID–/– mice, and compared PP naïve B cell average V$_H$ repertoire between WT and AID–/– mice.
Figure 28A:
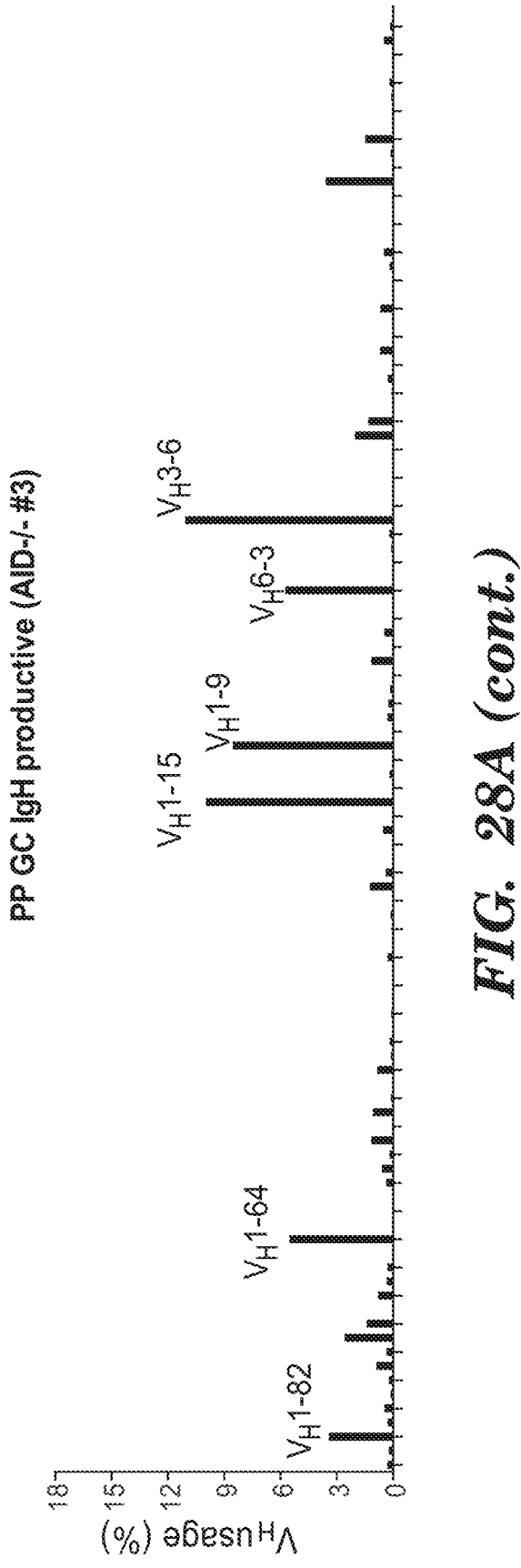

The $J_H$ ratios from the two baits matched pretty well, with a correlation co-efficiency r=0.94. Similarly, mixed $J_K$ and $J_L$ primers were also optimized to assay IgL repertoires in a truly unbiased way. By assaying the same PP GC samples for both IgH and IgL repertoires, both heavy and light chain V(D)J sequences can be identified (FIGS. 28A, 28C) and thus HTGTS-V(D)J SHM-seq is a discovery method that is able to identify new potentially physiologically important gut generated antibodies. Experimental conditions were also optimized to minimize the required cell number to tens of thousands so analysis could be done on GCs from a single PP.

TABLE 5

| Name | Sequence | Purpose | SEQ ID NO |
|------|----------|---------|-----------|
| JH1-bio-HC | /5BiosG/tgacatggggagatct gaga | mouse JH1 bio primer for HTGTS-V(D)J SHM seq | 43 |
| JH2-bio-HC | /5BiosG/ccccaacaaatgcag taaaatct | mouse JH2 bio primer for HTGTS-V(D)J SHM seq | 44 |
| JH3-bio-HC | /5BiosG/gagaatcttggtcctg aaggc | mouse JH3 bio primer for HTGTS-V(D)J SHM seq | 45 |
| JH4-bio-HC | /5BiosG/ctgcaatgctcagaaa actcc | mouse JH4 bio primer for HTGTS-V(D)J SHM seq | 46 |
| JHd-1,4 red-HC | cttacctgaggagacggtgac | mouse JH1,4 degenerative red primer for HTGTS-V(D)J SHM seq | 47 |
| JHd-2 red-HC | ctcacctgaggagactgtgag | mouseJH2 degenerative red primer for HTGTS-V(D)J SHM seq | 48 |
| JHd-3 redHC | ctcacctgcagagacagtgac | mouse JH3 degenerative red primer for HTGTS-V(D)J SHM seq | 49 |
| Jλ1-bio-HC | /5BiosG/agtgtgaagtataggt atgaagcag | mouse Jλ1 bio primer for HTGTS-V(D)J SHM seq | 50 |
| Jλ2-bio-HC | /5BiosG/cagtggagagcagat gagaaa | mouse Jλ2 bio primer for HTGTS-V(D)J SHM seq | 51 |
| Jλ3-bio-HC | /5BiosG/tctgaggagagcaga tgagaaa | mouse Jλ3 bio primer for HTGTS-V(D)J SHM seq | 52 |

TABLE 5-continued

| Name | Sequence | Purpose | SEQ ID NO |
|------|----------|---------|-----------|
| Jλ1-red-HC | cacctcaagtcttggagagaa | mouse Jλ1 degenerative red primer for HTGTS-V(D)J SHM seq | 53 |
| Jλ2-red-HC | caagacaacaagggctgg | mouse Jλ2 degenerative red primer for HTGTS-V(D) SHM seq | 54 |
| Jλ3-red-HC | caagataacaaggcctggac | mouse Jλ3 degenerative red primer for HTGTS-V(D)J SHM seq | 55 |
| Jκ1-red-HC | cagacatagacaacggaagaaag | mouse Jκ1 degenerative red primer for HTGTS-V(D)J SHM seq | 56 |
| Jκ2-red-HC | caaggttagacttagtgaacaaga g | mouse Jκ2 degenerative red primer for HTGTS-V(D)J SHM seq | 57 |
| Jκ4-red-HC | cagaaccaaaacgtcacaagtaa | mouse Jκ4 degenerative red primer for HTGTS-V(D)J SHM seq | 58 |
| Jκ5-red-HC | catgaaaacctgtgtcttacacat | mouse Jκ5 degenerative red primer for HTGTS-V(D)J SHM seq | 59 |

Figure 24:
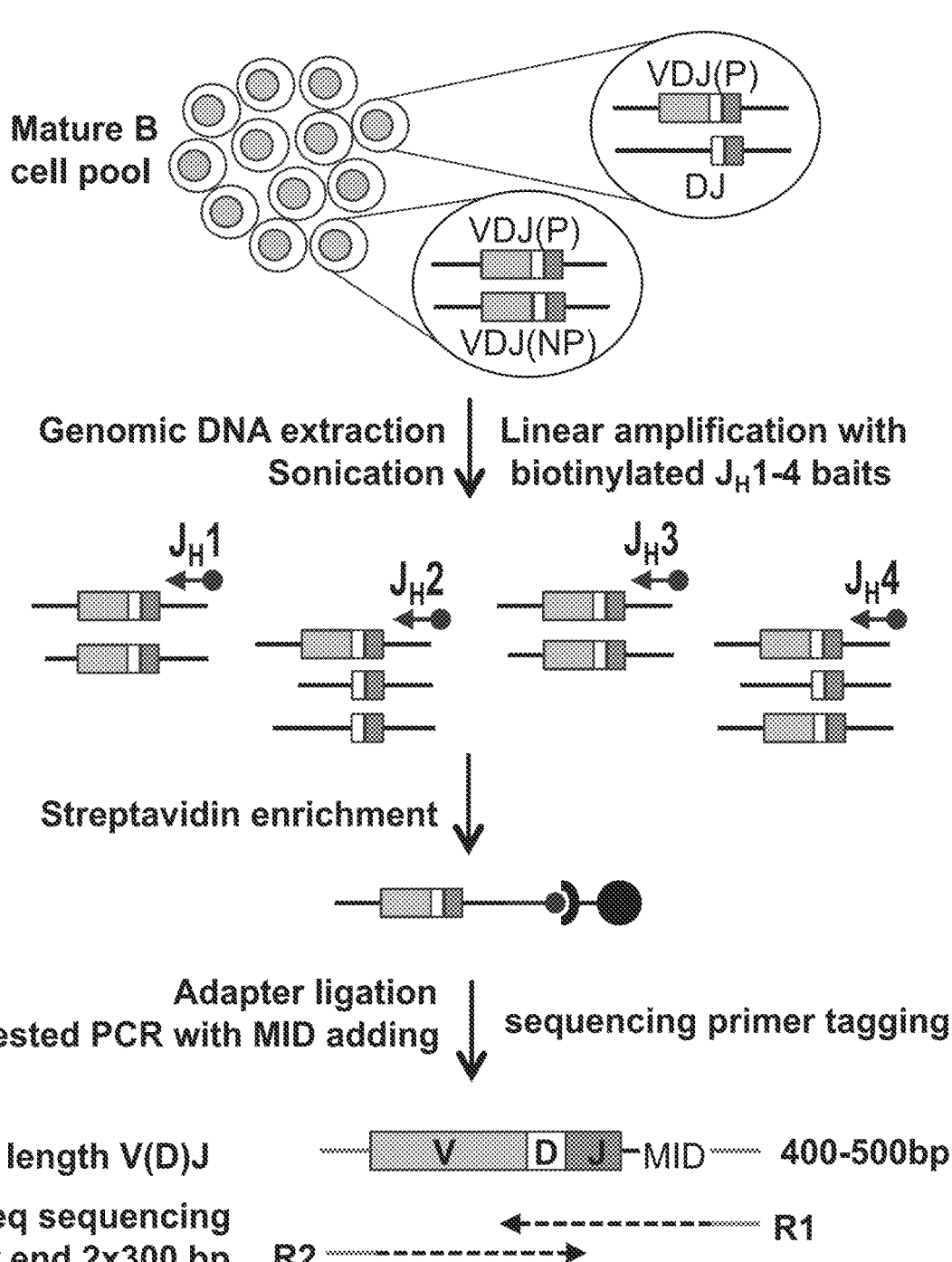
FIG. 24 depicts the experimental approach for detecting the IgH repertoire used in Example 5.

The bioinformatics pipeline was modified to implement more stringent filters to ensure quality control for junction reads used for SHM analysis, and incorporating comprehensive downstream analysis including SHM profiling, clonal clustering, mutation selection and lineage tree etc (FIG. 24). Unlike mRNA-based repertoire sequencing methods, which are affected by transcription levels, the HTGTS-V(D)J SHM-seq approach uses DNA as template and gives an accurate measurement of both productive and nonproductive VDJ joins[17]. By taking nonproductive VDJ sequences from multiple samples, an intrinsic mutation pattern database was generated for almost all mouse $V_H$s, which greatly facilitates SHM selection analysis in GC response.

NP-Induced Splenic GC IgH Repertoire

Figure 19A:
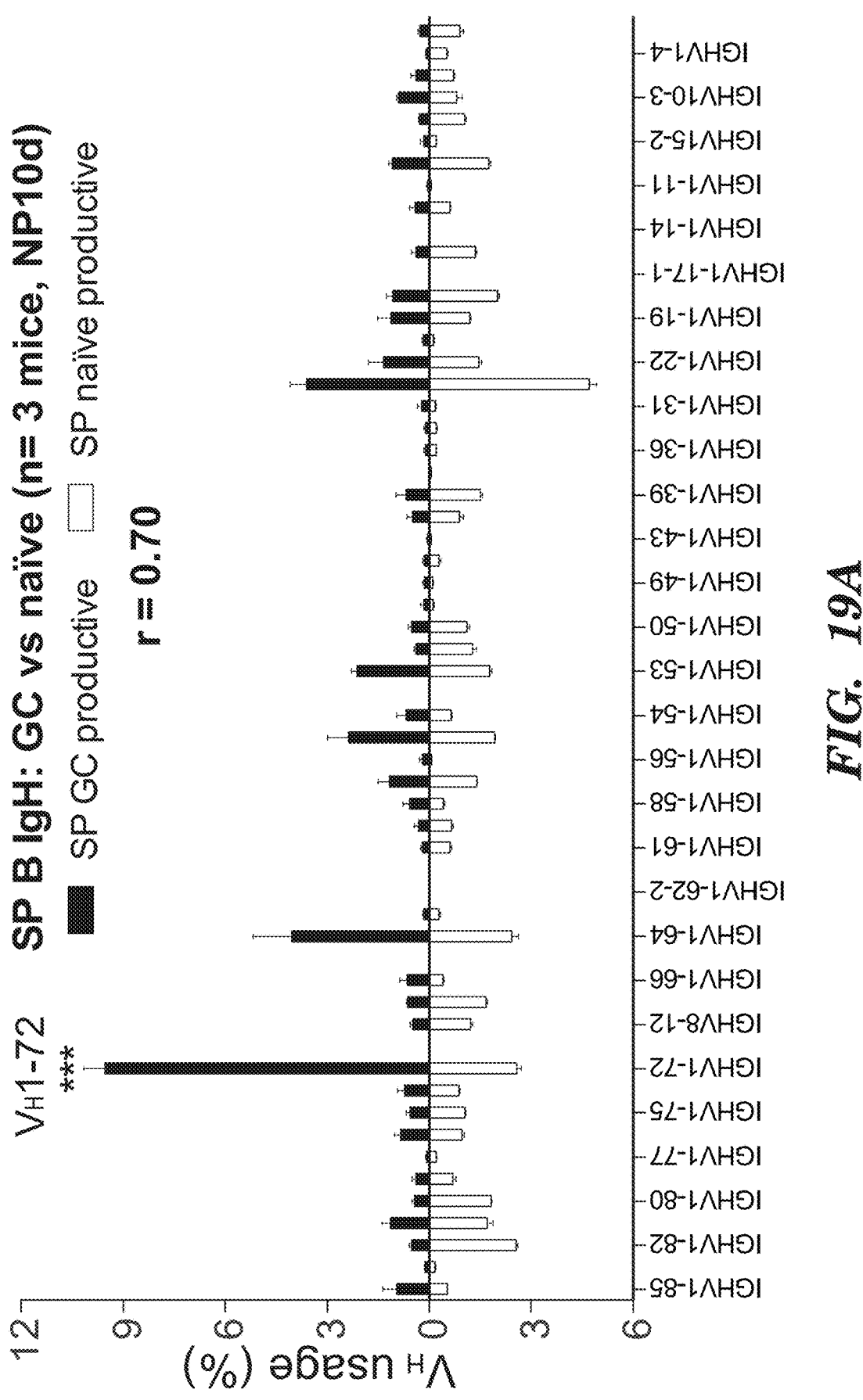
FIGS. 19A-19D depict V$_H$ usage, clonotype (CDR3) selection and SHM pattern of V$_H$1-72 from three NP-CGG immunized (10 d) C57BL/6 mice splenic GC and naïve B cells.
Figure 19A:
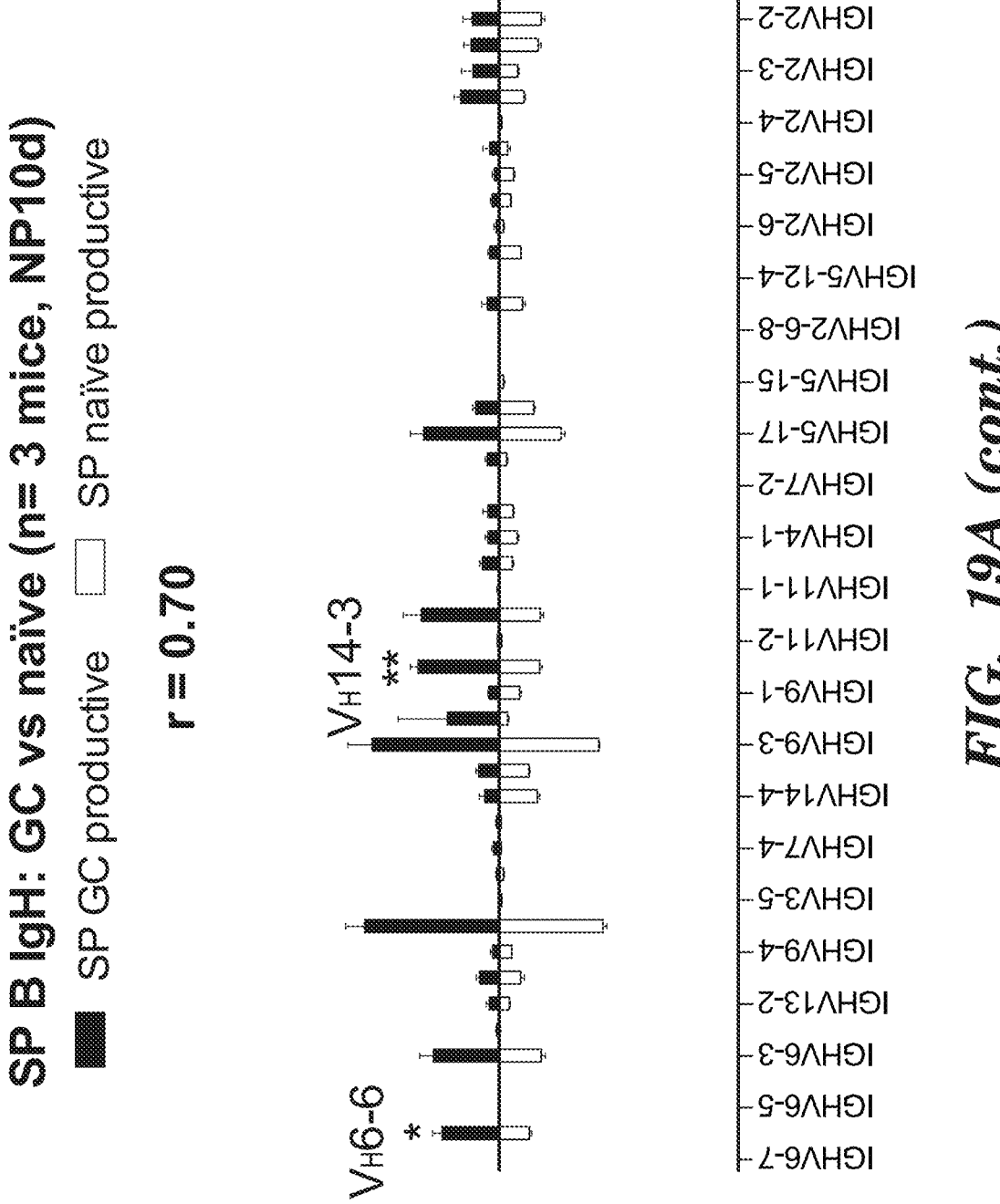
Figure 19B:
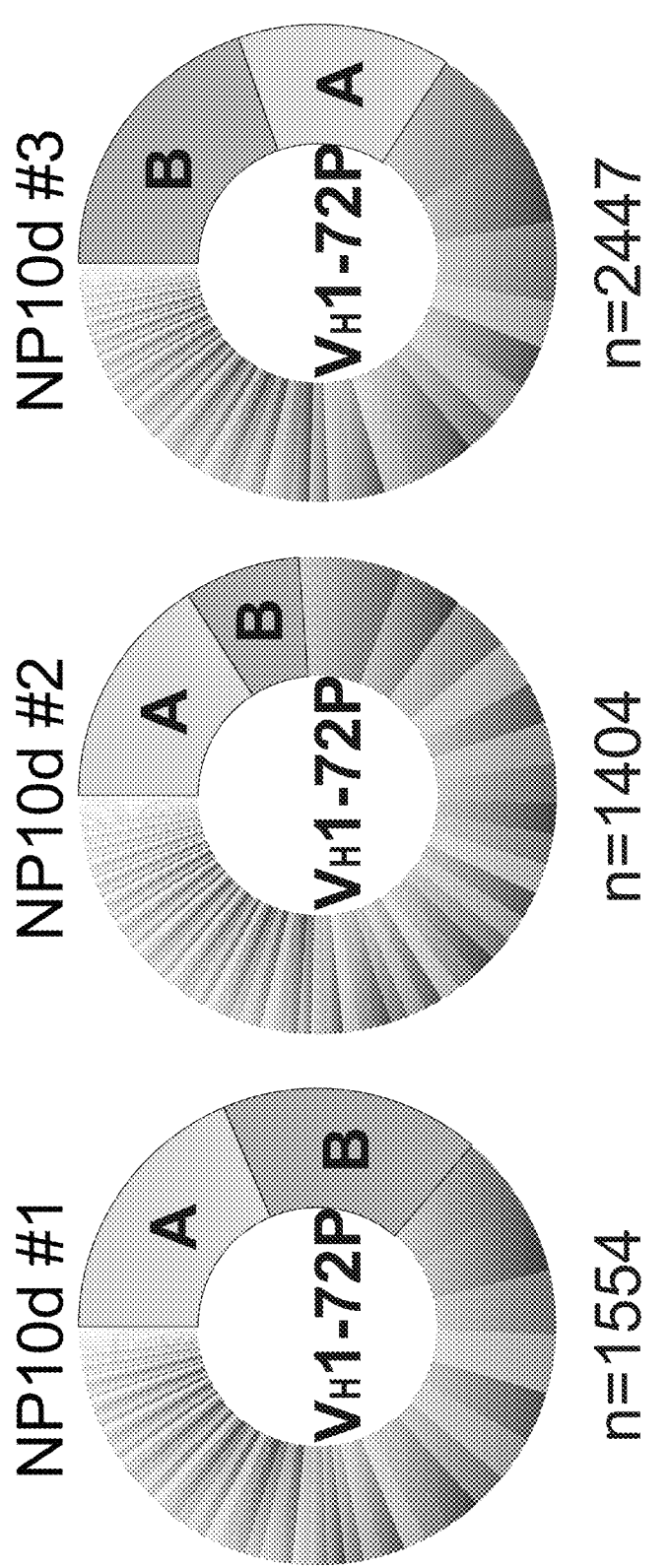
Figure 19B:
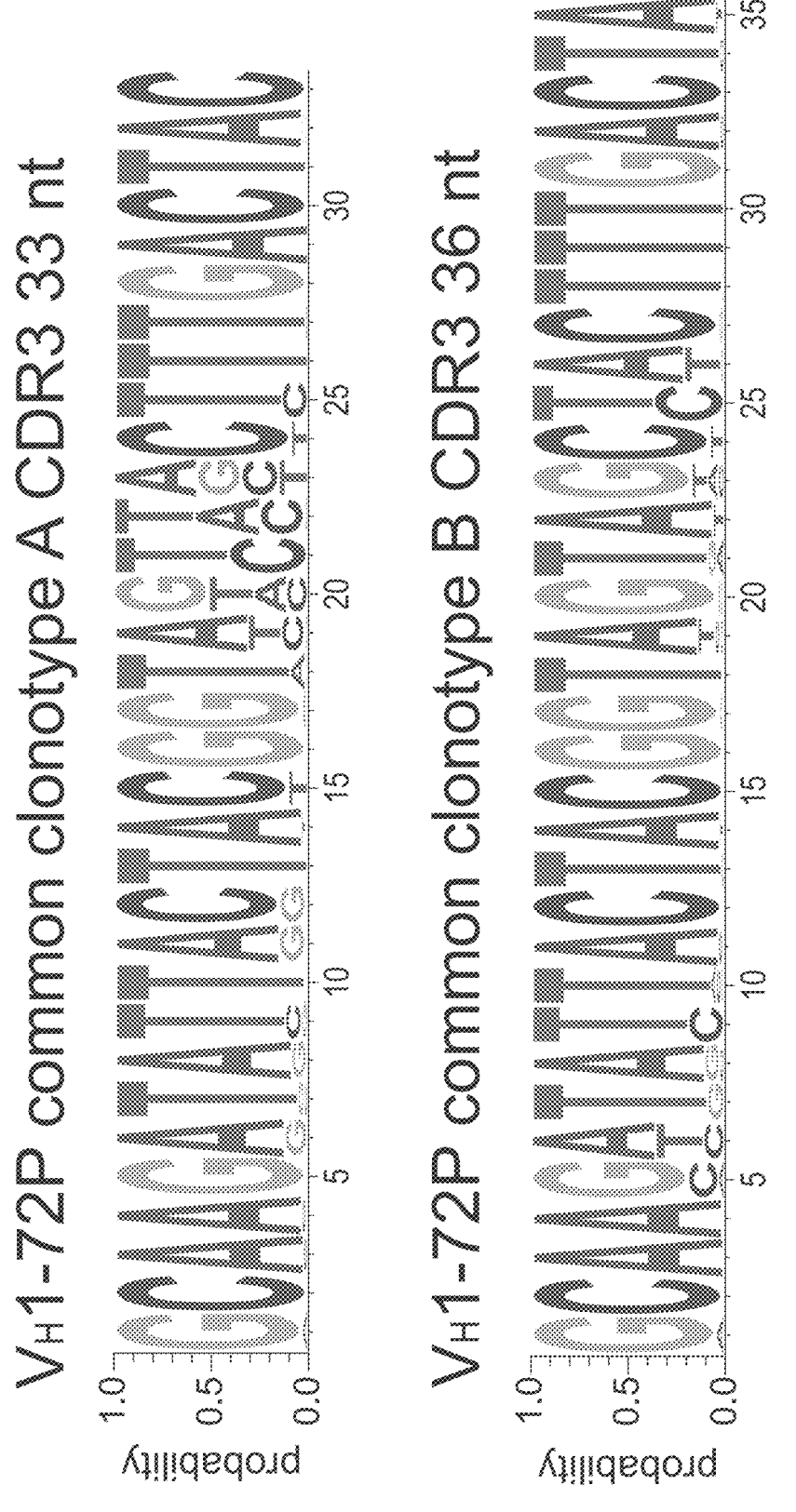

To validate HTGTS-V(D)J SHM-seq to follow a specific immune response, a well characterized immunogen was employed: NP conjugated to chicken gamma globulin (NP-CGG). C57BL/6 mice were immunized with NP-CGG intraperitoneally (IP) to stimulate splenic GC response. The spleen was collected 10 days post immunization and sorted for B220⁺GL7⁺CD38⁻ GC B cells and B220⁺GL7-CD38⁺ non-GC B cells by FACS and HTGTS-V(D)J SHM-seq libraries were constructed from both populations. To get purer populations of GC and naïve B cells for analysis and eliminate potential cross-contamination during FACS sorting, Miseq reads were further filtered by keeping mutated reads for B220⁺GL7⁺CD38⁻ samples as GC B cells and non-mutated reads for B220⁺GL7-CD38⁺ samples as naïve B cells. By comparing the IgH repertoire from splenic GC B cells versus naïve B cells, it was possible to detect a significant GC enrichment of $V_H$1-72 (V186.2) in productive VDJ junctions (FIG. 19A), the dominant $V_H$ used for NP antibody identified by earlier studies[20-22]. Clonal analysis revealed that the top two dominant clonotypes within the $V_H$1-72 junctions were shared by all three mice assayed as top clones (FIG. 19B) indicating strong BCR selection in splenic GC. Both clonotypes contained $D_H$1-1 (DFL16.1) and $J_H$2, the dominant D and J segments reported for NP response[20-22], with different CDR3 length: 33 nts and 36 nts respectively (FIG. 19B).

Figure 19C:
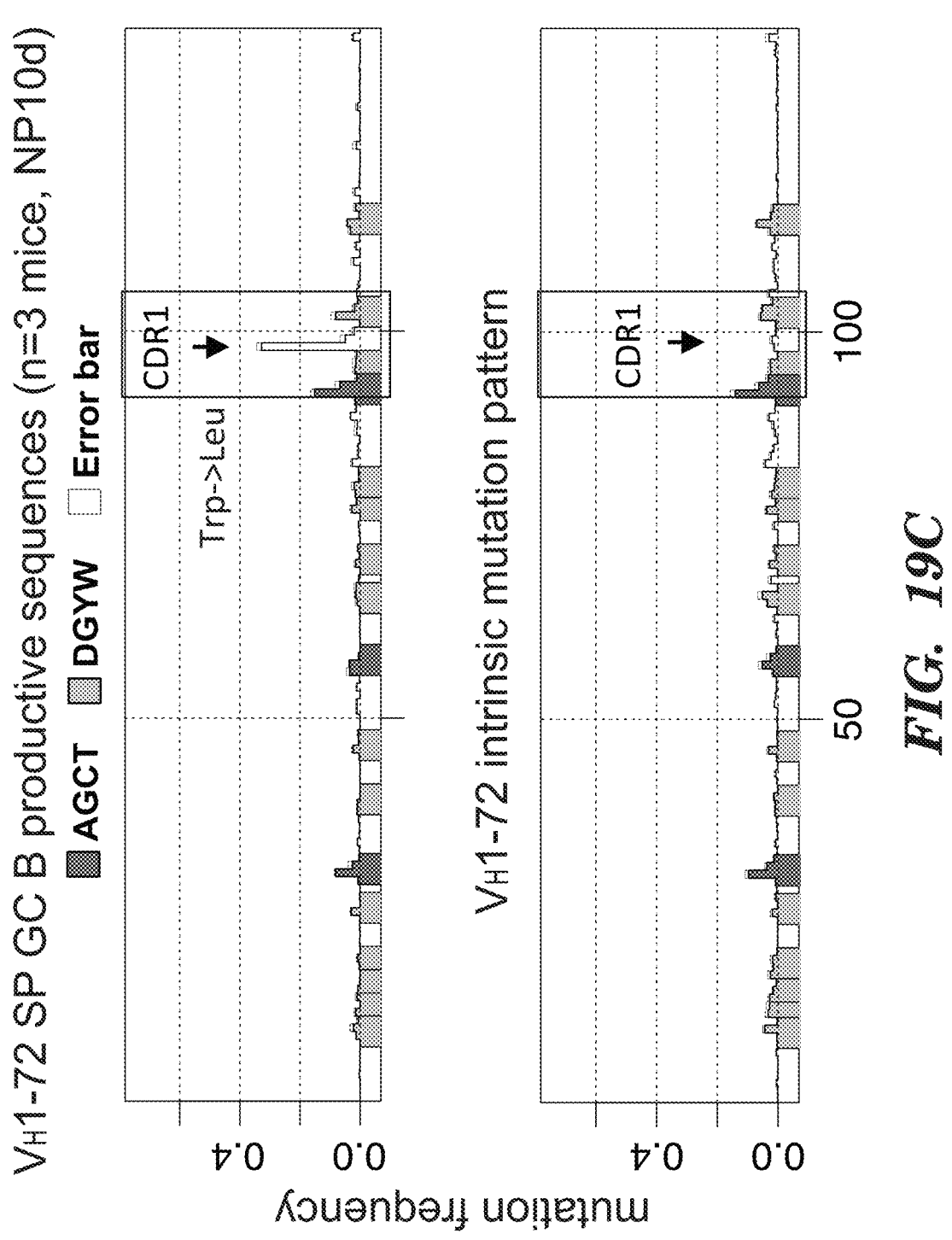
Figure 19C:
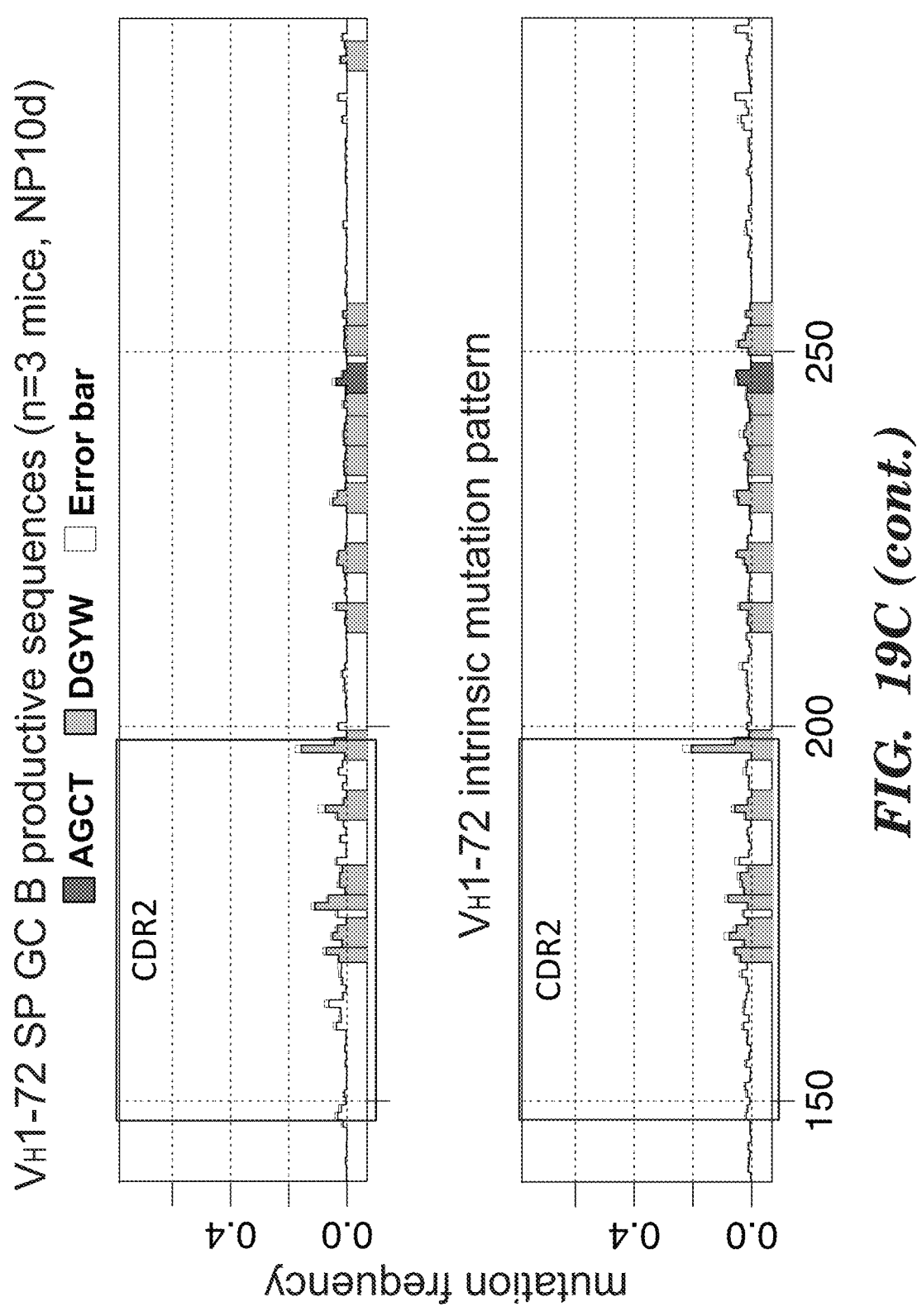
Figure 19D:
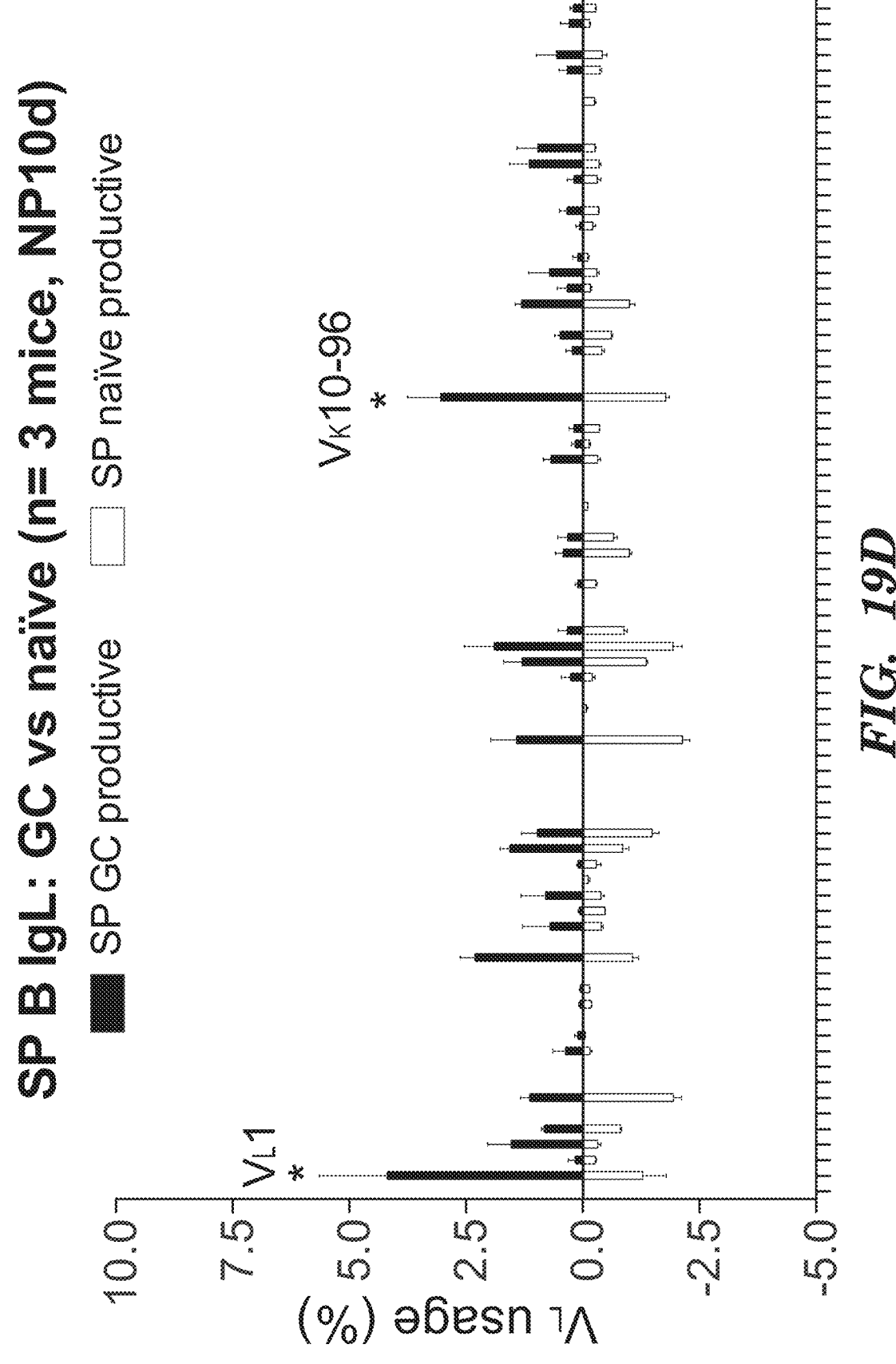
Figure 19D:

Moreover, a significant selection of a point mutation in $V_H$1-72 at position 98 encoding a Trp to Leu change in CDR1 (FIG. 19C), a hallmark for increased NP affinity[23]

was also detected. Note that this point mutation was not identified by traditional PCR assays on as early as day 10 post NP-CGG immunization[22,24]. Similarly, by comparing the IgL repertoire from splenic GC B cells versus naïve B cells, a significant GC enrichment of $V_L$1 in productive VDJ junctions was detected (FIG. 19D), this being the dominant $V_L$ used for NP antibody identified by earlier studies[20-22]. Thus with HTGTS-V(D)J SHM-seq, it was possible to identify all the known features of NP-specific BCR selection in the spleen at a fairly early stage upon immunization[25], demonstrating unprecedented sensitivity of this assay to follow a humoral immune response and its potential capability to accurately identify antigen-specific features for an uncharacterized immunogen.

Shared Naïve Repertoire by PPs and Spleen

Figure 20A:
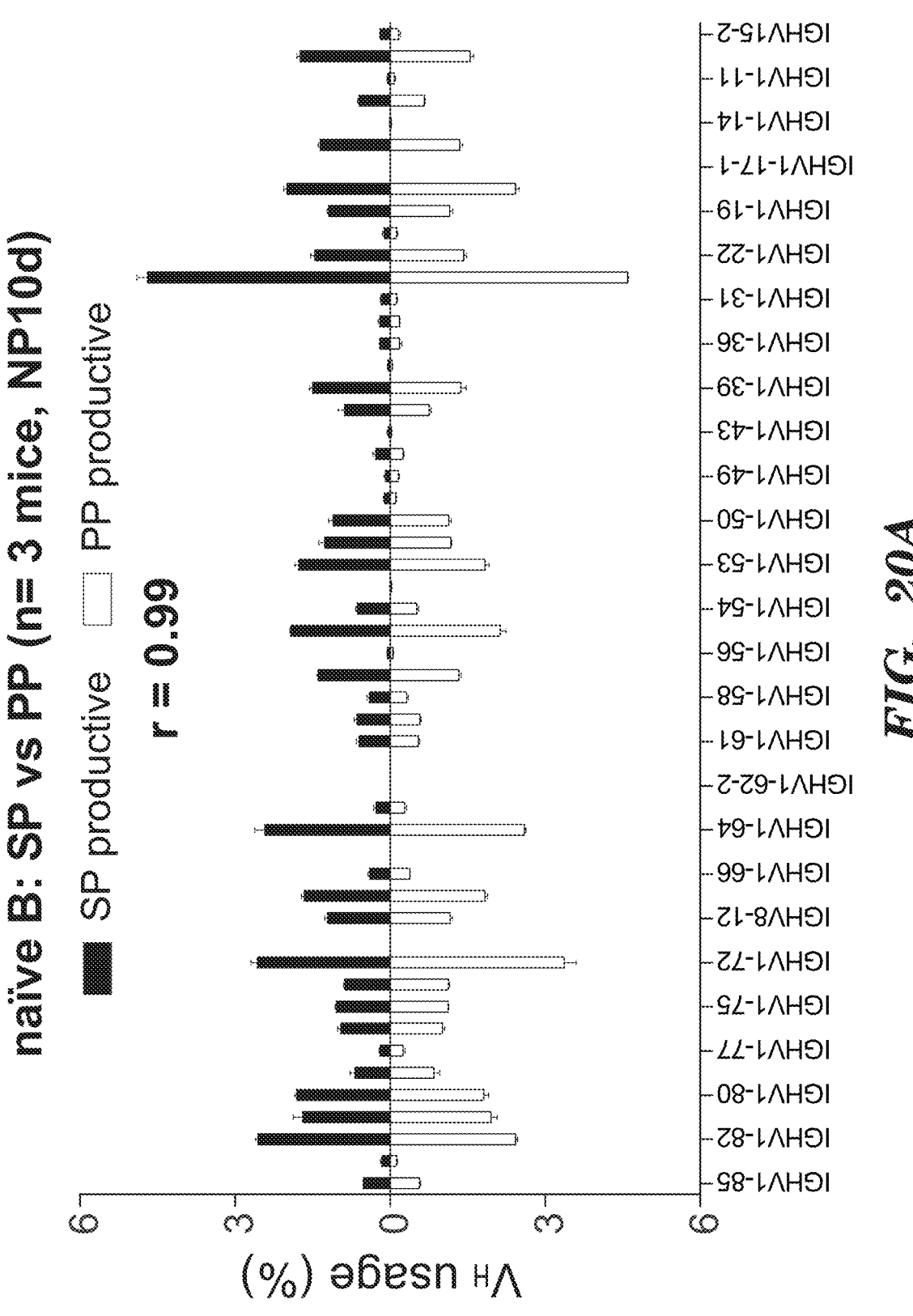
FIGS. 20A-20B depict comparison of V$_H$ usage between splenic and PPs naïve B cells, and between splenic and PPs GC B cells from three NP-CGG immunized (10 d) C57BL/6 mice.
Figure 20A:
Figure 20A:
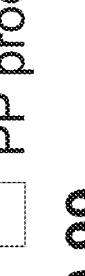
Figure 20A:
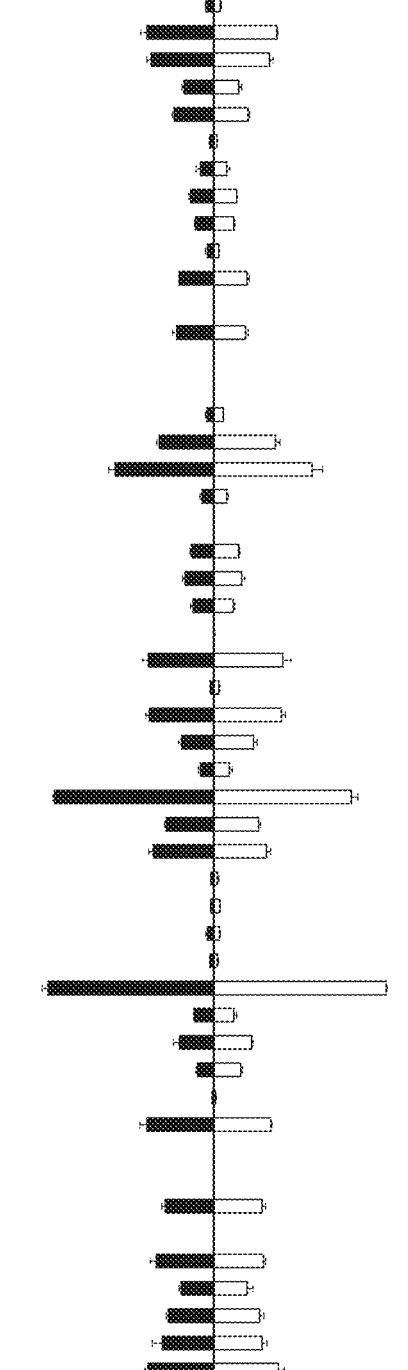

In the same NP-CGG IP immunized mice, all the PPs along the small intestine were also dissected out from each mouse and B220⁺GL7⁺CD38⁻ GC B cells and B220⁺GL7-CD38⁺ non-GC B cells isolated by FACS. With HTGTS-V(D)J SHM-seq, the naïve and GC B cell IgH repertoire in PPs were measured, and compared to those of spleen. Strikingly, the $V_H$ repertoires of PPs and splenic naïve B cells were identical in all three mice (FIG. 20A), with a correlation coefficient r=0.99, indicating circulation of naïve B cells between these tissues. In line with this, a study tracking the movements of endogenous PP B cells using photoconversion technique over a three-day period has found significant naïve B-cell exchange between PPs and spleen[26]. Moreover, the stable $V_H$ composition for naïve B cells among different mice, as reflected by the tiny error bars (FIG. 20A), indicates that a common baseline IgH repertoire is utilized across all mice.

Figure 20B:
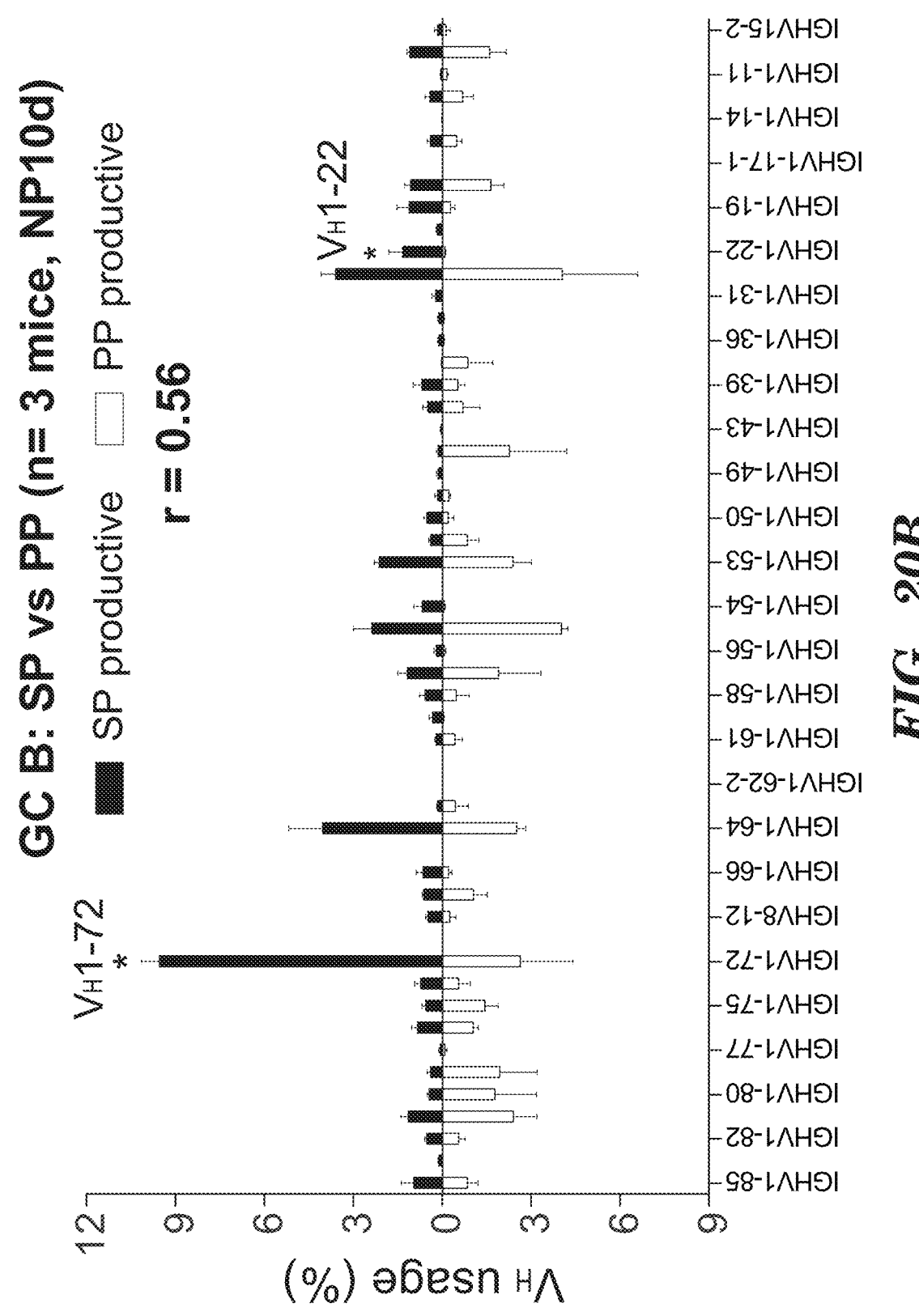
Figure 20B:
Figure 20B:
Figure 20B:
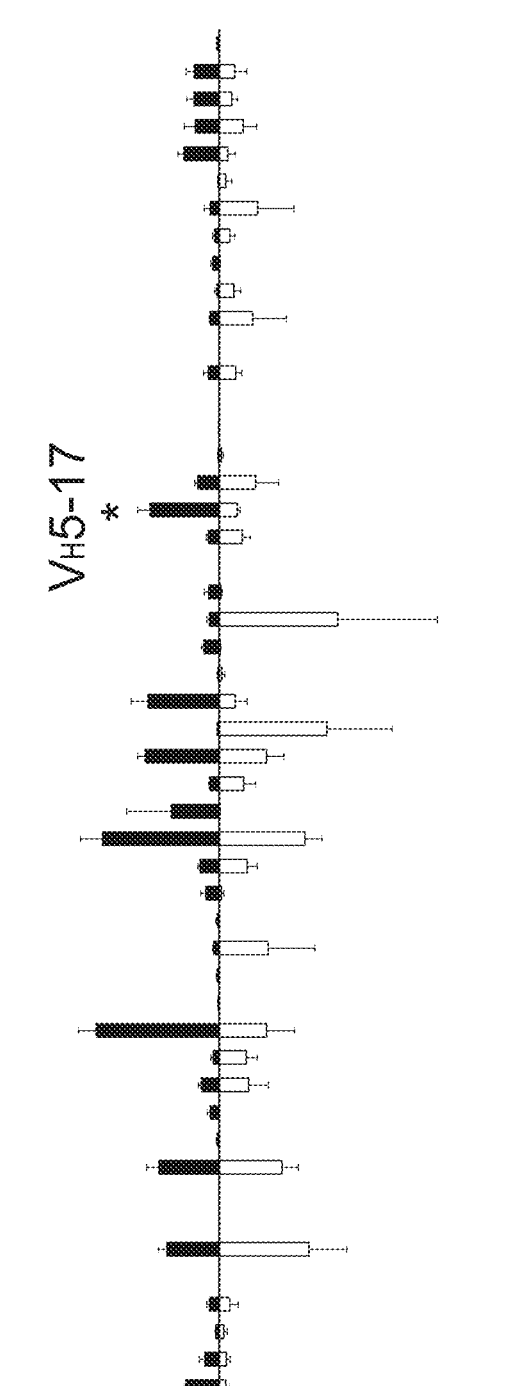
Figure 26A:
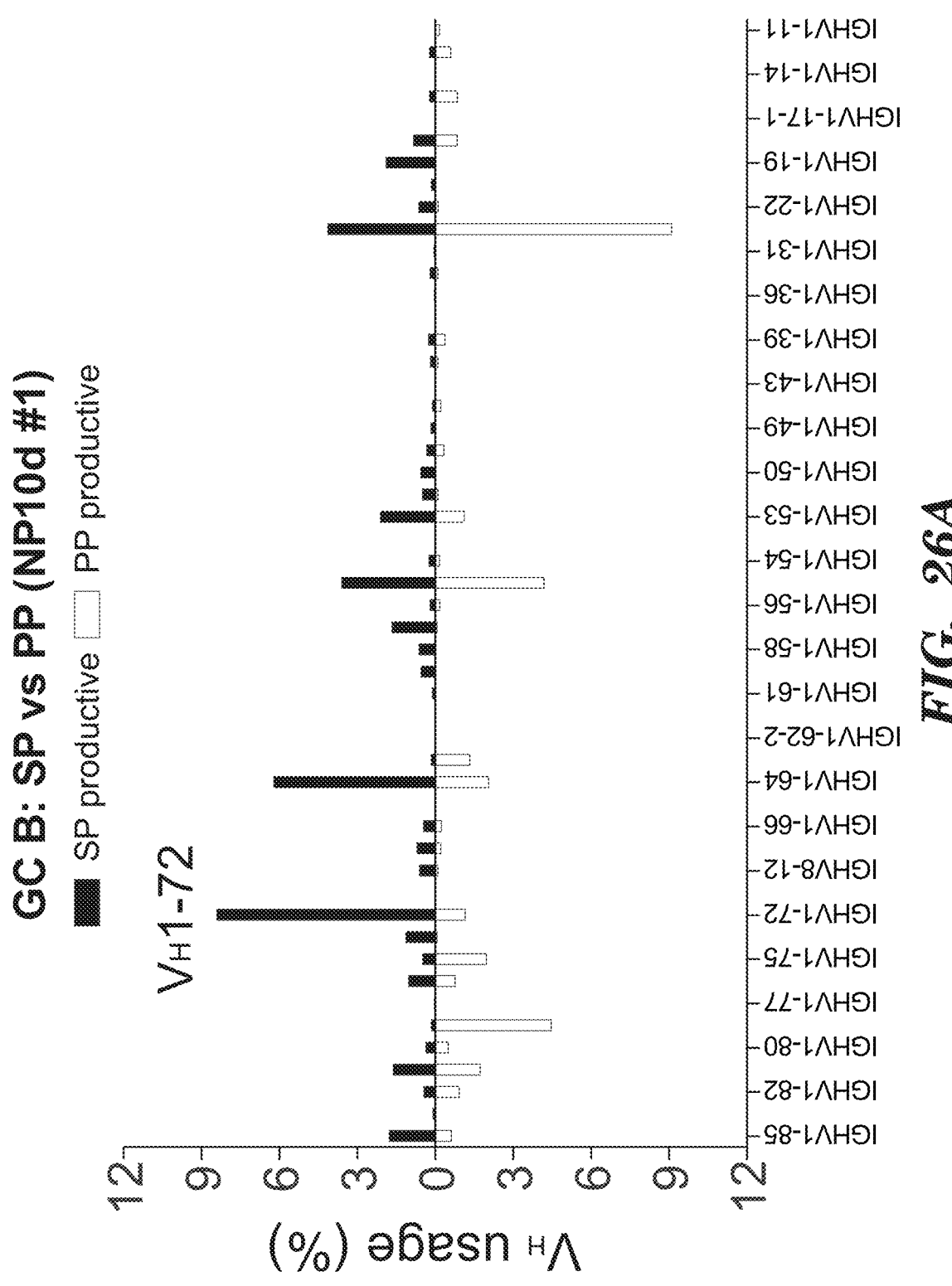
FIG. 26A depicts V$_H$ usage in splenic and PP GC in the indicated individual NP-CGG immunized mice.
Figure 26A:
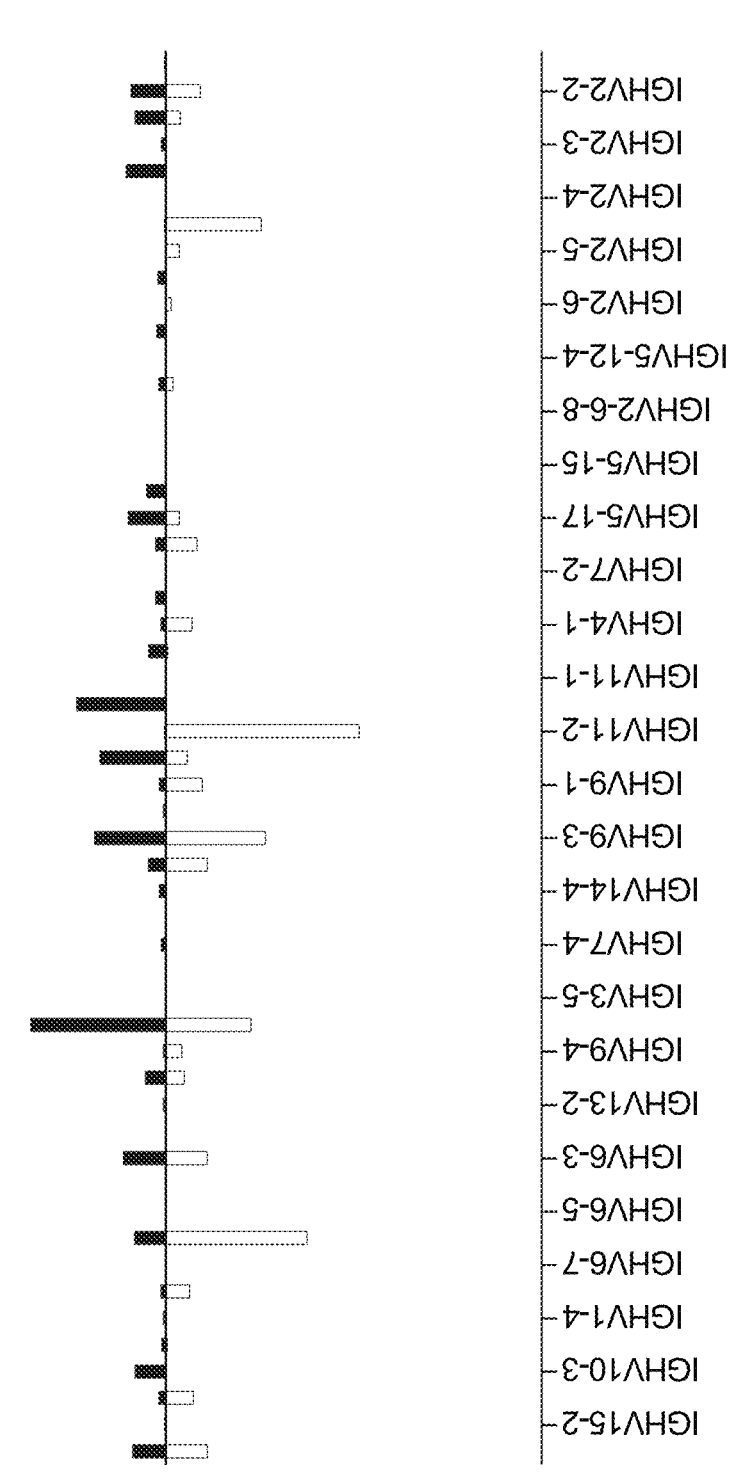
Figure 26A:
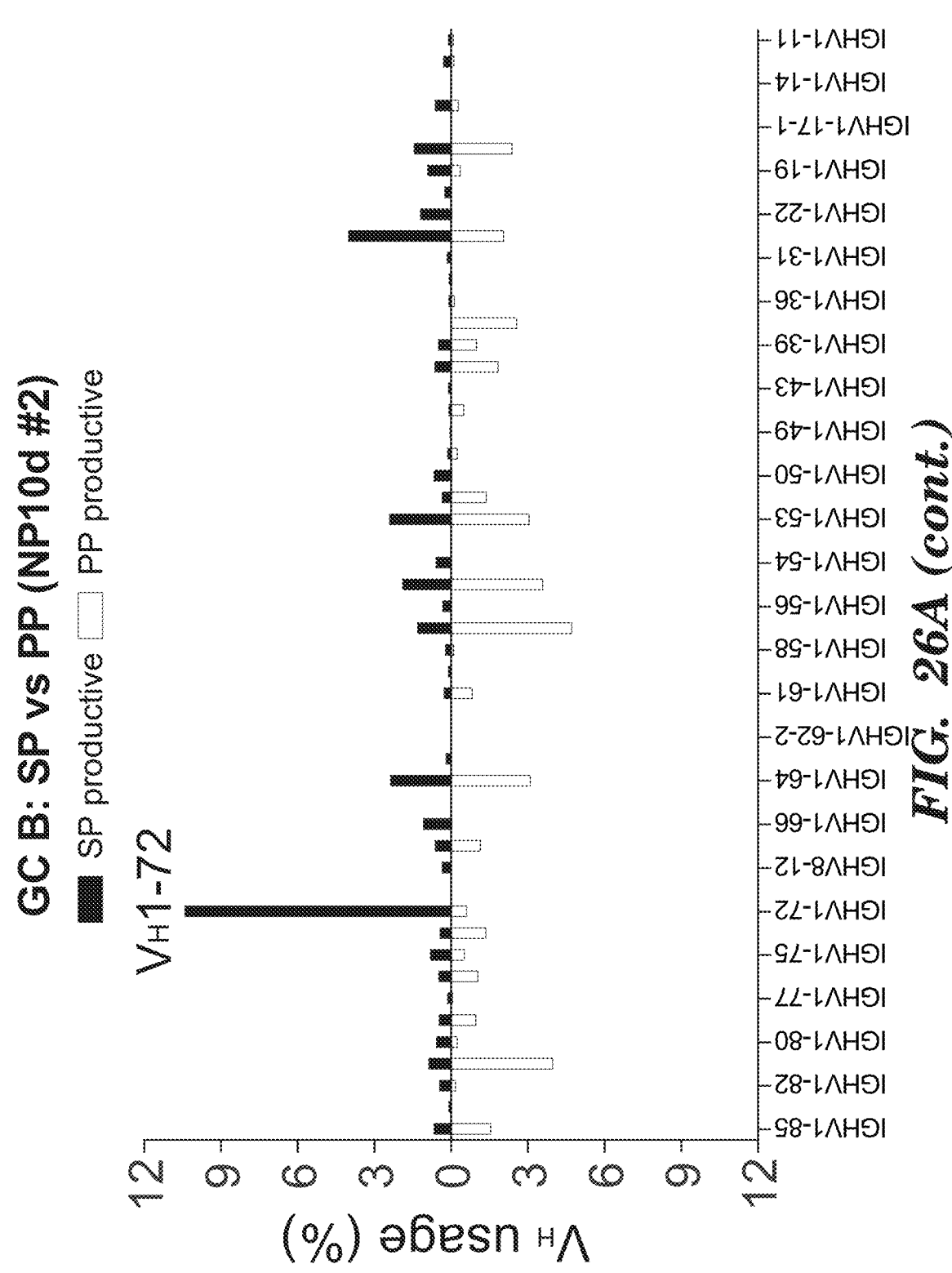
Figure 26A:
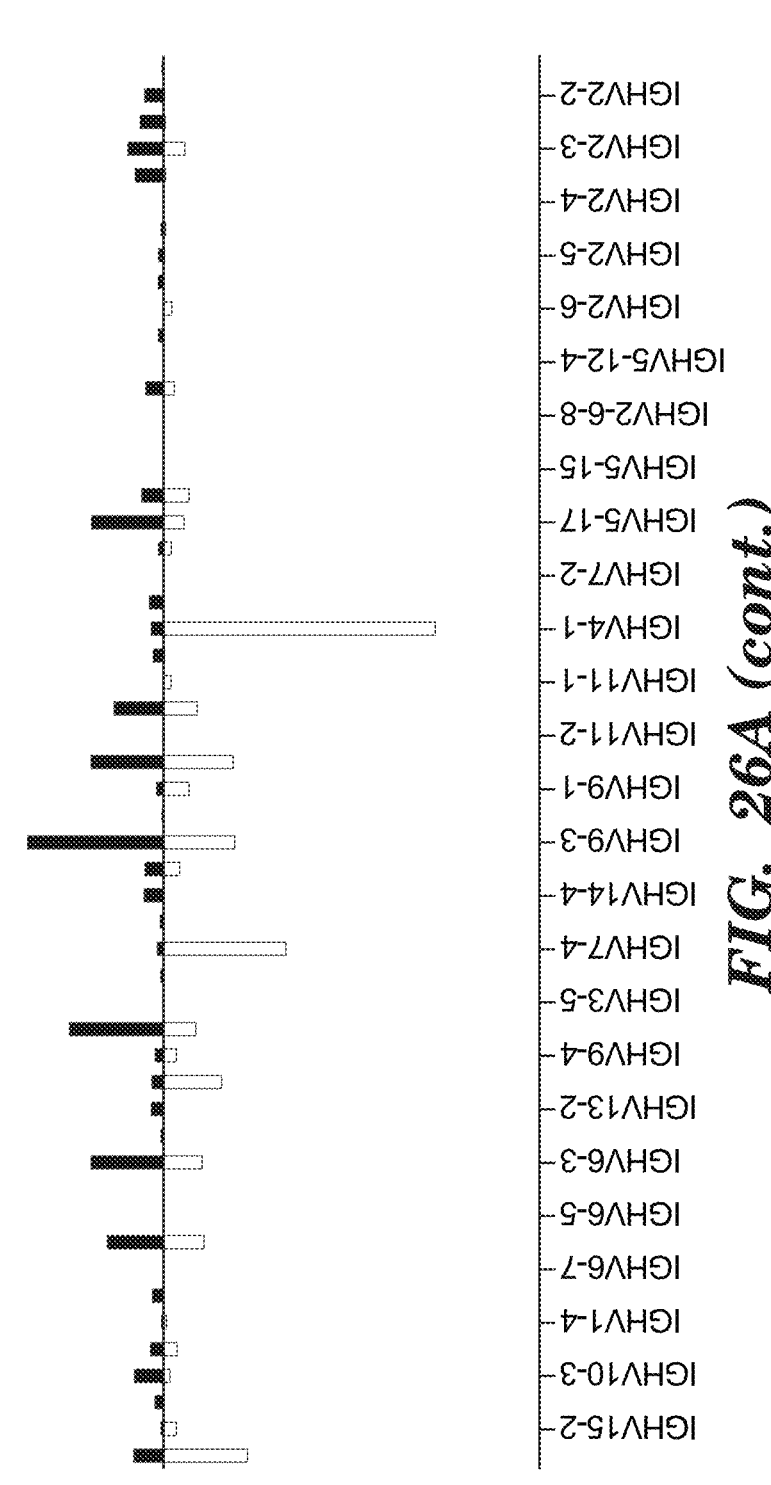
Figure 26A:
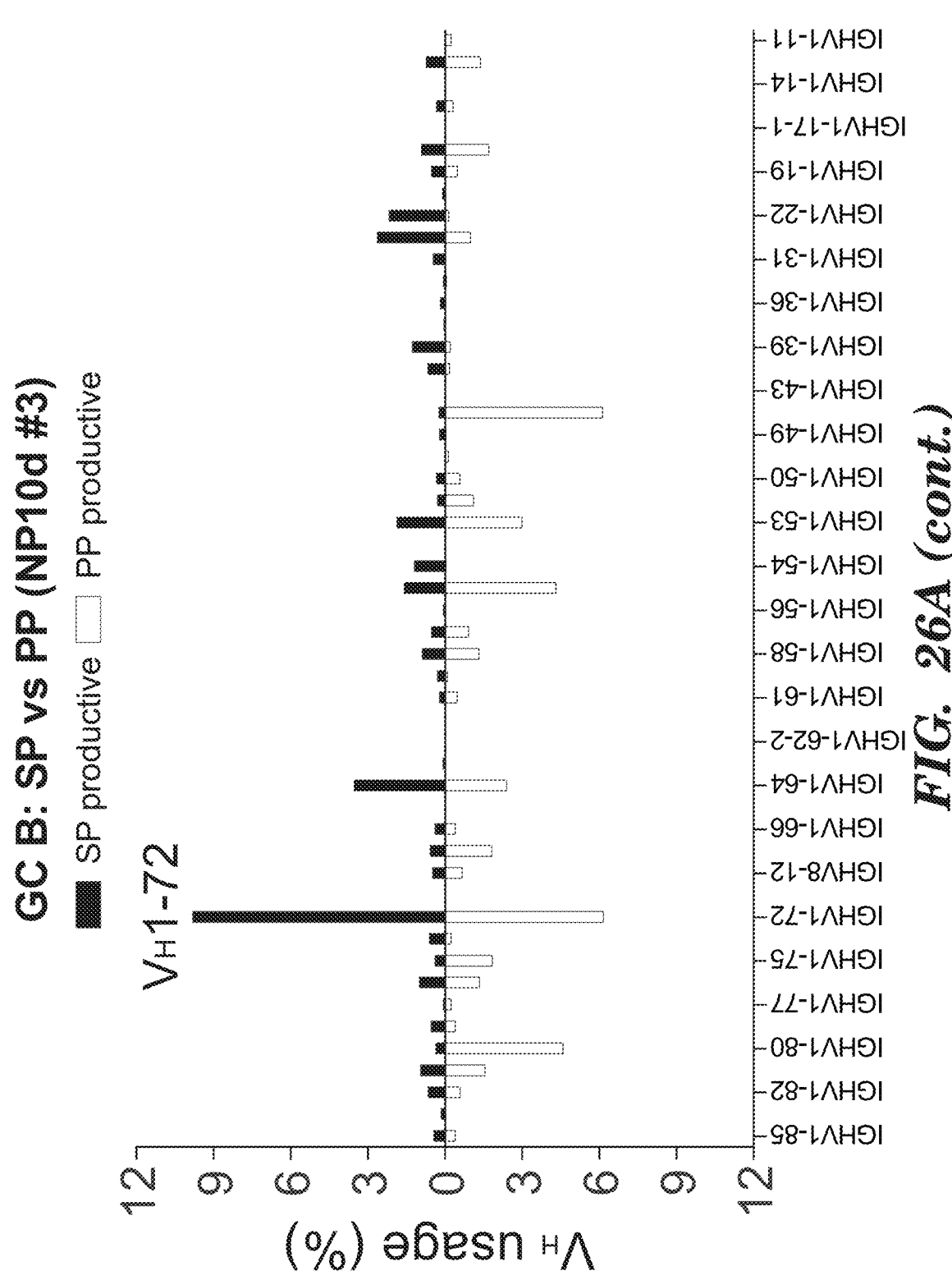
Figure 26A:
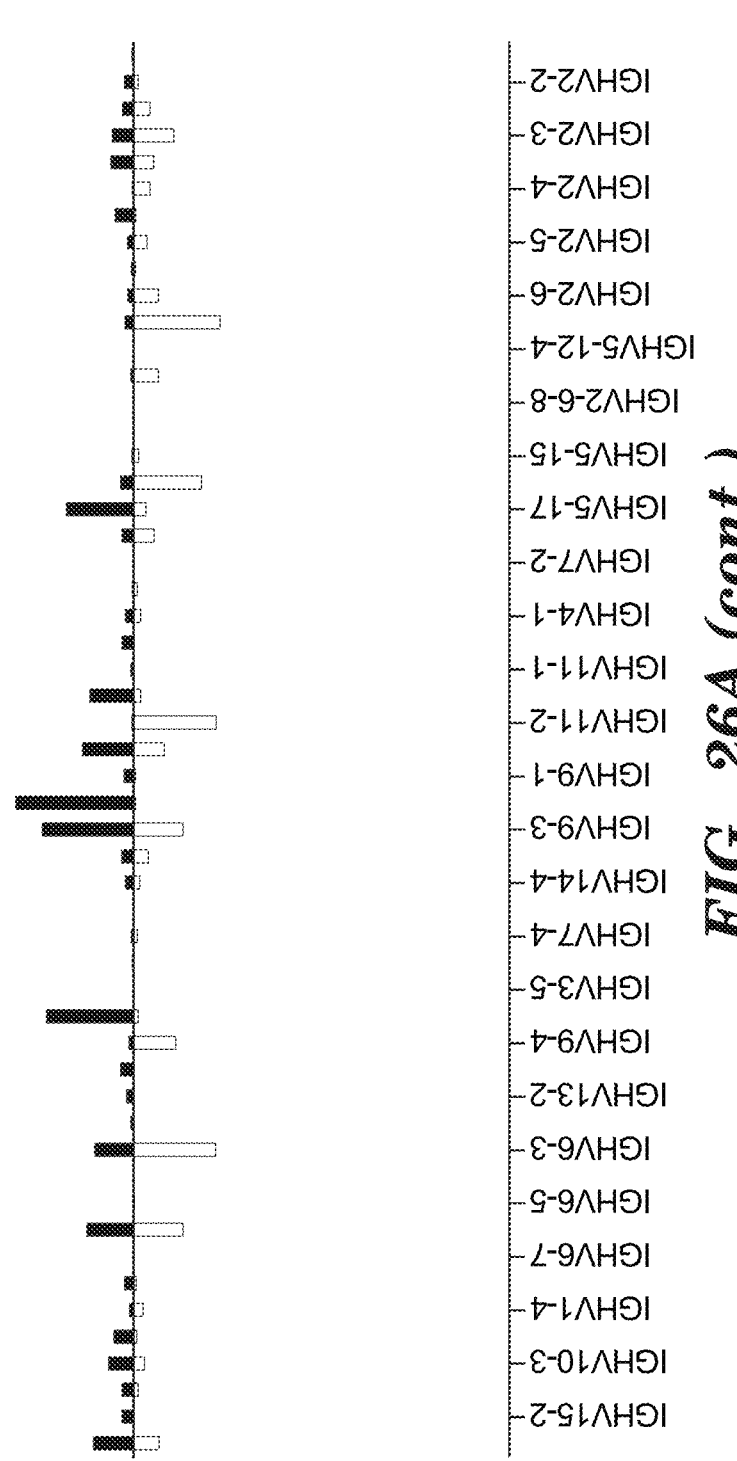
Figure 26B:
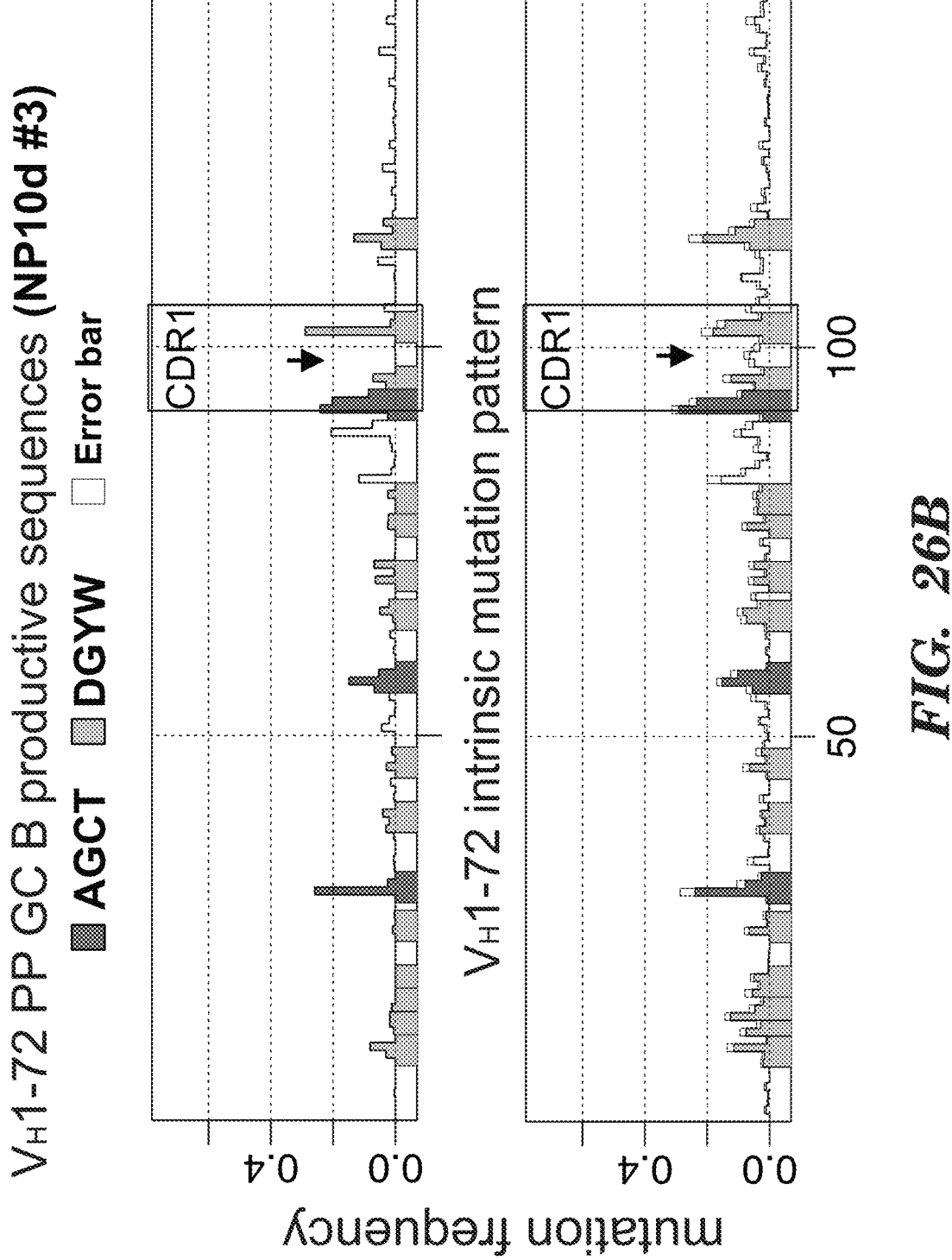
FIG. 26B depicts the SHM pattern of V$_H$1-72 in PP GC.
Figure 26B:
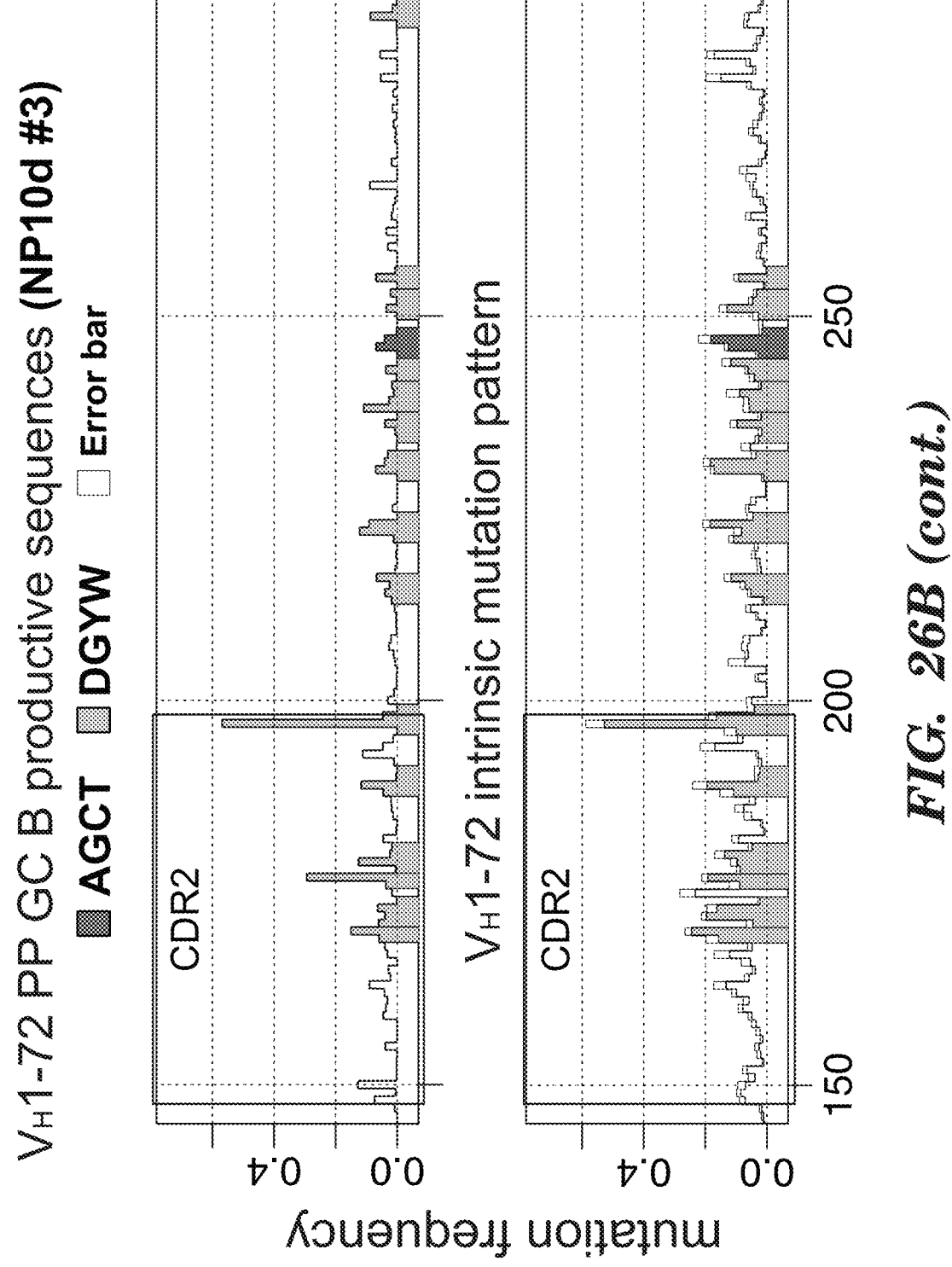

On the contrary, the GC $V_H$ repertoire of PPs was very different from that of spleen in each mouse (FIG. 20B, FIG. 26A), with a low correlation coefficient (r=0.56). NP-specific selection was not detected in PP GC as expected from the route of immunization. Specifically, $V_H$1-72 usage in PP GC was minimal in two mice and enriched in the third one compared to naïve B repertoire (FIG. 26A) but without the key mutation at position 98 (FIG. 26B) that increases NP binding affinity. Thus, PP GC and splenic GC are responding to different sources of stimuli. While the splenic GC $V_H$ repertoires only varied slightly among different NP-CGG immunized mice, the PP GC $V_H$ repertoires are highly variable from mouse to mouse (FIG. 20B, FIG. 26A), indicating PP GC repertoire is shaped by a pool of diverse antigens that appear to fluctuate between co-housed mice, likely commensal flora-associated antigens. Alternatively, it might be explained by antigen non-specific BCR diversification, as the case in the PP GCs from chicken, sheep and rabbits[13-15].

VDJ Selection Underlies PP GC Response

Figure 21A:
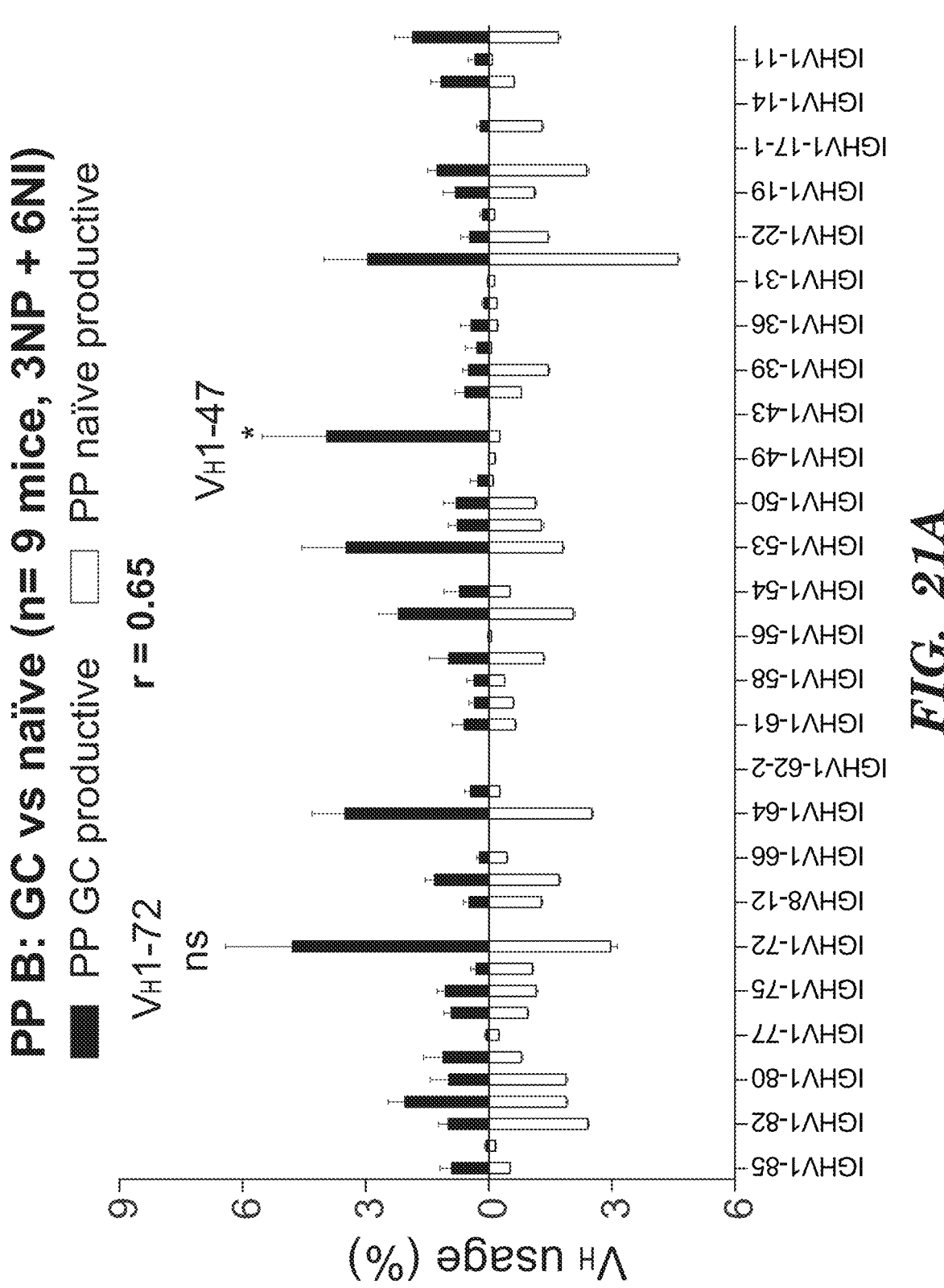
FIGS. 21A-21D depict V$_H$ usage of PP GC vs naïve B cells, and clonotype (CDR3) selection from WT and AID–/– C57BL/6 mice.
Figure 21A:
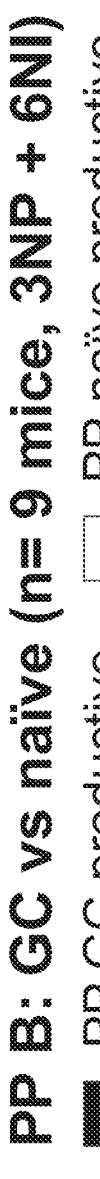
Figure 21A:
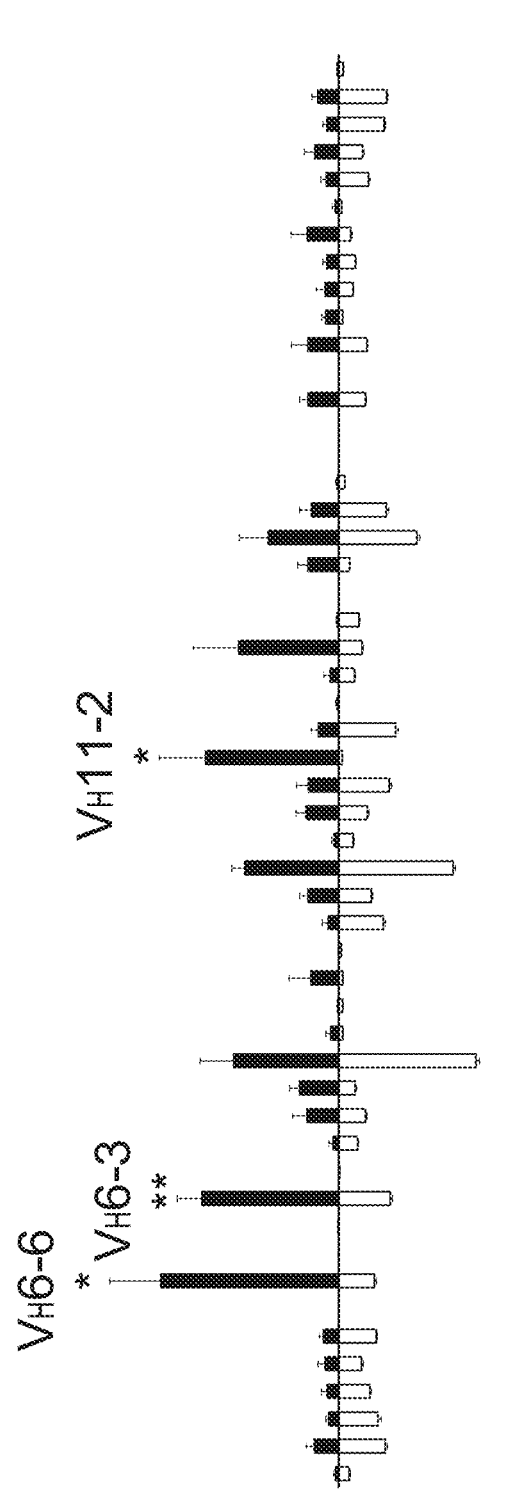
Figure 21B:
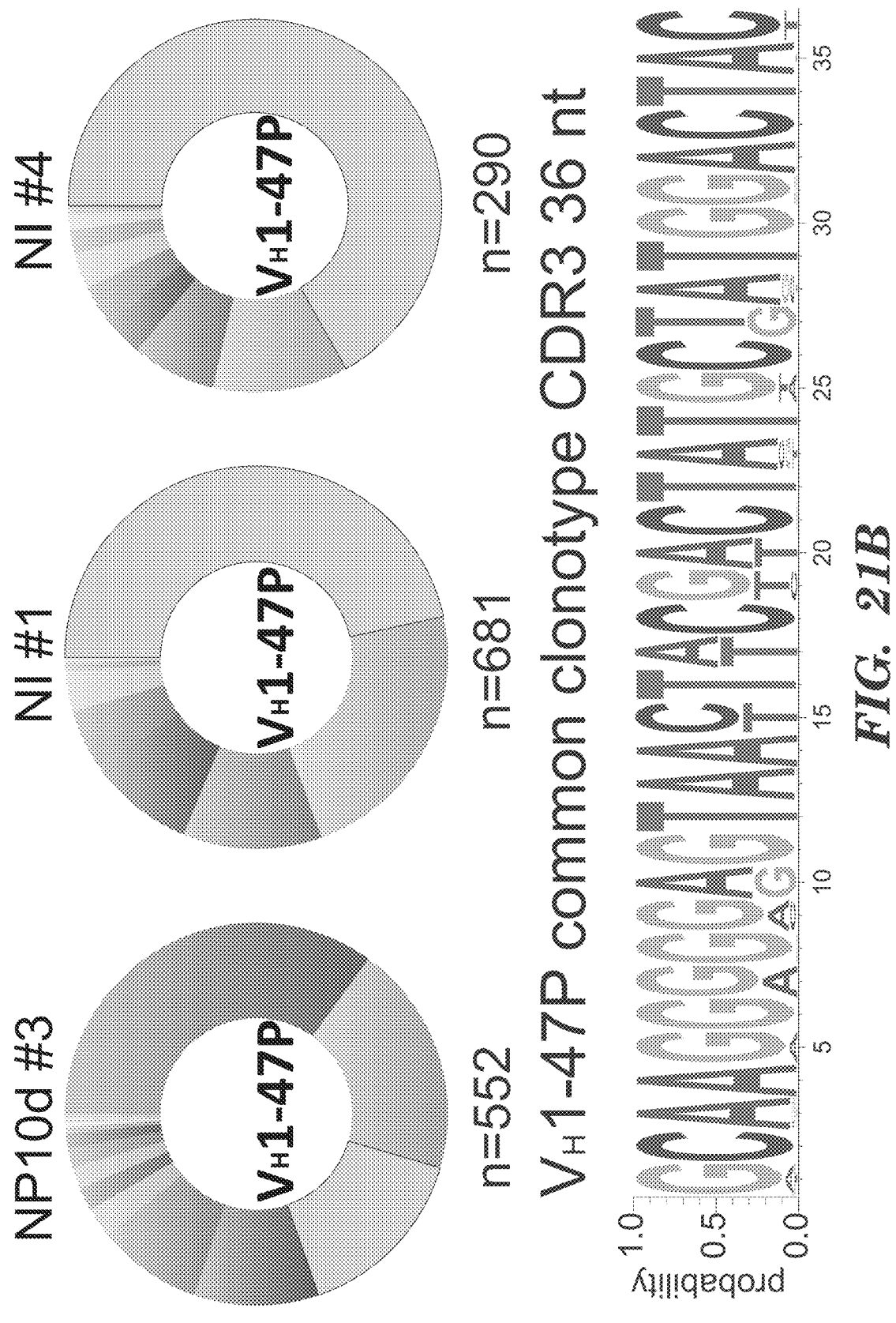
Figure 21C:
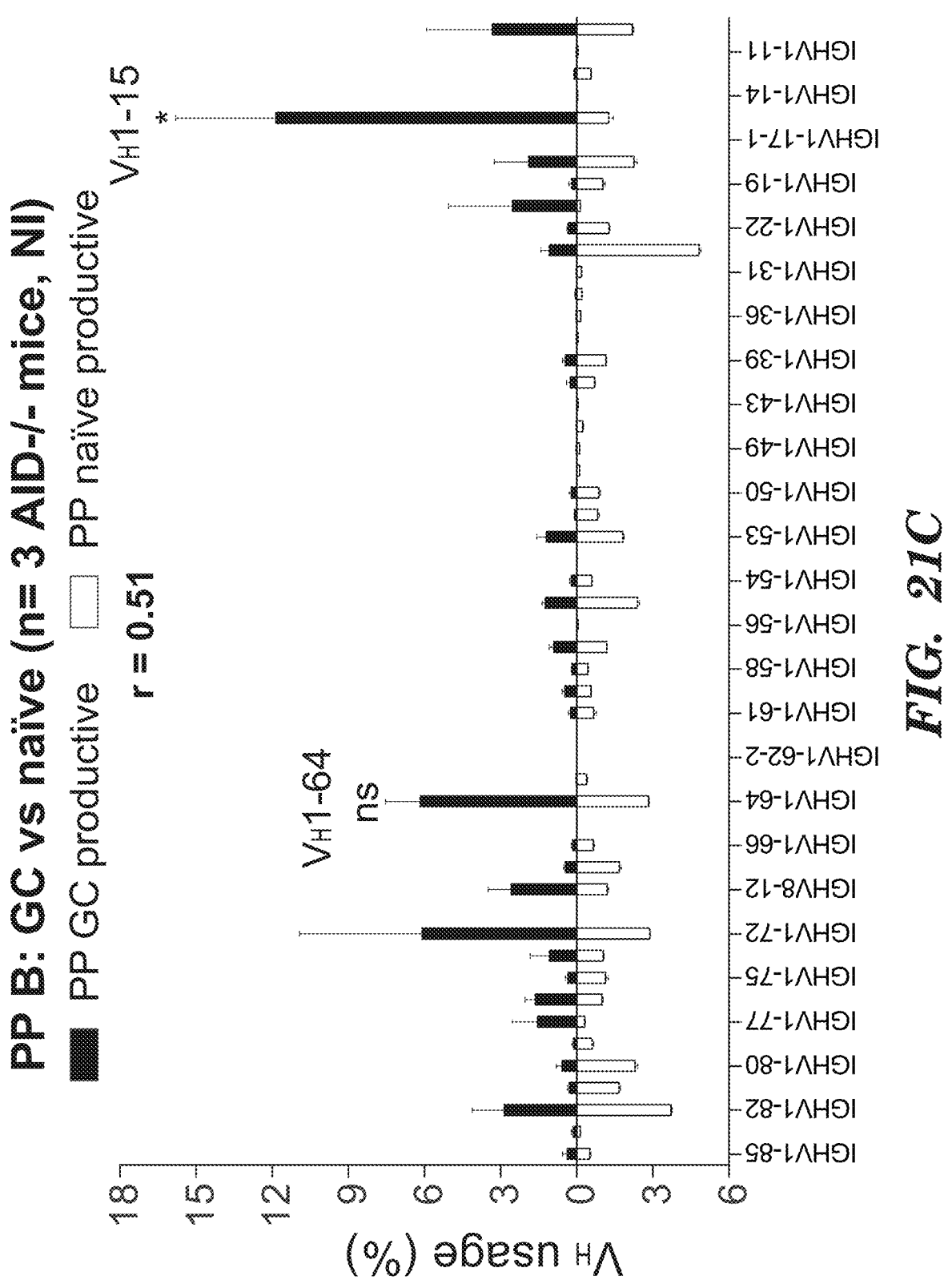
Figure 21C:
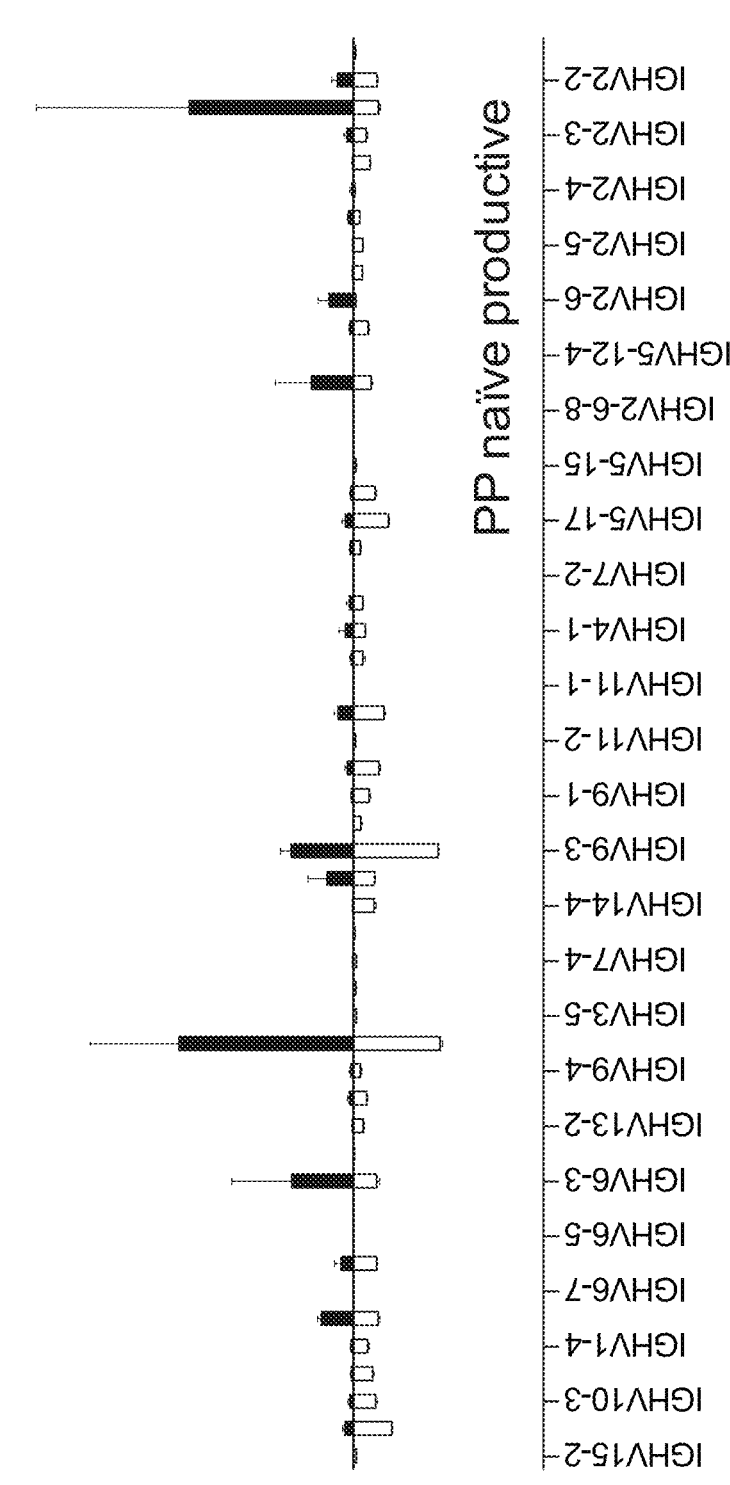
Figure 27A:
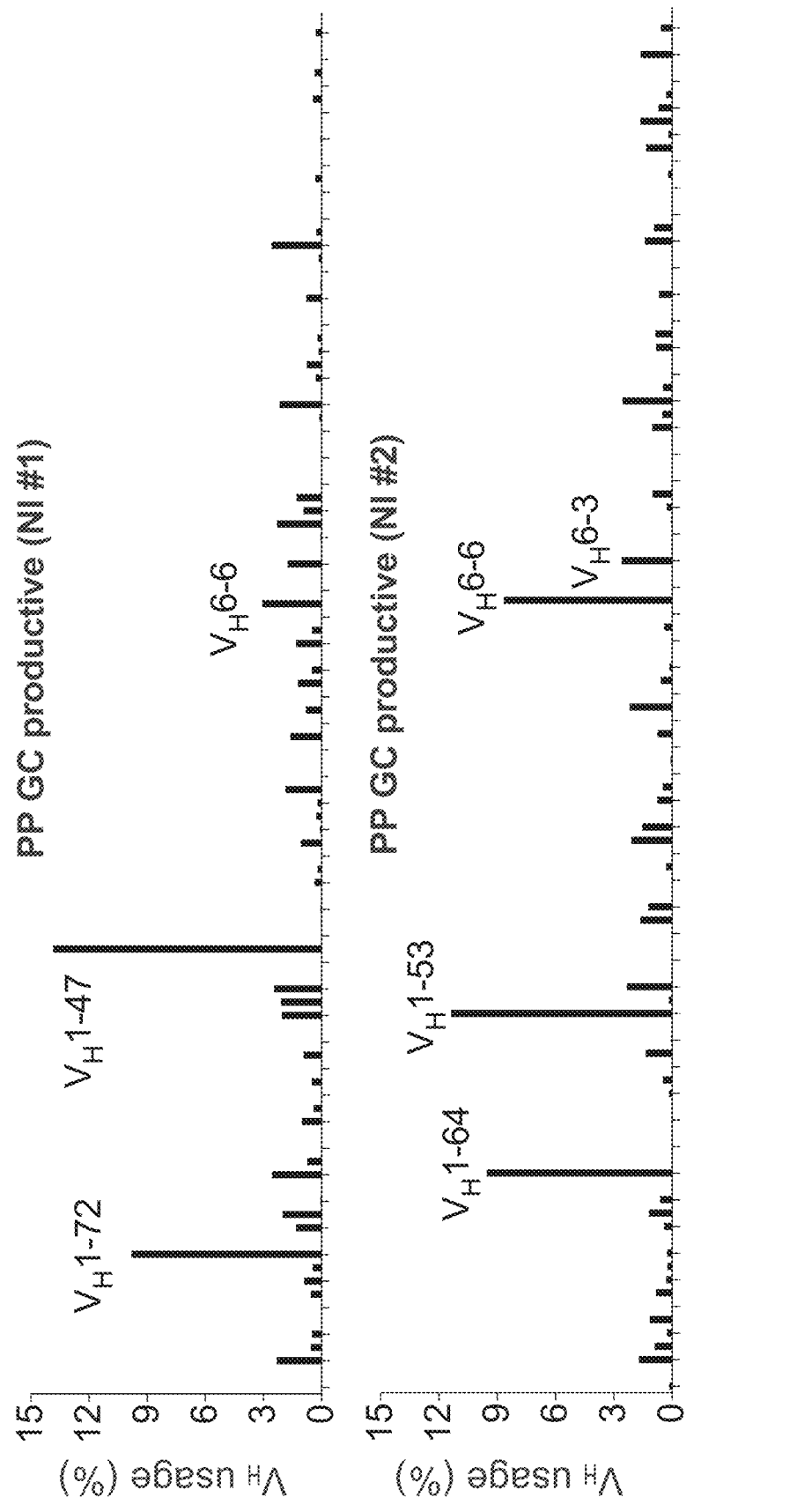
FIGS. 27A-27B depict V$_H$ usage and V$_H$11-2 clonotype selection of PP GC vs naïve B cells from individual unimmunized mice.
Figure 27A:
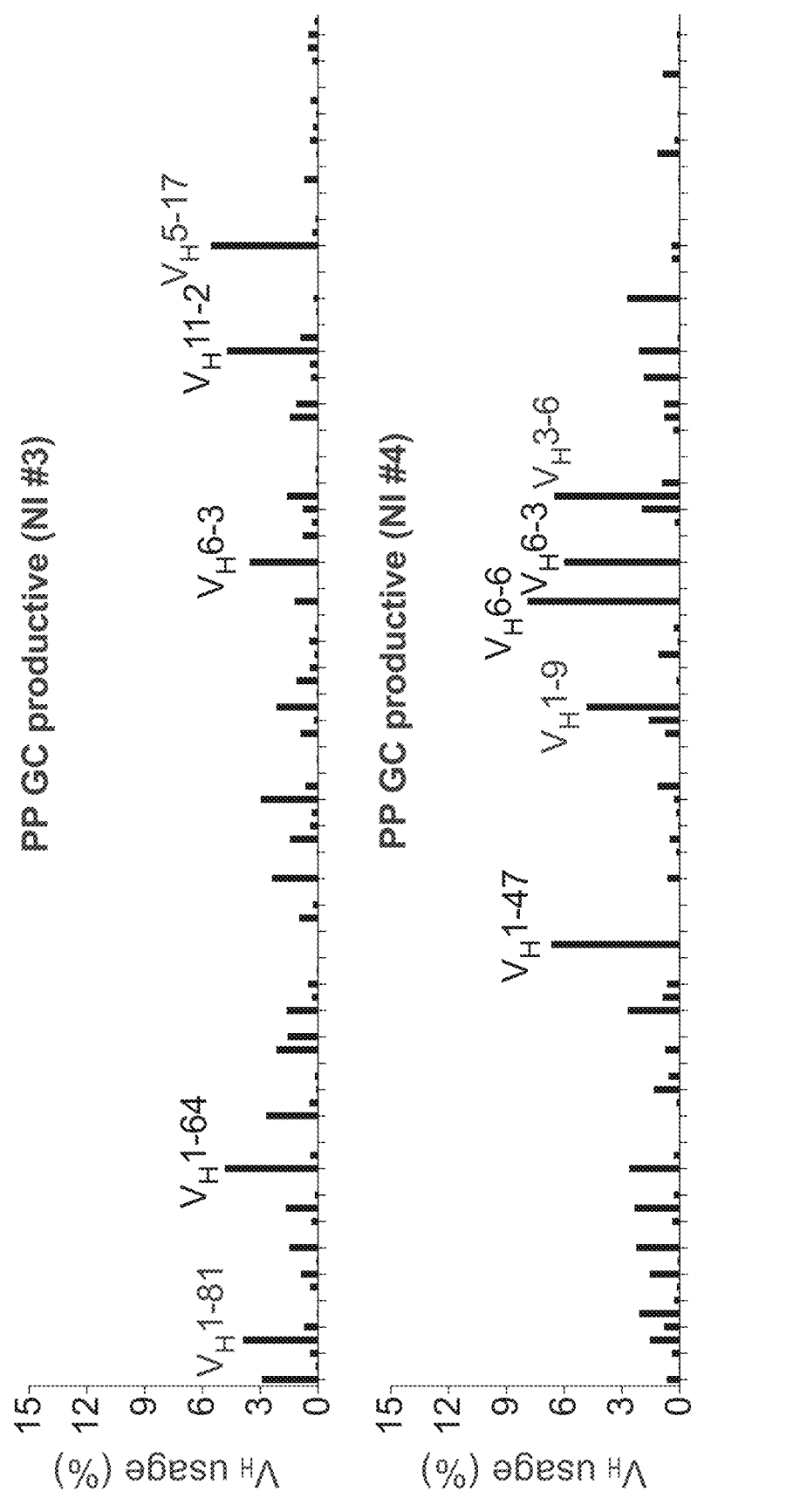
Figure 27A:
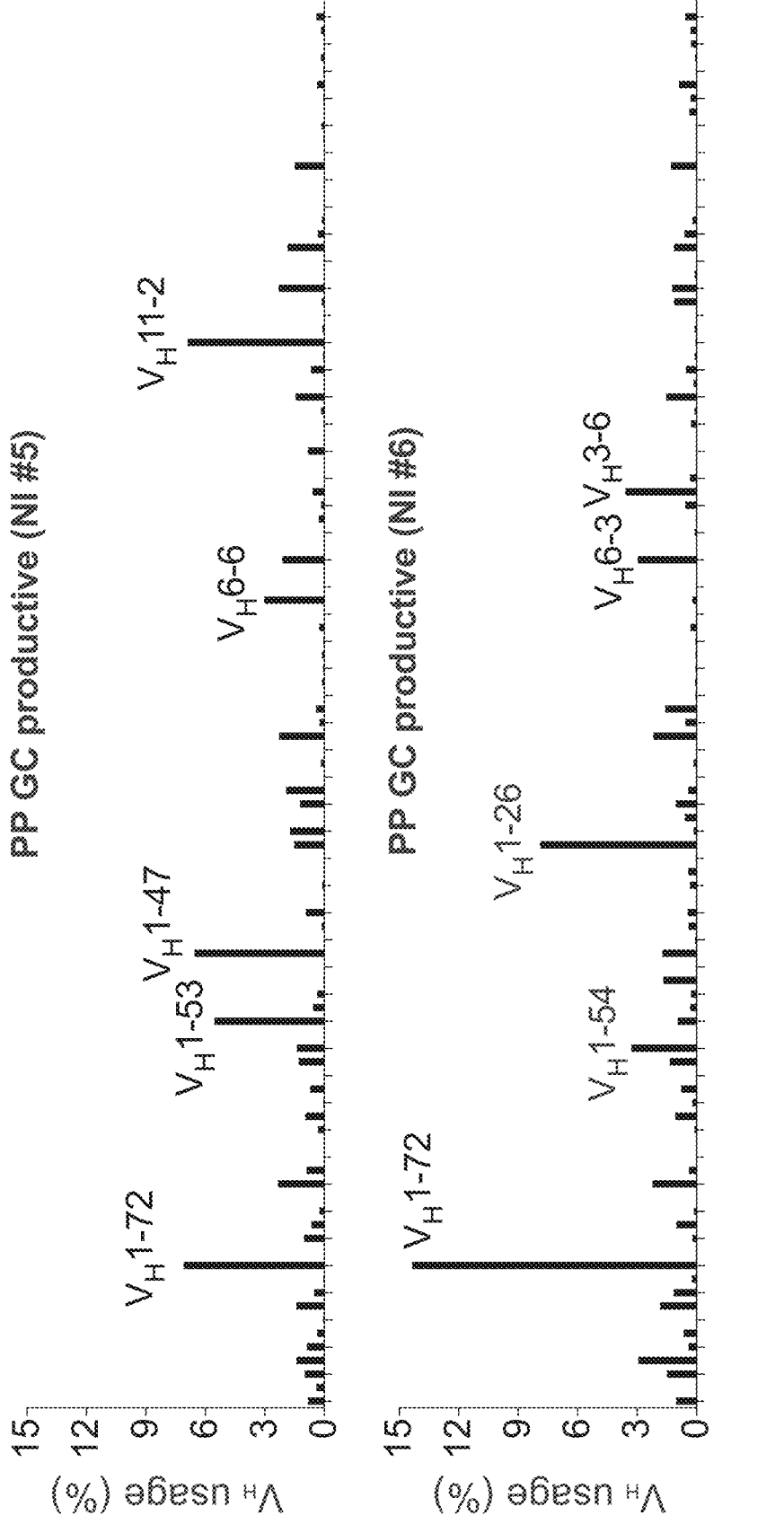
Figure 27B:
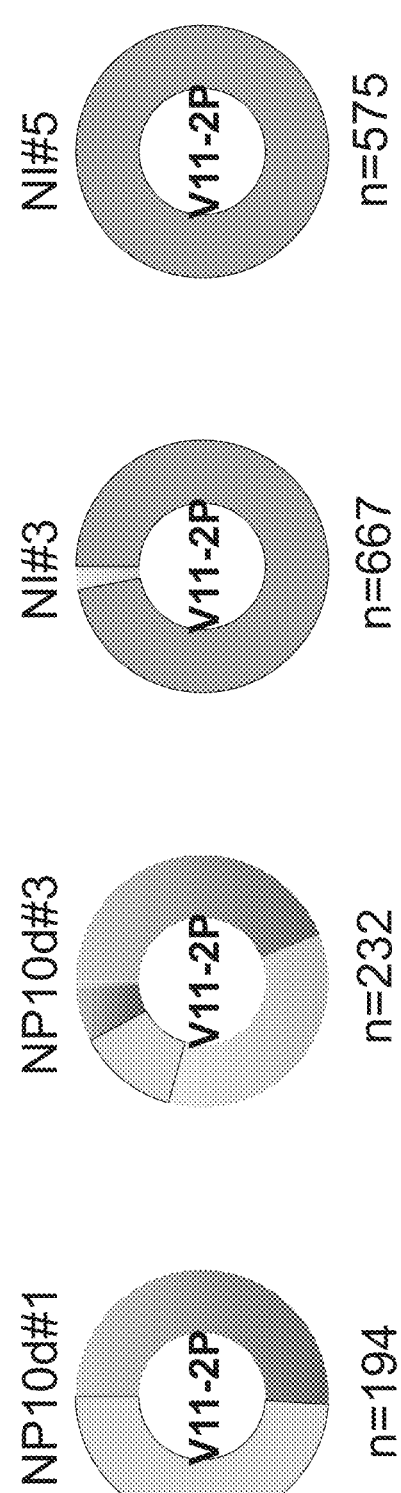

Given the relative big variation in PP GC repertoire across mice, to understand whether clonal selection plays a role in PP GC formation and function, the PP repertoire from six more naïve mice was assayed. Since NP-CGG IP immunization did not stimulate PP GC response, the NP-CGG-immunized mice were included with the six naïve mice for the analysis of PP GC versus naïve IgH repertoire. If there were no BCR-dependent clonal selection in PP GC, random enrichment of $V_{HS}$ for each mouse would be expected and thus the average $V_H$ repertoire from nine mice would resemble the common naïve B cell repertoire. Instead, the correlation coefficient between PP GC and naïve $V_H$ repertoire is low (r=0.65), with significant enrichment of several $V_{HS}$ ($V_H$1-47, $V_H$11-2, $V_H$6-6, $V_H$6-3) (FIG. 21A, FIG. 27A). Note that $V_H$1-47 and $V_H$11-2 were barely present in the naïve repertoire, with an average 14.3 fold and 43.6 fold increase respectively in their usage in PP GC repertoire. The frequency of $V_H$6-6 and $V_H$6-3 went up by 5.2 and 2.6 fold. Specifically, $V_H$1-47 was greatly enriched in four mice and its top clonotype, which contained $D_H$2-1, $J_H$4 and a 36-nt CDR3, was shared by three mice (FIG. 21). $V_H$11-2 was enriched in four mice with the top two clonotypes each shared by two mice (FIG. 27B). Therefore, a strong BCR-dependent clonal selection underlies GC response in the PPs.

Figure 21D:
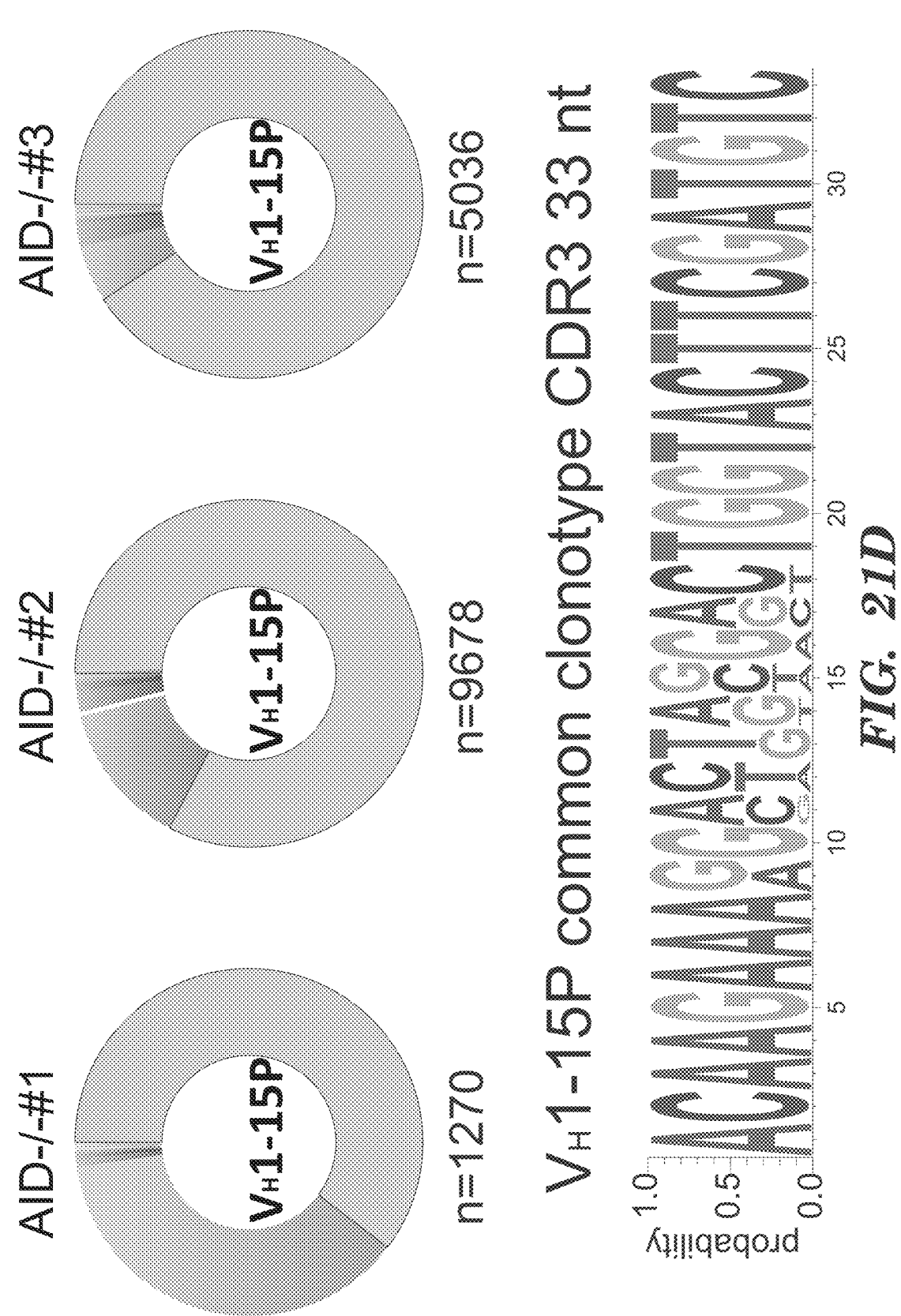
Figure 28B:
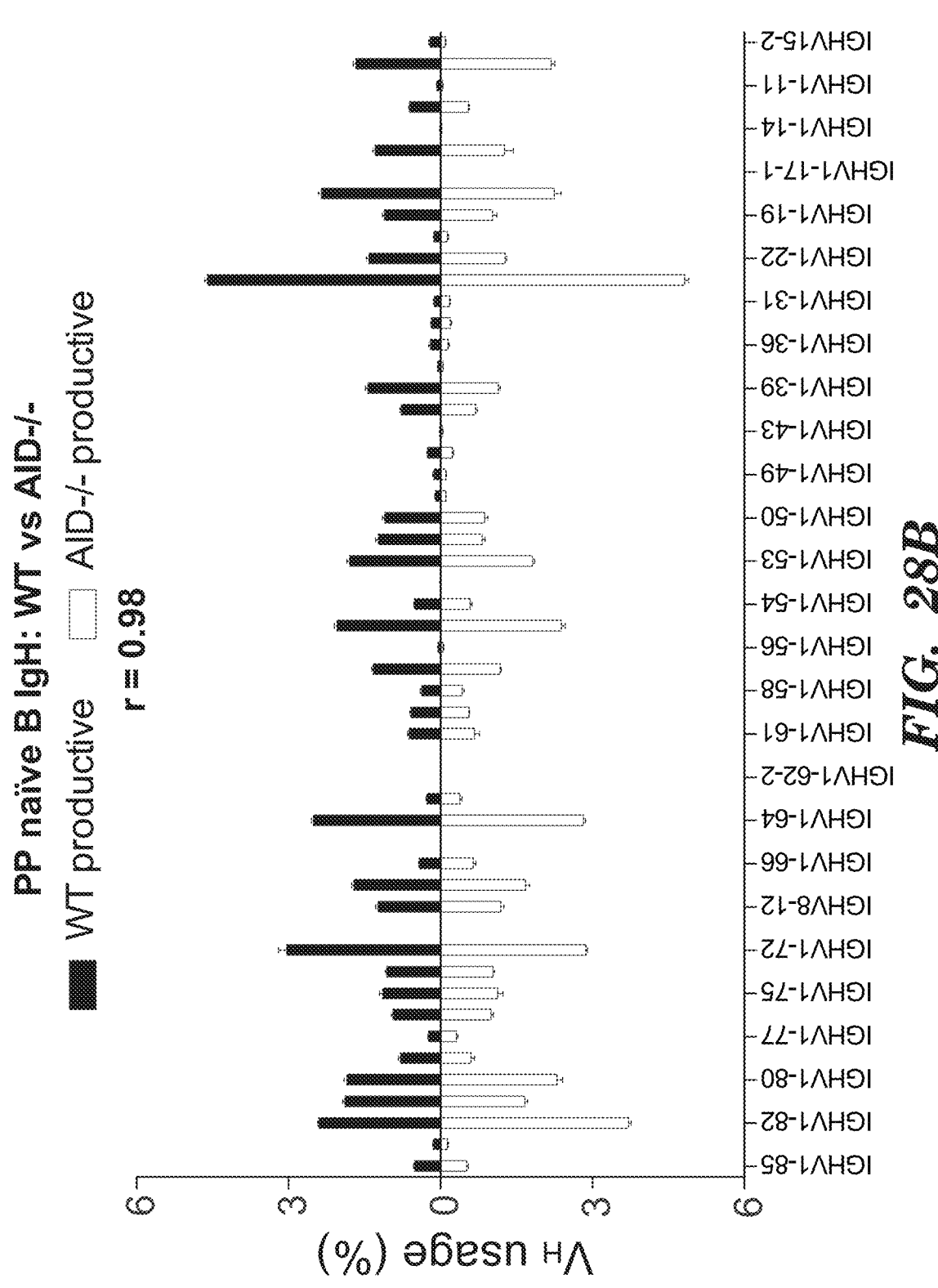
Figure 28B:
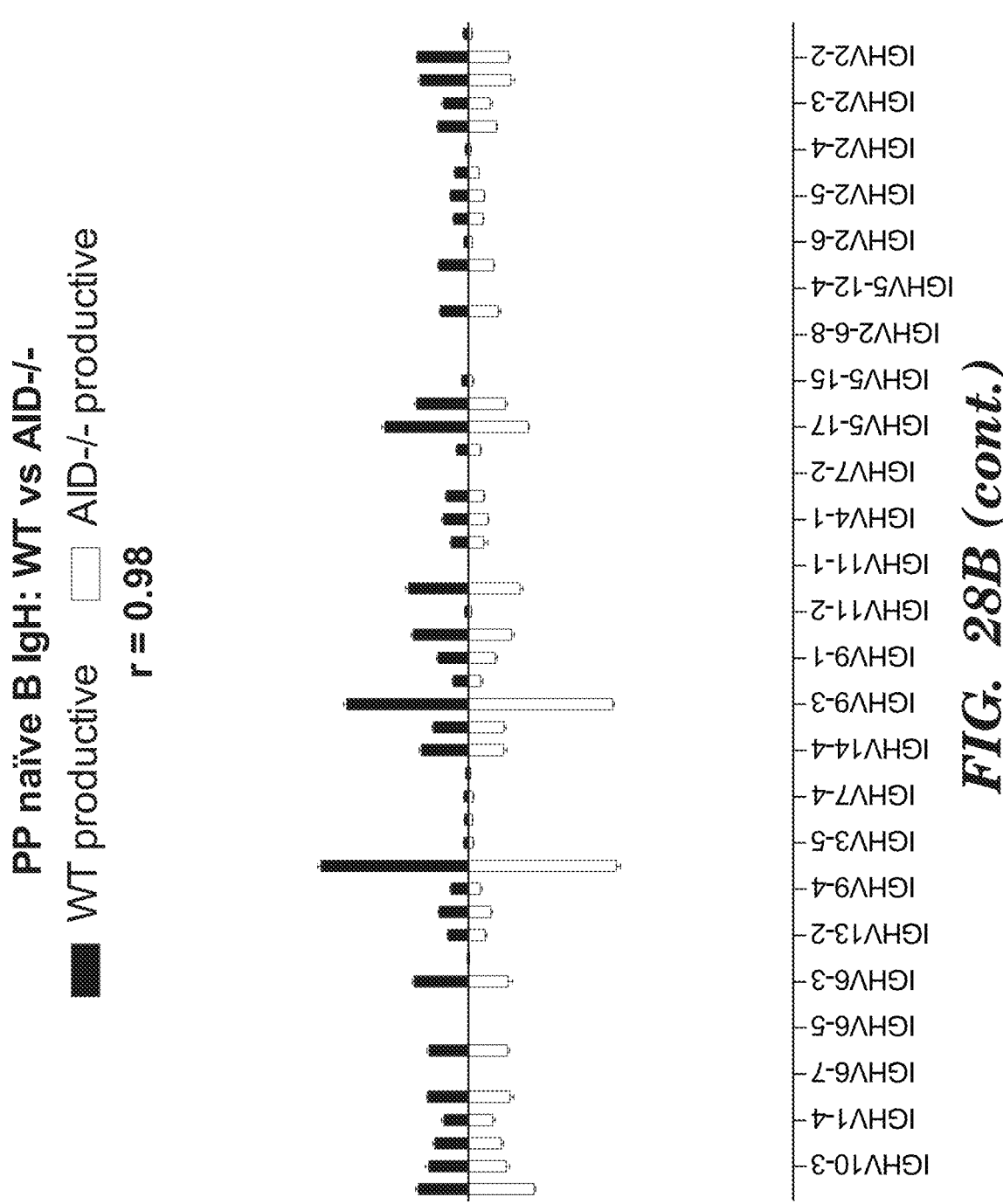
Figure 28C:
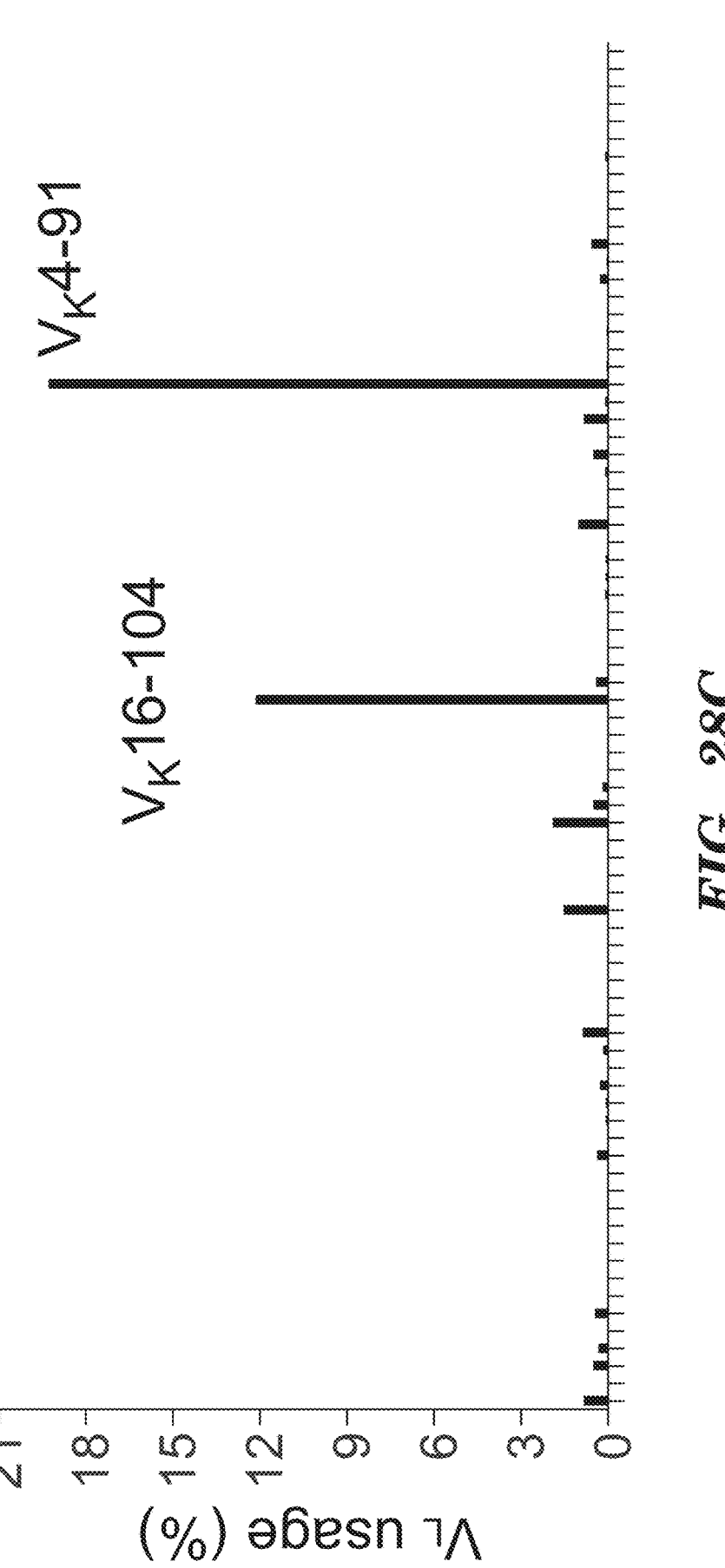
FIG. 28C depicts V$_L$ usage of PP GC vs naïve B cells from indicated AID–/– mouse.
Figure 28C:

This selection is not dependent on AID (FIG. 21C), which is specifically expressed in GC B cells[27], and its deficiency results in a defect in SHM and CSR[28,29] in mice and humans. CSR in PP preferentially generates IgA antibodies[30], the major Ig isoform guarding the gut mucosa system. In AID−/− mice, the $V_H$ repertoire of PP GC was again highly variable compared to the naïve repertoire (r=0.51) (FIG. 21C, FIG. 28A), with significant selection of $V_H$1-15, the top clonotype of which was shared by all three mice assayed (FIG. 21D). This clonotype contained a 33-nt CDR3 with $J_H$1 and several possible $D_{HS}$. Thus, the clonal selection in PP GCs can occur in the absence of SHM or CSR. Note that the VDJ selection pattern in PP GC of AID−/− mice appeared different from that of WT mice, even though they shared the same naïve repertoire (r=0.98) (FIG. 28B). It has been reported that AID deficiency results in GC hyperplasia in PP with a 100-fold expansion of anaerobic flora in the small intestine[31,32]. In this regard the different clonotype patterns of WT and AID−/− PP GC B cells may reflect the known differences in their gut flora composition.

Local Antigens Shape Single PP GC Pool 6-12 PPs were typically found in a C57BL/6 mouse, distributed along the length of small intestine[33]. It is known that the composition of gut microflora alters at different locations along the gastrointestinal (GI) tract, with more aerobic species in the upper intestine and anaerobes clustered in the lower intestine and large intestine[31]. As an example, segmented filamentous bacteria (SFB) were found to progressively increase in the proximal to distal direction along GI tract[34]. To understand whether PP GC response is affected by the local commensal bacteria, the HTGTS-V(D)J SHM-seq approach was used to look at GC and naïve B cell repertoire from individual PPs in the same mouse (FIG.

Figure 22A:
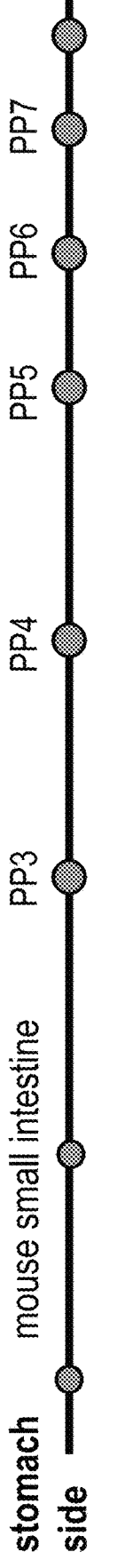
FIGS. 22A-22B depict V$_H$ usage of PP GC vs naïve B cells in different individual PP from the same mouse.
Figure 22B:
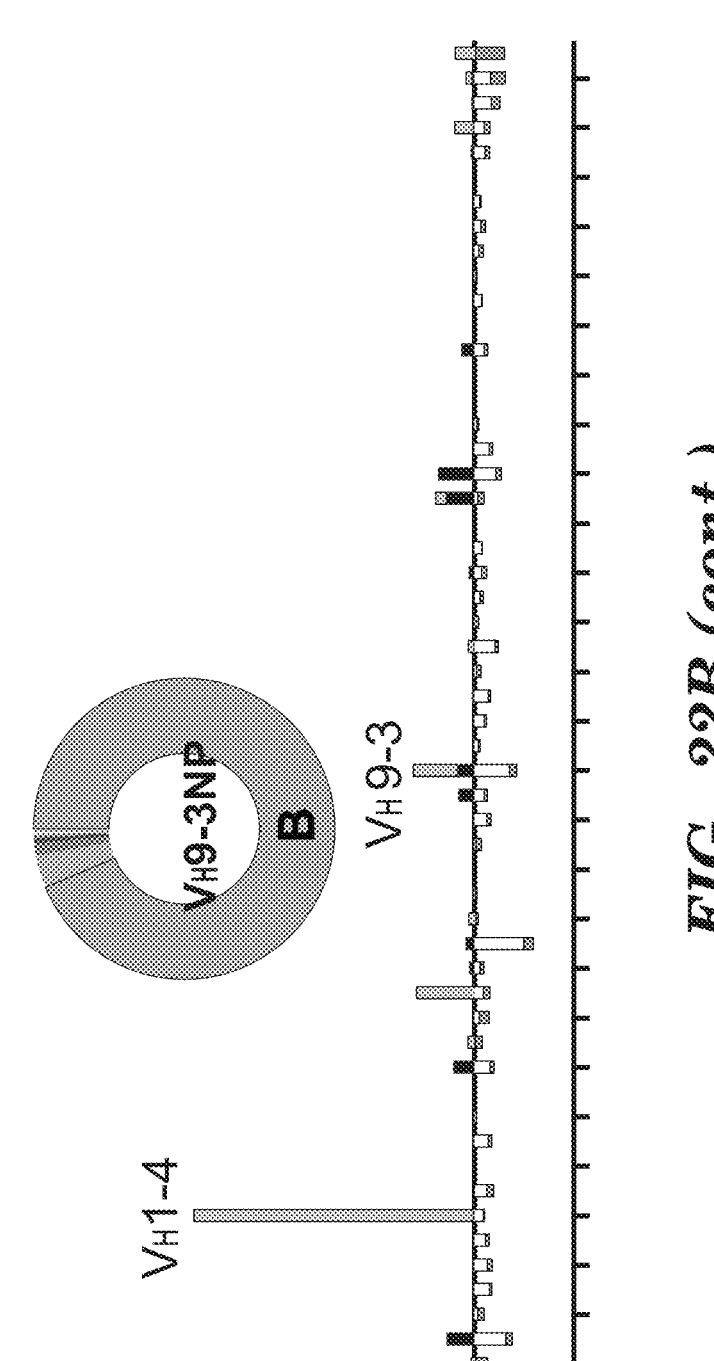
Figure 22B:
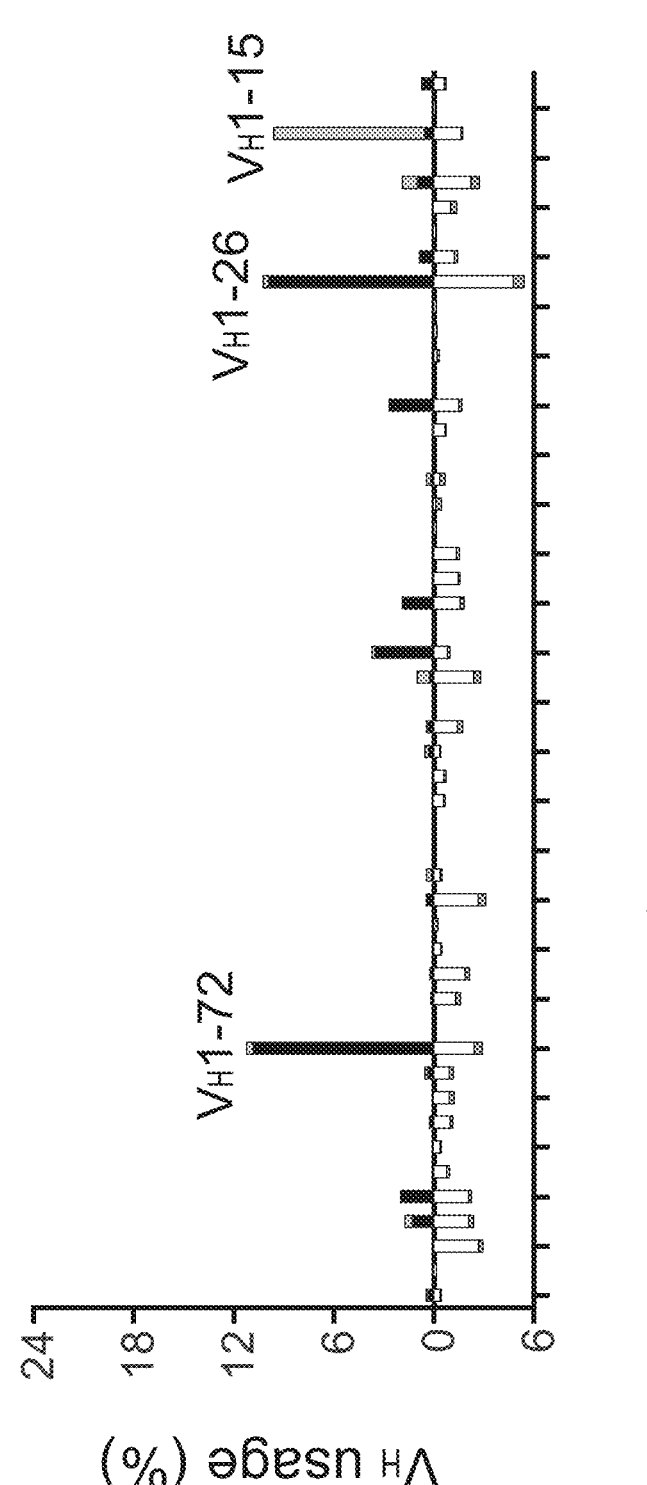
Figure 22B:
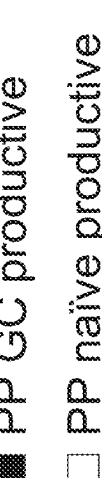
Figure 22B:
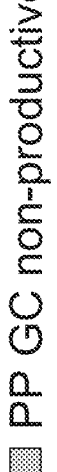
Figure 22B:
Figure 22B:
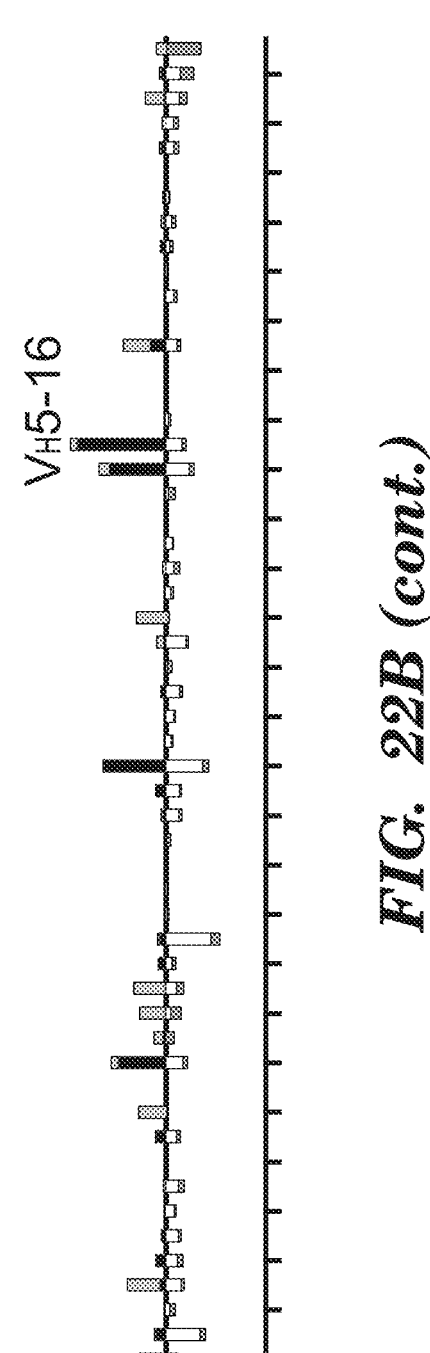
Figure 22B:
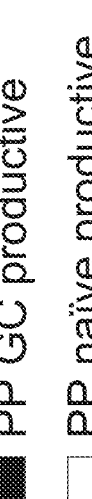
Figure 22B:
Figure 22B:
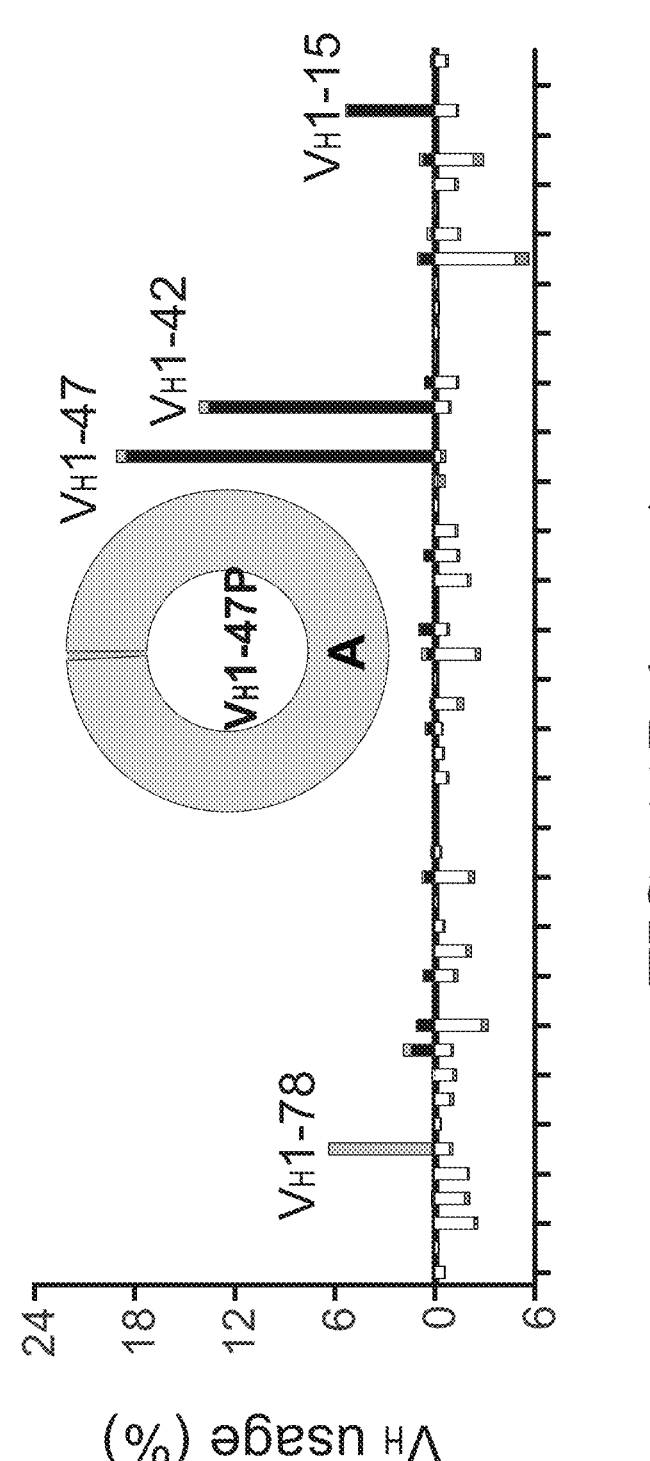
Figure 22B:
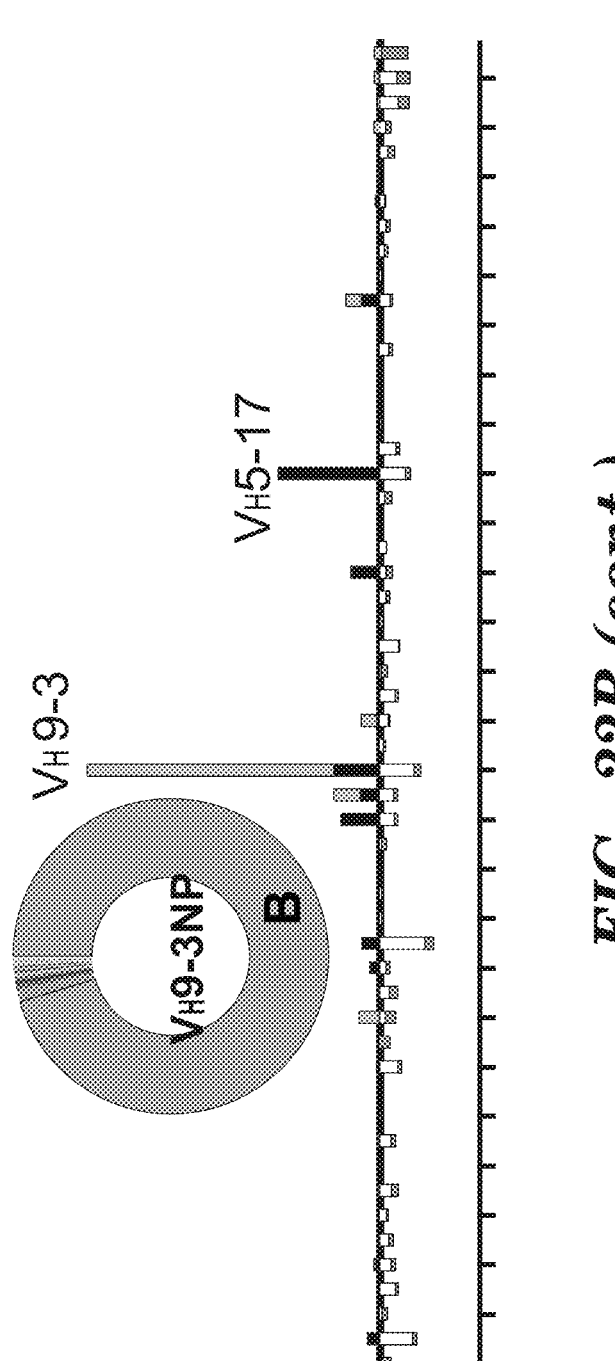
Figure 22B:
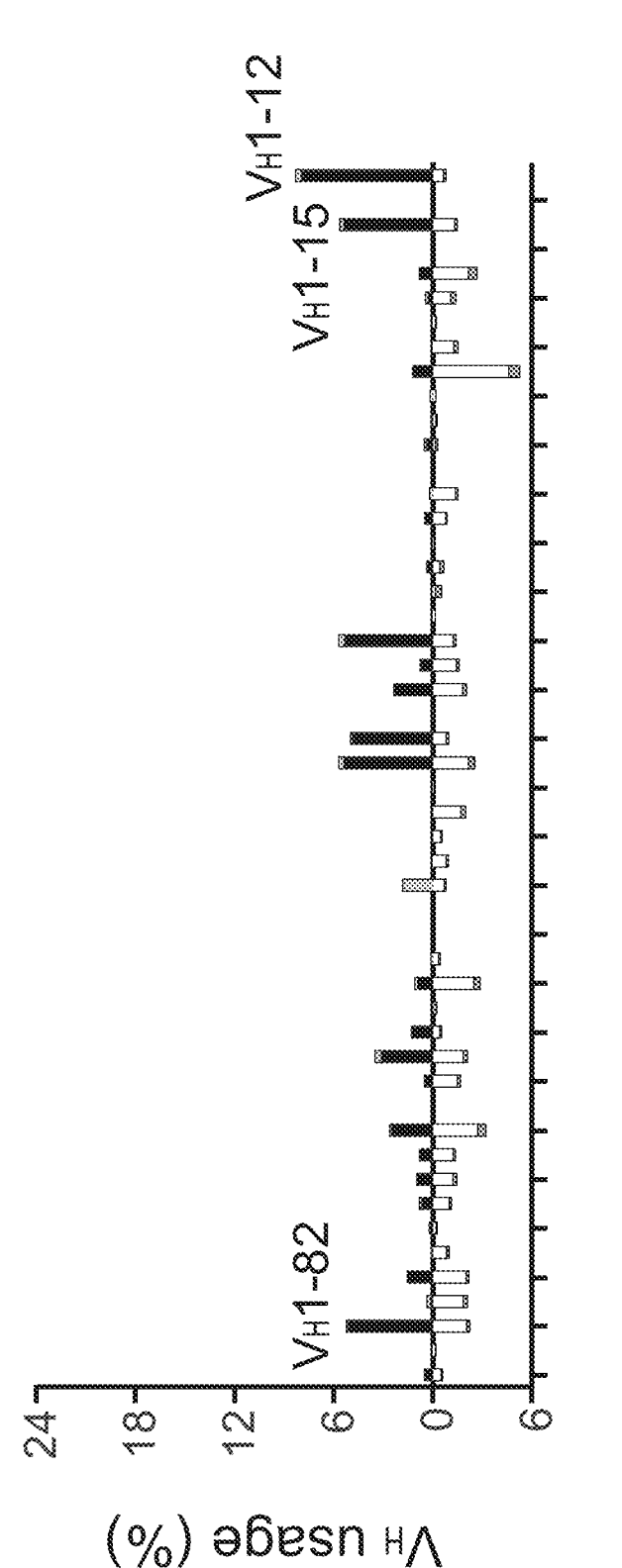
Figure 22B:
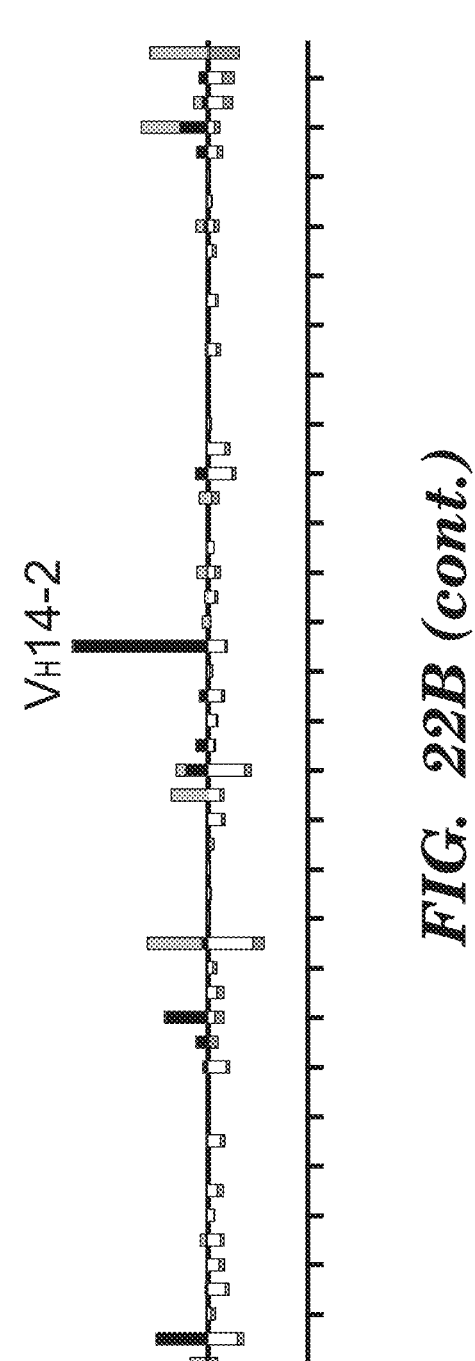
Figure 22B:
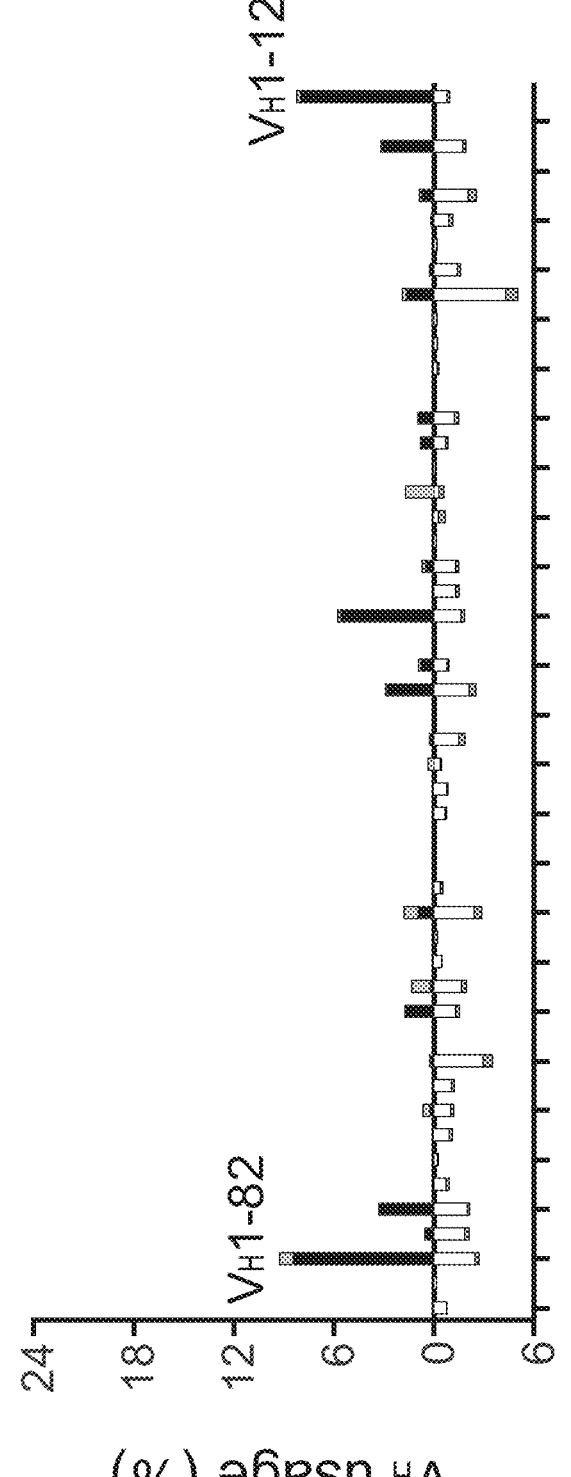
Figure 22B:
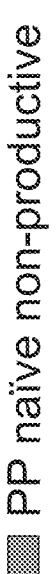
Figure 22B:
Figure 22B:
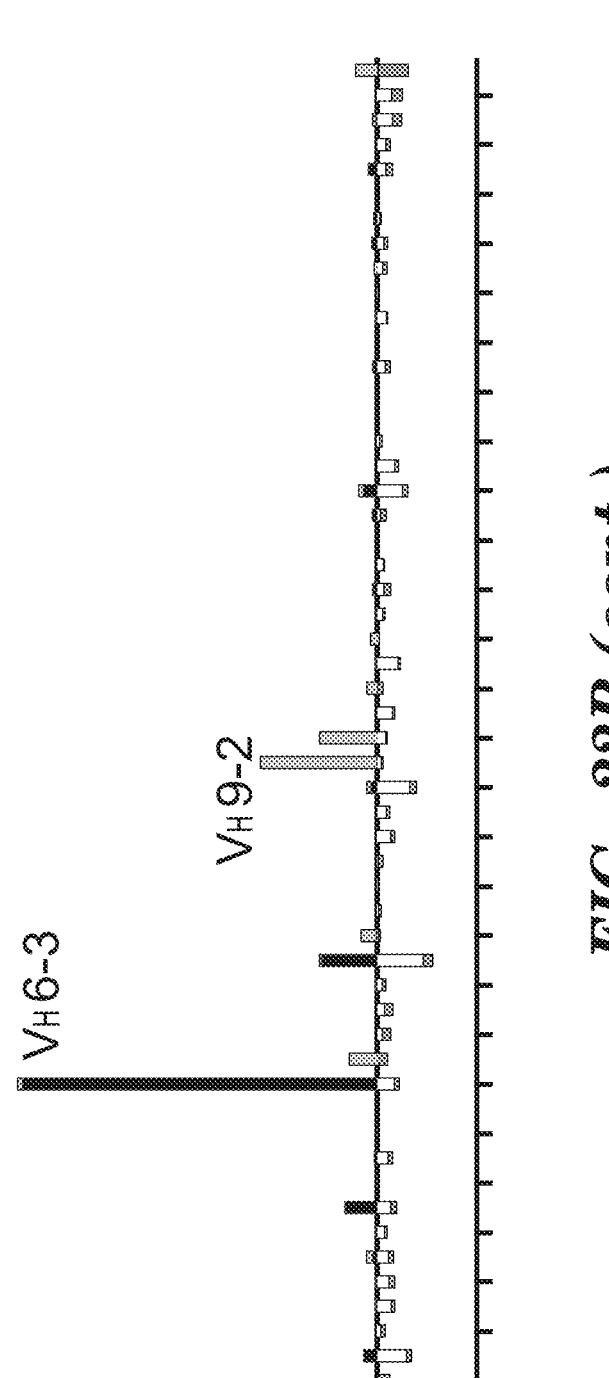

22A). The overall GC $V_H$ composition was highly variable among the five consecutive single PPs, despite their identical naïve repertoire (FIG. 22B). Nevertheless, several $V_{HS}$ were found to enrich in more than one PP: $V_H$1-47 in PP3 and PP5, $V_H$1-15 in PP5 and PP6, $V_H$1-82 and $V_H$1-12 in PP6 and PP7 (FIG. 22B), confirming an antigen-specific BCR selection in PP GCs. A distance effect was observed for this selection, where $V_H$1-47 was dominantly utilized in the more proximal PPs and $V_H$1-15, $V_H$1-82 and $V_H$1-12 were mostly involved in the distal PPs, likely correlated with the change of microflora species along the small intestine.

Interestingly, PP3 and PP5 shared a common clonotype for productive $V_H$1-47 (A) and nonproductive $V_H$9-3 (B) (FIG. 22B). The frequency of A and B was equal in either PP3 or PP5, indicating they were the two alleles from the same BCR clone that circulated between PPs and got selected against certain antigen in these two PPs. This is strong evidence for B cell exchange between PPs in the same mouse. In support of this view, both naïve and memory B cells have been reported to circulate among PPs by photo-conversion experiments[26]. Thus, it is demonstrated herein that BCR-dependent GC selection occurs in PPs both at the level of whole PPs from different mice and single PPs from the same mouse.

Selected BCRs Accumulate Intrinsic SHMs

Figure 23:
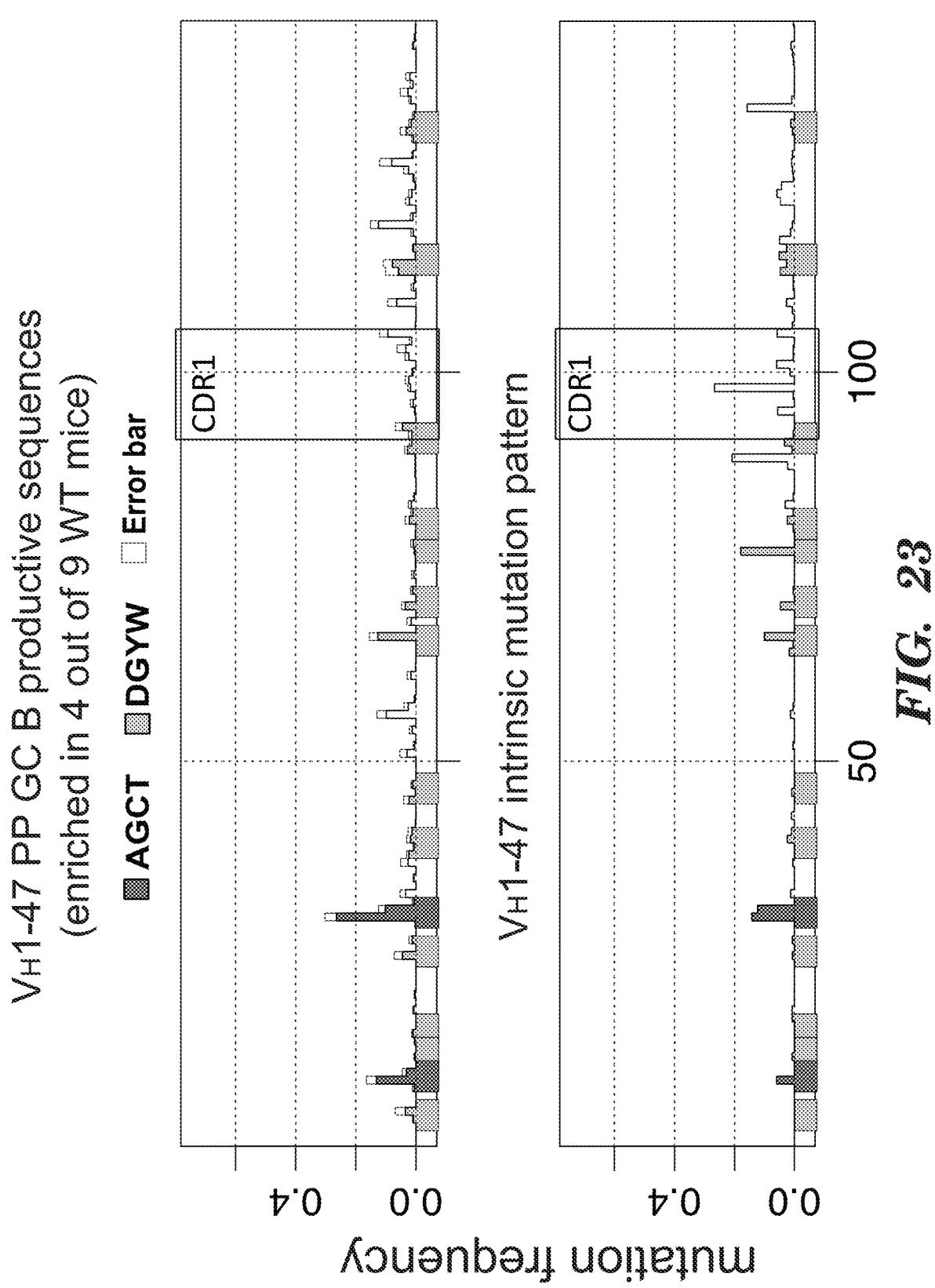
FIG. 23 demonstrates that the most highly enriched V$_H$1-47 and V$_H$11-2 in PP GCs did accumulate mutations but did not show any recurrent selection in CDR region mutations.
Figure 23:
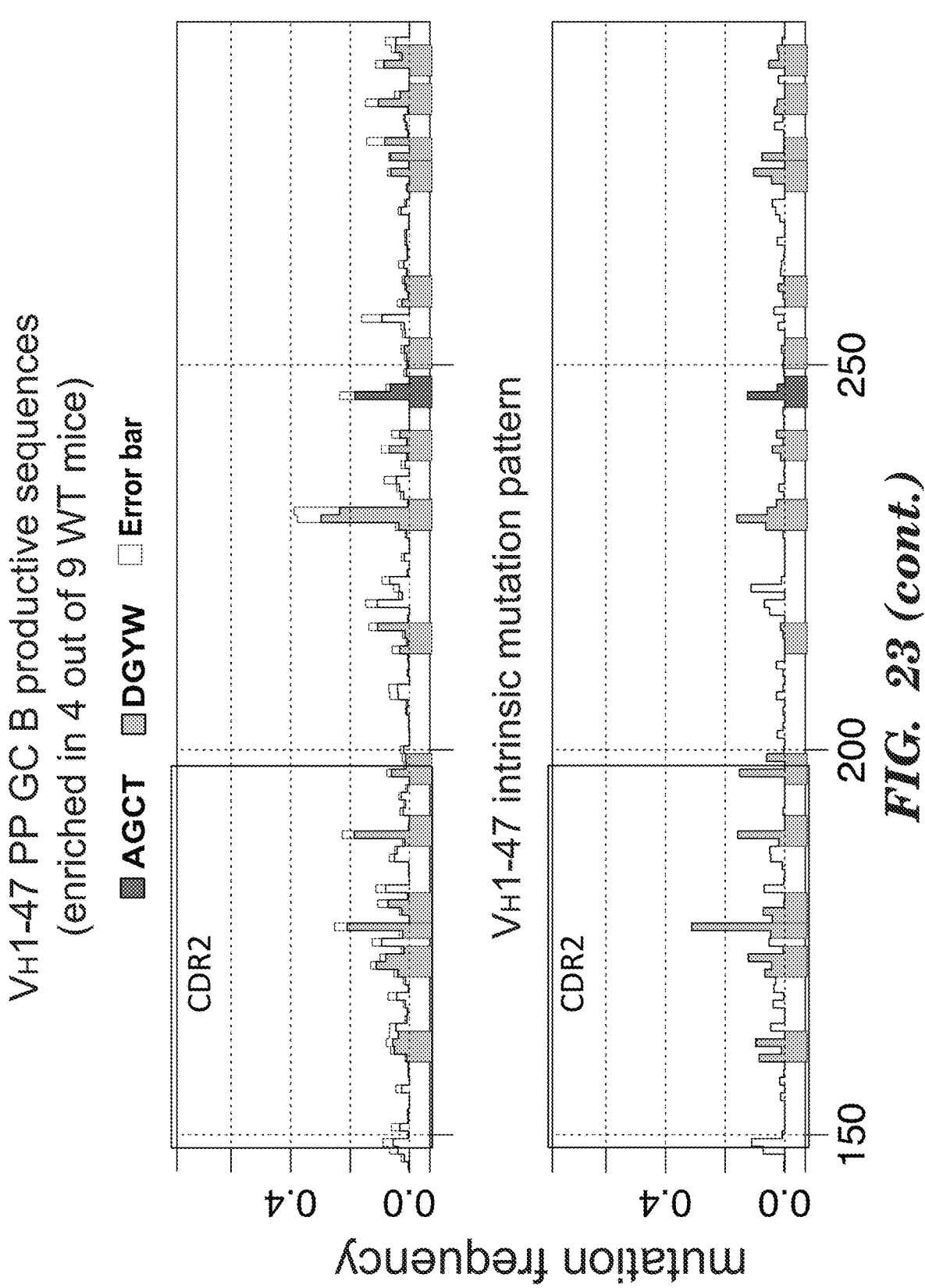
Figure 23:
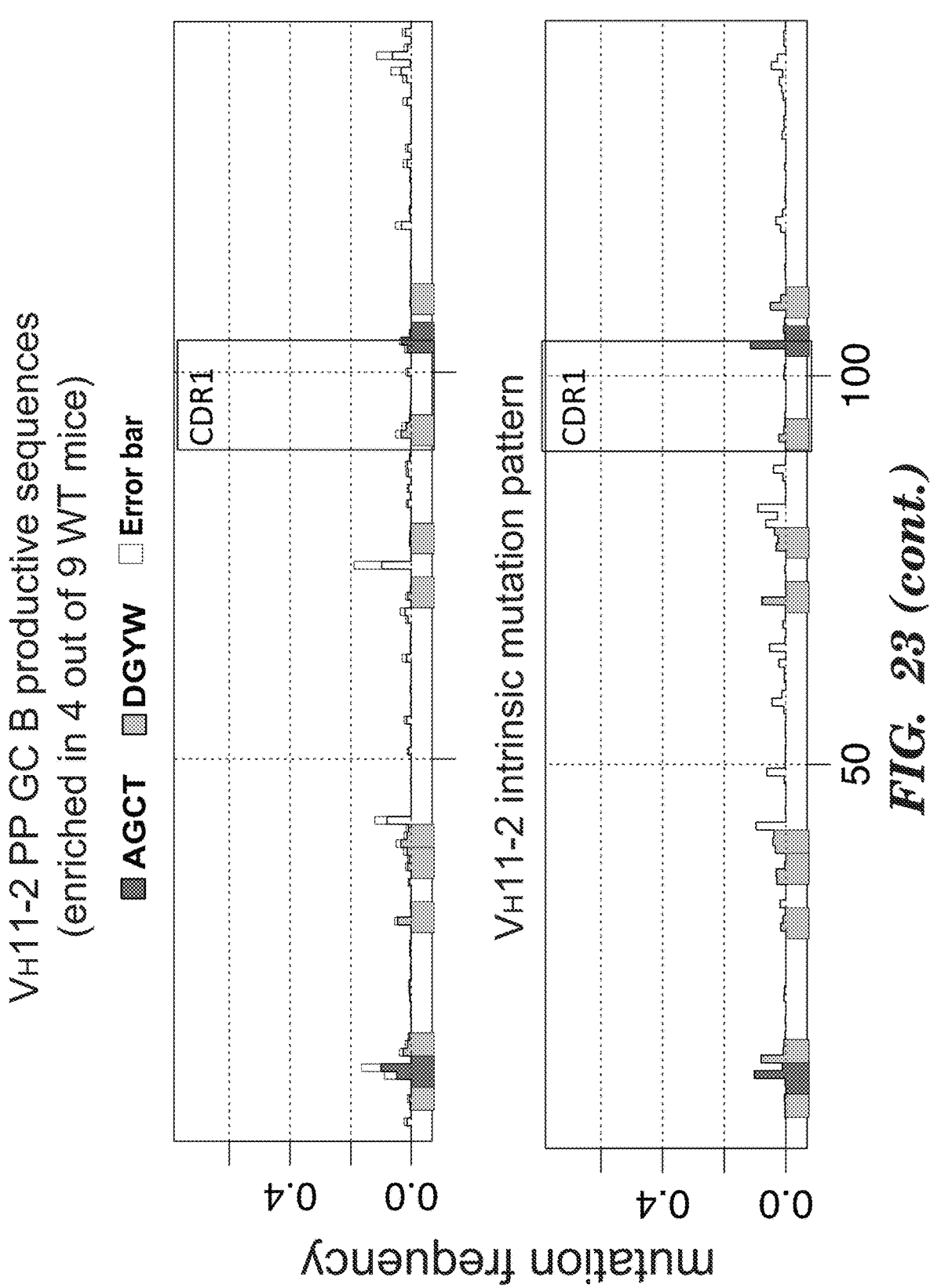
Figure 23:
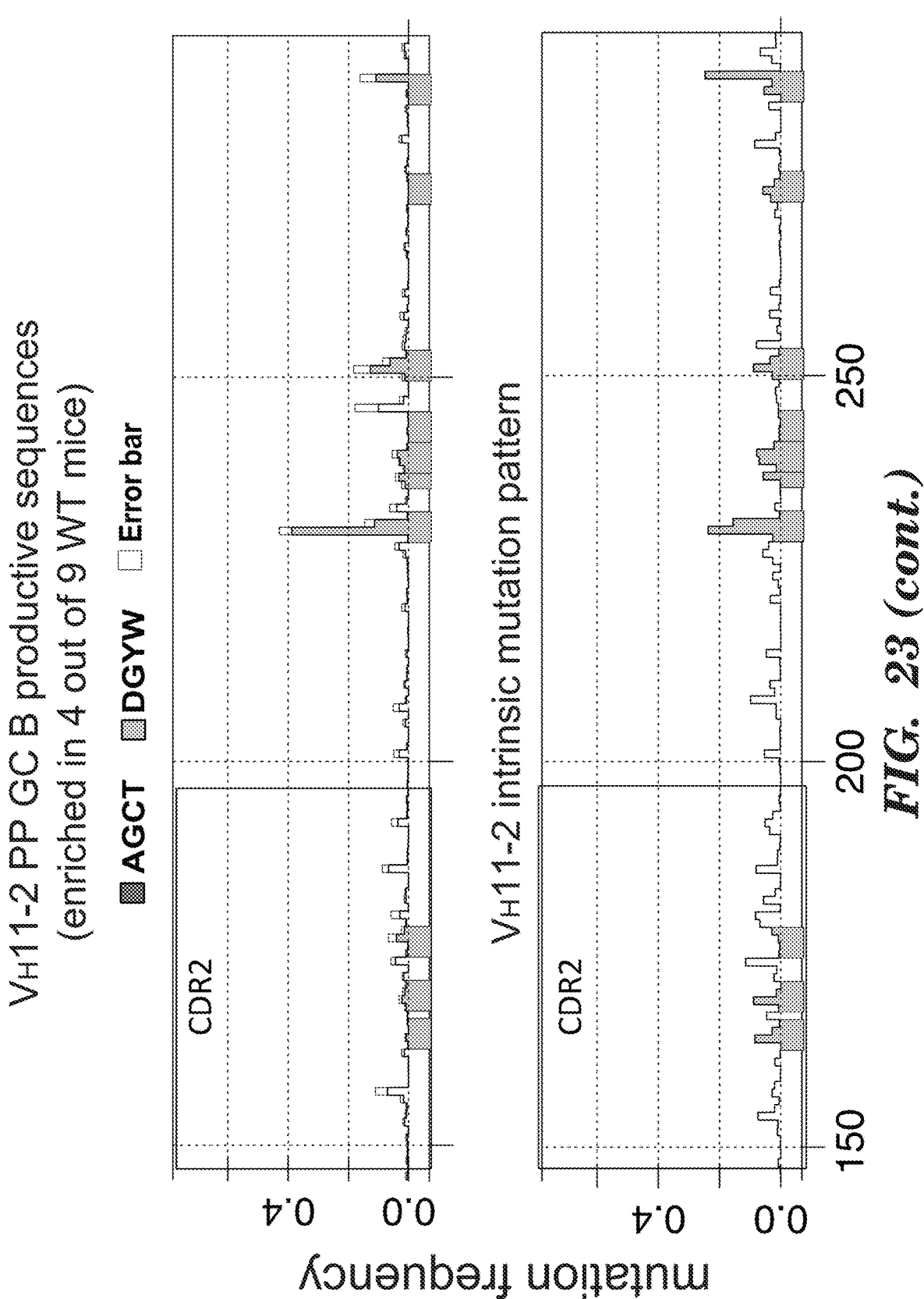
Figure 29A:
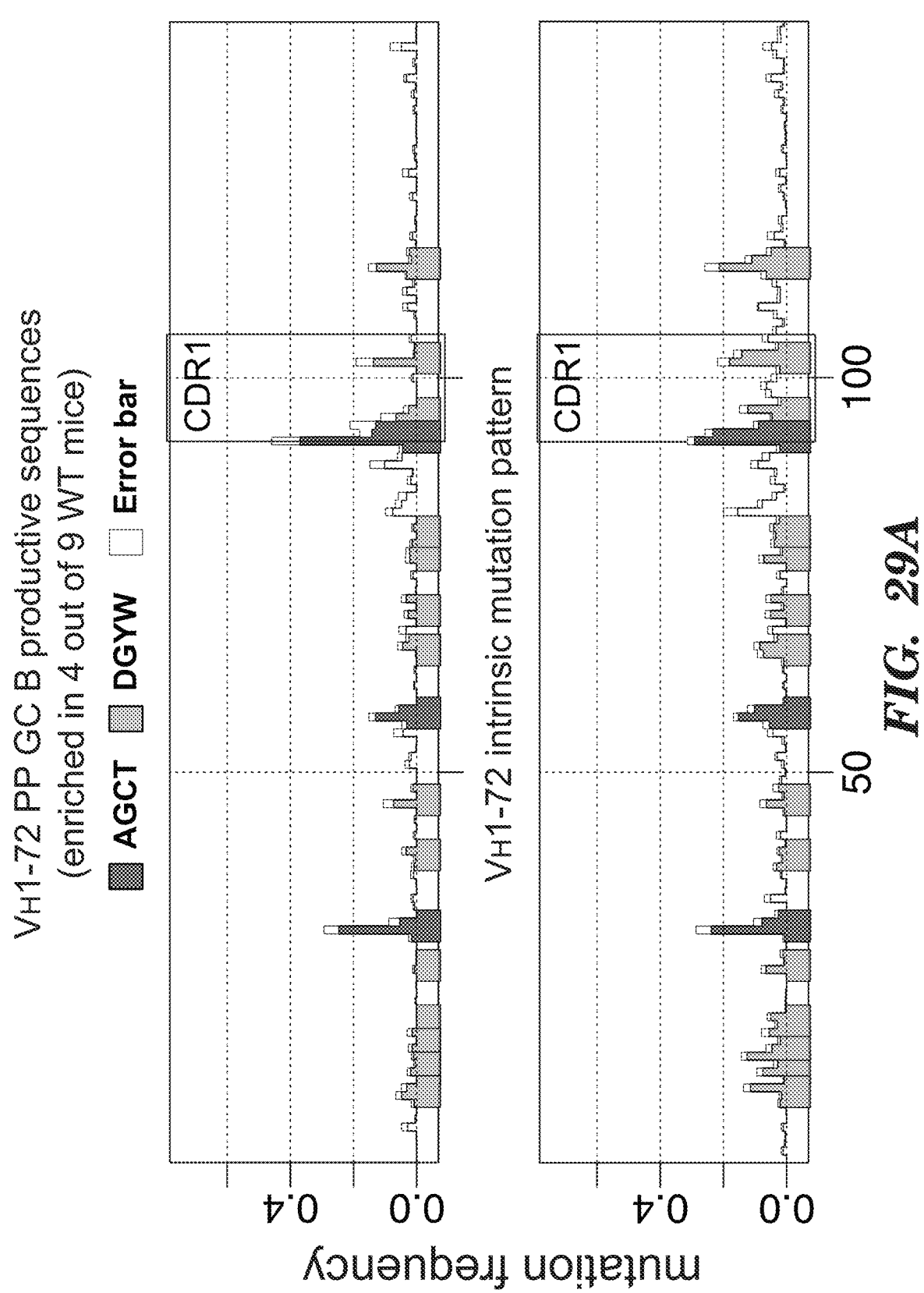
FIG. 29A demonstrates that V$_H$1-72, which was most frequently utilized in PP GCs albeit not significantly enriched, accumulated sequence-intrinsic SHMs.
Figure 29A:
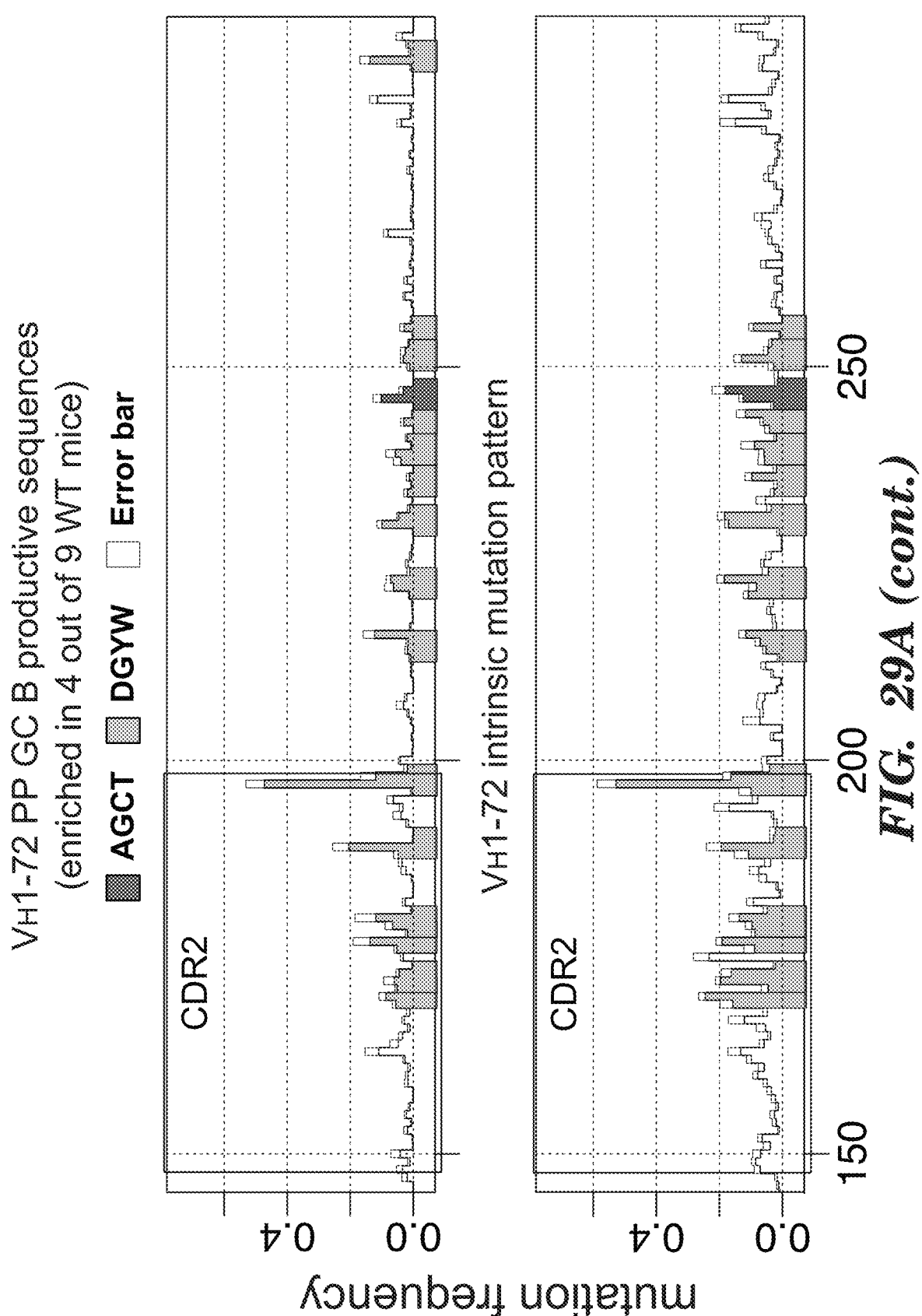
Figure 29B:
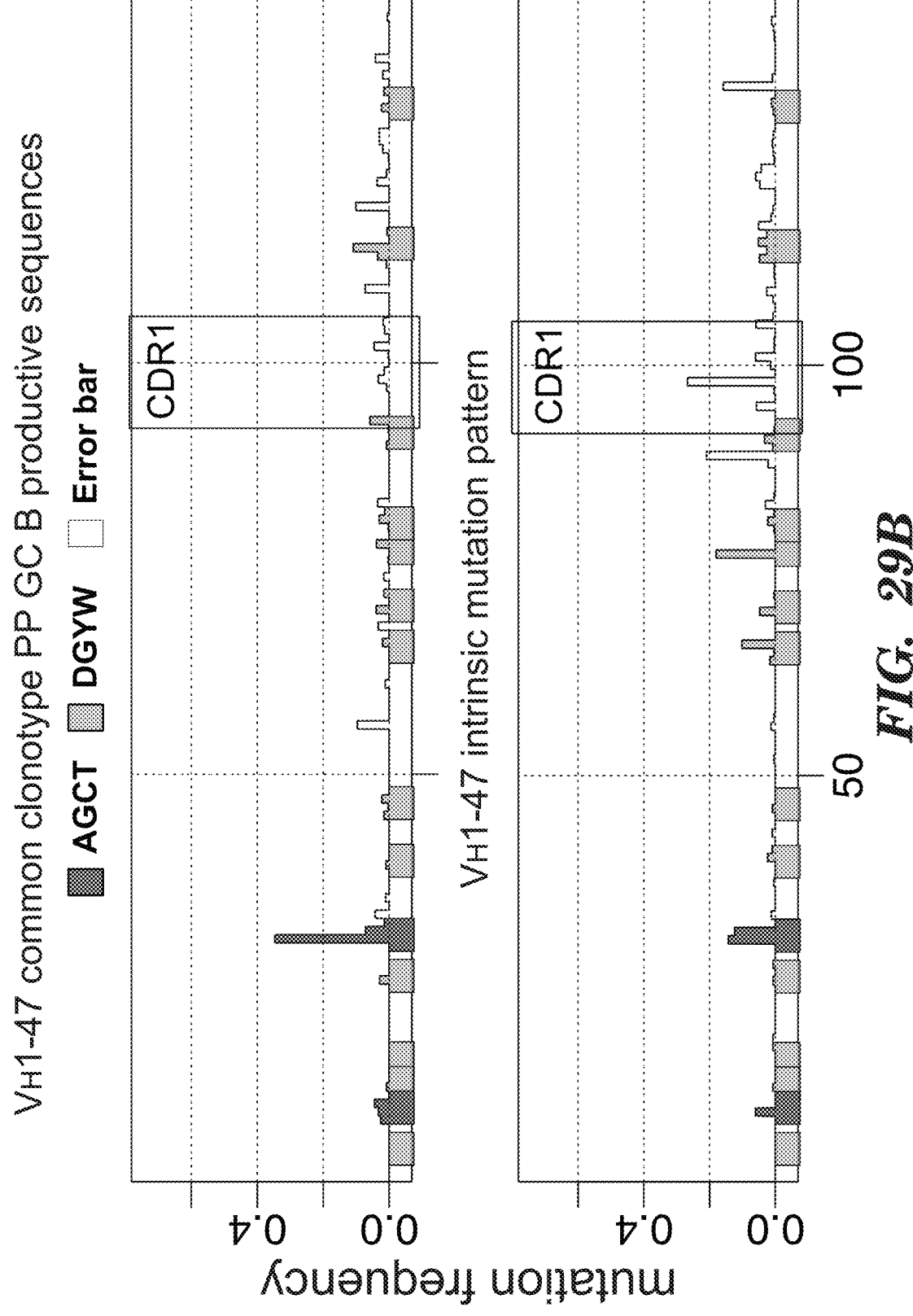
FIG. 29B depicts the SHM pattern of a top V$_H$1-47 clonotype.
Figure 29B:
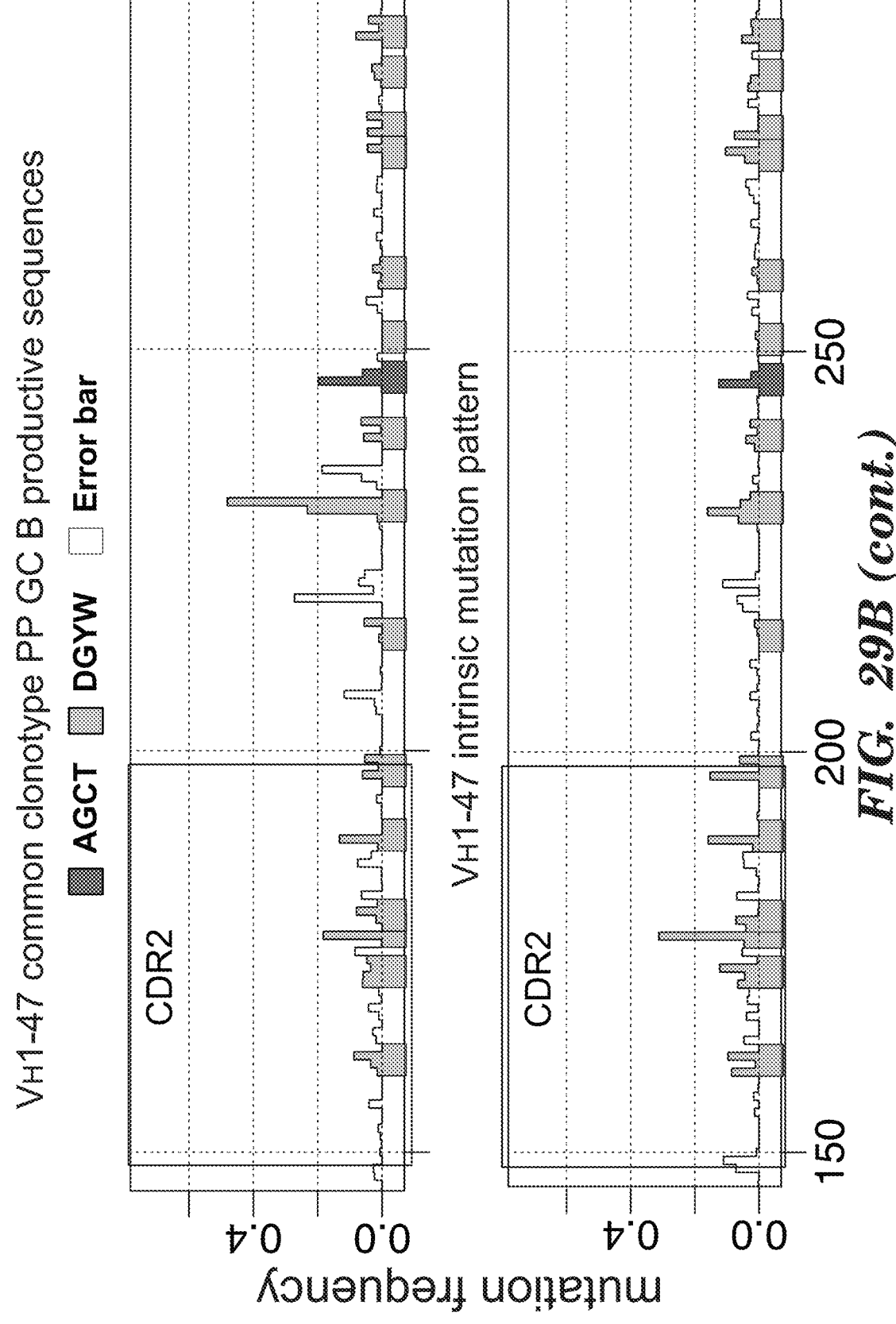

Using a mouse VB1-8 VDJ IgH exon, in PP GC the $V_H$ exon mutates without selection[12]. This finding raised the intriguing possibility that chronic activation of PP GC B cells might allow expansion of primary antibody repertoires via SHM in the absence of cellular selection. Alternatively, since there was only one productive VDJ sequence in the VB1-8 model, the lack of SHM selection could be due to the possibility that the VB1-8 exon does not match any gut antigen. Now that several $V_{HS}$ that were recurrently enriched in response to gut antigens in PP GCs (FIG. 21A) were identified, their mutation pattern was examined. Strikingly, compared to the intrinsic mutation pattern generated from pooled nonproductive sequences, the most highly enriched $V_H$1-47 and $V_H$11-2 in PP GCs did accumulate mutations but did not show any recurrent selection in CDR region mutations (FIG. 23), indicating a lack of affinity maturation in the PP. Consistent with past findings from the VB1-8 model, the same $V_H$1-72, which was most frequently utilized in PP GCs albeit not significantly enriched (FIG. 21A) likely due to its high baseline level in the naïve repertoire, also accumulated sequence-intrinsic SHMs (FIG. 29A). Thus, PP GCs appear to behave differently from conventional GCs in SHM selection.

REFERENCE

1. Alt, F. W., Zhang, Y., Meng, F.-L., Guo, C. & Schwer, B. Mechanisms of programmed DNA lesions and genomic instability in the immune system. *Cell* 152, 417-29 (2013).
2. De Silva, N. S. & Klein, U. Dynamics of B cells in germinal centres. *Nat. Rev. Immunol.* 15, 137-148 (2015).
3. Di Noia, J. M. & Neuberger, M. S. Molecular Mechanisms of Antibody Somatic Hypermutation. *Annu. Rev. Biochem.* 76, 1-22 (2007).
4. Shih, T.-A. Y., Meffre, E., Roederer, M. & Nussenzweig, M. C. Role of BCR affinity in T cell dependent antibody responses in vivo. *Nat. Immunol.* 3, 570-5 (2002).
5. Victora, G. D. et al. Germinal center dynamics revealed by multiphoton microscopy with a photoactivatable fluorescent reporter. *Cell* 143, 592-605 (2010).

6. Reboldi, A. & Cyster, J. G. Peyer's patches: Organizing B-cell responses at the intestinal frontier. *Immunol. Rev.* 271, 230-245 (2016).

7. Weinstein, P. D. & Cebra, J. J. The preference for switching to IgA expression by Peyer's patch germinal center B cells is likely due to the intrinsic influence of their microenvironment. *J. Immunol.* 147, 4126-4135 (1991).

8. Lécuyer, E. et al. Segmented filamentous bacterium uses secondary and tertiary lymphoid tissues to induce gut IgA and specific T helper 17 cell responses. *Immunity* 40, 608-620 (2014).

9. Bergqvist, P., Stensson, A., Lycke, N. Y. & Bemark, M. T Cell-Independent IgA Class Switch Recombination Is Restricted to the GALT and Occurs Prior to Manifest Germinal Center Formation. *J. Immunol.* 184, 3545-3553 (2010).

10. Bunker, J. J. et al. Innate and Adaptive Humoral Responses Coat Distinct Commensal Bacteria with Immunoglobulin A. *Immunity* 43, 541-553 (2015).

11. Casola, S. et al. B cell receptor signal strength determines B cell fate. *Nat. Immunol.* 5, 317-327 (2004).

12. Yeap, L., Hwang, J. K., Kepler, T. B., Wang, J. H. & Alt, F. W. Sequence-Intrinsic Mechanisms that Target AID Mutational Outcomes on Antibody Genes Article Sequence-Intrinsic Mechanisms that Target AID Mutational Outcomes on Antibody Genes. 1-14 (2015). doi:10.1016/j.cell.2015.10.042

13. Reynaud, C. A., Anquez, V., Grimal, H. & Weill, J. C. A hyperconversion mechanism generates the chicken light chain preimmune repertoire. *Cell* 48, 379-388 (1987).

14. Reynaud, C. A., Mackay, C. R., Müller, R. G. & Weill, J. C. Somatic generation of diversity in a mammalian primary lymphoid organ: The sheep ileal Peyer's patches. *Cell* 64, 995-1005 (1991).

15. Lanning, D., Zhu, X., Zhai, S.-K. K. & Knight, K. L. Development of the antibody repertoire in rabbit: gut-associated lymphoid tissue, microbes, and selection. *Immunological reviews* 175, 214-228 (2000).

16. Bergqvist, P. et al. Re-utilization of germinal centers in multiple Peyer's patches results in highly synchronized, oligoclonal, and affinity-matured gut IgA responses. *Mucosal Immunol.* 6, 122-135 (2012).

17. Lin, S. G. et al. Highly sensitive and unbiased approach for elucidating antibody repertoires. *Proc. Natl. Acad. Sci.* 113, 7846-7851 (2016).

18. Frock, R. L. et al. Genome-wide detection of DNA double-stranded breaks induced by engineered nucleases. *Nat. Biotechnol.* 33, (2014).

19. Tian, M. et al. Induction of HIV Neutralizing Antibody Lineages in Mice with Diverse Precursor Repertoires. *Cell* 166, 1471-1484.e18 (2016).

20. Bothwell, A. L. M. et al. Heavy chain variable region contribution to the NPb family of antibodies: somatic mutation evident in a 72a variable region. *Cell* 24, 625-637 (1981).

21. Curnano, A. Structure of prii nary anti-(4-hydroxy-3-nitro-phenyl) acetyl (N?) antibodies in normal and idio-typically suppressed C57BL/6 mice*. *Eur. J. Lmmunol* 512-520 (1985).

22. Jacob, J., Przylepa, J., Miller, C. & Kelsoe, G. In situ studies of the primary immune response to (4-hydroxy-3-nitrophenyl)acetyl. III. The kinetics of V region mutation and selection in germinal center B cells. *J. Exp. Med.* 178, 1293-307 (1993).

23. Allen, D., Simon, T., Sablitzky, F., Rajewsky, K. & Cumano, a. Antibody engineering for the analysis of affinity maturation of an anti-hapten response. *Embo J* 7, 1995-2001. (1988).

24. Weiss, U., Zoebelein, R. & Rajewsky, K. Accumulation of somatic mutants in the B cell compartment after primary immunization with a T cell-dependent antigen. *Eur. J. Immunol.* 22, 511-7 (1992).

25. Tas, J. M. J. et al. Visualizing antibody affinity maturation in germinal centers. *Science* (80-.). 58, 7250-7 (2016).

26. Lindner, C. et al. Diversification of memory B cells drives the continuous adaptation of secretory antibodies to gut microbiota. *Nat. Immunol.* 16, 880-8 (2015).

27. Muramatsu, M. et al. Specific expression of activation-induced cytidine deaminase (AID), a novel member of the RNA-editing deaminase family in germinal center B cells. *J. Biol. Chem.* 274, 18470-18476 (1999).

28. Muramatsu, M. et al. Class Switch Recombination and Hypermutation Require Activation-Induced Cytidine Deaminase (AID), a Potential RNA Editing Enzyme. *Cell* 102, 553-563 (2000).

29. Revy, P. et al. Activation-Induced Cytidine Deaminase (AID) Deficiency Causes the Autosomal Recessive Form of the Hyper-IgM Syndrome (HIGM2). *Cell* 102, 565-575 (2000).

30. Craig, S. W. & Cebra, J. J. Peyer's patches: an enriched source of precursors for IgA-producing immunocytes in the rabbit. *J. Exp. Med.* 134, 188-200 (1971).

31. Fagarasan, S. et al. Critical roles of activation-induced cytidine deaminase in the homeostasis of gut flora. *Science* (80-.). 298, 1424-1427 (2002).

32. Suzuki, K. et al. Aberrant expansion of segmented filamentous bacteria in IgA-deficient gut. *Proc. Natl. Acad. Sci. U.S.A.* 101, 1981-1986 (2004).

33. Heel, K. a, McCauley, R. D., Papadimitriou, J. M. & Hall, J. C. Review: Peyer's patches. *J. Gastroenterol. Hepatol.* 12, 122-136 (1997).

34. Jiang, D., Niwa, M., Koong, A. C. & Diego, S. Colonization and induction of Th17 cells by segmented filamentous bacteria in the murine intestine. 48-56 (2016). doi:10.1016/j.semcancer.2015.04.010.Targeting

Example 6

Figure 30:
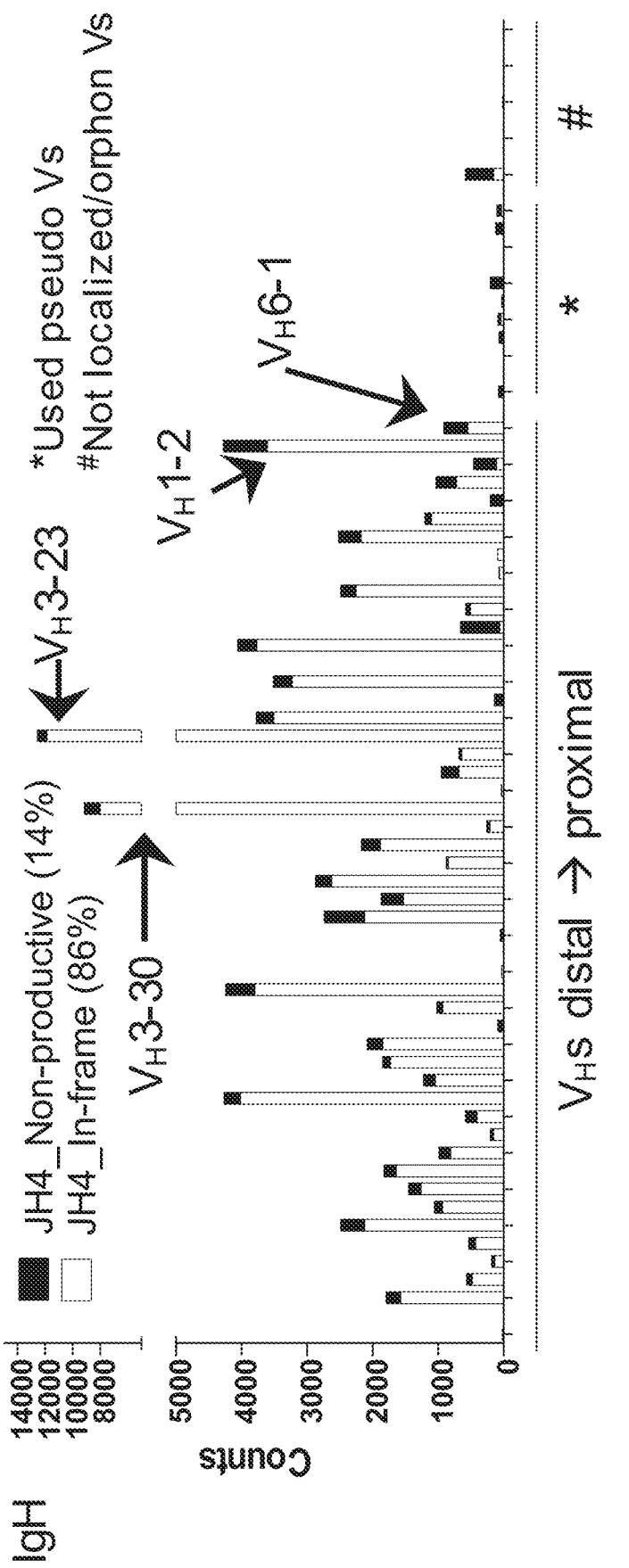
FIG. 30 depicts HTGTS-Rep-seq IGH, IGK, IGL repertoires from purified human peripheral blood B cells. Panels show IGH, IGL, and IGK V usage via primers for the coding ends of J$_H$4, Jλ2/3, and Jκ1, respectively. In-frame and non-productive rearrangements are shown. Functional Vs are listed from most D/J-distal to proximal (left to right), followed by utilized pseudo-Vs (*) and nonlocalized/orphon Vs (#).
Figure 30:
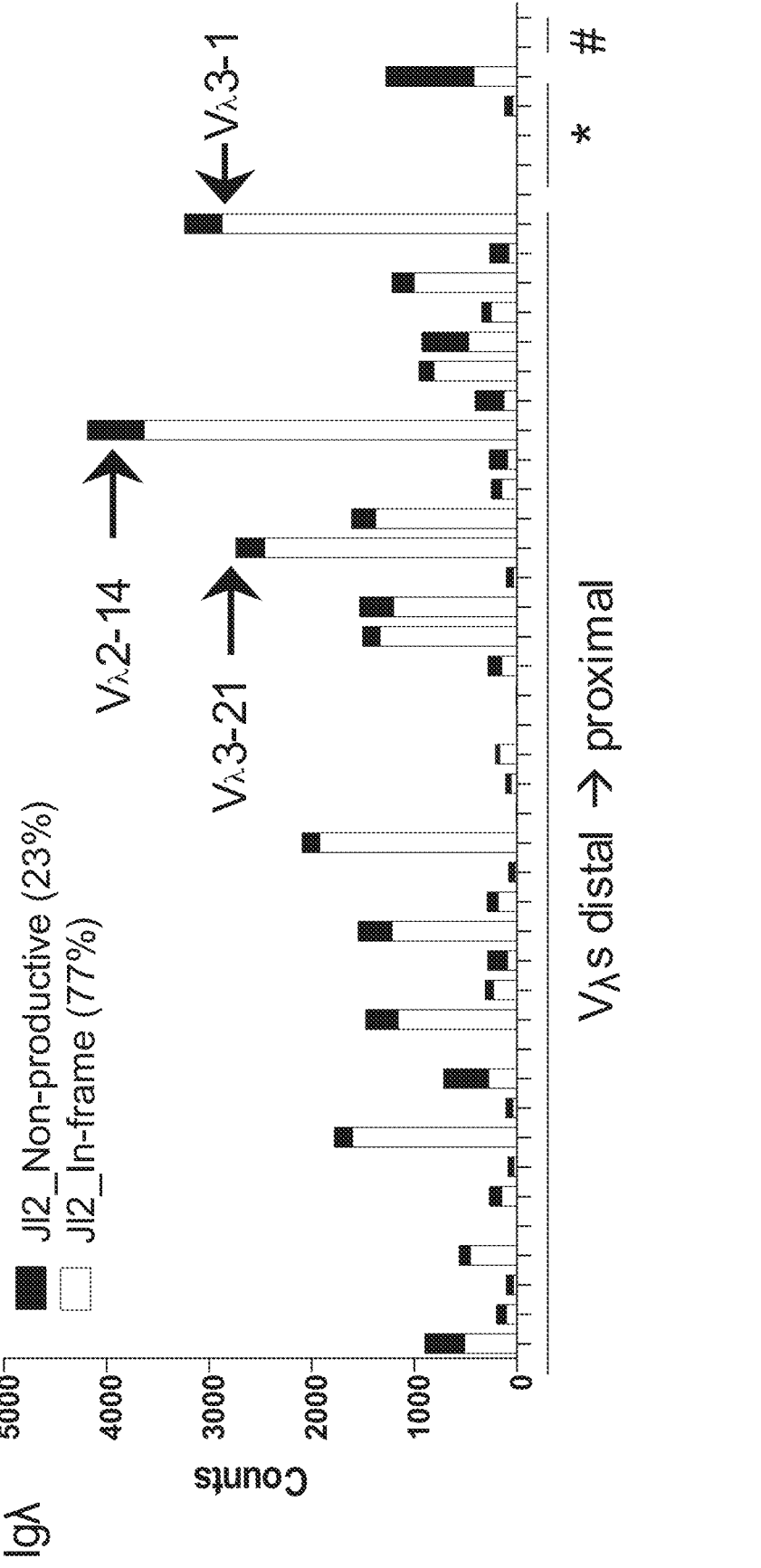
Figure 30:
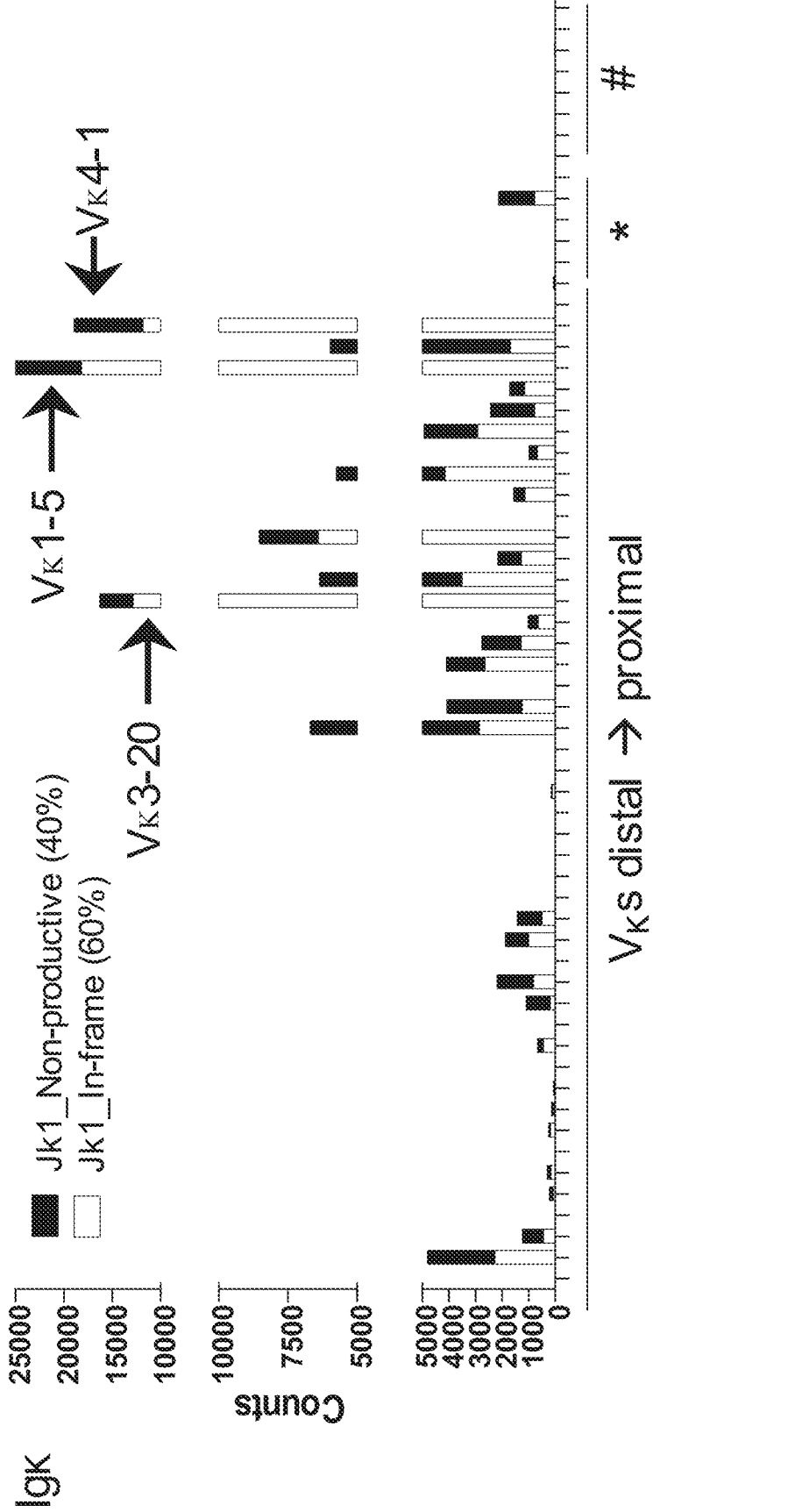

HTGTS-Rep-seq was used to analyze human IGH, IGK, and IGL repertoires from peripheral blood B cells (FIG. 30).

TABLE 6

| Name | Sequence | Purpose | SEQ ID NO |
|---|---|---|---|
| hJH4-bio-SL | /5BiosG/ACCCAGC ACCCTTATTTCCC | human JH4- bio primer | 60 |
| hJH4-red-SL | TGCAGCAAAACCCTT CAGAG | human JH4- red primer | 61 |
| hJκ1-bio-SL | /5BiosG/TGTGCAA TCAATTCTCGAGTTTG | human Jκ1- bio primer | 62 |
| hJκ1-red-SL | ACACAGGGAACAGAA GACACA | human Jκ1- red primer | 63 |
| hJλ2-bio-SL | /5BiosG/CAAGGGT CTGAACAGGGAGG | human Jλ2- bio primer | 64 |
| hJλ2-red-SL | ACCACAAGTTGAGAC AAGATACA | human Jλ2- red prime | 65 |

What is claimed herein is:

1. A method for high throughput, repertoire sequencing-based detection of Ig repertoire sequences in a cell, the method comprising the steps of:
   a) enriching a sample for a lymphocyte;
   b) extracting genomic DNA and/or mRNA from the lymphocyte;
   c) producing:
      a single-stranded PCR product from genomic DNA by Linear Amplification Mediated (LAM)-PCR with at least one primary locus-specific primer; and/or
      cDNA from mRNA by reverse-transcription with at least one primary locus-specific primer;
   d) producing a ligated DNA and/or cDNA product by ligating the single-stranded PCR product or cDNA produced in step (c) to a double-stranded adaptor, wherein the double-stranded adaptor comprises:
      a distal portion of known DNA sequence that can be used to design PCR primers for a nested PCR amplification;
      a proximal portion of random nucleotides; and
      a 3' overhang;
   e) producing a nested PCR product by performing a nested-PCR with an adaptor-specific primer and at least one secondary locus-specific primer using the ligated product of step (d), thereby amplifying the nucleic acid sequence comprising the Ig repertoire sequence, wherein the Ig repertoire comprises V(D)J recombination events and/or somatic hypermutations (SMH);
   f) producing a sequenced nested PCR product by sequencing the nested PCR product; and
   g) aligning the sequenced nested PCR product against a reference sequence or antigen receptor database.

2. The method of claim 1, further comprising producing a fragmented DNA and/or mRNA sample after step (a).

3. The method of claim 1, further comprising digesting the PCR product of step (e) with a restriction enzyme to block un-rearranged bait-containing fragments after step (e).

4. The method of claim 1, wherein the repertoire detected comprises Ig heavy chains, Ig light chains, V usage, and CDR3 repertoires.

5. The method of claim 1, wherein the cell is selected from a group consisting of:
   a mature B lymphocyte, a developing B lymphocyte, a mature T lymphocyte, a developing T lymphocyte, a lymphocyte obtained from a germinal center, and a lymphocyte obtained from a Peyer's Patch.

6. The method of claim 1, wherein the method further comprises providing the cell, wherein the cell was obtained from an animal immunized with an antigen.

7. The method of claim 1, wherein the sample was obtained from an animal immunized with an antigen.

8. The method of claim 1, wherein the at least one primary locus-specific primer specifically anneals to J gene segments.

9. The method of claim 1, wherein the method further comprises the use of multiple primary locus-specific primers and/or secondary locus-specific primers.

10. The method of claim 9, wherein each of the multiple primers specifically anneal to different V, D, and/or J gene segments; or
   wherein each of the multiple primers specifically anneal to each different J gene segment present in the genome of the cell or organism prior to V(D)J recombination.

11. The method of claim 10, wherein, collectively, the multiple primers specifically anneal to a sequence in each of $J_H1$, $J_H2$, $J_H3$, or $J_H4$; or
   wherein, collectively, the multiple primers specifically anneal to at least one sequence in each of the $J_H$, $J_K$, and $J_L$ gene segments present in the genome of the cell or organism prior to V(D)J recombination.

12. The method of claim 1, wherein the at least one primary locus-specific primer specifically anneals to a degenerate region(s) of the targeted gene segment(s).

13. The method of claim 1, further comprising a step of differentiating a source cell or tissue to initiate V(D)J recombination prior to performing step (a).

14. The method of claim 1, further comprising a step of contacting the lymphocyte with one or more reagents that initiate V(D)J recombination or SHM.

15. The method of claim 1, wherein the primary locus-specific primer comprises an affinity tag.

16. The method of claim 1, wherein the primers used for the nested PCR step comprise barcode sequences.

17. The method of claim 1, wherein the fragmenting is performed by sonication, restriction enzyme digest, randomly shearing genomic DNA, or a frequently cutting restriction enzyme.

18. The method of claim 1, wherein ligating the product of step (c) to a double-stranded adaptor comprises contacting the product with a population of double-stranded adaptors having the same distal portion and random proximal portion sequences.

19. The method of claim 1, wherein the double-stranded adaptor comprises barcode sequences between distal and proximal portions.

20. The method of claim 1, wherein end repair is not performed prior to step (c) and/or the PCR product of step (e) is not digested with a restriction enzyme to block un-rearranged bait-containing fragments after step (e).

* * * * *

SEQUENCE LISTING

Sequence total quantity: 65
SEQ ID NO: 1               moltype = DNA   length = 19
FEATURE                    Location/Qualifiers
misc_feature               1..19
                           note = Description of Artificial Sequence: Synthetic primer
source                     1..19
                           mol_type = other DNA
                           organism = synthetic construct
SEQUENCE: 1
ctgcagcatg cagagtgtg                                                    19

SEQ ID NO: 2               moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 2
tgacatgggg agatctgaga                                                   20

SEQ ID NO: 3               moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 3
accctttctg actcccaagg                                                   20

SEQ ID NO: 4               moltype = DNA   length = 23
FEATURE                    Location/Qualifiers
misc_feature               1..23
                           note = Description of Artificial Sequence: Synthetic primer
source                     1..23
                           mol_type = other DNA
                           organism = synthetic construct
SEQUENCE: 4
ccccaacaaa tgcagtaaaa tct                                               23

SEQ ID NO: 5               moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 5
gggacaaagg ggttgaatct                                                   20

SEQ ID NO: 6               moltype = DNA   length = 19
FEATURE                    Location/Qualifiers
misc_feature               1..19
                           note = Description of Artificial Sequence: Synthetic primer
source                     1..19
                           mol_type = other DNA
                           organism = synthetic construct
SEQUENCE: 6
cccgtttgca gagaatctt                                                    19

SEQ ID NO: 7               moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 7
ccctcaggga caaatatcca                                                   20

SEQ ID NO: 8               moltype = DNA   length = 21
FEATURE                    Location/Qualifiers
misc_feature               1..21
                           note = Description of Artificial Sequence: Synthetic primer
source                     1..21
                           mol_type = other DNA
                           organism = synthetic construct

```
SEQUENCE: 8
ctgcaatgct cagaaaactc c                                                    21

SEQ ID NO: 9              moltype = DNA   length = 21
FEATURE                   Location/Qualifiers
misc_feature              1..21
                          note = Description of Artificial Sequence: Synthetic primer
source                    1..21
                          mol_type = other DNA
                          organism = synthetic construct
SEQUENCE: 9
ttcccagctt tgcttacgga g                                                    21

SEQ ID NO: 10             moltype = DNA   length = 23
FEATURE                   Location/Qualifiers
misc_feature              1..23
                          note = Description of Artificial Sequence: Synthetic primer
source                    1..23
                          mol_type = other DNA
                          organism = synthetic construct
SEQUENCE: 10
agtgccagaa tctggtttca gag                                                  23

SEQ ID NO: 11             moltype = DNA   length = 22
FEATURE                   Location/Qualifiers
misc_feature              1..22
                          note = Description of Artificial Sequence: Synthetic primer
source                    1..22
                          mol_type = other DNA
                          organism = synthetic construct
SEQUENCE: 11
attccaacct cttgtgggac ag                                                   22

SEQ ID NO: 12             moltype = DNA   length = 24
FEATURE                   Location/Qualifiers
misc_feature              1..24
                          note = Description of Artificial Sequence: Synthetic primer
source                    1..24
                          mol_type = other DNA
                          organism = synthetic construct
SEQUENCE: 12
tccctcctta acacctgatc tgag                                                 24

SEQ ID NO: 13             moltype = DNA   length = 22
FEATURE                   Location/Qualifiers
misc_feature              1..22
                          note = Description of Artificial Sequence: Synthetic primer
source                    1..22
                          mol_type = other DNA
                          organism = synthetic construct
SEQUENCE: 13
cgctcagctt tcacactgac tc                                                   22

SEQ ID NO: 14             moltype = DNA   length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 14
caggttgcca ggaatggctc                                                      20

SEQ ID NO: 15             moltype = DNA   length = 22
FEATURE                   Location/Qualifiers
misc_feature              1..22
                          note = Description of Artificial Sequence: Synthetic primer
source                    1..22
                          mol_type = other DNA
                          organism = synthetic construct
SEQUENCE: 15
gcccctaatc tcactagctt ga                                                   22

SEQ ID NO: 16             moltype = DNA   length = 24
FEATURE                   Location/Qualifiers
misc_feature              1..24
                          note = Description of Artificial Sequence: Synthetic primer
source                    1..24
                          mol_type = other DNA
```

```
                            organism = synthetic construct
SEQUENCE: 16
gtcaactgat aatgagccct ctcc                                          24

SEQ ID NO: 17           moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 17
ctgcagcatg cagagtgtg                                                19

SEQ ID NO: 18           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 18
tgacatgggg agatctgaga                                               20

SEQ ID NO: 19           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 19
accctttctg actcccaagg                                               20

SEQ ID NO: 20           moltype = DNA  length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 20
ccccaacaaa tgcagtaaaa tct                                           23

SEQ ID NO: 21           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 21
gggacaaagg ggttgaatct                                               20

SEQ ID NO: 22           moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 22
cccgtttgca gagaatctt                                                19

SEQ ID NO: 23           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 23
ccctcaggga caaatatcca                                               20

SEQ ID NO: 24           moltype = DNA  length = 21
FEATURE                 Location/Qualifiers
misc_feature            1..21
                        note = Description of Artificial Sequence: Synthetic primer
source                  1..21
```

```
                        mol_type = other DNA
                        organism = synthetic construct
SEQUENCE: 24
ctgcaatgct cagaaaactc c                                          21

SEQ ID NO: 25          moltype = DNA   length = 21
FEATURE                Location/Qualifiers
misc_feature           1..21
                       note = Description of Artificial Sequence: Synthetic primer
source                 1..21
                       mol_type = other DNA
                       organism = synthetic construct
SEQUENCE: 25
ttcccagctt tgcttacgga g                                          21

SEQ ID NO: 26          moltype = DNA   length = 23
FEATURE                Location/Qualifiers
misc_feature           1..23
                       note = Description of Artificial Sequence: Synthetic primer
source                 1..23
                       mol_type = other DNA
                       organism = synthetic construct
SEQUENCE: 26
agtgccagaa tctggtttca gag                                        23

SEQ ID NO: 27          moltype = DNA   length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 27
attccaacct cttgtgggac ag                                         22

SEQ ID NO: 28          moltype = DNA   length = 24
FEATURE                Location/Qualifiers
misc_feature           1..24
                       note = Description of Artificial Sequence: Synthetic primer
source                 1..24
                       mol_type = other DNA
                       organism = synthetic construct
SEQUENCE: 28
tccctcctta acacctgatc tgag                                       24

SEQ ID NO: 29          moltype = DNA   length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 29
cgctcagctt tcacactgac tc                                         22

SEQ ID NO: 30          moltype = DNA   length = 20
FEATURE                Location/Qualifiers
misc_feature           1..20
                       note = Description of Artificial Sequence: Synthetic primer
source                 1..20
                       mol_type = other DNA
                       organism = synthetic construct
SEQUENCE: 30
caggttgcca ggaatggctc                                            20

SEQ ID NO: 31          moltype = DNA   length = 22
FEATURE                Location/Qualifiers
misc_feature           1..22
                       note = Description of Artificial Sequence: Synthetic primer
source                 1..22
                       mol_type = other DNA
                       organism = synthetic construct
SEQUENCE: 31
gcccctaatc tcactagctt ga                                         22

SEQ ID NO: 32          moltype = DNA   length = 24
FEATURE                Location/Qualifiers
misc_feature           1..24
                       note = Description of Artificial Sequence: Synthetic primer
```

-continued

```
source                    1..24
                          mol_type = other DNA
                          organism = synthetic construct
SEQUENCE: 32
gtcaactgat aatgagccct ctcc                                       24

SEQ ID NO: 33             moltype = DNA   length = 460
FEATURE                   Location/Qualifiers
misc_feature              1..460
                          note = Description of Artificial Sequence: Synthetic
                           polynucleotide
source                    1..460
                          mol_type = other DNA
                          organism = synthetic construct
SEQUENCE: 33
ctgcaatgct cagaaaactc cataacaaag gttaaaaata aagacctgga gaggccattc   60
ttacctgagg agacggtgac tgaggttcct tgacccagt agtccatagc cccactacta   120
ccgtagtaat aatttgcatc tcttgcacag taataaatgg cagtgtcctc agctctcagg   180
gcattcatct gaaggtagag gatgctttgg gaagtgtctc tggagacgat gaaccgaccc   240
ttcacagatg cactgtactc tgttgtataa tcattagctt tgtttctact tgcagcaatc   300
cactccagtc tcttccctgg aggctggcgg acccactcca tgtagaaatc actgaaggtg   360
aacccagaag ttgcacagga gagtctcaga gaaccccag gctgtaccaa gcctcctcca   420
gattccacca gcttcacctc accacgcgtg ccctatagtc                         460

SEQ ID NO: 34             moltype = DNA   length = 493
FEATURE                   Location/Qualifiers
misc_feature              1..493
                          note = Description of Artificial Sequence: Synthetic
                           polynucleotide
source                    1..493
                          mol_type = other DNA
                          organism = synthetic construct
SEQUENCE: 34
ccggttgcca ggaatggctc atttagccaa aatgtcacaa attcacacaa gttacccaaa   60
cagaaccaaa acgtcacaag taaatgagca aaagtctact tacgttttat ttccaacttt   120
gtccccgagc cgaacgtgaa tgggaggatc ctcattactt tgctgacagt aataggttgc   180
agcatcctcc tcctccacag gatggatgtt gagggtgaag tctgtcccag acccactgcc   240
actaaacctg gctgggatcc cagattctag attggatgca gcatagatga ggagtttggg   300
tggctgtcct ggtttctgtt ggtaccagtt catataacta tcaccatcat aatcaacact   360
ttggctggcc ttgcaggaga tggtggccct ctgccctaga gacacagcca aagaagctgg   420
agattgggtc agcacaatgt caccagtgga gcctggaatg ataaacacac agacccacgc   480
gtgccctata gtc                                                     493

SEQ ID NO: 35             moltype = DNA   length = 53
FEATURE                   Location/Qualifiers
source                    1..53
                          mol_type = unassigned DNA
                          organism = Mus musculus
SEQUENCE: 35
ctactggtac ttcgatgtct ggggcacagg gaccacggtc accgtctcct cag           53

SEQ ID NO: 36             moltype = DNA   length = 48
FEATURE                   Location/Qualifiers
source                    1..48
                          mol_type = unassigned DNA
                          organism = Mus musculus
SEQUENCE: 36
actactttga ctactggggc caaggcacca ctctcacagt ctcctcag                 48

SEQ ID NO: 37             moltype = DNA   length = 48
FEATURE                   Location/Qualifiers
source                    1..48
                          mol_type = unassigned DNA
                          organism = Mus musculus
SEQUENCE: 37
cctggtttgc ttactggggc caagggactc tggtcactgt ctctgcag                 48

SEQ ID NO: 38             moltype = DNA   length = 54
FEATURE                   Location/Qualifiers
source                    1..54
                          mol_type = unassigned DNA
                          organism = Mus musculus
SEQUENCE: 38
attactatgc tatggactac tggggtcaag gaacctcagt caccgtctcc tcag           54

SEQ ID NO: 39             moltype = DNA   length = 137
FEATURE                   Location/Qualifiers
source                    1..137
                          mol_type = unassigned DNA
```

```
                          organism = Mus musculus
SEQUENCE: 39
ctactggtac ttcgatgtct ggggcacagg gaccacggtc accgtctcct caggtaagct   60
ggcttttttc tttctgcaca ttccattctg aaacgggaaa agatattctc agatctcccc  120
atgtcaggcc atctgcc                                                  137

SEQ ID NO: 40         moltype = DNA  length = 134
FEATURE               Location/Qualifiers
source                1..134
                      mol_type = unassigned DNA
                      organism = Mus musculus
SEQUENCE: 40
actactttga ctactggggc caaggcacca ctctcacagt ctcctcaggt gagtccttac   60
aacctctctc ttctattcag cttaaataga ttttactgca tttgttgggg gggaaatgtg  120
tgtatctgaa tttc                                                     134

SEQ ID NO: 41         moltype = DNA  length = 131
FEATURE               Location/Qualifiers
source                1..131
                      mol_type = unassigned DNA
                      organism = Mus musculus
SEQUENCE: 41
cctggtttgc ttactggggc caagggactc tggtcactgt ctctgcaggt gagtcctaac   60
ttctcccatt ctaaatgcat gttgggggga ttctgggcct tcaggaccaa gattctctgc  120
aaacgggaat c                                                        131

SEQ ID NO: 42         moltype = DNA  length = 134
FEATURE               Location/Qualifiers
source                1..134
                      mol_type = unassigned DNA
                      organism = Mus musculus
SEQUENCE: 42
attactatgc tatggactac tggggtcaag gaacctcagt caccgtctcc tcaggtaaga   60
atggcctctc caggtcttta tttttaacct ttgttatgga gttttctgag cattgcagac  120
taatcttgga tatt                                                     134

SEQ ID NO: 43         moltype = DNA  length = 20
FEATURE               Location/Qualifiers
misc_feature          1..20
                      note = Description of Artificial Sequence: Synthetic primer
source                1..20
                      mol_type = other DNA
                      organism = synthetic construct
SEQUENCE: 43
tgacatgggg agatctgaga                                                20

SEQ ID NO: 44         moltype = DNA  length = 23
FEATURE               Location/Qualifiers
misc_feature          1..23
                      note = Description of Artificial Sequence: Synthetic primer
source                1..23
                      mol_type = other DNA
                      organism = synthetic construct
SEQUENCE: 44
ccccaacaaa tgcagtaaaa tct                                            23

SEQ ID NO: 45         moltype = DNA  length = 21
FEATURE               Location/Qualifiers
misc_feature          1..21
                      note = Description of Artificial Sequence: Synthetic primer
source                1..21
                      mol_type = other DNA
                      organism = synthetic construct
SEQUENCE: 45
gagaatcttg gtcctgaagg c                                              21

SEQ ID NO: 46         moltype = DNA  length = 21
FEATURE               Location/Qualifiers
misc_feature          1..21
                      note = Description of Artificial Sequence: Synthetic primer
source                1..21
                      mol_type = other DNA
                      organism = synthetic construct
SEQUENCE: 46
ctgcaatgct cagaaaactc c                                              21

SEQ ID NO: 47         moltype = DNA  length = 21
FEATURE               Location/Qualifiers
misc_feature          1..21
```

-continued

```
                              note = Description of Artificial Sequence: Synthetic primer
source                        1..21
                              mol_type = other DNA
                              organism = synthetic construct
SEQUENCE: 47
cttacctgag gagacggtga c                                              21

SEQ ID NO: 48                 moltype = DNA   length = 21
FEATURE                       Location/Qualifiers
misc_feature                  1..21
                              note = Description of Artificial Sequence: Synthetic primer
source                        1..21
                              mol_type = other DNA
                              organism = synthetic construct
SEQUENCE: 48
ctcacctgag gagactgtga g                                              21

SEQ ID NO: 49                 moltype = DNA   length = 21
FEATURE                       Location/Qualifiers
misc_feature                  1..21
                              note = Description of Artificial Sequence: Synthetic primer
source                        1..21
                              mol_type = other DNA
                              organism = synthetic construct
SEQUENCE: 49
ctcacctgca gagacagtga c                                              21

SEQ ID NO: 50                 moltype = DNA   length = 25
FEATURE                       Location/Qualifiers
misc_feature                  1..25
                              note = Description of Artificial Sequence: Synthetic primer
source                        1..25
                              mol_type = other DNA
                              organism = synthetic construct
SEQUENCE: 50
agtgtgaagt ataggtatga agcag                                          25

SEQ ID NO: 51                 moltype = DNA   length = 21
FEATURE                       Location/Qualifiers
misc_feature                  1..21
                              note = Description of Artificial Sequence: Synthetic primer
source                        1..21
                              mol_type = other DNA
                              organism = synthetic construct
SEQUENCE: 51
cagtggagag cagatgagaa a                                              21

SEQ ID NO: 52                 moltype = DNA   length = 22
FEATURE                       Location/Qualifiers
misc_feature                  1..22
                              note = Description of Artificial Sequence: Synthetic primer
source                        1..22
                              mol_type = other DNA
                              organism = synthetic construct
SEQUENCE: 52
tctgaggaga gcagatgaga aa                                             22

SEQ ID NO: 53                 moltype = DNA   length = 21
FEATURE                       Location/Qualifiers
misc_feature                  1..21
                              note = Description of Artificial Sequence: Synthetic primer
source                        1..21
                              mol_type = other DNA
                              organism = synthetic construct
SEQUENCE: 53
cacctcaagt cttggagaga a                                              21

SEQ ID NO: 54                 moltype = DNA   length = 18
FEATURE                       Location/Qualifiers
misc_feature                  1..18
                              note = Description of Artificial Sequence: Synthetic primer
source                        1..18
                              mol_type = other DNA
                              organism = synthetic construct
SEQUENCE: 54
caagacaaca agggctgg                                                  18

SEQ ID NO: 55                 moltype = DNA   length = 20
FEATURE                       Location/Qualifiers
```

-continued

```
misc_feature            1..20
                        note = Description of Artificial Sequence: Synthetic primer
source                  1..20
                        mol_type = other DNA
                        organism = synthetic construct
SEQUENCE: 55
caagataaca aggcctggac                                                    20

SEQ ID NO: 56           moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 56
cagacataga caacggaaga aag                                                23

SEQ ID NO: 57           moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 57
caaggttaga cttagtgaac aagag                                              25

SEQ ID NO: 58           moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 58
cagaaccaaa acgtcacaag taa                                                23

SEQ ID NO: 59           moltype = DNA   length = 24
FEATURE                 Location/Qualifiers
misc_feature            1..24
                        note = Description of Artificial Sequence: Synthetic primer
source                  1..24
                        mol_type = other DNA
                        organism = synthetic construct
SEQUENCE: 59
catgaaaacc tgtgtcttac acat                                               24

SEQ ID NO: 60           moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 60
acccagcacc cttatttccc                                                    20

SEQ ID NO: 61           moltype = DNA   length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 61
tgcagcaaaa cccttcagag                                                    20

SEQ ID NO: 62           moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 62
tgtgcaatca attctcgagt ttg                                                23

SEQ ID NO: 63           moltype = DNA   length = 21
```

```
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 63
acacagggaa cagaagacac a                                              21

SEQ ID NO: 64           moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 64
caagggtctg aacagggagg                                               20

SEQ ID NO: 65           moltype = DNA  length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 65
accacaagtt gagacaagat aca                                           23
```